United States Patent
Pasteris et al.

(10) Patent No.: US 11,708,358 B2
(45) Date of Patent: Jul. 25, 2023

(54) FUNGICIDAL OXADIAZOLES

(71) Applicant: FMC Corporation, Philadelphia, PA (US)

(72) Inventors: Robert James Pasteris, Newark, DE (US); Srinivas Chittaboina, Bibipet (IN); Travis Chandler McMahon, Middletown, DE (US); Balreddy Kamireddy, Hockessin, DE (US); Ravisekhara Pochimireddy Reddy, Secunderabad (IN)

(73) Assignee: FMC Corporation, Philadelphia, PA (US)

( * ) Notice: Subject to any disclaimer, the term of this patent is extended or adjusted under 35 U.S.C. 154(b) by 479 days.

(21) Appl. No.: 16/603,449

(22) PCT Filed: Apr. 5, 2018

(86) PCT No.: PCT/US2018/026232
§ 371 (c)(1),
(2) Date: Oct. 7, 2019

(87) PCT Pub. No.: WO2018/187553
PCT Pub. Date: Oct. 11, 2018

(65) Prior Publication Data
US 2020/0148672 A1 May 14, 2020

Related U.S. Application Data

(60) Provisional application No. 62/542,949, filed on Aug. 9, 2017, provisional application No. 62/482,343, filed on Apr. 6, 2017.

(51) Int. Cl.

| | | |
|---|---|---|
| *C07D 271/06* | (2006.01) | |
| *C07D 413/10* | (2006.01) | |
| *C07D 413/04* | (2006.01) | |
| *C07D 413/12* | (2006.01) | |
| *C07D 413/14* | (2006.01) | |
| *C07D 417/10* | (2006.01) | |
| *C07D 471/04* | (2006.01) | |
| *C07D 487/04* | (2006.01) | |
| *C07D 498/04* | (2006.01) | |
| *A01N 43/82* | (2006.01) | |
| *A01N 43/84* | (2006.01) | |

(52) U.S. Cl.
CPC .......... *C07D 413/10* (2013.01); *A01N 43/82* (2013.01); *A01N 43/84* (2013.01); *C07D 271/06* (2013.01); *C07D 413/04* (2013.01); *C07D 413/12* (2013.01); *C07D 413/14* (2013.01); *C07D 417/10* (2013.01); *C07D 471/04* (2013.01); *C07D 487/04* (2013.01); *C07D 498/04* (2013.01)

(58) Field of Classification Search
None
See application file for complete search history.

(56) References Cited

U.S. PATENT DOCUMENTS

2005/0203188 A1    9/2005    Ammermann et al.

FOREIGN PATENT DOCUMENTS

| EP | 276432 | | 12/1987 |
|---|---|---|---|
| EP | 577218 | | 1/1994 |
| EP | 2065377 | A1 | 6/2009 |
| EP | 2246338 | | 11/2010 |
| EP | 2729454 | B1 | 5/2014 |
| JP | 11-171877 | | 6/1999 |
| WO | 1994/05153 | | 3/1994 |
| WO | 2000/15637 | | 3/2000 |
| WO | 2013/066839 | | 5/2013 |
| WO | 20130066838 | | 5/2013 |
| WO | 20130066839 | | 5/2013 |
| WO | 20130080120 | | 6/2013 |
| WO | 20140154612 | | 10/2014 |
| WO | 20150185485 | | 12/2015 |
| WO | 20170055473 | | 4/2017 |
| WO | 20170076740 | | 5/2017 |
| WO | 20170085098 | | 5/2017 |
| WO | 20170085100 | | 5/2017 |
| WO | 20170093348 | | 6/2017 |
| WO | 20170118689 | | 7/2017 |
| WO | 20170178549 | | 10/2017 |
| WO | 20170213252 | | 12/2017 |

(Continued)

OTHER PUBLICATIONS

International Search Report for corresponding PCT/US2018/026232 dated Oct. 11, 2018.

(Continued)

*Primary Examiner* — Alton N Pryor

(74) *Attorney, Agent, or Firm* — Charlene G. Sternberg; FMC Corporation

(57) ABSTRACT

Disclosed are compounds of Formula 1, including all geometric and stereoisomers, tautomers, N-oxides, and salts thereof, wherein $R^1$, L and J are as defined in the disclosure. Also disclosed are compositions containing the compounds of Formula 1 and methods for controlling plant disease caused by a fungal pathogen comprising applying an effective amount of a compound or a composition of the invention.

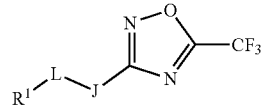

14 Claims, No Drawings

(56) References Cited

FOREIGN PATENT DOCUMENTS

| WO | 20170220485 | 12/2017 |
|----|-------------|---------|
| WO | 20180080859 | 5/2018  |
| WO | 20180118781 | 6/2018  |
| WO | 2018/158365 | 9/2018  |

OTHER PUBLICATIONS

Lima et al., "Bioisosterism: A Useful Strategy for Molecular Modification and Drug Design", Current Medicinal Chemistry, 2005, vol. 12, No. 1, p. 23-49.

FUNGICIDAL OXADIAZOLES

FIELD OF THE INVENTION

This invention relates to certain oxadiazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publications WO 2017/118689 and WO 2017/085100 disclose oxadiazole derivatives and their use as fungicides.

SUMMARY OF THE INVENTION

This invention is directed to compounds of Formula 1 (including all stereoisomers), N-oxides, hydrates (and solvates thereof), and salts thereof, agricultural compositions containing them and their use as fungicides:

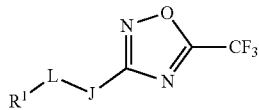

1 wherein
- $R^1$ is a phenyl ring optionally substituted with up to 3 substituents independently selected from $R^2$; or
- $R^1$ is a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 3 substituents independently selected from $R^2$; or
- $R^1$ is a 3- to 7-membered nonaromatic ring or an 8- to 11-membered bicyclic ring system, each ring or ring system containing ring members selected from carbon atoms and optionally up to 4 heteroatoms independently selected from up to 2 O, up to 2 S and up to 4 N atoms, wherein up to 2 ring members are independently selected from C(=O), C(=S), S(=O) and S(=O)$_2$, each ring or ring system optionally substituted with up to 3 substituents independently selected from $R^2$;
- L is O, $NR^3$, $NR^3CH_2$, $CH_2NR^3$, $NR^3CH_2CH_2$, $CH_2CH_2NR^3$, $(CR^{4a}R^{4b})_n$, $OCH_2$, $CH_2O$, $OCH_2CH_2$, $CH_2CH_2O$ or $CH_2OCH_2$, wherein the atom to the left is connected to $R^1$, and the atom to the right is connected to J, each carbon atom is optionally substituted with up to 2 substituents independently selected from halogen, cyano, hydroxy, nitro, $C_1$-$C_3$ alkyl, $C_1$-$C_3$ haloalkyl, $C_1$-$C_2$ alkoxy and $C_1$-$C_2$ haloalkoxy;
- J is a phenyl ring or a naphthalenyl ring system, each optionally substituted with up to 2 substituents independently selected from $R^5$; or a 3- to 7-membered carbocyclic ring, wherein up to 3 ring members are independently selected from C(=O) and C(=S), each ring optionally substituted with up to 2 substituents independently selected from $R^5$; or
- J is a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^5$;
- each $R^2$ is independently halogen, cyano, hydroxy, nitro, thioyl, —$SF_5$, —CH(=O), —C(=O)OH, —$NR^{3a}R^{3b}$, —C(=O)$NR^{3a}R^{3b}$, —C(=O)C(=O)$NR^{3a}R^{3b}$, —C(=S)$NR^{3a}R^{3b}$, —C($R^6$)=$NR^7$, —N=$CR^8NR^{9a}R^{9b}$ or —U—V-Q; or $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_1$-$C_6$ alkylsulfinyl, $C_1$-$C_6$ alkylsulfonyl, $C_1$-$C_6$ alkylaminosulfinyl, $C_2$-$C_6$ dialkylaminosulfinyl, $C_1$-$C_6$ alkylsulfonyloxy, $C_1$-$C_6$ alkylsulfonylamino, $C_2$-$C_6$ alkylcarbonyl, $C_4$-$C_7$ cycloalkylcarbonyl, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_3$-$C_6$ alkyloxycarbonylcarbonyl, $C_2$-$C_6$ alkylcarbonyloxy, $C_4$-$C_7$ cycloalkylcarbonyloxy, $C_2$-$C_6$ alkoxycarbonyloxy, $C_4$-$C_7$ cycloalkoxycarbonyloxy, $C_2$-$C_6$ alkylaminocarbonyloxy, $C_4$-$C_7$ cycloalkylaminocarbonyloxy, $C_2$-$C_6$ alkylcarbonylamino, $C_4$-$C_7$ cycloalkylcarbonylamino, $C_2$-$C_6$ alkoxycarbonylamino, $C_4$-$C_7$ cycloalkoxycarbonylamino, $C_2$-$C_6$ alkylaminocarbonylamino, $C_4$-$C_7$ cycloalkylaminocarbonylamino or $C_2$-$C_6$ dialkoxyphosphinyl, each optionally substituted with up to 3 substituents independently selected from $R^{10}$;
- each $R^3$ and $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_5$ alkoxy, $C_2$-$C_4$ alkoxyalkyl, $C_1$-$C_4$ alkylsulfonyl, $C_1$-$C_4$ haloalkylsulfonyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_4$-$C_7$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl;
- each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ hydroxyalkyl, $C_2$-$C_6$ cyanoalkyl, $C_3$-$C_8$ cycloalkyl, $C_3$-$C_8$ halocycloalkyl, $C_3$-$C_8$ cycloalkenyl, $C_3$-$C_8$ halocycloalkenyl, $C_4$-$C_{10}$ alkylcycloalkyl, $C_4$-$C_{10}$ cycloalkylalkyl, $C_4$-$C_{10}$ halocycloalkylalkyl, $C_6$-$C_{14}$ cycloalkylcycloalkyl, $C_5$-$C_{10}$ alkylcycloalkylalkyl, $C_2$-$C_6$ alkoxyalkyl, $C_2$-$C_6$ haloalkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_2$-$C_6$ haloalkylaminoalkyl, $C_3$-$C_8$ dialkylaminoalkyl or $C_4$-$C_{10}$ cycloalkylaminoalkyl, each optionally substituted with up to 1 substituent selected from cyano, hydroxy, nitro, $C_2$-$C_4$ alkylcarbonyl, $C_2$-$C_4$ alkoxycarbonyl, $C_3$-$C_{15}$ trialkylsilyl and $C_3$-$C_{15}$ halotrialkylsilyl; or a pair of $R^{3a}$ and $R^{3b}$ substituents are taken together with the nitrogen atom to which they are attached to form a 4- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 3 substituents independently selected from halogen and $C_1$-$C_3$ alkyl;

each $R^{4a}$ and $R^{4b}$ is independently H, halogen, cyano, hydroxy, nitro, $C_1$-$C_3$ alkyl, $C_1$-$C_3$ haloalkyl, $C_1$-$C_2$ alkoxy or $C_1$-$C_2$ haloalkoxy; or a pair of $R^{4a}$ and $R^{4b}$ substituents attached to the same carbon atom are taken together to form a $C_3$-$C_5$ cycloalkyl ring optionally substituted with up to 2 substituents independently selected from halogen, methyl, methoxy and methylthio;

each $R^5$ is independently hydroxy, cyano, nitro, halogen, $C_1$-$C_4$ alkyl, $C_1$-$C_4$ haloalkyl, $C_2$-$C_4$ alkenyl or $C_1$-$C_4$ alkoxy;

each $R^6$ is independently H, cyano, halogen, methyl, methoxy, methylthio or methoxycarbonyl;

each $R^7$ is independently hydroxy or $NR^{11a}R^{11b}$; or $C_1$-$C_4$ alkoxy, $C_2$-$C_4$ alkenyloxy, $C_2$-$C_4$ alkynyloxy, $C_2$-$C_4$ alkylcarbonyloxy, $C_2$-$C_5$ alkoxycarbonyloxy, $C_2$-$C_5$ alkylaminocarbonyloxy or $C_3$-$C_5$ dialkylaminocarbonyloxy, each optionally substituted with up to 1 substituent selected from halogen, cyano, hydroxy and —C(=O)OH;

each $R^8$ is independently H, methyl, methoxy or methylthio;

each $R^{9a}$ and $R^{9b}$ is independently H or $C_1$-$C_4$ alkyl; or a pair of $R^{9a}$ and $R^{9b}$ substituents are taken together with the nitrogen atom to which they are attached to form a 5- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 2 methyl;

each $R^{10}$ is independently halogen, amino, cyano, hydroxy, nitro, thioyl, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_2$-$C_4$ alkoxyalkoxy, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_1$-$C_6$ alkylamino, $C_2$-$C_6$ dialkylamino, $C_2$-$C_5$ alkylaminocarbonyl, $C_3$-$C_5$ dialkylaminocarbonyl, $C_3$-$C_5$ alkylthioalkylcarbonyl, $C_3$-$C_{15}$ trialkylsily, $C_3$-$C_{15}$ halotrialkylsilyl, —C($R^{13}$)=NOR$^{14}$ or —C($R^{15}$)=NR$^{16}$;

each U is independently a direct bond, C(=O)O, C(=O)NR$^{17}$ or C(=S)NR$^{18}$, wherein the atom to the left is connected to $R^1$, and the atom to the right is connected to V;

each V is independently a direct bond; or $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, each optionally substituted with up to 3 substituents independently selected from halogen, cyano, nitro, hydroxy, $C_1$-$C_2$ alkyl, $C_1$-$C_2$ haloalkyl, $C_1$-$C_2$ alkoxy and $C_1$-$C_2$ haloalkoxy;

each Q is independently phenyl or phenoxy, each optionally substituted with up to 2 substituents independently selected from $R^{12}$; or each Q is independently a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$; or each Q is independently a 3- to 7-membered nonaromatic heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$;

each $R^{11a}$ is independently H, $C_1$-$C_4$ alkyl or $C_2$-$C_4$ alkylcarbonyl;

each $R^{11b}$ is independently H, cyano, $C_1$-$C_5$ alkyl, $C_2$-$C_5$ alkylcarbonyl, $C_2$-$C_5$ haloalkylcarbonyl, $C_4$-$C_7$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl; or a pair of $R^{11a}$ and $R^{11b}$ substituents are taken together with the nitrogen atom to which they are attached to form a 5- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 2 methyl;

each $R^{12}$ is independently halogen, cyano, hydroxy, nitro, $C_1$-$C_4$ alkyl, $C_1$-$C_4$ haloalkyl, $C_2$-$C_4$ alkenyl, $C_1$-$C_4$ alkoxy, $C_2$-$C_4$ alkylcarbonyl or $C_2$-$C_4$ alkoxycarbonyl;

each $R^{13}$ and $R^{15}$ is independently H, cyano, halogen, $C_1$-$C_3$ alkyl, $C_1$-$C_3$ haloalkyl, $C_3$-$C_6$ cycloalkyl or $C_1$-$C_3$ alkoxy; or a phenyl ring optionally substituted with up to 2 substituents independently selected from halogen and $C_1$-$C_3$ alkyl;

each $R^{14}$ is independently H, $C_1$-$C_5$ alkyl, $C_1$-$C_5$ haloalkyl, $C_2$-$C_5$ alkenyl, $C_2$-$C_5$ haloalkenyl, $C_2$-$C_5$ alkynyl, $C_3$-$C_6$ cycloalkyl, $C_3$-$C_6$ halocycloalkyl, $C_2$-$C_5$ alkylcarbonyl or $C_2$-$C_5$ alkoxycarbonyl; or each $R^{14}$ is a phenyl ring optionally substituted with up to 2 substituents independently selected from halogen and $C_1$-$C_3$ alkyl; or a 5- to 6-membered fully saturated heterocyclic ring, each ring containing ring members selected from carbon atoms and up to 2 heteroatoms independently selected from up to 2 O, up to 2 S and up to 2 N atoms, each ring optionally substituted with up to 2 substituents independently selected from halogen and $C_1$-$C_3$ alkyl;

each $R^{16}$ is independently H, cyano, $C_1$-$C_3$ alkyl, $C_1$-$C_3$ haloalkyl, $C_1$-$C_4$ alkoxy, $C_2$-$C_4$ alkylcarbonyl or $C_2$-$C_4$ alkoxycarbonyl;

each $R^{17}$ and $R^{18}$ is independently H, cyano, hydroxy, $C_1$-$C_4$ alkyl, $C_1$-$C_4$ haloalkyl, $C_2$-$C_4$ alkylcarbonyl, $C_2$-$C_4$ haloalkylcarbonyl, $C_2$-$C_4$ alkoxycarbonyl or $C_2$-$C_4$ haloalkoxycarbonyl; and n is 1, 2 or 3;

provided that:
(a) when L is CH$_2$, and J is unsubstituted phenyl, then $R^1$ is other than 3-(methoxyimino)-1-pyrrolidinyl, 5-(methylsulfinyl)-1H-1,2,4-triazol-3-yl, 5-(ethylthio)-1H-1,2,4-triazol-3-yl, 5-(propylthio)-1H-1,2,4-triazol-3-yl, 2,3-dihydro-5-methyl-3-oxo-1H-pyrazol-1-yl, 1-piperidinyl, 4-(methoxyimino)-1-piperidinyl, 4-morpholinyl, 2,6-dimethyl-4-morpholinyl, 4-(methylsulfonyl)-1-piperazinyl, 4-thiomorpholinyl, 6-methoxy-3-pyridinyl or 1,2,3,6-tetrahydro-1,3-dimethyl-2,6-dioxo-7H-purin-7-yl;

(b) when R¹ is a 5-membered heterocyclic ring containing 2 to 4 nitrogen atoms, each ring optionally substituted with up to 3 substituents independently selected from cyano, Br, Cl, I, CH₃, C₁-C₂ alkoxycarbonyl and 4-chlorophenyl, and L is CH₂, then J is other than pyridine;

(c) when R¹ is 1H-pyrazol-1-yl substituted with 1-2 substituents independently selected from CH₃ and CH₃CH₂C(=O), and J is unsubstituted phenyl, then L is other than CH₂CH₂, CH₂CHF or CH(CH₃);

(d) when L is CH₂, and J is unsubstituted phenyl, then R¹ is other than 1H-indazole, 2H-indazole, 1H-indole, 1H-pyrrole, 2-piperidinone or 2-pyrrolidinone, each optionally substituted with up to 3 substituents independently selected from —CH(=O), CH₃C(=O), cyano, Cl, F, CH₃, (CH₃)₂CHCH₂, CF₃, CH₃O and CH₃OC(=O);

(e) the compound of Formula 1 is not a compound of F-1

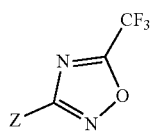

F-1 wherein
Z is

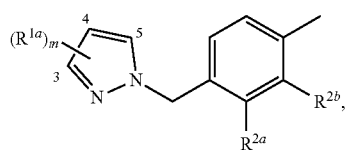

Z-1

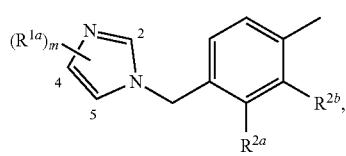

Z-2

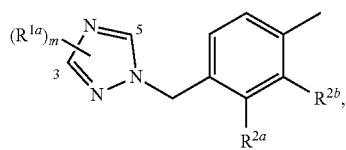

Z-3

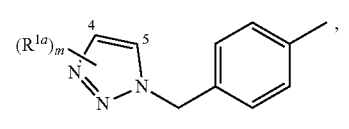

Z-4

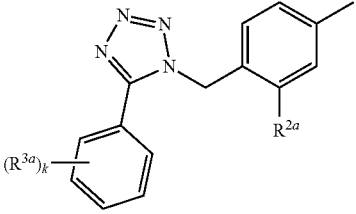

Z-5

-continued

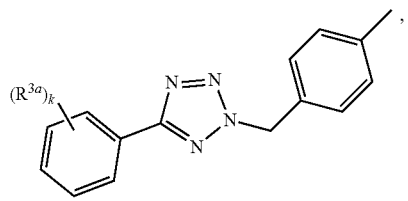

Z-6

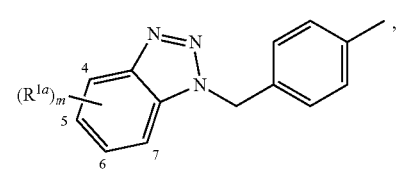

Z-7

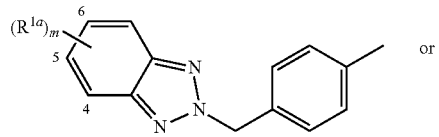

Z-8 or

Z-9 wherein for Z-1 through Z-9, the substituents R¹ᵃ and R³ᵃ may be the same or different; and wherein for Z-1:
  m is 0; and R²ᵃ and R²ᵇ are each H; or
  m is 1; R¹ᵃ is at the 3-position and is 3-(CH₃CH₂OC(=O))-2-pyridinyl, Cl, CF₃ or —CH(=O); and R²ᵃ and R²ᵇ are each H; or
  m is 1; R¹ᵃ is at the 4-position and is halogen, cyano, CF₃, —CH(=O), OHC(=O), C₂-C₅ alkoxycarbonyl, NH₂C(=O), CH₃NHC(=O), CH₃CH₂NHC(=O), (CH₃)₂NCH₂CH₂OC(=O), cyclopropyl-NHC(=O), cyclopropyl-CH₂NHC(=O), (CH₃)₂NC(=O), (CH₃CH₂)₂NC(=O), CH₃ONHC(=O), CH₃OCH₂CH₂NHC(=O), CH≡CCH₂NHC(=O), CH₃ON(CH₃)C(=O), CH₃ON=CH, CH₃CH₂ON=CH, CH₃CH₂CH₂ON=CH, (CH₃)₂CHON=CH, CH≡CCH₂ON=CH, phenyl-CH₂ON=CH or 4-morpholinylcarbonyl; and R²ᵃ and R²ᵇ are each H; or
  m is 1; R¹ᵃ is at the 4-position and is CH₃CH₂C(=O); R²ᵃ is H; and R²ᵇ is F; or
  m is 1; R¹ᵃ is at the 4-position and is Br, Cl or I; R²ᵃ is F or Cl; and R²ᵇ is H; or
  m is 2; R¹ᵃ is at the 3- and 4-positions and is cyano, CF₂H, CF₃, CH₃OCH₂, C₂-C₃ alkoxycarbonyl, cyclopropyl, phenyl or 4-chlorophenyl; and R²ᵃ and R²ᵇ are each H; or
  m is 2; R¹ᵃ is at the 3- and 5-positions and is cyano, CH₃, —CH(=O), CF₂H, CF₃, cyclopropyl, C₂-C₃ alkoxycarbonyl, 4-fluorophenyl, 2,4-difluorophenyl, 2,5-difluorophenyl or 4-methoxyphenyl; and R²ᵃ and R²ᵇ are each H; or
  m is 2; R¹ᵃ is at the 3- and 5-positions and is CH₃; R²ᵃ is F or Cl; and R²ᵇ is H; or
  m is 2; R¹ᵃ is at the 3- and 5-positions and is CH₃; R²ᵃ is H; and R²ᵇ is F; or m is 2; $R^{1a}$ is at the 4- and 5-positions and is $CF_2H$, cyclopropyl, $CH_3OCH_2$ or $C_2$-$C_3$ alkoxycarbonyl; and $R^{2a}$ and $R^{2b}$ are each H; or m is 3; $R^{1a}$ is at the 3-, 4- and 5-positions and is cyano, Cl, $CH_3$, $CF_3$, 4-chlorophenyl, 2,4-dichlorophenyl or 2,2-difluoro-1,3-benzodioxol-4-yl; and $R^{2a}$ and $R^{2b}$ are each H; or m is 3; $R^{1a}$ is at the 3-, 4- and 5-positions and is Cl or $CH_3$; $R^{2a}$ is F; and $R^{2b}$ is H;

wherein for Z-2:

m is 0; $R^{2a}$ is H, Cl or F; and $R^{2b}$ is H; or m is 1; $R^{1a}$ is at the 2-position and is Br, $CH_3$, $(CH_3)_2CH$, —CH(=O), phenyl or 4-fluorophenyl; and $R^{2a}$ and $R^{2b}$ are each H; or m is 1; $R^{1a}$ is at the 2-position and is $CH_3$; $R^{2a}$ is F; and $R^{2b}$ is H; or m is 1; $R^{1a}$ is at the 4-position and is cyano, Br, I, $CH_3$, $CF_3$, —CH(=O), $CH_3OC(=O)$, $CH_3C(=O)NHCH_2CH_2$, phenyl or 4-chlorophenyl; and $R^{2a}$ and $R^{2b}$ are each H; or m is 1; $R^{1a}$ is at the 4-position and is Br or $CH_3$; $R^{2a}$ is Cl, F, $CF_3$ or $CH_3O$; and $R^{2b}$ is H; or m is 1; $R^{1a}$ is at the 5-position and is $CH_3OC(=O)$; $R^{2a}$ and $R^{2b}$ are each H; or m is 1; $R^{1a}$ is at the 5-position and is Br; $R^{2a}$ is $CH_3O$; and $R^{2b}$ is H; or m is 2; $R^{1a}$ is at the 2- and 4-positions and is Br, Cl, $CH_3$, $CHF_2S$ or 4-chlorophenyl; and $R^{2a}$ and $R^{2b}$ are each H; or m is 2; $R^{1a}$ is at the 2- and 4-positions and is $CH_3$; $R^{2a}$ is Cl or F; and $R^{2b}$ is H; or m is 2; $R^{1a}$ is at the 4- and 5-positions and is cyano, Cl, $CH_3$, $CH_3CH_2CH_2$, $C_2$-$C_3$ alkoxycarbonyl or phenyl; and $R^{2a}$ and $R^{2b}$ are each H; or m is 2; $R^{1a}$ is at the 4- and 5-positions and is Cl, cyano or $CH_3OC(=O)$; $R^{2a}$ is F or Cl; and $R^{2b}$ is H; or m is 3; $R^{1a}$ is at the 2-, 4- and 5-positions and is Br, Cl, $CF_3$, $CF_3S$, $CH_3CH_2OC(=O)$ or 4-chlorophenyl; and $R^{2a}$ and $R^{2b}$ are each H; or wherein for Z-3:

m is 0; $R^{2a}$ is H, Cl, F, $CF_3$ or $CH_3O$; and $R^{2b}$ is H; or m is 1; $R^{1a}$ is at the 3-position and is cyano, $CF_3$, $CH_3S$, $CH_3CH_2CH_2S$, $CH_3S(=O)$, $CH_3S(=O)_2$, phenyl-$CH_2S$, $CH_3OC(=O)$ or $(CH_3)_2N$; and $R^{2a}$ and $R^{2b}$ are each H; or m is 1; $R^{1a}$ is at the 3-position and is cyano; $R^{2a}$ is H; and $R^{2b}$ is F; or m is 1; $R^{1a}$ is at the 3-position and is $CH_3OC(=O)$; $R^{2a}$ is F or Cl; and $R^{2b}$ is H; or m is 1; $R^{1a}$ is at the 5-position and is cyano, $CF_3$, $CH_3S$, $CH_3CH_2S$, $CH_3S(=O)_2$ or $CH_3OC(=O)$; and $R^{2a}$ and $R^{2b}$ are each H; or m is 1; $R^{1a}$ is at the 5-position and is cyano; $R^{2a}$ is H; and $R^{2b}$ is F; or m is 2; $R^{1a}$ is at the 3- and 5-positions and is Br, $CF_2H$, $CF_3$, $CH_3O$ or $NH_2$; and $R^{2a}$ and $R^{2b}$ are each H; or wherein for Z-4:

m is 1; $R^{1a}$ is at the 4-position and is cyano, OHC(=O), $C_1$-$C_5$ alkyl, cyclopropyl, cyclopentyl, $CH_3CH_2OCH_2$, $C_2$-$C_4$ alkoxycarbonyl, $C_2$-$C_3$ alkylaminocarbonyl, $CH_3ONHC(=O)$, 4-chlorophenyl-NHC(=O), 4-methoxyphenyl-NHC(=O), 4-pyrdinyl-NHC(=O), $(CH_3)_2NC(=O)$, $CH_3ON(CH_3)C(=O)$, 3-thienyl, phenyl-C(=O)NHC(Me)$_2$, phenyl, 4-fluorophenyl, 4-methylphenyl, 4-methoxyphenyl, 2-pyridinyl, 3-pyridinyl, 1-ethyl-3-methyl-1H-pyrazol-4-yl, 1-ethyl-5-methyl-1H-pyrazol-4-yl, 1-methyl-1H-imidazol-5-yl or $(CH_3)_3Si$; and $R^{2a}$ and $R^{2b}$ are each H; or m is 1; $R^{1a}$ is at the 5-position and is phenyl, $CH_3OC(=O)$ or $CH_3NHC(=O)$; and $R^{2a}$ and $R^{2b}$ are each H; or wherein for Z-5:

k is 1 or 2; each $R^{3a}$ is independently Cl, Br or $CH_3$; and $R^{2a}$ is H, Cl or F;

wherein for Z-6:

k is 1 or 2; each $R^{3a}$ is independently Br, Cl, $CH_3$ or —CH(=O);

wherein for Z-7:

m is 0; or m is 1; and $R^{1a}$ is at the 5-position and is $CH_3CH_2OC(=O)$; or m is 2; and $R^{1a}$ is at the 4- and 5-positions and is Cl, $CH_3$, $CF_3$ or 4-fluorophenoxy; or m is 2; and $R^{1a}$ is at the 4- and 6-positions and is Cl or $CF_3$; or m is 2; and $R^{1a}$ is at the 5- and 6-positions and is Cl or 4-methoxyphenoxy; or m is 2; and $R^{1a}$ is at the 5- and 7-positions and is Cl or $CF_3$; or m is 2; and $R^{1a}$ is at the 6- and 7-positions and is Cl or 4-fluorophenoxy; or m is 3; and $R^{1a}$ is at the 4-, 5- and 6-positions and is Br or $CH_3$;

wherein for Z-8:

m is 0; or m is 1; and $R^{1a}$ is at the 5-position and is $CH_3CH_2OC(=O)$; or m is 2; and $R^{1a}$ is at the 4- and 5-positions and is Cl, $CH_3$ or 4-fluorophenoxy; or m is 2; and $R^{1a}$ is at the 4- and 6-positions and is $CF_3$ or Cl; or m is 2; and $R^{1a}$ is at the 5- and 6-positions and is Cl or 4-methoxyphenoxy; or m is 3; and $R^{1a}$ is at the 4-, 5- and 6-positions and is Br or $CH_3$;

wherein for Z-9:

m is 0; and $R^{2a}$ is Cl or F; or m is 1; $R^{1a}$ is at the 2-position and is $CF_3$, $CH_3CH_2$, N=CCH$_2$ or 4-pyridinyl; and $R^{2a}$ is H; or m is 1; $R^{1a}$ is at the 4-position and is Cl; and $R^{2a}$ is H; or m is 1; $R^{1a}$ is at the 7-position and is Cl; and $R^{2a}$ is H; or m is 2; $R^{1a}$ is at the 2- and 5-positions and is $CH_3$ or $CF_3$; and $R^{2a}$ is H; or m is 2; $R^{1a}$ is at the 2- and 5-positions and is $CH_3$ or F; and $R^{2a}$ is F; or m is 2; $R^{1a}$ is at the 2- and 6-positions and is $CH_3$ or $CF_3$; and $R^{2a}$ is H; or m is 2; $R^{1a}$ is at the 2- and 6-positions and is $CH_3$ or F; and $R^{2a}$ is F; or m is 2; $R^{1a}$ is at the 5- and 6-positions and is Cl or F; and $R^{2a}$ is H; and (f) the compound of Formula 1 is not α-[4-[5-(trifluoromethyl)-1,2,4-oxadiazol-3-yl]phenyl]-4-morpholineacetonitrile;

3-[[4-[5-(trifluoromethyl)-1,2,4-oxadiazol-3-yl]phenyl]methyl]-3H-1,2,3-triazolo[4,5-b]pyridine;

2-[[4-[5-(trifluoromethyl)-1,2,4-oxadiazol-3-yl]phenyl]methyl]-2H-1,2,3-triazolo[4,5-b]pyridine;

1-[[4-[5-(trifluoromethyl)-1,2,4-oxadiazol-3-yl]phenyl]methyl]-1H-1,2,3-triazolo[4,5-b]pyridine;

4-[[4-[5-(trifluoromethyl)-1,2,4-oxadiazol-3-yl]phenyl]methyl]-4H-1,2,3-triazolo[4,5-b]pyridine;

5-(2,6-difluorophenyl)-2-[[4-[5-(trifluoromethyl)-1,2,4-oxadiazol-3-yl]phenyl]methyl]-2H-1,2,3-triazole-4-carbonitrile;
3-[4-(4H-1,2,4-triazol-4-ylmethyl)phenyl]-5-(trifluoromethyl)-1,2,4-oxadiazole;
3-[4-[[3-[(phenylmethyl)thio]-4H-1,2,4-triazol-4-yl]methyl]phenyl]-5-(trifluoromethyl)-1,2,4-oxadiazole;
1-[[4-[5-(trifluoromethyl)-1,2,4-oxadiazol-3-yl]phenyl]methyl]-1H-pyrrolo[3,2-b]pyridine-2-carbonitrile;
7-[[2-fluoro-4-[5-(trifluoromethyl)-1,2,4-oxadiazol-3-yl]phenyl]methyl]-7H-pyrrolo[2,3-b]pyridine;
3-[3-fluoro-4-[(5-methyl-1H-imidazol-2-yl)methyl]phenyl]-5-(trifluoromethyl)-1,2,4-oxadiazole;
5,6-dihydro-2-[[4-[5-(trifluoromethyl)-1,2,4-oxadiazol-3-yl]phenyl]methyl]-cyclopenta[c]pyrrol-4(2H)-one
2-methoxy-5-[1-[4-[5-(trifluoromethyl)-1,2,4-oxadiazol-3-yl]phenyl]ethyl]-pyridine;
3-[4-[(4,5-dihydro-5,5-dimethyl-2-oxazolyl)methyl]phenyl]-5-(trifluoromethyl)-1,2,4-oxadiazole;
N-(2,2,2-trifluoro-1-(4-(5-(trifluoromethyl)-1,2,4-oxadiazol-3-yl)phenyl)ethyl)cyclopropanamine;
4-[[4-[5-(trifluoromethyl)-1,2,4-oxadiazol-3-yl]phenyl]methyl]-1H-pyrrolo[3,2-b]pyridine-2-carbonitrile;
3-[4-(2H-1,2,3-triazol-2-ylmethyl)phenyl]-5-(trifluoromethyl)-1,2,4-oxadiazole; or
3-[4-(1H-1,2,3-triazol-1-ylmethyl)phenyl]-5-(trifluoromethyl)-1,2,4-oxadiazole.

More particularly, this invention pertains to a compound of Formula 1 (including all geometric and stereoisomers), tautomers, an N-oxide, or a salt thereof.

This invention also relates to a fungicidal composition comprising (a) a compound of Formula 1; and (b) at least one additional component selected from the group consisting of surfactants, solid diluents and liquid diluents.

This invention also relates to a fungicidal composition comprising (a) a compound of Formula 1; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains," "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As referred to in this disclosure, the terms "fungal pathogen" and "fungal plant pathogen" include pathogens in the Ascomycota, Basidiomycota and Zygomycota phyla, and the fungal-like Oomycota class that are the causal agents of a broad spectrum of plant diseases of economic importance, affecting ornamental, turf, vegetable, field, cereal and fruit crops. In the context of this disclosure, "protecting a plant from disease" or "control of a plant disease" includes preventative action (interruption of the fungal cycle of infection, colonization, symptom development and spore production) and/or curative action (inhibition of colonization of plant host tissues).

As used herein, the term "mode of action" (MOA) is as define by the Fungicide Resistance Action Committee (FRAC), and is used to distinguish fungicides according to their biochemical mode of action in the biosynthetic pathways of plant pathogens. FRAC-defined modes of actions include (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis, (I) melanin synthesis in cell wall, (P) host plant defense induction, (U) unknown mode of action, (NC) not classified and (M) multi-site contact activity. Each mode of action (i.e. letters A through M) contain one or more subgroups (e.g., A includes subgroups A1, A2, A3 and A4) based either on individual validated target sites of action, or in cases where the precise target site is unknown, based on cross resistance profiles within a group or in relation to other groups. Each of these subgroups (e.g., A1, A2, A3 and A4) is assigned a FRAC code (a number and/or letter). For example, the FRAC code for subgroup A1 is 4. Additional information on target sites and FRAC codes can be obtained from publicly available databases maintained, for example, by FRAC.

As used herein, the term "cross resistance" refers to the phenomenon that occurs when a pathogen develops resistance to one fungicide and simultaneously becomes resistant to one or more other fungicides. These other fungicides are typically, but not always, in the same chemical class or have the same target site of action, or can be detoxified by the same mechanism.

Generally when a molecular fragment (i.e. radical) is denoted by a series of atom symbols (e.g., C, H, N, O and S) the implicit point or points of attachment will be easily recognized by those skilled in the art. In some instances herein, particularly when alternative points of attachment are possible, the point or points of attachment may be explicitly indicated by a hyphen ("-"). For example, "—SCN" indicates that the point of attachment is the sulfur atom (i.e. thiocyanato, not isothiocyanato).

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified, for example, for $R^2$.

In the above recitations, the term "alkyl", used either alone or in compound words such as "alkylthio" or "haloalkyl" includes straight-chain and branched alkyl, such as, methyl, ethyl, n-propyl, i-propyl, and the different butyl, pentyl and hexyl isomers. "Alkenyl" includes straight-chain and branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain and branched alkynes such as ethynyl, 1-propynyl, 2-propynyl, and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene isomers. "Alkenylene" denotes a straight-chain or branched alkenediyl containing one olefinic bond. Examples of "alkenylene" include $CH=CH$, $CH_2CH=CH$, $CH=C(CH_3)$ and the different butenylene isomers. The term "cycloalkylene" denotes a cycloalkanediyl ring. Examples of "cycloalkylene" include cyclopropylene, cyclobutylene, cyclopentylene and cyclohexylene. The term "cycloalkenylene" denotes a cycloalkenediyl ring containing one olefinic bond. Examples of "cycloalkenylene" include cylopropenediyl and cyclpentenediyl.

"Alkoxy" includes, for example, methoxy, ethoxy, n-propyloxy, i-propyloxy, and the different butoxy, pentoxy and hexyloxy isomers. "Alkenyloxy" includes straight-chain and branched alkenyl attached to and linked through an oxygen atom. Examples of "alkenyloxy" include $H_2C=CHCH_2O$ and $CH_3CH=CHCH_2O$. "Alkynyloxy" includes straight-chain and branched alkynyloxy moieties. Examples of "alkynyloxy" include $HC\equiv CCH_2O$ and $CH_3C\equiv CCH_2O$.

The term "alkylthio" includes straight-chain and branched alkylthio moieties such as methylthio, ethylthio, and the different propylthio and butylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$, and the different butylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different butylsulfonyl isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2SCH_2$ and $CH_3CH_2SCH_2CH_2$; "alkylsulfinylalkyl" and "alkylsulfonylalkyl" include the corresponding sulfoxides and sulfones, respectively.

"Alkylamino" includes an NH radical substituted with a straight-chain or branched alkyl group. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2NHCH_2$ and $CH_3CH_2NHCH_2CH_2$.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3OC(=O)$, $CH_3CH_2OC(=O)$, $CH_3CH_2CH_2OC(=O)$, $(CH_3)_2CHOC(=O)$, and the different butoxy- and pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$, and the different butylamino- and pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CH(CH_3)NC(=O)$ and $CH_3CH_2CH_2(CH_3)NC(=O)$.

The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$. The term "alkoxycarbonylamino" denotes alkoxy bonded to a $C(=O)NH$ moiety. Examples of "alkoxycarbonylamino" include $CH_3OC(=O)NH$ and $CH_3CH_2OC(=O)NH$.

"Alkylsulfonylamino" denotes an NH radical substituted with alkylsulfonyl. Examples of "alkylsulfonylamino" include $CH_3CH_2S(=O)_2NH$ and $(CH_3)_2CHS(=O)_2NH$. The term "alkylsulfonyloxy" denotes an alkylsulfonyl group bonded to an oxygen atom. Examples of "alkylsulfonyloxy" include $CH_3S(=O)_2O$, $CH_3CH_2S(=O)_2O$, $CH_3CH_2CH_2S(=O)_2O$, $(CH_3)_2CHS(=O)_2O$, and the different butylsulfonyloxy, pentylsulfonyloxy and hexylsulfonyloxy isomers.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkoxyalkoxy" denotes alkoxy substitution on another alkoxy moiety. "Alkoxyalkoxyalkyl" denotes alkoxyalkoxy substitution on alkyl. Examples of "alkoxyalkoxyalkyl" include $CH_3OCH_2OCH_2$ $CH_3OCH_2OCH_2CH_2$ and $CH_3CH_2OCH_2OCH_2$.

The term "alkylcarbonyloxy" denotes a straight-chain or branched alkyl bonded to a $C(=O)O$ moiety. Examples of "alkylcarbonyloxy" include $CH_3CH_2C(=O)O$ and $(CH_3)$ $_2$CHC(=O)O. Examples of "alkoxycarbonyloxy" include CH$_3$CH$_2$CH$_2$OC(=O)O and (CH$_3$)$_2$CHOC(=O)O. The term "alkoxycarbonylalkyl" denotes alkoxycarbonyl substitution on alkyl. Examples of "alkoxycarbonylalkyl" include CH$_3$CH$_2$OC(=O)CH$_2$, (CH$_3$)$_2$CHOC(=O)CH$_2$ and CH$_3$OC(=O)CH$_2$CH$_2$. The term "alkylaminocarbonyloxy" denotes a straight-chain or branched alkylaminocarbonyl attached to and linked through an oxygen atom. Examples of "alkylaminocarbonyloxy" include (CH$_3$)$_2$CHCH$_2$NHC (=O)O and CH$_3$CH$_2$NHC(=O)O.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to a straight-chain or branched alkyl group. The term "alkylcycloalkyl" denotes alkyl substitution on a cycloalkyl moiety and includes, for example, ethylcyclopropyl, i-propylcyclobutyl, methylcyclopentyl and methylcyclohexyl. "Alkylcycloalkylalkyl" denotes an alkyl group substituted with alkylcycloalkyl. Examples of "alkylcycloalkylalkyl" include methylcyclohexylmethyl and ethylcycloproylmethyl. "Cycloalkenyl" includes groups such as cyclopentenyl and cyclohexenyl as well as groups with more than one double bond such as 1,3- or 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "cycloalkoxy" denotes cycloalkyl attached to and linked through an oxygen atom including, for example, cyclopentyloxy and cyclohexyloxy. The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy groups bonded to a straight-chain or branched alkyl moiety.

The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to a straight-chain or branched alkyl group.

"Cycloalkylcarbonyl" denotes cycloalkyl bonded to a C(=O) group including, for example, cyclopropylcarbonyl and cyclopentylcarbonyl. Cycloalkylcarbonyloxy" denotes cycloalkylcarbonyl attached to and linked through an oxygen atom. Examples of "cycloalkylcarbonyloxy" include cyclohexylcarbonyloxy and cyclopentylcarbonyloxy. The term "cycloalkoxycarbonyl" means cycloalkoxy bonded to a C(=O) group, for example, cyclopropyloxycarbonyl and cyclopentyloxycarbonyl. "Cycloalkylaminocarbonylamino" denotes cycloalkylamino bonded to a C(=O)NH group, for example, cyclopentylaminocarbonylamino and cyclohexylaminocarbonylamino.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The terms "haloalkenyl", "haloalkynyl" "haloalkoxy", "haloalkylsulfonyl", "halocycloalkyl", and the like, are defined analogously to the term "haloalkyl". Examples of "haloalkenyl" include Cl$_2$C=CHCH$_2$ and CF$_3$CH$_2$CH=CHCH$_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, F$_2$CHCH$_2$CH$_2$O and CF$_3$CH$_2$O. Examples of "haloalkylsulfonyl" include CF$_3$S(=O)$_2$, CCl$_3$S(=O)$_2$, CF$_3$CH$_2$S(=O)$_2$ and CF$_3$CF$_2$S(=O)$_2$. Examples of "halocycloalkyl" include 2-chlorocyclopropyl, 2-fluorocyclobutyl, 3-bromocyclopentyl and 4-chorocyclohexyl.

"Cyanoalkyl" denotes an alkyl group substituted with one cyano group. Examples of "cyanoalkyl" include NCCH$_2$, NCCH$_2$CH$_2$ and CH$_3$CH(CN)CH$_2$. "Hydroxyalkyl" denotes an alkyl group substituted with one hydroxy group. Examples of "hydroxyalkyl" include HOCH$_2$CH$_2$, CH$_3$CH (OH)CH and HOCH$_2$CH$_2$CH$_2$.

The total number of carbon atoms in a substituent group is indicated by the "$C_i$-$C_j$" prefix where i and j are numbers from 1 to 14. For example, $C_1$-$C_4$ alkylsulfonyl designates methylsulfonyl through butylsulfonyl; $C_2$ alkoxyalkyl designates CH$_3$OCH$_2$; $C_3$ alkoxyalkyl designates, for example, CH$_3$CH(OCH$_3$), CH$_3$OCH$_2$CH$_2$ or CH$_3$CH$_2$OCH$_2$; and $C_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$.

The term "unsubstituted" in connection with a group such as a ring or ring system means the group does not have any substituents other than its one or more attachments to the remainder of Formula 1. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3. As used herein, the term "optionally substituted" is used interchangeably with the phrase "substituted or unsubstituted" or with the term "(un) substituted."

The number of optional substituents may be restricted by an expressed limitation. For example, the phrase "optionally substituted with up to 3 substituents independently selected from $R^2$" means that 0, 1, 2 or 3 substituents can be present (if the number of potential connection points allows). When a range specified for the number of substituents (e.g., x being an integer from 0 to 2 in Exhibit A) exceeds the number of positions available for substituents on a ring (e.g., 1 position available for $(R^2)_x$ on U-7 in Exhibit A), the actual higher end of the range is recognized to be the number of available positions.

When a compound is substituted with a substituent bearing a subscript that indicates the number of said substituents can vary (e.g., $(R^2)_x$ in Exhibit A wherein x is 1 to 2), then said substituents are independently selected from the group of defined substituents, unless otherwise indicated. When a variable group is shown to be optionally attached to a position, for example $(R^2)_x$ in Exhibit A wherein x may be 0, then hydrogen may be at the position even if not recited in the definition of the variable group.

Naming of substituents in the present disclosure uses recognized terminology providing conciseness in precisely conveying to those skilled in the art the chemical structure. For sake of conciseness, locant descriptors may be omitted.

Unless otherwise indicated, a "ring" or "ring system" as a component of Formula 1 (e.g., $R^1$ and J) is carbocyclic or heterocyclic. The term "ring system" denotes two or more connected rings. The term "spirocyclic ring system" denotes a ring system consisting of two rings connected at a single atom (so the rings have a single atom in common). The term "bicyclic ring system" denotes a ring system consisting of two rings sharing two or more common atoms. In a "fused bicyclic ring system" the common atoms are adjacent, and therefore the rings share two adjacent atoms and a bond connecting them.

The term "ring member" refers to an atom (e.g., C, O, N or S) or other moiety (e.g., C(=O), C(=S), S(=O) and S(=O)$_2$) forming the backbone of a ring or ring system. The term "aromatic" indicates that each of the ring atoms is essentially in the same plane and has a p-orbital perpendicular to the ring plane, and that (4n+2) π electrons, where n is a positive integer, are associated with the ring to comply with Hückel's rule The term "carbocyclic ring" denotes a ring wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

As used herein, the term "partially unsaturated ring" or "partially unsaturated heterocycle" refers to a ring which contains unsaturated ring atoms and one or more double bonds but is not aromatic.

The terms "heterocyclic ring" or "heterocycle" denotes a ring wherein at least one of the atoms forming the ring backbone is other than carbon. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or aromatic heterocyclic ring. "Saturated heterocyclic ring" refers to a heterocyclic ring containing only single bonds between ring members.

Unless otherwise indicated, heterocyclic rings and ring systems are attached to the remainder of Formula 1 through any available carbon or nitrogen atom by replacement of a hydrogen on said carbon or nitrogen atom.

Compounds of this invention can exist as one or more stereoisomers. Stereoisomers are isomers of identical constitution but differing in the arrangement of their atoms in space and include enantiomers, diastereomers, cis- and trans-isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. For a comprehensive discussion of all aspects of stereoisomerism, see Ernest L. Eliel and Samuel H. Wilen, *Stereochemistry of Organic Compounds*, John Wiley & Sons, 1994.

Compounds of this invention can exist as one or more conformational isomers due to restricted rotation about an amide bond (e.g., C(=O)—N) in Formula 1. This invention comprises mixtures of conformational isomers. In addition, this invention includes compounds that are enriched in one conformer relative to others.

This invention comprises all stereoisomers, conformational isomers and mixtures thereof in all proportions as well as isotopic forms such as deuterated compounds.

One skilled in the art will appreciate that not all nitrogen containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts, solvates and hydrates thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due to the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

The compounds herein, and the agriculturally acceptable salts thereof, may exist in a continuum of solid states ranging from fully amorphous to fully crystalline. They may also exist in unsolvated and solvated forms. The term "solvate" describes a molecular complex comprising the compound and one or more agriculturally acceptable solvent molecules (e.g., EtOH). The term "hydrate" is a solvate in which the solvent is water. Agriculturally acceptable solvates include those in which the solvent may be isotopically substituted (e.g., $D_2O$, $d_6$-acetone, $d_6$-DMSO).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

Embodiments of the present invention as described in the Summary of the Invention include those described below. In the following Embodiments, Formula 1 includes stereoisomers, N-oxides, hydrates, and salts thereof, and reference to "a compound of Formula 1" includes the definitions of substituents specified in the Summary of the Invention unless further defined in the Embodiments.

Embodiment 1

A compound of Formula 1 wherein $R^1$ is selected from U-1 through U-118 as depicted in Exhibit A Exhibit A

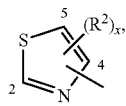
U-1

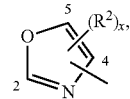
U-2

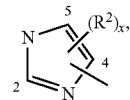
U-3

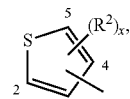
U-4

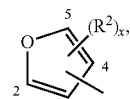
U-5

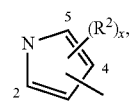
U-6

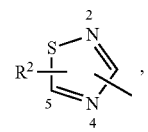
U-7

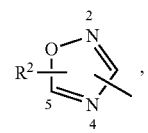
U-8

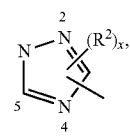
U-9

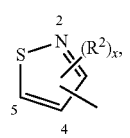
U-10

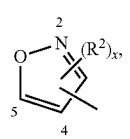
U-11

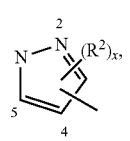
U-12

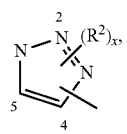 U-13
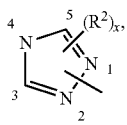 U-14
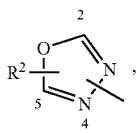 U-15
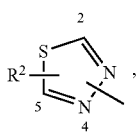 U-16
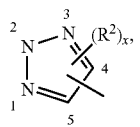 U-17
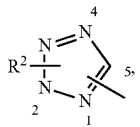 U-18
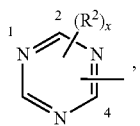 U-19
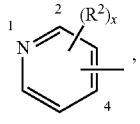 U-20
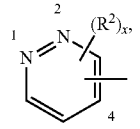 U-21
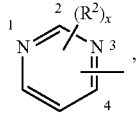 U-22
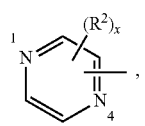 U-23
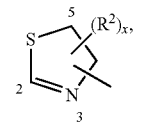 U-24
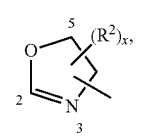 U-25
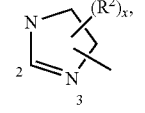 U-26
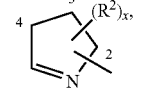 U-27
 U-28
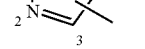 U-29
 U-30
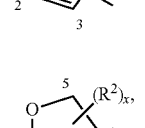 U-31
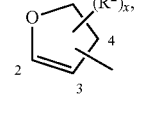 U-32
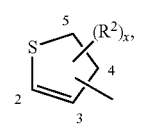 U-33

| | |
|---|---|
| U-34 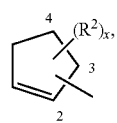 | U-45 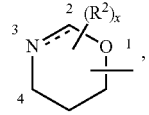 |
| U-35 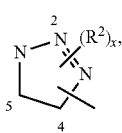 | U-46 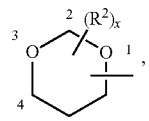 |
| U-36 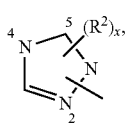 | U-47 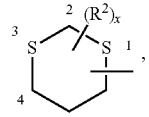 |
| U-37 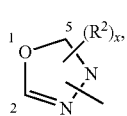 | U-48 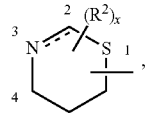 |
| U-38 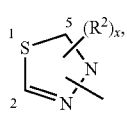 | U-49 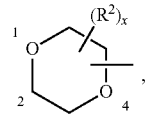 |
| U-39 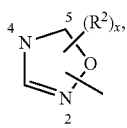 | U-50 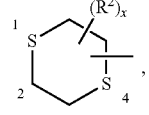 |
| U-40 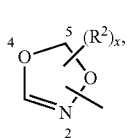 | U-51 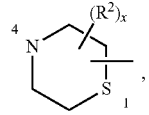 |
| U-41 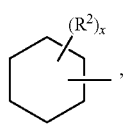 | U-52 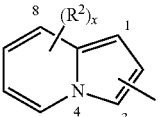 |
| U-42 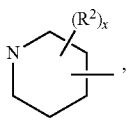 | U-53 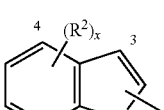 |
| U-43 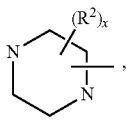 | U-54 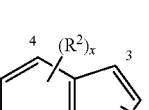 |
| U-44 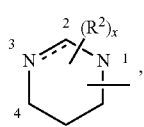 | U-55 |

-continued
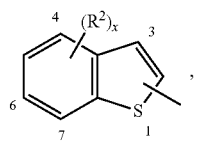 U-56
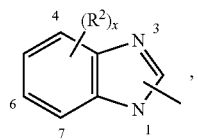 U-57
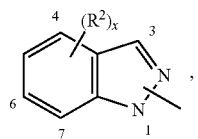 U-58
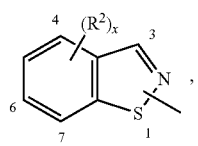 U-59
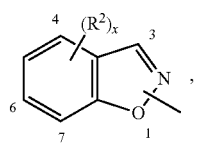 U-60
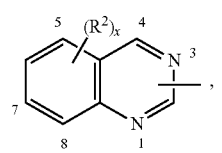 U-61
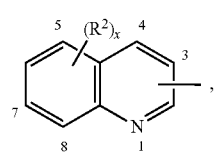 U-62
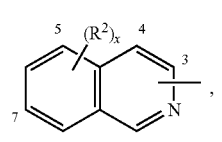 U-63
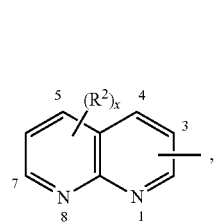 U-64
-continued
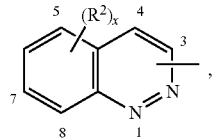 U-65
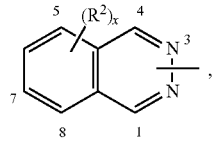 U-66
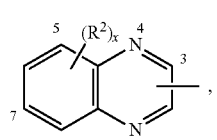 U-67
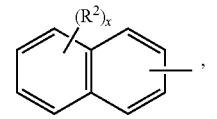 U-68
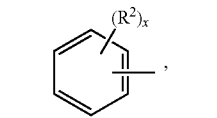 U-69
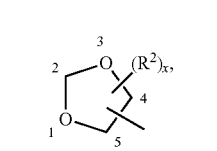 U-70
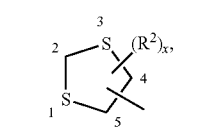 U-71
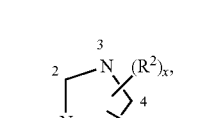 U-72
U-73
U-74
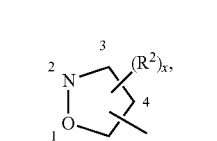 U-75

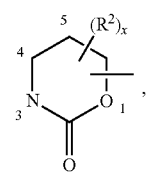, U-76
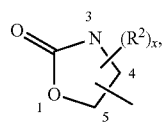, U-77
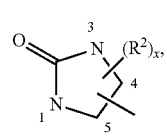, U-78
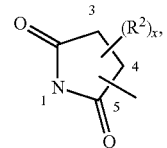, U-79
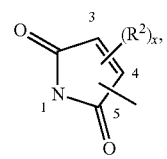, U-80
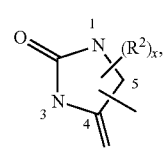, U-81
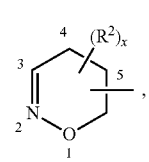, U-82
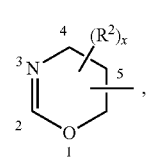, U-83
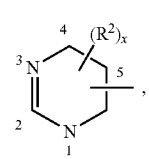, U-84
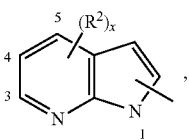, U-85
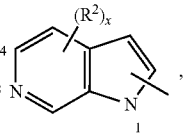, U-86
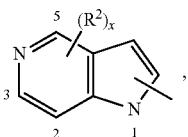, U-87
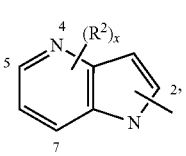, U-88
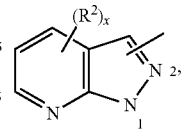, U-89
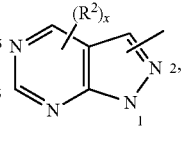, U-90
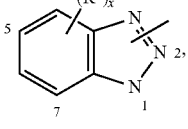, U-91
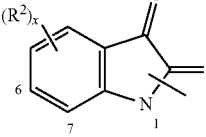, U-92
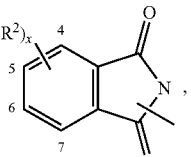, U-93
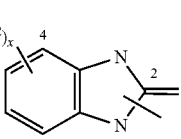, U-94

-continued
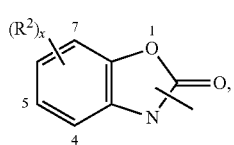 U-95
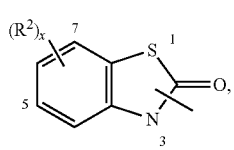 U-96
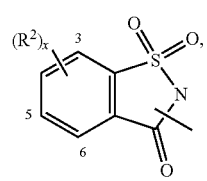 U-97
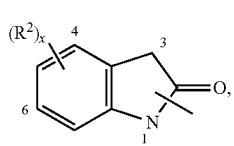 U-98
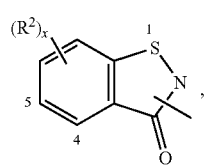 U-99
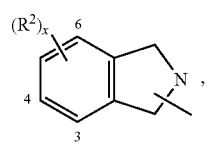 U-100
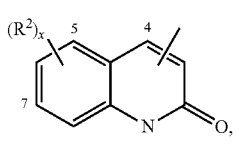 U-101
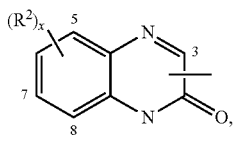 U-102
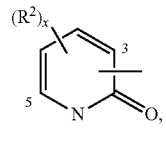 U-103
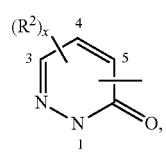 U-104
-continued
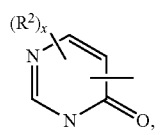 U-105
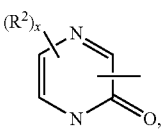 U-106
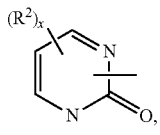 U-107
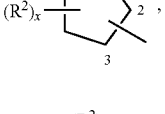 U-108
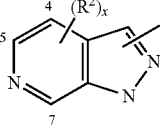 U-109
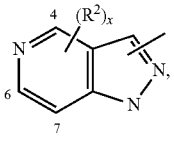 U-110
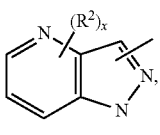 U-111
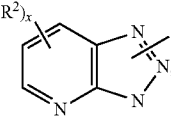 U-112
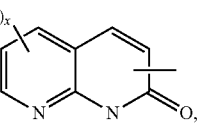 U-113
U-114
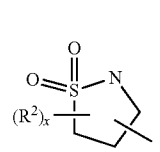 U-115

-continued

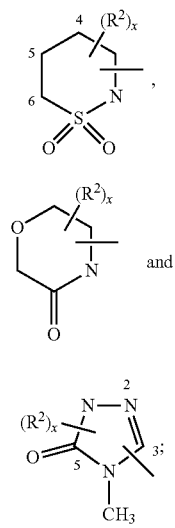

wherein the floating bond is connected to L in Formula 1 through any available carbon or nitrogen atom of the depicted ring or ring system; and x is 0, 1 or 2.

Embodiment 2

A compound of Embodiment 1 wherein $R^1$ is U-1 through U-16, U-20, U-22, U-24, U-25, U-26, U-28, U-29, U-30, U-37, U-38, U-42 through U-47 or U-71 through U-114.

Embodiment 3

A compound of Embodiment 2 wherein $R^1$ is U-12, U-24, U-26, U-28, U-29, U-30, U-37, U-38, U-42 through U-46, U-71, U-74, U-76, U-77, U-78, U-82, U-83, U-84 through U-91, U-93 through U-96, U-99 or U-101 through U-114.

Embodiment 4

A compound of Embodiment 3 wherein $R^1$ is U-12, U-24, U-26, U-28, U-29, U-30, U-42 through U-46, U-71, U-76, U-77, U-78, U-82, U-83, U-84, U-89, U-90, U-91, U-93, U-103, U-104 or U-109 through U-112.

Embodiment 5

A compound of Embodiment 4 wherein $R^1$ is U-12, U-26, U-29, U-30, U-42 through U-46, U-71, U-76, U-77, U-78, U-82, U-83, U-89, U-90, U-103 or U-104.

Embodiment 6

A compound of Embodiment 5 wherein $R^1$ is U-12, U-29, U-42, U-43, U-71, U-76, U-77, U-89, U-90, U-103 or U-104.

Embodiment 7

A compound of Embodiment 6 wherein $R^1$ is U-12, U-29, U-89 or U-90.

Embodiment 8

A compound of Embodiment 7 wherein $R^1$ is U-89.

Embodiment 9

A compound of Embodiment 7 wherein $R^1$ is U-90.

Embodiment 10

A compound of Embodiment 1 wherein $R^1$ is U-1, U-2, U-4, U-5, U-8, U-12, U-29, U-58, U-69, U-79, U-80, U-104, U-115, U-116, U-117 or U-118.

Embodiment 11

A compound of Embodiment 10 wherein $R^1$ is U-1, U-2, U-4, U-5, U-12 or U-29.

Embodiment 12

A compound of Embodiment 11 wherein $R^1$ is U-1, U-2, U-12 or U-29.

Embodiment 13

A compound of Embodiment 12 wherein $R^1$ is U-2 or U-12.

Embodiment 14

A compound of Embodiment 12 wherein $R^1$ is U-1.

Embodiment 14a

A compound of Embodiment 14 wherein U-1 is connected at its 2-position to L.

Embodiment 14b

A compound of Embodiment 14 wherein U-1 is connected at its 5-position to L.

Embodiment 15

A compound of Embodiment 12 wherein $R^1$ is U-2.

Embodiment 15a

A compound of Embodiment 15 wherein U-2 is connected at its 2-position to L.

Embodiment 15b

A compound of Embodiment 15 wherein U-2 is connected at its 4-position to L.

Embodiment 15c

A compound of Embodiment 15 wherein U-2 is connected at its 5-position to L.

Embodiment 16

A compound of Embodiment 12 wherein $R^1$ is U-12.

Embodiment 16a

A compound of Embodiment 16 wherein U-12 is connected at its 1-position to L.

Embodiment 16b

A compound of Embodiment 16 wherein U-12 is connected at its 3-position to L.

Embodiment 16c

A compound of Embodiment 16 wherein U-12 is connected at its 4-position to L.

Embodiment 17

A compound of Embodiment 12 wherein $R^1$ is U-29.

Embodiment 17a

A compound of Embodiment 17 wherein U-29 is connected at its 5-position to L.

Embodiment 18

A compound of any one of Embodiments 1 through 17a wherein x is 1 or 2.

Embodiment 19

A compound of Embodiment 18 wherein x is 1.

Embodiment 20

A compound of Embodiment 18 wherein x is 2.

Embodiment 21

A compound of Formula 1 or any one of Embodiments 1 through 20 wherein L is O, $(CR^{4a}R^{4b})_n$, $OCH_2$, $CH_2O$, $OCH_2CH_2$, $CH_2CH_2O$ or $CH_2OCH_2$, wherein the atom to the left is connected to $R^1$, and the atom to the right is connected to J, each carbon atom is optionally substituted with up to 2 substituents independently selected from halogen, cyano, hydroxy, $C_1$-$C_3$ alkyl, $C_1$-$C_3$ haloalkyl, $C_1$-$C_2$ alkoxy and $C_1$-$C_2$ haloalkoxy.

Embodiment 22

A compound of Embodiment 21 wherein L is $(CR^{4a}R^{4b})_n$, $OCH_2$, $CH_2O$, $OCH_2CH_2$, $CH_2CH_2O$ or $CH_2OCH_2$, wherein the atom to the left is connected to $R^1$, and the atom to the right is connected to J, each carbon atom is optionally substituted with up to 1 substituent selected from halogen, cyano, hydroxy, methyl, halomethyl or methoxy.

Embodiment 23

A compound of Embodiment 22 wherein L is $(CR^{4a}R^{4b})_n$, $OCH_2$, $CH_2O$, $OCH_2CH_2$, $CH_2CH_2O$ or $CH_2OCH_2$, wherein the atom to the left is connected to $R^1$, and the atom to the right is connected to J.

Embodiment 24

A compound of Formula 1 or any one of Embodiments 1 through 21 wherein L is $(CR^{4a}R^{4b})_n$, $OCH_2$ or $CH_2O$, wherein the atom to the left is connected to $R^1$, and the atom to the right is connected to J, each carbon atom optionally substituted with up to 2 substituents independently selected from halogen, cyano, hydroxy, $C_1$-$C_3$ alkyl, $C_1$-$C_3$ haloalkyl, $C_1$-$C_2$ alkoxy and $C_1$-$C_2$ haloalkoxy.

Embodiment 25

A compound of Embodiment 24 wherein L is $(CR^{4a}R^{4b})_n$, $OCH_2$ or $CH_2O$, wherein the atom to the left is connected to $R^1$, and the atom to the right is connected to J, each carbon atom optionally substituted with up to 1 substituent selected from halogen, cyano, hydroxy, $C_1$-$C_3$ alkyl, $C_1$-$C_3$ haloalkyl, $C_1$-$C_2$ alkoxy and $C_1$-$C_2$ haloalkoxy.

Embodiment 26

A compound of Embodiment 25 wherein L is $(CR^{4a}R^{4b})_n$, $OCH_2$ or $CH_2O$, wherein the atom to the left is connected to $R^1$, and the atom to the right is connected to J.

Embodiment 27

A compound of Embodiment 25 wherein L is $(CR^{4a}R^{4b})_n$.

Embodiment 28

A compound of Formula 1 or any one of Embodiments 1 through 27 wherein n is 1 or 2.

Embodiment 29

A compound of Embodiment 28 wherein n is 1.

Embodiment 30

A compound of Embodiment 28 wherein n is 2.

Embodiment 31

A compound of Formula 1 or any one of Embodiments 1 through 27 wherein n is 3.

Embodiment 32

A compound of Formula 1 or any one of Embodiments 1 through 31 wherein J is a phenyl ring optionally substituted with up to 2 substituents independently selected from $R^5$; or a 3- to 7-membered carbocyclic ring, wherein up to 2 ring members are independently selected from C(=O) and C(=S), each ring optionally substituted with up to 2 substituents independently selected from $R^5$; or a 5- to 6-membered heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O) and C(=S), each ring optionally substituted with up to 2 substituents independently selected from $R^5$.

Embodiment 33

A compound of Formula 1 or any one of Embodiments 1 through 32 wherein J is selected from J-1 through J-93 as depicted in Exhibit B Exhibit B

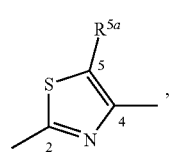

J-1

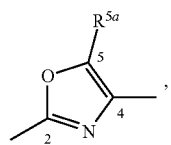
J-2
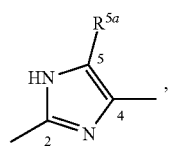
J-3
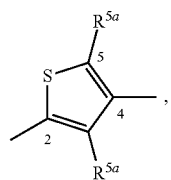
J-4
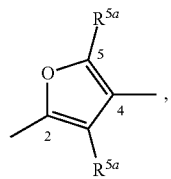
J-5
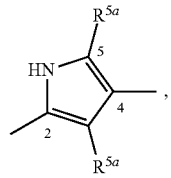
J-6
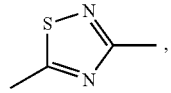
J-7
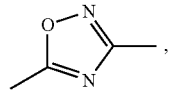
J-8
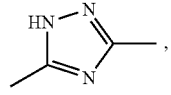
J-9
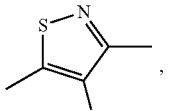
J-10
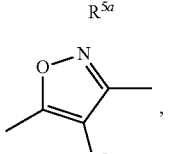
J-11
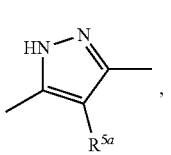
J-12
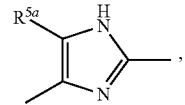
J-13
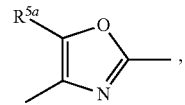
J-14
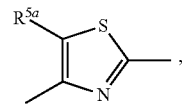
J-15
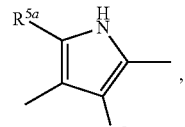
J-16
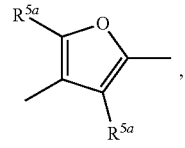
J-17
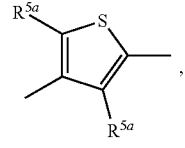
J-18
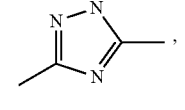
J-19
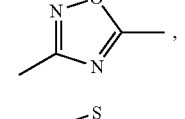
J-20
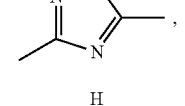
J-21
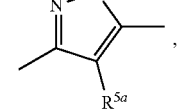
J-22
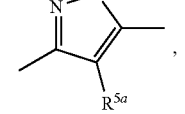
J-23
J-24

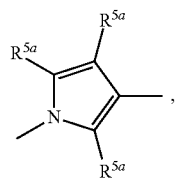 J-25
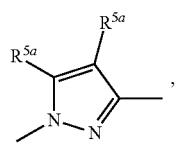 J-26
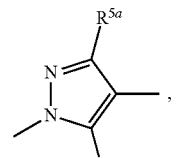 J-27
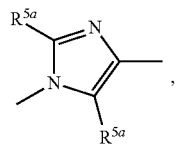 J-28
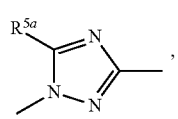 J-29
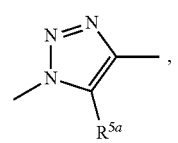 J-30
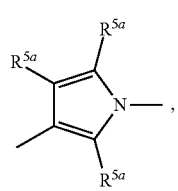 J-31
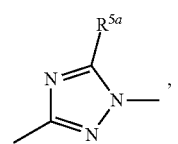 J-32
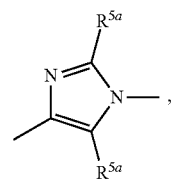 J-33
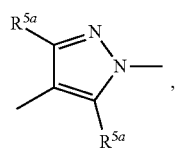 J-34
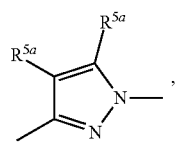 J-35
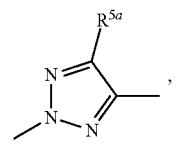 J-36
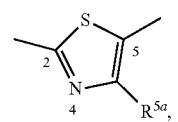 J-37
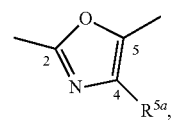 J-38
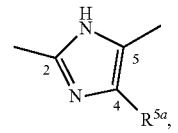 J-39
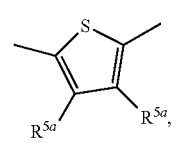 J-40
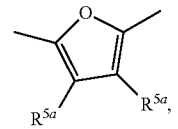 J-41
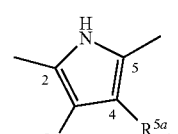 J-42
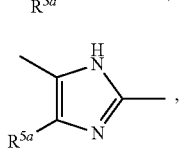 J-43
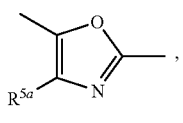 J-44
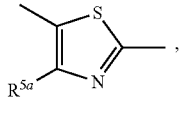 J-45
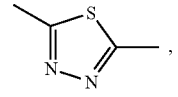 J-46

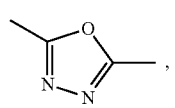  J-47
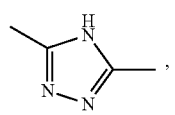  J-48
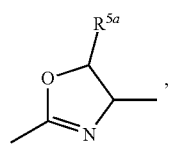  J-49
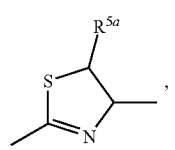  J-50
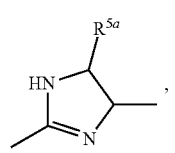  J-51
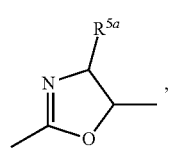  J-52
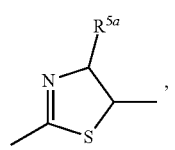  J-53
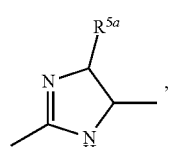  J-54
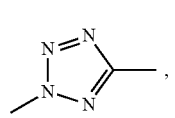  J-55
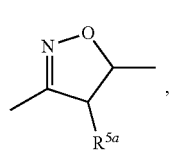  J-56
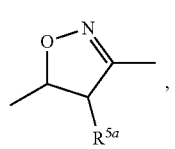  J-57
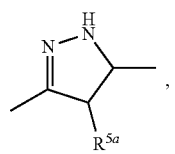  J-58
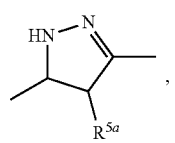  J-59
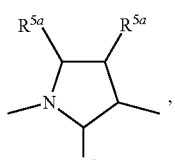  J-60
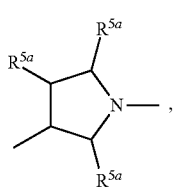  J-61
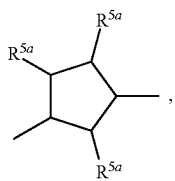  J-62
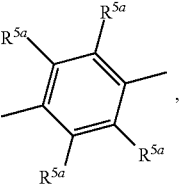  J-63
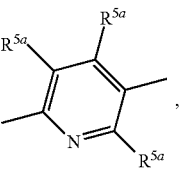  J-64
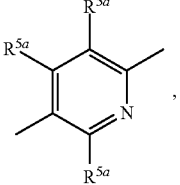  J-65
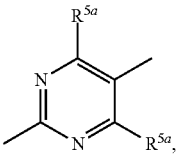  J-66

-continued
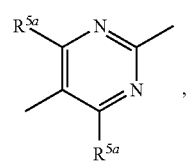 J-67
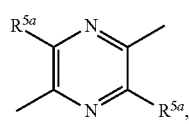 J-68
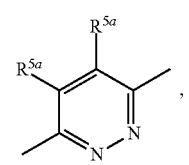 J-69
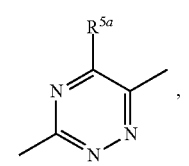 J-70
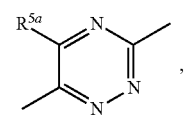 J-71
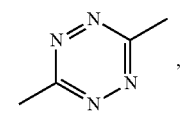 J-72
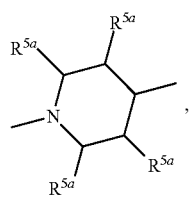 J-73
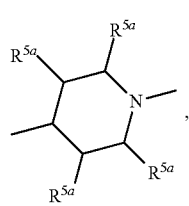 J-74
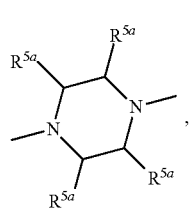 J-75
-continued
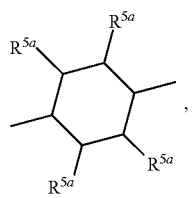 J-76
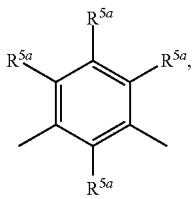 J-77
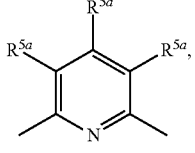 J-78
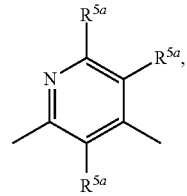 J-79
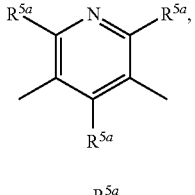 J-80
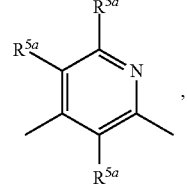 J-81
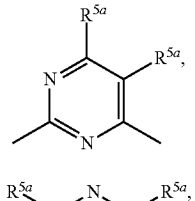 J-82
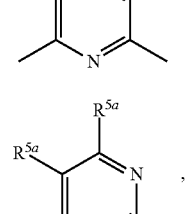 J-83
J-84

-continued

J-85 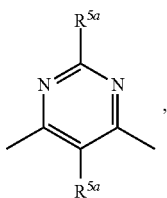

J-86 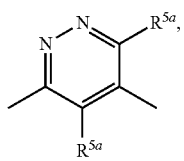

J-87 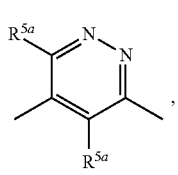

J-88 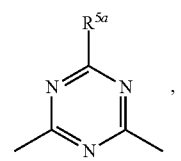

J-89 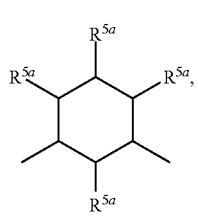

J-90 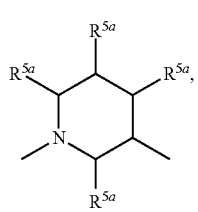

J-91 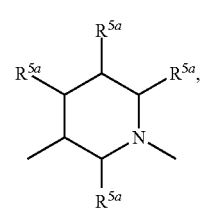

J-92 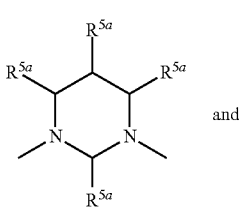 and

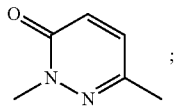 J-93 wherein the bond projecting to the left is bonded to L, and the bond projecting to the right is bonded to the oxadiazole ring in Formula 1; and each $R^{5a}$ is independently H or $R^5$; provided that at most only two $R^{5a}$ substituents are other than H.

Embodiment 34

A compound of Embodiment 33 wherein J is J-1 through J-5, J-17, J-18, J-37 through J-41, J-60, J-63 through J-71, J-73, J-74, J-75 or J-77 through J-85.

Embodiment 35

A compound of Embodiment 34 wherein J is J-4, J-5, J-18, J-37, J-40, J-41, J-63 through J-69, J-73 or J-77 through J-85.

Embodiment 36

A compound of Embodiment 35 wherein J is J-4, J-18, J-37, J-40, J-63 through J-69 or J-73.

Embodiment 37

A compound of Embodiment 36 wherein J is J-37, J-40 or J-63 through J-67.

Embodiment 38

A compound of Embodiment 37 wherein J is J-37.

Embodiment 39

A compound of Embodiment 37 wherein J is J-40.

Embodiment 40

A compound of Embodiment 37 wherein J is J-63 through J-65.

Embodiment 41

A compound of Embodiment 40 wherein J is J-63.

Embodiment 42

A compound of Embodiment 40 wherein J is J-64.

Embodiment 43

A compound of Embodiment 33 wherein J is J-4, J-18, J-27, J-40, J-41, J-63, J-73 or J-93.

Embodiment 44

A compound of Embodiment 43 wherein J is J-4, J-18, J-27, J-40 or J-63.

Embodiment 45

A compound of Embodiment 44 wherein J is J-27, J-40 or J-63.

Embodiment 45a

A compound of Embodiment 45 wherein J is J-40 or J-63.

Embodiment 46

A compound of Embodiment 45 wherein J is J-27.

Embodiment 47

A compound of Embodiment 45 wherein J is J-40.

Embodiment 48

A compound of Embodiment 45 wherein J is J-63.

Embodiment 49

A compound of any one of Embodiments 33 through 48 wherein $R^{5a}$ is H, cyano, halogen, methyl or methoxy.

Embodiment 50

A compound of Embodiment 49 wherein $R^{5a}$ is H, halogen, methyl or methoxy.

Embodiment 51

A compound of Embodiment 50 wherein $R^{5a}$ is H, methyl or methoxy.

Embodiment 52

A compound of Embodiment 51 wherein $R^{5a}$ is H.

Embodiment 53

A compound of Formula 1 or anyone of Embodiments 1 through 52 wherein each $R^2$ is independently halogen, cyano, —$NR^{3a}R^{3b}$, —C(=O)$NR^{3a}R^{3b}$, —C(=S)$NR^{3a}R^{3b}$ or —C($R^6$)=$NR^7$; or $C_1$-$C_6$ alkyl, $C_3$-$C_7$ cycloalkyl, $C_1$-$C_6$ alkoxy, $C_3$-$C_7$ cycloalkoxy, $C_1$-$C_6$ alkylthio, $C_1$-$C_6$ alkylsulfinyl, $C_1$-$C_6$ alkylsulfonyl, $C_1$-$C_6$ alkylsulfonyloxy, $C_1$-$C_6$ alkylsulfonylamino, $C_2$-$C_6$ alkylcarbonyl, $C_4$-$C_7$ cycloalkylcarbonyl, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy, $C_4$-$C_7$ cycloalkylcarbonyloxy, $C_2$-$C_6$ alkoxycarbonyloxy, $C_4$-$C_7$ cycloalkoxycarbonyloxy, $C_2$-$C_6$ alkylaminocarbonyloxy, $C_4$-$C_7$ cycloalkylaminocarbonyloxy, $C_2$-$C_6$ alkylcarbonylamino, $C_4$-$C_7$ cycloalkylcarbonylamino, $C_2$-$C_6$ alkoxycarbonylamino, $C_4$-$C_7$ cycloalkoxycarbonylamino, $C_2$-$C_6$ alkylaminocarbonylamino or $C_4$-$C_7$ cycloalkylaminocarbonylamino, each optionally substituted with up to 3 substituents independently selected from $R^{10}$.

Embodiment 54

A compound of Embodiment 53 wherein each $R^2$ is independently cyano, —$NR^{3a}R^{3b}$, —C(=O)$NR^{3a}R^{3b}$, —C(=S)$NR^{3a}R^{3b}$ or —C($R^6$)=$NR^7$; or $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, $C_1$-$C_3$ alkylsulfonyloxy, $C_1$-$C_4$ alkylsulfonylamino, $C_2$-$C_3$ alkylcarbonyl, $C_2$-$C_3$ alkoxycarbonyl, $C_3$-$C_4$ alkenyloxycarbonyl, $C_3$-$C_4$ alkynyloxycarbonyl, $C_4$-$C_5$ cycloalkoxycarbonyl, $C_2$-$C_3$ alkylcarbonyloxy, $C_2$-$C_4$ alkoxycarbonyloxy, $C_2$-$C_4$ alkylaminocarbonyloxy, $C_2$-$C_4$ alkylcarbonylamino, $C_2$-$C_4$ alkoxycarbonylamino or $C_2$-$C_4$ alkylaminocarbonylamino, each optionally substituted with up to 1 substituent selected from $R^{10}$.

Embodiment 55

A compound of Embodiment 54 wherein each $R^2$ is independently —$NR^{3a}R^{3b}$, —C(=O)$NR^{3a}R^{3b}$, —C(=S)$NR^{3a}R^{3b}$ or —C($R^6$)=$NR^7$; or $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, $C_1$-$C_3$ alkylsulfonyloxy, $C_2$-$C_3$ alkylcarbonyl, $C_2$-$C_3$ alkoxycarbonyl, $C_3$-$C_4$ alkenyloxycarbonyl, $C_3$-$C_4$ alkynyloxycarbonyl, $C_4$-$C_5$ cycloalkoxycarbonyl or $C_2$-$C_3$ alkylcarbonyloxy, each optionally substituted with up to 1 substituent selected from $R^{10}$.

Embodiment 56

A compound of Formula 1 or anyone of Embodiments 1 through 53 wherein each $R^2$ is independently halogen, cyano, —CH(=O), —C(=O)OH, —C(=O)$NR^{3a}R^{3b}$, —C($R^6$)=$NR^7$ or —U—V-Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 3 substituents independently selected from $R^{10}$.

Embodiment 56a

A compound of Embodiment 56 wherein each $R^2$ is independently halogen, —CH(=O), —C(=O)OH, —C(=O)$NR^{3a}R^{3b}$, —C($R^6$)=$NR^7$ or —U—V-Q; or $C_1$-$C_6$ alkyl, $C_1$-$C_6$ alkoxy, $C_2$-$C_6$ alkenyloxy, $C_2$-$C_6$ alkynyloxy, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 3 substituents independently selected from $R^{10}$.

Embodiment 56b

A compound of Embodiment 56a wherein each $R^2$ is independently halogen, —CH(=O), —C(=O)OH, —C(=O)$NR^{3a}R^{3b}$ or —C($R^6$)=$NR^7$; or $C_1$-$C_6$ alkyl, $C_1$-$C_6$ alkoxy, $C_2$-$C_6$ alkenyloxy, $C_2$-$C_6$ alkynyloxy, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 3 substituents independently selected from $R^{10}$.

Embodiment 57

A compound of Embodiment 56 wherein each $R^2$ is independently halogen, cyano, —CH(=O), —C(=O)OH, —C(=O)$NR^{3a}R^{3b}$, —C($R^6$)=$NR^7$ or —U—V-Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 2 substituents independently selected from $R^{10}$.

Embodiment 58

A compound of Embodiment 57 wherein each $R^2$ is independently halogen, cyano, —CH(=O), —C(=O)OH, —C(=O)NR$^{3a}$R$^{3b}$, —C(R$^6$)=NR$^7$ or —U—V-Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 1 substituent selected from $R^{10}$.

Embodiment 59

A compound of Embodiment 58 wherein each $R^2$ is independently halogen, cyano, —CH(=O), —C(=O)OH, —C(=O)NR$^{3a}$R$^{3b}$, —C(R$^6$)=NR$^7$ or —U—V-Q; or $C_1$-$C_6$ alkyl, $C_2$-$C_6$ alkenyl, $C_2$-$C_6$ alkynyl, $C_1$-$C_6$ alkoxy, $C_2$-$C_6$ alkoxycarbonyl, $C_3$-$C_6$ alkenyloxycarbonyl, $C_3$-$C_6$ alkynyloxycarbonyl or $C_4$-$C_7$ cycloalkoxycarbonyl, each optionally substituted with up to 1 substituent selected from $R^{10}$.

Embodiment 60

A compound of Embodiment 59 wherein each $R^2$ is independently —C(=O)NR$^{3a}$R$^{3b}$, —C(R$^6$)=NR$^7$ or —U—V-Q; or $C_2$-$C_6$ alkoxycarbonyl, $C_3$-$C_6$ alkenyloxycarbonyl or $C_3$-$C_6$ alkynyloxycarbonyl, each optionally substituted with up to 1 substituent selected from $R^{10}$.

Embodiment 61

A compound of Embodiment 60 wherein each $R^2$ is independently —C(=O)NR$^{3a}$R$^{3b}$ or —C(R$^6$)=NR$^7$; or $C_2$-$C_6$ alkoxycarbonyl, $C_3$-$C_6$ alkenyloxycarbonyl or $C_3$-$C_6$ alkynyloxycarbonyl, each optionally substituted with up to 1 substituent selected from $R^{10}$.

Embodiment 62

A compound of Embodiment 56 wherein each $R^2$ is independently —C(=O)NR$^{3a}$R$^{3b}$; or $C_2$-$C_6$ alkoxycarbonyl, optionally substituted with up to 3 substituents independently selected from $R^{10}$.

Embodiment 63

A compound of Embodiment 62 wherein each $R^2$ is independently —C(=O)NR$^{3a}$R$^{3b}$; or $C_2$-$C_6$ alkoxycarbonyl, optionally substituted with up to 2 substituents independently selected from $R^{10}$.

Embodiment 64

A compound of Embodiment 63 wherein each $R^2$ is independently —C(=O)NR$^{3a}$R$^{3b}$; or $C_2$-$C_6$ alkoxycarbonyl, optionally substituted with up to 1 substituent selected from $R^{10}$.

Embodiment 65

A compound of Embodiment 64 wherein each $R^2$ is independently —C(=O)NR$^{3a}$R$^{3b}$ or $C_2$-$C_6$ alkoxycarbonyl.

Embodiment 66

A compound of Formula 1 or any one of Embodiments 1 through 65 wherein $R^3$ is H, cyano, hydroxy, $C_1$-$C_4$ alkyl, $C_1$-$C_4$ haloalkyl, $C_2$-$C_4$ alkenyl, $C_2$-$C_4$ alkynyl or $C_1$-$C_4$ alkoxy.

Embodiment 67

A compound of Embodiment 66 wherein $R^3$ is H, cyano, hydroxy, $C_1$-$C_4$ alkyl or $C_1$-$C_4$ alkoxy.

Embodiment 68

A compound of Embodiment 67 wherein $R^3$ is H, cyano, hydroxy, methyl or methoxy.

Embodiment 69

A compound of Embodiment 68 wherein $R^3$ is H.

Embodiment 70

A compound of Formula 1 or any one of Embodiments 1 through 69 wherein when each $R^{3a}$ is separate (i.e. not taken together with $R^{3b}$), then each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_1$-$C_4$ alkylsulfonyl, $C_1$-$C_4$ haloalkylsulfonyl, $C_2$-$C_4$ alkylthioalkyl, $C_2$-$C_4$ alkylcarbonyl, $C_2$-$C_4$ haloalkylcarbonyl, $C_4$-$C_6$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl.

Embodiment 71

A compound of Embodiment 70 wherein each $R^{3a}$ is independently H, cyano, $C_1$-$C_4$ alkyl, $C_1$-$C_4$ haloalkyl, $C_2$-$C_4$ alkenyl, $C_2$-$C_4$ alkynyl, $C_2$-$C_4$ alkoxyalkyl, $C_1$-$C_4$ alkylsulfonyl, $C_1$-$C_4$ haloalkylsulfonyl, $C_2$-$C_4$ alkylthioalkyl, $C_2$-$C_4$ alkylcarbonyl, $C_2$-$C_4$ haloalkylcarbonyl, $C_4$-$C_6$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl.

Embodiment 72

A compound of Embodiment 71 wherein each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_2$-$C_4$ alkoxyalkyl, $C_1$-$C_3$ alkylsulfonyl, $C_2$-$C_4$ alkylthioalkyl, $C_2$-$C_3$ alkylcarbonyl, $C_2$-$C_3$ alkoxycarbonyl, $C_2$-$C_3$ alkylaminocarbonyl or $C_3$-$C_4$ dialkylaminocarbonyl.

Embodiment 73

A compound of Formula 1 or any one of Embodiments 1 through 69 wherein when each $R^{3a}$ is separate (i.e. not taken together with $R^{3b}$), then each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_5$ alkoxy, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_4$-$C_6$ cycloalkylcarbonyl, $C_2$-$C_5$ alkoxycarbonyl or $C_3$-$C_5$ alkoxycarbonylalkyl.

Embodiment 74

A compound of Embodiment 73 wherein each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl.

Embodiment 74a

A compound of Embodiment 74 wherein each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl.

Embodiment 75

A compound of Embodiment 74 wherein each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_2$-$C_4$ alkoxyalkyl or $C_3$-$C_5$ alkoxycarbonylalkyl.

Embodiment 76

A compound of Formula 1 or any one of Embodiments 1 through 75 wherein when each $R^{3b}$ is separate (i.e. not taken together with $R^{3a}$), then each $R^{3b}$ is independently H, $C_1$-$C_4$ alkyl, $C_1$-$C_4$ haloalkyl, $C_3$-$C_6$ cycloalkyl, $C_2$-$C_6$ alkoxyalkyl, $C_2$-$C_6$ haloalkoxyalkyl, $C_3$-$C_8$ alkoxyalkoxyalkyl, $C_2$-$C_6$ alkylthioalkyl, $C_2$-$C_6$ alkylaminoalkyl or $C_3$-$C_8$ dialkylaminoalkyl.

Embodiment 77

A compound of Embodiment 76 wherein each $R^{3b}$ is independently H, $C_1$-$C_3$ alkyl, $C_1$-$C_3$ haloalkyl, $C_3$-$C_6$ cycloalkyl, $C_2$-$C_4$ alkoxyalkyl, $C_2$-$C_4$ alkylthioalkyl, $C_2$-$C_4$ alkylaminoalkyl or $C_3$-$C_6$ dialkylaminoalkyl.

Embodiment 78

A compound of Embodiment 77 wherein each $R^{3b}$ is independently H, $C_1$-$C_3$ alkyl, $C_1$-$C_3$ haloalkyl, $C_3$-$C_6$ cycloalkyl, $C_2$-$C_4$ alkoxyalkyl or $C_2$-$C_4$ alkylthioalkyl.

Embodiment 79

A compound of Formula 1 or any one of Embodiments 1 through 75 wherein when each $R^{3b}$ is separate (i.e. not taken together with $R^{3a}$), then each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ hydroxyalkyl, $C_2$-$C_6$ cyanoalkyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_2$-$C_6$ alkoxyalkyl, $C_2$-$C_6$ haloalkoxyalkyl or $C_4$-$C_{10}$ cycloalkoxyalkyl, each optionally substituted with up to 1 substituent selected from cyano, hydroxy, $C_2$-$C_4$ alkylcarbonyl, $C_2$-$C_4$ alkoxycarbonyl, $C_3$-$C_{15}$ trialkylsilyl and $C_3$-$C_{15}$ halotrialkylsilyl.

Embodiment 80

A compound of Embodiment 79 wherein each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ halocycloalkyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from cyano, $C_2$-$C_4$ alkylcarbonyl, $C_2$-$C_4$ alkoxycarbonyl and $C_3$-$C_{15}$ trialkylsilyl.

Embodiment 81

A compound of Embodiment 80 wherein each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from $C_2$-$C_4$ alkylcarbonyl and $C_2$-$C_4$ alkoxycarbonyl.

Embodiment 82

A compound of Embodiment 81 wherein each $R^{3b}$ is independently H, $C_1$-$C_6$ alkyl, $C_1$-$C_6$ haloalkyl, $C_2$-$C_6$ alkenyl or $C_2$-$C_6$ haloalkenyl, each optionally substituted with up to 1 substituent selected from $C_2$-$C_4$ alkylcarbonyl and $C_2$-$C_4$ alkoxycarbonyl.

Embodiment 83

A compound of Embodiment 82 wherein each $R^{3b}$ is independently H, $C_1$-$C_3$ alkyl, $C_1$-$C_3$ haloalkyl, $C_2$-$C_4$ alkenyl or $C_2$-$C_4$ haloalkenyl, each optionally substituted with up to 1 substituent selected from $C_2$-$C_4$ alkylcarbonyl and $C_2$-$C_4$ alkoxycarbonyl.

Embodiment 84

A compound of Embodiment 83 wherein each $R^{3b}$ is independently H, $C_1$-$C_3$ alkyl, $C_1$-$C_3$ haloalkyl, $C_2$-$C_4$ alkenyl or $C_2$-$C_4$ haloalkenyl.

Embodiment 85

A compound of Formula 1 or any one Embodiments 1 through 84 wherein when a pair of $R^{3a}$ and $R^{3b}$ substituents attached to the same nitrogen atom are taken together to form a 5- to 6-membered fully saturated heterocyclic ring, then said ring contains ring members, in addition to the connecting nitrogen atom, selected from carbon atoms and up to 1 heteroatom selected from up to 1 O, up to 1 S and up to 1 N atom, each ring optionally substituted with up to 2 methyl.

Embodiment 86

A compound of Embodiment 85 wherein a pair of $R^{3a}$ and $R^{3b}$ substituents attached to the same nitrogen atom are taken together to form an azetidinyl, morpholinyl, pyrrolidinyl, piperidinyl, piperazinyl or thiomorpholinyl ring, each ring optionally substituted with up to 2 methyl.

Embodiment 87

A compound of Formula 1 or any one of Embodiments 1 through 86 wherein when each $R^{4a}$ and $R^{4b}$ is separate (i.e. not taken together), then each $R^{4a}$ and $R^{4b}$ is independently H, halogen, cyano, hydroxy, methyl or methoxy.

Embodiment 88

A compound of Embodiment 87 wherein each $R^{4a}$ and $R^{4b}$ is independently H, halogen, hydroxy, methyl or methoxy.

Embodiment 89

A compound of Embodiment 88 wherein each $R^{4a}$ and $R^{4b}$ is independently H or methyl.

Embodiment 90

A compound of Embodiment 89 wherein each $R^{4a}$ and $R^{4b}$ is H.

Embodiment 91

A compound of Formula 1 or any one of Embodiments 1 through 90 wherein each $R^{4a}$ and $R^{4b}$ is taken alone.

Embodiment 92

A compound of Formula 1 or any one Embodiments 1 through 91 wherein when a pair of $R^{4a}$ and $R^{4b}$ substituents attached to the same carbon atom are taken together to form a ring, said ring is a cyclopropyl ring optionally substituted with up to 2 substituents independently selected from halogen, methyl, methoxy or methylthio.

Embodiment 93

A compound of Embodiment 92 wherein a pair of $R^{4a}$ and $R^{4b}$ substituents attached to the same carbon atom are taken together to form a cyclopropyl ring.

Embodiment 94

A compound of Formula 1 or any one of Embodiments 1 through 93 wherein each $R^5$ is independently cyano, halogen, $C_1$-$C_4$ alkyl, $C_1$-$C_4$ haloalkyl or $C_1$-$C_4$ alkoxy.

Embodiment 95

A compound of Embodiment 94 wherein each $R^5$ is independently cyano, halogen, $C_1$-$C_3$ alkyl, $C_1$-$C_3$ haloalkyl or $C_1$-$C_3$ alkoxy.

Embodiment 96

A compound of Embodiment 95 wherein each $R^5$ is independently cyano, halogen, methyl or methoxy.

Embodiment 97

A compound of Embodiment 96 wherein each $R^5$ is independently methyl or methoxy.

Embodiment 98

A compound of Formula 1 or any one of Embodiments 1 through 97 wherein each $R^6$ is independently H, cyano, halogen methyl or methoxy.

Embodiment 99

A compound of Embodiment 98 wherein each $R^6$ is independently H, Cl or methyl.

Embodiment 100

A compound of Embodiment 99 wherein each $R^6$ is independently H or methyl.

Embodiment 101

A compound of Embodiment 100 wherein each $R^6$ is H.

Embodiment 102

A compound of Formula 1 or any one of Embodiments 1 through 101 wherein each $R^7$ is independently hydroxy, $NR^{11a}R^{11b}$, $C_1$-$C_4$ alkoxy, $C_2$-$C_4$ alkenyloxy, $C_2$-$C_4$ alkylcarbonyloxy or $C_2$-$C_4$ alkoxycarbonyloxy.

Embodiment 103

A compound of Embodiment 102 wherein each $R^7$ is independently hydroxy, $NR^{11a}R^{11b}$ or $C_1$-$C_2$ alkoxy.

Embodiment 104

A compound of Embodiment 103 wherein each $R^7$ is independently hydroxy, $NR^{11a}R^{11b}$ or methoxy.

Embodiment 105

A compound of Embodiment 104 wherein each $R^7$ is hydroxy.

Embodiment 106

A compound of Formula 1 or any one of Embodiments 1 through 101 wherein each $R^7$ is independently hydroxy or $NR^{11a}R^{11b}$; or $C_1$-$C_4$ alkoxy, $C_2$-$C_4$ alkenyloxy, $C_2$-$C_4$ alkynyloxy or $C_2$-$C_4$ alkylcarbonyloxy, each optionally substituted with up to 1 substituent selected cyano, hydroxy and —C(=O)OH.

Embodiment 107

A compound of Embodiment 106 wherein each $R^7$ is independently $C_1$-$C_4$ alkoxy, $C_2$-$C_4$ alkenyloxy or $C_2$-$C_4$ alkynyloxy, each optionally substituted with up to 1 substituent selected cyano, hydroxy and —C(=O)OH.

Embodiment 108

A compound of Embodiment 107 wherein each $R^7$ is independently $C_1$-$C_4$ alkoxy, $C_2$-$C_4$ alkenyloxy or $C_2$-$C_4$ alkynyloxy.

Embodiment 109

A compound of Formula 1 or any one of Embodiments 1 through 108 wherein each $R^8$ is independently H, methyl or methoxy.

Embodiment 110

A compound of Embodiment 109 wherein each $R^8$ is independently H or methyl.

Embodiment 111

A compound of Embodiment 110 wherein each $R^8$ is H.

Embodiment 112

A compound of Formula 1 or any one of Embodiments 1 through 111 wherein when each $R^{9a}$ and $R^{9b}$ is separate (i.e. not taken together), then each $R^{9a}$ and $R^{9b}$ is independently H, methyl or ethyl.

Embodiment 113

A compound of Embodiment 112 wherein each $R^{9a}$ and $R^{9b}$ is independently H or methyl.

Embodiment 114

A compound of Formula 1 or any one Embodiments 1 through 113 wherein when a pair of $R^{9a}$ and $R^{9b}$ substituents are taken together with the nitrogen atom to which they are attached to form a 5- to 6-membered fully saturated heterocyclic ring, then said ring contains ring members, in addition to the connecting nitrogen atom, selected from carbon atoms and up to 1 heteroatom selected from up to 1 O, up to 1 S and up to 1 N atom, each ring optionally substituted with up to 2 methyl.

Embodiment 115

A compound of Embodiment 114 wherein a pair of $R^{9a}$ and $R^{9b}$ are substituents taken together with the nitrogen atom to which they are attached to form an azetidinyl, morpholinyl, pyrrolidinyl, piperidinyl, piperazinyl, or thiomorpholinyl ring, each ring optionally substituted with up to 2 methyl.

Embodiment 116

A compound of Formula 1 or any one of Embodiments 1 through 115 wherein each $R^{10}$ is independently halogen, cyano, hydroxy, nitro, $C_1$-$C_4$ alkyl, $C_1$-$C_4$ haloalkyl, $C_3$-$C_6$ cycloalkyl, $C_1$-$C_4$ alkoxy, $C_1$-$C_4$ haloalkoxy, $C_2$-$C_4$ alkoxyalkoxy, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_2$-$C_5$ alkylaminocarbonyl or $C_3$-$C_5$ dialkylaminocarbonyl.

Embodiment 117

A compound of Embodiment 116 wherein each $R^{10}$ is independently halogen, cyano, hydroxy, nitro, $C_1$-$C_3$ alkyl, $C_1$-$C_3$ haloalkyl, $C_3$-$C_6$ cycloalkyl, $C_1$-$C_3$ alkoxy, $C_1$-$C_3$ haloalkoxy, $C_2$-$C_3$ alkoxyalkoxy, $C_1$-$C_3$ alkylthio, $C_1$-$C_3$ alkylsulfinyl, $C_1$-$C_3$ alkylsulfonyl, $C_1$-$C_3$ haloalkylsulfonyl, $C_2$-$C_3$ alkylcarbonyl, $C_2$-$C_3$ haloalkylcarbonyl, $C_2$-$C_3$ alkoxycarbonyl, $C_2$-$C_3$ alkylaminocarbonyl or $C_3$-$C_5$ dialkylaminocarbonyl.

Embodiment 118

A compound of Embodiment 117 wherein each $R^{10}$ is independently halogen, hydroxy, cyano, $C_1$-$C_2$ alkyl, $C_1$-$C_2$ haloalkyl, $C_1$-$C_2$ alkoxy, $C_1$-$C_2$ haloalkoxy, $C_1$-$C_2$ alkylthio, $C_1$-$C_2$ alkylsulfinyl, $C_1$-$C_2$ alkylsulfonyl, $C_1$-$C_2$ haloalkylsulfonyl, $C_2$-$C_3$ alkylcarbonyl, $C_2$-$C_3$ haloalkylcarbonyl, $C_2$-$C_3$ alkoxycarbonyl, $C_2$-$C_3$ alkylaminocarbonyl or $C_3$-$C_5$ dialkylaminocarbonyl.

Embodiment 119

A compound of Formula 1 or any one of Embodiments 1 through 115 wherein each $R^{10}$ is independently halogen, cyano, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_2$-$C_4$ alkoxyalkoxy, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_3$-$C_5$ alkylthioalkylcarbonyl, $C_3$-$C_{15}$ trialkylsily or —C($R^{13}$)=NOR$^{14}$.

Embodiment 120

A compound of Embodiment 119 wherein each $R^{10}$ is independently halogen, cyano, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkoxy, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl or —C($R^{13}$)=NOR$^{14}$.

Embodiment 121

A compound of Embodiment 120 wherein each $R^{10}$ is independently halogen, $C_1$-$C_4$ alkyl, $C_1$-$C_4$ haloalkyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_5$ alkoxycarbonyl or —C($R^{13}$)=NOR$^{14}$.

Embodiment 122

A compound of Embodiment 121 wherein each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl, $C_2$-$C_5$ alkoxycarbonyl or —C($R^{13}$)=NOR$^{14}$.

Embodiment 123

A compound of Embodiment 122 wherein each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl or $C_2$-$C_5$ alkoxycarbonyl.

Embodiment 124

A compound of Formula 1 or any one of Embodiments 1 through 123 wherein each U is independently a direct bond, C(=O)O or C(=O)NR$^{17}$.

Embodiment 125

A compound of Embodiment 124 wherein each U is a direct bond.

Embodiment 126

A compound of Embodiment 125 wherein each U is independently C(=O)O or C(=O)NR$^{17}$.

Embodiment 127

A compound of Formula 1 or any one of Embodiments 1 through 126 wherein each V is independently a direct bond; or $C_1$-$C_6$ alkylene, $C_2$-$C_6$ alkenylene or $C_3$-$C_6$ alkynylene, each optionally substituted with up to 2 substituents independently selected from halogen, cyano, nitro, hydroxy, $C_1$-$C_2$ alkyl, $C_1$-$C_2$ haloalkyl, $C_1$-$C_2$ alkoxy and $C_1$-$C_2$ haloalkoxy.

Embodiment 128

A compound of Embodiment 127 wherein each V is independently a direct bond; or $C_1$-$C_3$ alkylene, $C_2$-$C_4$ alkenylene or $C_3$-$C_4$ alkynylene, each optionally substituted with up to 2 substituents independently selected from halogen, hydroxy, $C_1$-$C_2$ alkyl, $C_1$-$C_2$ alkoxy and $C_1$-$C_2$ haloalkoxy.

Embodiment 129

A compound of Embodiment 128 wherein each V is independently a direct bond, $C_1$-$C_3$ alkylene, $C_2$-$C_4$ alkenylene or $C_3$-$C_4$ alkynylene.

Embodiment 130

A compound of Embodiment 129 wherein each V is independently a direct bond, $C_1$-$C_3$ alkylene or $C_2$-$C_4$ alkenylene.

Embodiment 131

A compound of Embodiment 130 wherein each V is a direct bond.

Embodiment 132

A compound of Embodiment 130 wherein each V is independently $C_1$-$C_3$ alkylene.

Embodiment 133

A compound of Formula 1 or any one of Embodiments 1 through 132 wherein each Q is independently phenyl, each optionally substituted with up to 2 substituents independently selected from $R^{12}$; or a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$; or a 3- to 7-membered nonaromatic heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$.

Embodiment 134

A compound of Embodiment 133 wherein each Q is independently phenyl, each optionally substituted with up to 2 substituents independently selected from $R^{12}$; or pyridinyl, pyrazolyl, imidazolyl, triazolyl, thiazolyl, oxazolyl, isoxazolyl, thienyl, isoxazolinyl, piperidinyl, morpholinyl or piperazinyl, each ring optionally substituted with up to 2 substituents independently selected from $R^{12}$.

Embodiment 135

A compound of Embodiment 134 wherein each Q is independently phenyl, each optionally substituted with up to 2 substituents independently selected from $R^{12}$; or pyridinyl, pyrazolyl, imidazolyl, triazolyl, thiazolyl or oxazolyl, each ring optionally substituted with up to 2 substituents independently selected from $R^{12}$.

Embodiment 136

A compound of Embodiment 135 wherein each Q is independently phenyl, each optionally substituted with up to 2 substituents independently selected from $R^{12}$; or pyridinyl or pyrazolyl, each ring optionally substituted with up to 2 substituents independently selected from $R^{12}$.

Embodiment 137

A compound of Formula 1 or any one of Embodiments 1 through 136 wherein when each $R^{11a}$ is separate (i.e. not taken together with $R^{11b}$), then each $R^{11a}$ is independently H, $C_1$-$C_2$ alkyl or $C_2$-$C_3$ alkylcarbonyl.

Embodiment 138

A compound of Embodiment 137 wherein each $R^{11a}$ is independently H, methyl or methylcarbonyl.

Embodiment 139

A compound of Formula 1 or any one of Embodiments 1 through 138 wherein when each $R^{11b}$ is separate (i.e. not taken together with $R^{11a}$), then each $R^{11b}$ is independently H, cyano, $C_1$-$C_2$ alkyl, $C_2$-$C_4$ alkylcarbonyl, $C_2$-$C_4$ alkoxycarbonyl, $C_3$-$C_5$ alkoxycarbonylalkyl, $C_2$-$C_5$ alkylaminocarbonyl or $C_3$-$C_5$ dialkylaminocarbonyl.

Embodiment 140

A compound of Embodiment 139 wherein each $R^{11b}$ is independently H, cyano, methyl, methylcarbonyl, methoxycarbonyl, methoxycarbonylmethyl, methylaminocarbonyl or dimethylaminocarbonyl.

Embodiment 141

A compound of Embodiment 140 wherein each $R^{11b}$ is independently H, methyl, methylcarbonyl or methoxycarbonyl.

Embodiment 142

A compound of Formula 1 or any one Embodiments 1 through 141 wherein when a pair of $R^{11a}$ and $R^{11b}$ substituents are taken together with the nitrogen atom to which they are attached to form a 5- to 6-membered fully saturated heterocyclic ring, then said ring contains ring members, in addition to the connecting nitrogen atom, selected from carbon atoms and up to 1 heteroatom selected from up to 1 O, up to 1 S and up to 1 N atom, each ring optionally substituted with up to 2 methyl.

Embodiment 143

A compound of Embodiment 142 wherein a pair of $R^{11a}$ and $R^{11b}$ substituents are taken together with the nitrogen atom to which they are attached to form an azetidinyl, morpholinyl, pyrrolidinyl, piperidinyl, piperazinyl or thiomorpholinyl ring, each ring optionally substituted with up to 2 methyl.

Embodiment 144

A compound of Formula 1 or any one of Embodiments 1 through 143 wherein each $R^{12}$ is independently halogen, cyano, $C_1$-$C_4$ alkyl, $C_1$-$C_4$ haloalkyl or $C_1$-$C_4$ alkoxy.

Embodiment 145

A compound of Embodiment 144 wherein each $R^{12}$ is independently halogen, cyano, $C_1$-$C_3$ alkyl, $C_1$-$C_3$ haloalkyl or $C_1$-$C_3$ alkoxy.

Embodiment 146

A compound of Embodiment 145 wherein each $R^{12}$ is independently halogen, cyano, $C_1$-$C_2$ alkyl, $C_1$-$C_2$ haloalkyl or $C_1$-$C_2$ alkoxy.

Embodiment 147

A compound of Embodiment 146 wherein each $R^{12}$ is independently halogen, methyl or methoxy.

Embodiment 148

A compound of Formula 1 or any one Embodiments 1 through 147 wherein each $R^{13}$ and $R^{15}$ is independently H, cyano, halogen, methyl, halomethyl or methoxy.

Embodiment 149

A compound of Embodiment 148 wherein each $R^{13}$ and $R^{15}$ is independently H, halogen, methyl or methoxy.

Embodiment 150

A compound of Embodiment 149 wherein each $R^{13}$ and $R^{15}$ is H.

Embodiment 151

A compound of Formula 1 or any one Embodiments 1 through 150 wherein each $R^{14}$ is H, $C_1$-$C_5$ alkyl, $C_1$-$C_5$ haloalkyl, $C_2$-$C_5$ alkenyl, $C_2$-$C_5$ haloalkenyl, $C_2$-$C_5$ alkylcarbonyl or $C_2$-$C_5$ alkoxycarbonyl.

Embodiment 152

A compound of Embodiment 151 wherein each $R^{14}$ is independently H, $C_1$-$C_2$ alkyl, $C_1$-$C_2$ haloalkyl, $C_2$-$C_4$ alkenyl, $C_2$-$C_4$ alkylcarbonyl or $C_2$-$C_4$ alkoxycarbonyl.

Embodiment 153

A compound of Embodiment 152 wherein each $R^{14}$ is independently H, methyl, halomethyl, $C_2$-$C_4$ alkylcarbonyl or $C_2$-$C_4$ alkoxycarbonyl.

Embodiment 154

A compound of Formula 1 or any one Embodiments 1 through 153 wherein each $R^{16}$ is independently H, cyano, methyl, halomethyl, methoxy, $C_2$-$C_4$ alkylcarbonyl or $C_2$-$C_4$ alkoxycarbonyl.

Embodiment 155

A compound of Embodiment 154 wherein each $R^{16}$ is independently H, cyano, methyl, halomethyl or methoxy.

Embodiment 156

A compound of Embodiment 155 wherein each $R^{16}$ is independently H or methyl.

Embodiment 157

A compound of Embodiment 156 wherein each $R^{16}$ is H.

Embodiment 158

A compound of Formula 1 or any one Embodiments 1 through 157 wherein each $R^{17}$ and $R^{18}$ is independently H, cyano, methyl or halomethyl.

Embodiments of this invention, including Embodiments 1-158 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-158 above as well as any other embodiments described herein, and any combination thereof, pertain to the compositions and methods of the present invention.

Combinations of Embodiments 1-158 are illustrated by:

Embodiment A

A compound of Formula 1 wherein
$R^1$ is selected from U-1 through U-118

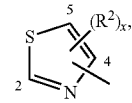
U-1

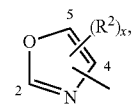
U-2

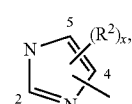
U-3

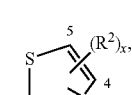
U-4

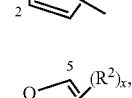
U-5

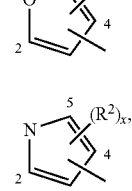
U-6

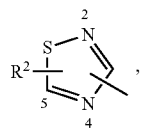 U-7
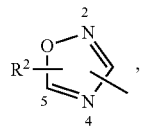 U-8
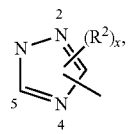 U-9
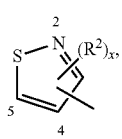 U-10
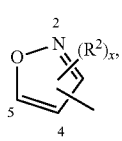 U-11
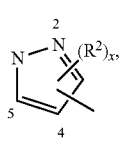 U-12
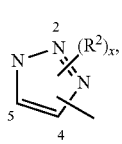 U-13
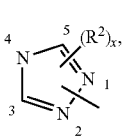 U-14
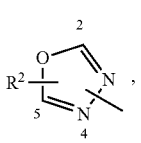 U-15
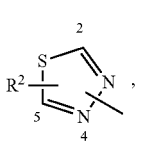 U-16
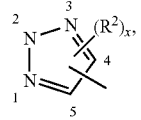 U-17
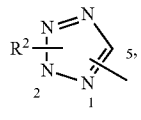 U-18
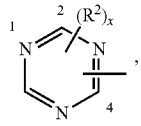 U-19
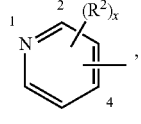 U-20
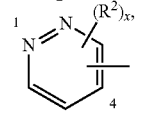 U-21
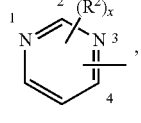 U-22
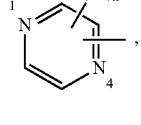 U-23
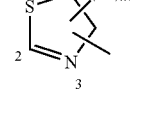 U-24
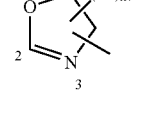 U-25
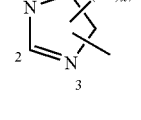 U-26
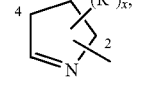 U-27

U-28 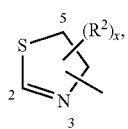
U-29 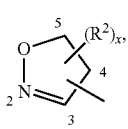
U-30 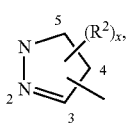
U-31 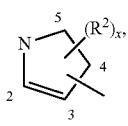
U-32 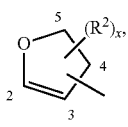
U-33 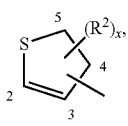
U-34 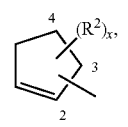
U-35 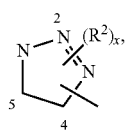
U-36 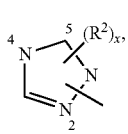
U-37 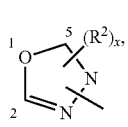
U-38 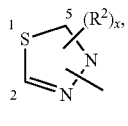
U-39 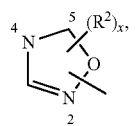
U-40 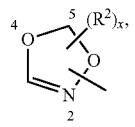
U-41 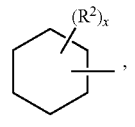
U-42 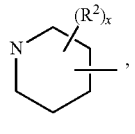
U-43 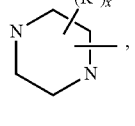
U-44 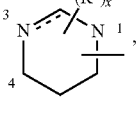
U-45 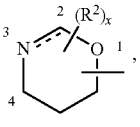
U-46 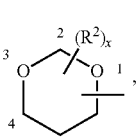
U-47 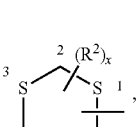
U-48 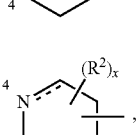
U-49 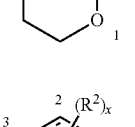

| U-50 | 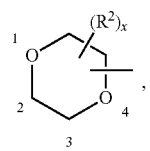 |
| --- | --- |
| U-51 | 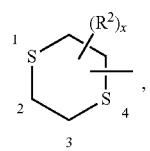 |
| U-52 | 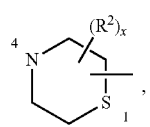 |
| U-53 | 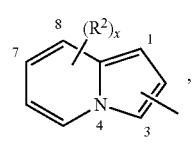 |
| U-54 | 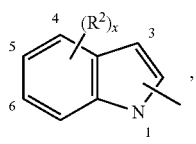 |
| U-55 | 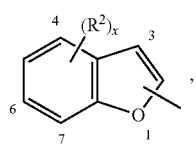 |
| U-56 | 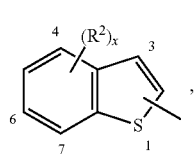 |
| U-57 | 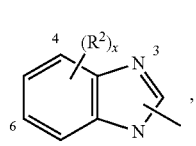 |
| U-58 | 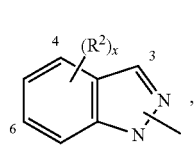 |
| U-59 | 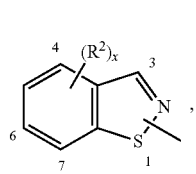 |
| U-60 | 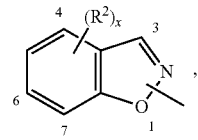 |
| U-61 | 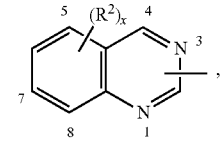 |
| U-62 | 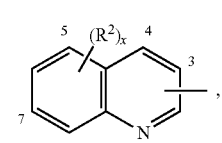 |
| U-63 | 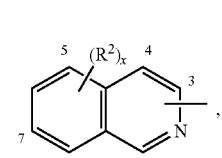 |
| U-64 | 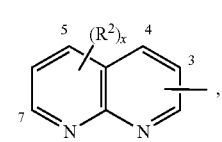 |
| U-65 | 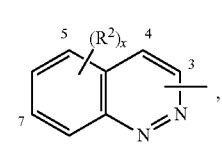 |
| U-66 | 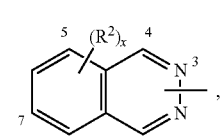 |
| U-67 | 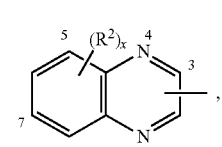 |
| U-68 | 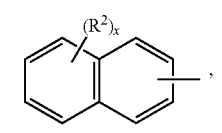 |
| U-69 | 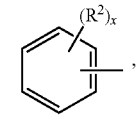 |

-continued
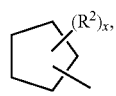 U-70
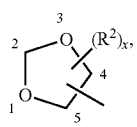 U-71
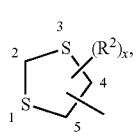 U-72
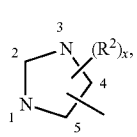 U-73
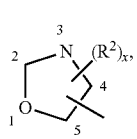 U-74
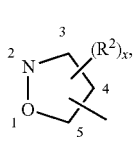 U-75
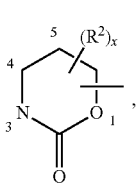 U-76
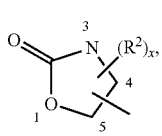 U-77
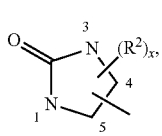 U-78
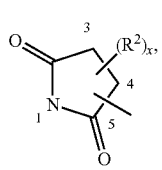 U-79
-continued
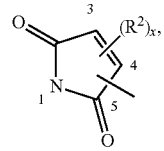 U-80
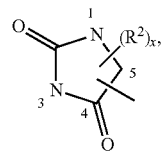 U-81
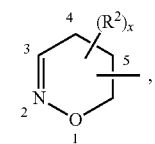 U-82
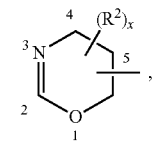 U-83
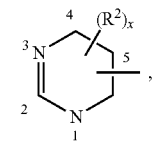 U-84
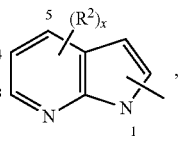 U-85
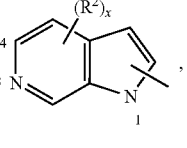 U-86
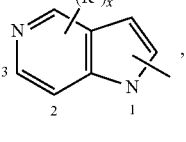 U-87
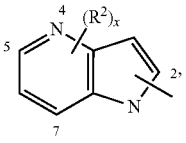 U-88

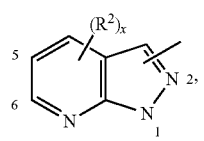 U-89
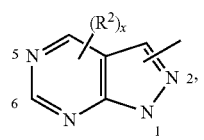 U-90
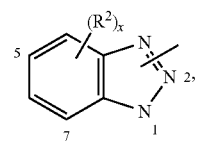 U-91
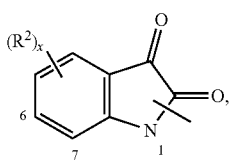 U-92
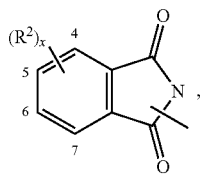 U-93
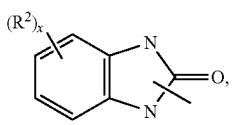 U-94
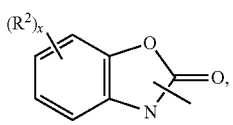 U-95
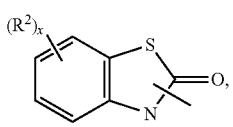 U-96
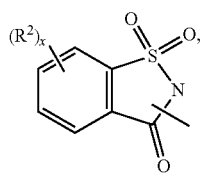 U-97
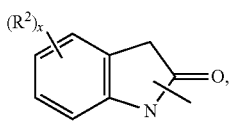 U-98
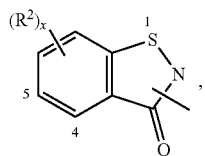 U-99
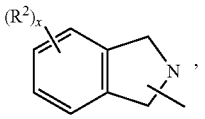 U-100
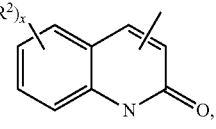 U-101
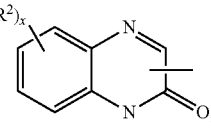 U-102
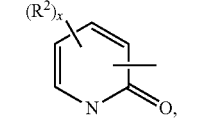 U-103
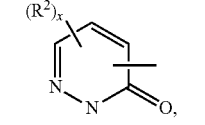 U-104
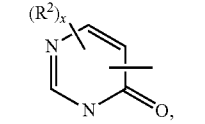 U-105
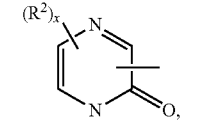 U-106
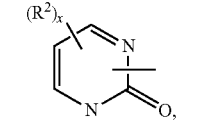 U-107
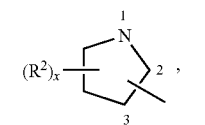 U-108
U-109

-continued

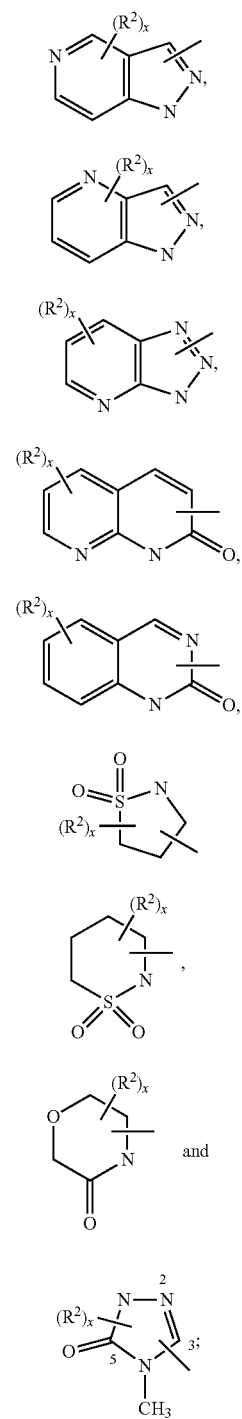

J is selected from J-1 through J-93

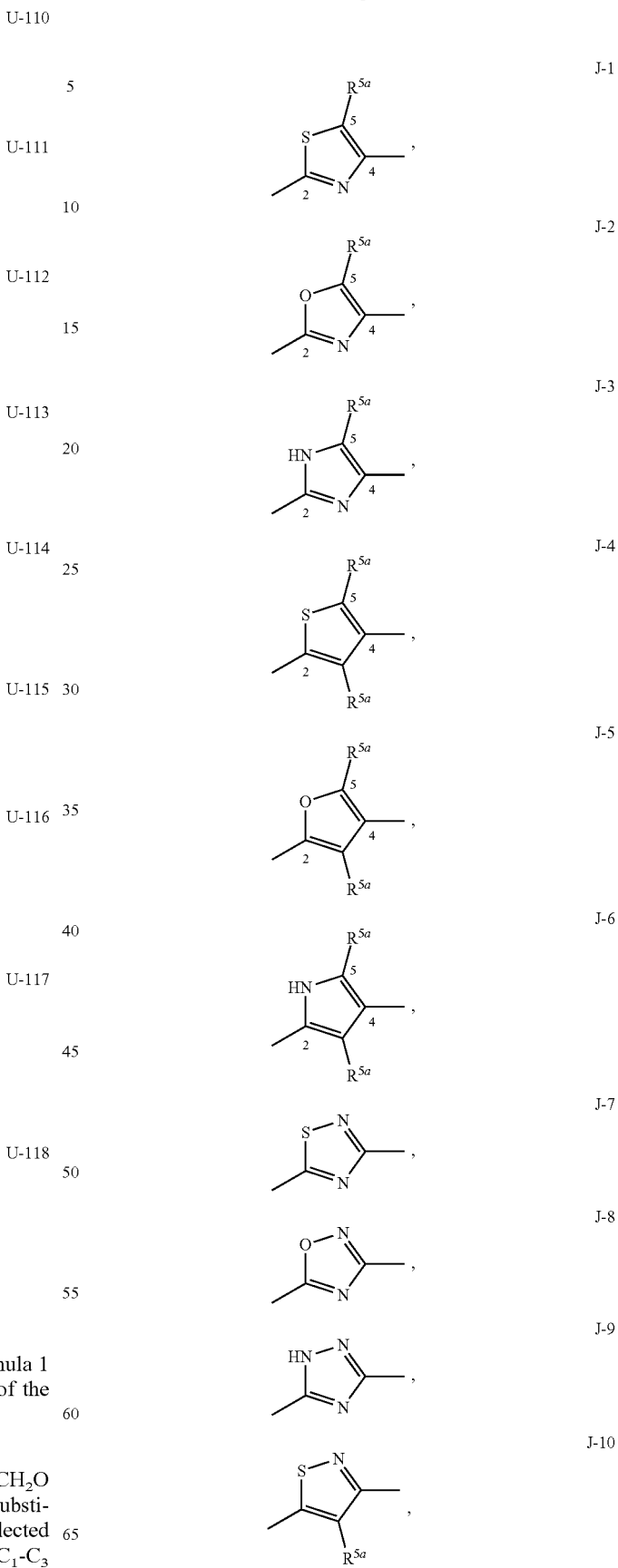

wherein the floating bond is connected to L in Formula 1 through any available carbon or nitrogen atom of the depicted ring or ring system;

x is 0, 1 or 2;

L is O, $(CR^{4a}R^{4b})_n$, $OCH_2$, $CH_2O$, $OCH_2CH_2$, $CH_2CH_2O$ or $CH_2OCH_2$, each carbon atom is optionally substituted with up to 2 substituents independently selected from halogen, cyano, hydroxy, $C_1$-$C_3$ alkyl, $C_1$-$C_3$ haloalkyl, $C_1$-$C_2$ alkoxy and $C_1$-$C_2$ haloalkoxy;

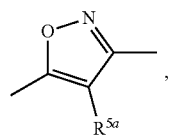 J-11
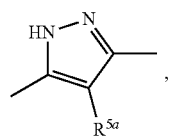 J-12
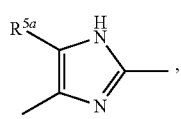 J-13
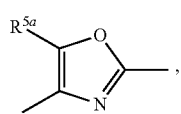 J-14
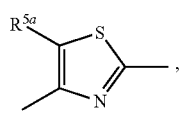 J-15
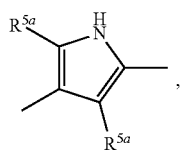 J-16
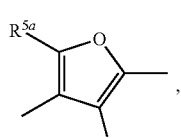 J-17
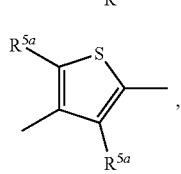 J-18
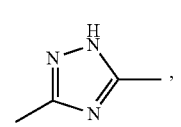 J-19
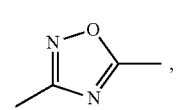 J-20
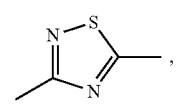 J-21
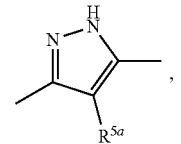 J-22
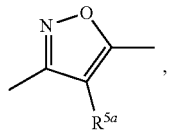 J-23
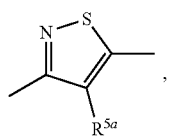 J-24
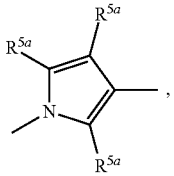 J-25
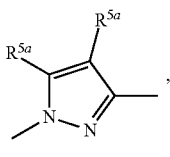 J-26
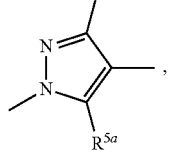 J-27
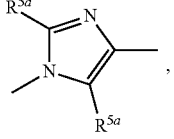 J-28
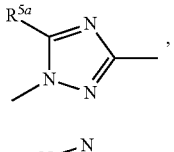 J-29
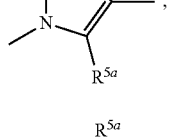 J-30
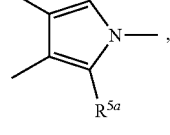 J-31
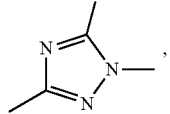 J-32

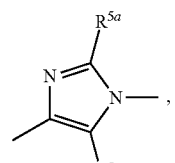 J-33,
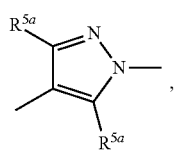 J-34,
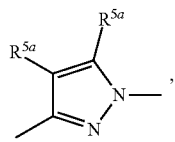 J-35,
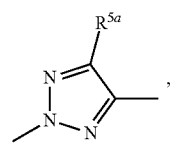 J-36,
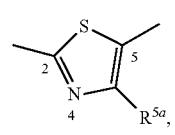 J-37,
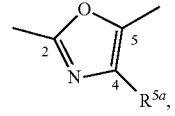 J-38,
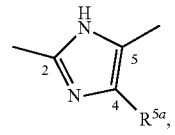 J-39,
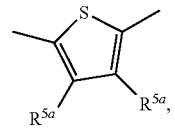 J-40,
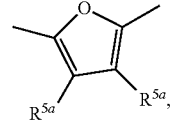 J-41,
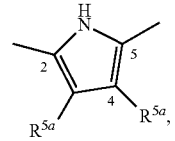 J-42,
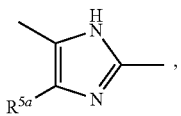 J-43
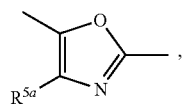 J-44,
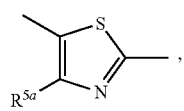 J-45,
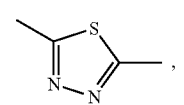 J-46,
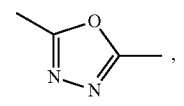 J-47,
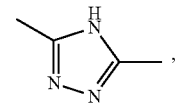 J-48,
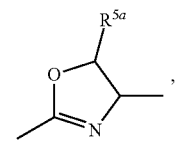 J-49,
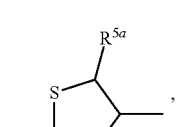 J-50,
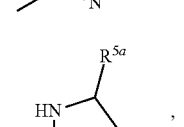 J-51,
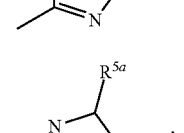 J-52,
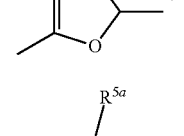 J-53,
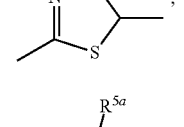 J-54,
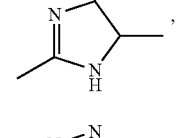 J-55,
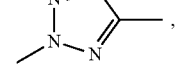

-continued
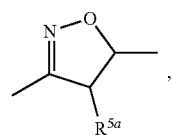 J-56
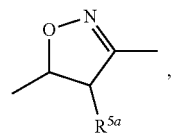 J-57
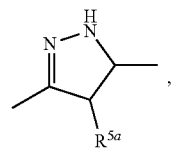 J-58
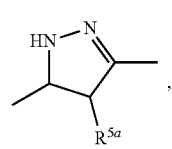 J-59
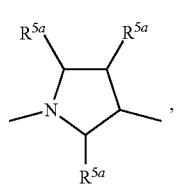 J-60
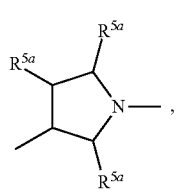 J-61
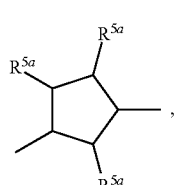 J-62
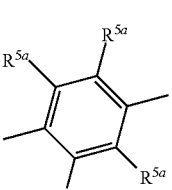 J-63
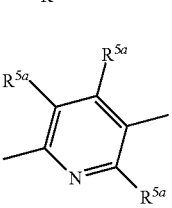 J-64
-continued
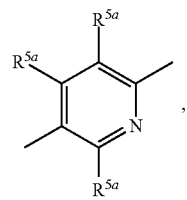 J-65
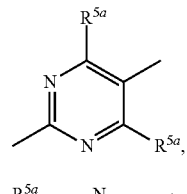 J-66
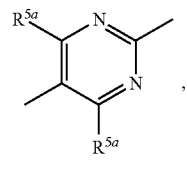 J-67
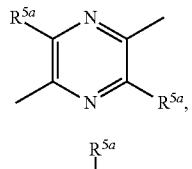 J-68
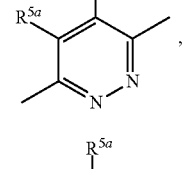 J-69
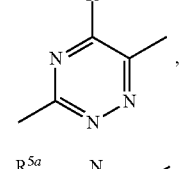 J-70
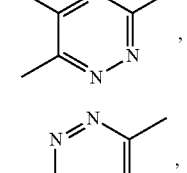 J-71
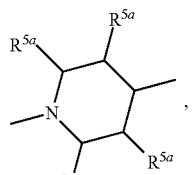 J-72
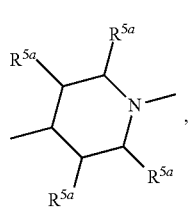 J-73
J-74

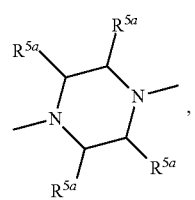 J-75
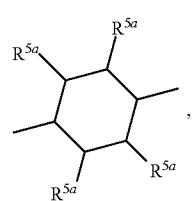 J-76
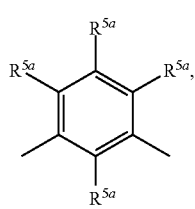 J-77
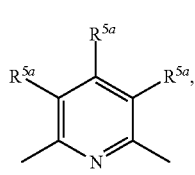 J-78
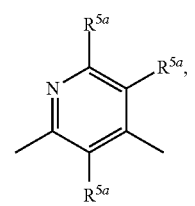 J-79
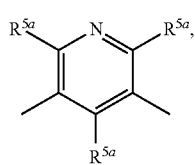 J-80
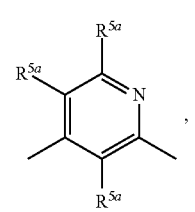 J-81
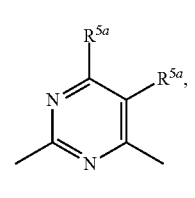 J-82
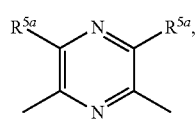 J-83
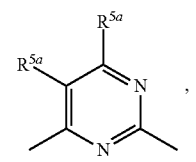 J-84
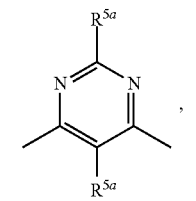 J-85
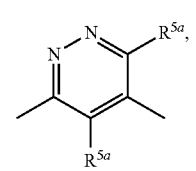 J-86
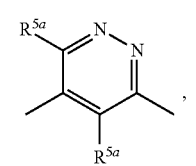 J-87
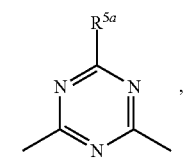 J-88
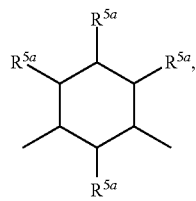 J-89
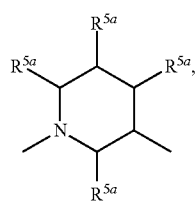 J-90
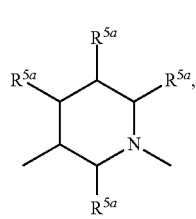 J-91

-continued

J-92

J-93 wherein the bond projecting to the left is bonded to L, and the bond projecting to the right is bonded to the oxadiazole ring in Formula 1;

each $R^{5a}$ is independently H or $R^5$; provided that at most only two $R^{5a}$ substituents are other than H;

each $R^2$ is independently halogen, cyano, —CH(=O), —C(=O)OH, —C(=O)NR$^{3a}$R$^{3b}$, —C(R$^6$)=NR$^7$ or —U—V—Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 3 substituents independently selected from $R^{10}$;

each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_5$ alkoxy, $C_2$-$C_4$ alkoxyalkyl, $C_2$-$C_4$ alkylthioalkyl, $C_2$-$C_4$ alkylcarbonyl, $C_2$-$C_4$ haloalkylcarbonyl, $C_4$-$C_6$ cycloalkylcarbonyl, $C_2$-$C_5$ alkoxycarbonyl or $C_3$-$C_5$ alkoxycarbonylalkyl;

each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ hydroxyalkyl, $C_2$-$C_6$ cyanoalkyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_4$-$C_{10}$ halocycloalkylalkyl, $C_2$-$C_6$ alkoxyalkyl, $C_2$-$C_6$ haloalkoxyalkyl or $C_4$-$C_{10}$ cycloalkoxyalkyl, each optionally substituted with up to 1 substituent selected from cyano, hydroxy, $C_2$-$C_4$ alkylcarbonyl, $C_2$-$C_4$ alkoxycarbonyl, $C_3$-$C_{15}$ trialkylsilyl and $C_3$-$C_{15}$ halotrialkylsilyl; or a pair of $R^{3a}$ and $R^{3b}$ substituents attached to the same nitrogen atom are taken together to form an azetidinyl, morpholinyl, pyrrolidinyl, piperidinyl, piperazinyl or thiomorpholinyl ring, each ring optionally substituted with up to 2 methyl;

each $R^{4a}$ and $R^{4b}$ is independently H, halogen, cyano, hydroxy, methyl or methoxy; or a pair of $R^{4a}$ and $R^{4b}$ substituents attached to the same carbon atom are taken together to form a cyclopropyl ring optionally substituted with up to 2 substituents independently selected from halogen, methyl, methoxy or methylthio;

each $R^5$ is independently cyano, halogen, $C_1$-$C_4$ alkyl, $C_1$-$C_4$ haloalkyl or $C_1$-$C_4$ alkoxy;

each $R^6$ is independently H, cyano, halogen, methyl or methoxy;

each $R^7$ is independently hydroxy or NR$^{11a}$R$^{11b}$; or $C_1$-$C_4$ alkoxy, $C_2$-$C_4$ alkenyloxy, $C_2$-$C_4$ alkynyloxy or $C_2$-$C_4$ alkylcarbonyloxy, each optionally substituted with up to 1 substituent selected cyano, hydroxy and —C(=O)OH;

each $R^{10}$ is independently halogen, cyano, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_2$-$C_4$ alkoxyalkoxy, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_3$-$C_5$ alkylthioalkylcarbonyl, $C_3$-$C_{15}$ trialkylsily or —C(R$^{13}$)=NOR$^{14}$;

each U is independently a direct bond, C(=O)O or C(=O)NR$^{17}$;

each V is independently a direct bond; or $C_1$-$C_6$ alkylene, $C_2$-$C_6$ alkenylene or $C_3$-$C_6$ alkynylene, each optionally substituted with up to 2 substituents independently selected from halogen, cyano, nitro, hydroxy, $C_1$-$C_2$ alkyl, $C_1$-$C_2$ haloalkyl, $C_1$-$C_2$ alkoxy and $C_1$-$C_2$ haloalkoxy;

each Q is independently phenyl, each optionally substituted with up to 2 substituents independently selected from $R^{12}$; or pyridinyl, pyrazolyl, imidazolyl, triazolyl, thiazolyl, oxazolyl, isoxazolyl, thienyl, isoxazolinyl, piperidinyl, morpholinyl or piperazinyl, each ring optionally substituted with up to 2 substituents independently selected from $R^{12}$;

each $R^{11a}$ is independently H, $C_1$-$C_2$ alkyl or $C_2$-$C_3$ alkylcarbonyl;

each $R^{11b}$ is independently H, cyano, $C_1$-$C_2$ alkyl, $C_2$-$C_4$ alkylcarbonyl, $C_2$-$C_4$ alkoxycarbonyl, $C_3$-$C_5$ alkoxycarbonylalkyl, $C_2$-$C_5$ alkylaminocarbonyl or $C_3$-$C_5$ dialkylaminocarbonyl; or a pair of $R^{11a}$ and $R^{11b}$ substituents are taken together with the nitrogen atom to which they are attached to form an azetidinyl, morpholinyl, pyrrolidinyl, piperidinyl, piperazinyl or thiomorpholinyl ring, each ring optionally substituted with up to 2 methyl;

each $R^{12}$ is independently halogen, cyano, $C_1$-$C_4$ alkyl, $C_1$-$C_4$ haloalkyl or $C_1$-$C_4$ alkoxy;

each $R^{13}$ is independently H, cyano, halogen, methyl, halomethyl or methoxy;

each $R^{14}$ is H, $C_1$-$C_5$ alkyl, $C_1$-$C_5$ haloalkyl, $C_2$-$C_5$ alkenyl, $C_2$-$C_5$ haloalkenyl, $C_2$-$C_5$ alkylcarbonyl or $C_2$-$C_5$ alkoxycarbonyl; and each $R^{17}$ is independently H, cyano, methyl or halomethyl.

Embodiment B

A compound of Embodiment A wherein
$R^1$ is U-1, U-2, U-4, U-5, U-8, U-12, U-29, U-58, U-69, U-79, U-80, U-104, U-115, U-116, U-117 or U-118;
L is (CR$^{4a}$R$^{4b}$)$_n$, OCH$_2$, CH$_2$O, OCH$_2$CH$_2$, CH$_2$CH$_2$O or CH$_2$OCH$_2$;
J is J-4, J-18, J-27, J-40, J-41, J-63, J-73 or J-93;
each $R^2$ is independently halogen, cyano, —CH(=O), —C(=O)OH, —C(=O)NR$^{3a}$R$^{3b}$, —C(R$^6$)=NR$^7$ or —U—V—Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 2 substituents independently selected from $R^{10}$;
each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl;

each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ halocycloalkyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from cyano, $C_2$-$C_4$ alkylcarbonyl, $C_2$-$C_4$ alkoxycarbonyl and $C_3$-$C_{15}$ trialkylsilyl;

each $R^{4a}$ and $R^{4b}$ is independently H, halogen, hydroxy, methyl or methoxy;

each $R^5$ is independently methyl or methoxy;

each $R^6$ is independently H or methyl;

each $R^7$ is independently $C_1$-$C_4$ alkoxy, $C_2$-$C_4$ alkenyloxy or $C_2$-$C_4$ alkynyloxy, each optionally substituted with up to 1 substituent selected cyano, hydroxy and —C(=O)OH;

each $R^{10}$ is independently halogen, cyano, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkoxy, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl or —C($R^{13}$)=NOR$^{14}$;

each V is independently a direct bond, $C_1$-$C_3$ alkylene, $C_2$-$C_4$ alkenylene or $C_3$-$C_4$ alkynylene;

each $R^{12}$ is independently halogen, cyano, $C_1$-$C_2$ alkyl, $C_1$-$C_2$ haloalkyl or $C_1$-$C_2$ alkoxy;

each $R^{13}$ is independently H, halogen, methyl or methoxy; and each $R^{14}$ is independently H, $C_1$-$C_2$ alkyl, $C_1$-$C_2$ haloalkyl, $C_2$-$C_4$ alkenyl, $C_2$-$C_4$ alkylcarbonyl or $C_2$-$C_4$ alkoxycarbonyl.

Embodiment C

A compound of Embodiment B wherein
$R^1$ is U-1, U-2, U-12 or U-29;
L is $(CR^{4a}R^{4b})_n$;
J is J-27, J-40 or J-63;
each $R^2$ is independently —C(=O)NR$^{3a}$R$^{3b}$, —C(R$^6$)=NR$^7$ or —U—V-Q; or $C_2$-$C_6$ alkoxycarbonyl, $C_3$-$C_6$ alkenyloxycarbonyl or $C_3$-$C_6$ alkynyloxycarbonyl, each optionally substituted with up to 1 substituent selected from $R^{10}$;
each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl;
each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from $C_2$-$C_4$ alkylcarbonyl and $C_2$-$C_4$ alkoxycarbonyl;
each $R^{4a}$ and $R^{4b}$ is independently H or methyl;
each $R^6$ is independently H;
each $R^7$ is independently $C_1$-$C_4$ alkoxy, $C_2$-$C_4$ alkenyloxy or $C_2$-$C_4$ alkynyloxy;
each $R^{10}$ is independently halogen, $C_1$-$C_4$ alkyl, $C_1$-$C_4$ haloalkyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_5$ alkoxycarbonyl or —C($R^{13}$)=NOR$^{14}$;
each V is independently a direct bond, $C_1$-$C_3$ alkylene or $C_2$-$C_4$ alkenylene;
each Q is independently phenyl, each optionally substituted with up to 2 substituents independently selected from $R^{12}$; or pyridinyl, pyrazolyl, imidazolyl, triazolyl, thiazolyl or oxazolyl, each ring optionally substituted with up to 2 substituents independently selected from $R^{12}$;
each $R^{12}$ is independently halogen, methyl or methoxy; and
each $R^{14}$ is independently H, methyl, halomethyl, $C_2$-$C_4$ alkylcarbonyl or $C_2$-$C_4$ alkoxycarbonyl.

Embodiment D

A compound of Embodiment C wherein
$R^1$ is U-2 or U-12;
J is J-40 or J-63;
$R^{5a}$ is H;
each $R^2$ is independently —C(=O)NR$^{3a}$R$^{3b}$; or $C_2$-$C_6$ alkoxycarbonyl, optionally substituted with up to 1 substituent selected from $R^{10}$;
each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_2$-$C_4$ alkoxyalkyl or $C_3$-$C_5$ alkoxycarbonylalkyl;
each $R^{3b}$ is independently H, $C_1$-$C_6$ alkyl, $C_1$-$C_6$ haloalkyl, $C_2$-$C_6$ alkenyl or $C_2$-$C_6$ haloalkenyl, each optionally substituted with up to 1 substituent selected from $C_2$-$C_4$ alkylcarbonyl and $C_2$-$C_4$ alkoxycarbonyl; and
each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl or $C_2$-$C_5$ alkoxycarbonyl.

Embodiment E

A compound of Embodiment D wherein
$R^1$ is U-2 connected at its 2-position to L; or
$R^1$ is U-12 connected at its 1-position to L;
each $R^2$ is independently —C(=O)NR$^{3a}$R$^{3b}$ or $C_2$-$C_6$ alkoxycarbonyl; and n is 1.

Embodiment F

A compound of Formula 1 wherein
$R^1$ is a phenyl ring optionally substituted with up to 3 substituents independently selected from $R^2$; or
$R^1$ is a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 3 substituents independently selected from $R^2$; provided that $R^1$ is linked to L via a carbon atom ring member;
J is

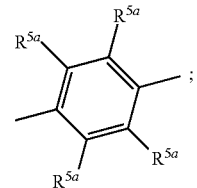

J-63 wherein the bond projecting to the left is bonded to L, and the bond projecting to the right is bonded to the oxadiazole ring in Formula 1;
each $R^{5a}$ is independently H or $R^5$; provided that at most only two $R^{5a}$ substituents are other than H; and
n is 3.

Embodiment G

A compound of Formula 1 wherein
R¹ is a phenyl ring optionally substituted with up to 3 substituents independently selected from R²; or
R¹ is a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 3 substituents independently selected from R²; and
each R² is independently $C_5$-$C_6$ alkyl, $C_5$-$C_6$ alkenyl, $C_5$-$C_6$ alkynyl, $C_5$-$C_6$ alkoxy, $C_5$-$C_6$ alkenyloxy or $C_5$-$C_6$ alkynyloxy, each optionally substituted with up to 3 substituents independently selected from R¹⁰.

This invention provides a fungicidal composition comprising a compound of Formula 1 (including all stereoisomers, N-oxides, hydrates, and salts thereof), and at least one other fungicide. Of note as embodiments of such compositions are compositions comprising a compound corresponding to any of the compound embodiments described above.

This invention provides a fungicidal composition comprising a compound of Formula 1 (including all stereoisomers, N-oxides, hydrates, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, N-oxides, hydrates, and salts thereof). Of note as embodiments of such methods are methods comprising applying a fungicidally effective amount of a compound corresponding to any of the compound embodiments describe above. Of particular note are embodiments where the compounds are applied as compositions of this invention.

Of note are compounds of Formula 1 that are compounds of Formula 1G (including all geometric and stereoisomers), N-oxides, hydrates and salts thereof, and agricultural compositions containing them and their use as fungicides:

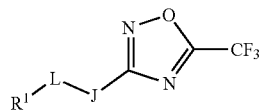

1G wherein
R¹ is a phenyl ring optionally substituted with up to 3 substituents independently selected from R²; or
R¹ is a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 3 substituents independently selected from R²; or
R¹ is a 3- to 7-membered nonaromatic ring or an 8- to 11-membered bicyclic ring system, each ring or ring system containing ring members selected from carbon atoms and optionally up to 4 heteroatoms independently selected from up to 2 O, up to 2 S and up to 4 N atoms, wherein up to 2 ring members are independently selected from C(=O), C(=S), S(=O) and S(=O)$_2$, each ring or ring system optionally substituted with up to 3 substituents independently selected from R²;
L is O, NR³, NR³CH$_2$, CH$_2$NR³, NR³CH$_2$CH$_2$, CH$_2$CH$_2$NR³, (CR$^{4a}$R$^{4b}$)$_n$, OCH$_2$, CH$_2$O, OCH$_2$CH$_2$, CH$_2$CH$_2$O or CH$_2$OCH$_2$, wherein the atom to the left is connected to R¹, and the atom to the right is connected to J, each carbon atom is optionally substituted with up to 2 substituents independently selected from halogen, cyano, hydroxy, nitro, $C_1$-$C_3$ alkyl, $C_1$-$C_3$ haloalkyl, $C_1$-$C_2$ alkoxy and $C_1$-$C_2$ haloalkoxy;
J is

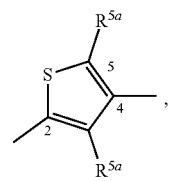

J-4

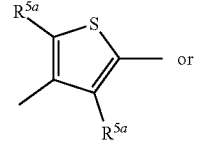

J-18

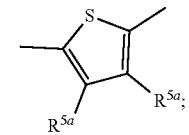

J-40 wherein the bond projecting to the left is bonded to L, and the bond projecting to the right is bonded to the oxadiazole ring in Formula 1;
each R$^{5a}$ is independently H or R⁵;
each R² is independently halogen, cyano, hydroxy, nitro, thioyl, —SF$_5$, —CH(=O), —C(=O)OH, —NR$^{3a}$R$^{3b}$, —C(=O)NR$^{3a}$R$^{3b}$, —C(=O)C(=O)NR$^{3a}$R$^{3b}$, —C(=S)NR$^{3a}$R$^{3b}$, —C(R⁶)=NR⁷, —N=CR⁸NR$^{9a}$R$^{9b}$ or —U—V-Q; or $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkenyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_1$-$C_6$ alkylsulfinyl, $C_1$-$C_6$ alkylsulfonyl, $C_1$-$C_6$ alkylaminosulfinyl, $C_2$-$C_6$ dialkylaminosulfinyl, $C_1$-$C_6$ alkylsulfonyloxy, $C_1$-$C_6$ alkylsulfonylamino, $C_2$-$C_6$ alkylcarbonyl, $C_4$-$C_7$ cycloalkylcarbonyl, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_3$-$C_6$ alkyloxycarbonylcarbonyl, $C_2$-$C_6$ alkylcarbonyloxy, $C_4$-$C_7$ cycloalkylcarbonyloxy, $C_2$-$C_6$ alkoxycarbonyloxy, $C_4$-$C_7$ cycloalkoxycarbonyloxy, $C_2$-$C_6$ alkylaminocarbonyloxy, $C_4$-$C_7$ cycloalkylaminocarbonyloxy, $C_2$-$C_6$ alkylcarbonylamino, $C_4$-$C_7$ cycloalkylcarbonylamino, $C_2$-$C_6$ alkoxycarbonylamino, $C_4$-$C_7$ cycloalkoxycarbonylamino, $C_2$-$C_6$ alkylaminocarbonylamino, $C_4$-$C_7$ cycloalkylaminocarbonylamino or $C_2$-$C_6$ dialkoxyphosphinyl, each optionally substituted with up to 3 substituents independently selected from $R^{10}$;

each $R^3$ and $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_5$ alkoxy, $C_2$-$C_4$ alkoxyalkyl, $C_1$-$C_4$ alkylsulfonyl, $C_1$-$C_4$ haloalkylsulfonyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_4$-$C_7$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl;

each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ hydroxyalkyl, $C_2$-$C_6$ cyanoalkyl, $C_3$-$C_8$ cycloalkyl, $C_3$-$C_8$ halocycloalkyl, $C_3$-$C_8$ cycloalkenyl, $C_3$-$C_8$ halocycloalkenyl, $C_4$-$C_{10}$ alkylcycloalkyl, $C_4$-$C_{10}$ cycloalkylalkyl, $C_4$-$C_{10}$ halocycloalkylalkyl, $C_6$-$C_{14}$ cycloalkylcycloalkyl, $C_5$-$C_{10}$ alkylcycloalkylalkyl, $C_2$-$C_6$ alkoxyalkyl, $C_2$-$C_6$ haloalkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_2$-$C_6$ haloalkylaminoalkyl, $C_3$-$C_8$ dialkylaminoalkyl or $C_4$-$C_{10}$ cycloalkylaminoalkyl, each optionally substituted with up to 1 substituent selected from cyano, hydroxy, nitro, $C_2$-$C_4$ alkylcarbonyl, $C_2$-$C_4$ alkoxycarbonyl, $C_3$-$C_{15}$ trialkylsilyl and $C_3$-$C_{15}$ halotrialkylsilyl; or a pair of $R^{3a}$ and $R^{3b}$ substituents are taken together with the nitrogen atom to which they are attached to form a 4- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 3 substituents independently selected from halogen and $C_1$-$C_3$ alkyl;

each $R^{4a}$ and $R^{4b}$ is independently H, halogen, cyano, hydroxy, nitro, $C_1$-$C_3$ alkyl, $C_1$-$C_3$ haloalkyl, $C_1$-$C_2$ alkoxy or $C_1$-$C_2$ haloalkoxy; or a pair of $R^{4a}$ and $R^{4b}$ substituents attached to the same carbon atom are taken together to form a $C_3$-$C_5$ cycloalkyl ring optionally substituted with up to 2 substituents independently selected from halogen, methyl, methoxy and methylthio;

each $R^5$ is independently hydroxy, cyano, nitro, halogen, $C_1$-$C_4$ alkyl, $C_1$-$C_4$ haloalkyl, $C_2$-$C_4$ alkenyl or $C_1$-$C_4$ alkoxy;

each $R^6$ is independently H, cyano, halogen, methyl, methoxy, methylthio or methoxycarbonyl;

each $R^7$ is independently hydroxy or $NR^{11a}R^{11b}$; or $C_1$-$C_4$ alkoxy, $C_2$-$C_4$ alkenyloxy, $C_2$-$C_4$ alkynyloxy, $C_2$-$C_4$ alkylcarbonyloxy, $C_2$-$C_5$ alkoxycarbonyloxy, $C_2$-$C_5$ alkylaminocarbonyloxy or $C_3$-$C_5$ dialkylaminocarbonyloxy, each optionally substituted with up to 1 substituent selected from halogen, cyano, hydroxy and —C(=O)OH;

each $R^8$ is independently H, methyl, methoxy or methylthio;

each $R^{9a}$ and $R^{9b}$ is independently H or $C_1$-$C_4$ alkyl; or a pair of $R^{9a}$ and $R^{9b}$ substituents are taken together with the nitrogen atom to which they are attached to form a 5- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 2 methyl;

each $R^{10}$ is independently halogen, amino, cyano, hydroxy, nitro, thioyl, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_2$-$C_4$ alkoxyalkoxy, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_1$-$C_6$ alkylamino, $C_2$-$C_6$ dialkylamino, $C_2$-$C_5$ alkylaminocarbonyl, $C_3$-$C_5$ dialkylaminocarbonyl, $C_3$-$C_5$ alkylthioalkylcarbonyl, $C_3$-$C_{15}$ trialkylsily, $C_3$-$C_{15}$ halotrialkylsilyl, —C($R^{13}$)=NOR$^{14}$ or —C($R^{15}$)=NR$^{16}$;

each U is independently a direct bond, C(=O)O, C(=O)NR$^{17}$ or C(=S)NR$^{18}$, wherein the atom to the left is connected to $R^1$, and the atom to the right is connected to V;

each V is independently a direct bond; or $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, each optionally substituted with up to 3 substituents independently selected from halogen, cyano, nitro, hydroxy, $C_1$-$C_2$ alkyl, $C_1$-$C_2$ haloalkyl, $C_1$-$C_2$ alkoxy and $C_1$-$C_2$ haloalkoxy;

each Q is independently phenyl or phenoxy, each optionally substituted with up to 2 substituents independently selected from $R^{12}$; or each Q is independently a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$; or each Q is independently a 3- to 7-membered nonaromatic heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from $R^{12}$;

each $R^{11a}$ is independently H, $C_1$-$C_4$ alkyl or $C_2$-$C_4$ alkylcarbonyl;

each $R^{11b}$ is independently H, cyano, $C_1$-$C_5$ alkyl, $C_2$-$C_5$ alkylcarbonyl, $C_2$-$C_5$ haloalkylcarbonyl, $C_4$-$C_7$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl; or a pair of $R^{11a}$ and $R^{11b}$ substituents are taken together with the nitrogen atom to which they are attached to form a 5- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 2 methyl;

each $R^{12}$ is independently halogen, cyano, hydroxy, nitro, $C_1$-$C_4$ alkyl, $C_1$-$C_4$ haloalkyl, $C_2$-$C_4$ alkenyl, $C_1$-$C_4$ alkoxy, $C_2$-$C_4$ alkylcarbonyl or $C_2$-$C_4$ alkoxycarbonyl;

each $R^{13}$ and $R^{15}$ is independently H, cyano, halogen, $C_1$-$C_3$ alkyl, $C_1$-$C_3$ haloalkyl, $C_3$-$C_6$ cycloalkyl or C$_1$-C$_3$ alkoxy; or a phenyl ring optionally substituted with up to 2 substituents independently selected from halogen and C$_1$-C$_3$ alkyl;

each R$^{14}$ is independently H, C$_1$-C$_5$ alkyl, C$_1$-C$_5$ haloalkyl, C$_2$-C$_5$ alkenyl, C$_2$-C$_5$ haloalkenyl, C$_2$-C$_5$ alkynyl, C$_3$-C$_6$ cycloalkyl, C$_3$-C$_6$ halocycloalkyl, C$_2$-C$_5$ alkylcarbonyl or C$_2$-C$_5$ alkoxycarbonyl; or each R$^{14}$ is a phenyl ring optionally substituted with up to 2 substituents independently selected from halogen and C$_1$-C$_3$ alkyl; or a 5- to 6-membered fully saturated heterocyclic ring, each ring containing ring members selected from carbon atoms and up to 2 heteroatoms independently selected from up to 2 O, up to 2 S and up to 2 N atoms, each ring optionally substituted with up to 2 substituents independently selected from halogen and C$_1$-C$_3$ alkyl;

each R$^{16}$ is independently H, cyano, C$_1$-C$_3$ alkyl, C$_1$-C$_3$ haloalkyl, C$_1$-C$_4$ alkoxy, C$_2$-C$_4$ alkylcarbonyl or C$_2$-C$_4$ alkoxycarbonyl;

each R$^{17}$ and R$^{18}$ is independently H, cyano, hydroxy, C$_1$-C$_4$ alkyl, C$_1$-C$_4$ haloalkyl, C$_2$-C$_4$ alkylcarbonyl, C$_2$-C$_4$ haloalkylcarbonyl, C$_2$-C$_4$ alkoxycarbonyl or C$_2$-C$_4$ haloalkoxycarbonyl; and n is 1, 2 or 3;

Accordingly, of note is a compound selected from Formula 1G (including all geometric and stereoisomers), N-oxides, hydrates, and salts thereof, as defined above. Also of note are counterpart embodiments to Embodiments 1 through 158 and Embodiments A through F wherein in said counterpart embodiments "Formula 1" is replaced by "Formula 1G" and the scope of said counterpart embodiments does not exceed the scope defined above for Formula 1G. Examples of combinations of Embodiments 1 through 158 as applied to Formula 1G, as well as any other embodiments described herein, are Embodiments AG and BG below.

Embodiment AG

A compound of Formula 1G wherein
R$^1$ is U-1, U-2, U-4, U-5, U-8, U-12, U-29, U-58, U-69, U-79, U-104, U-115, U-116, U-117 or U-118;
wherein the floating bond is connected to L in Formula 1 through any available carbon or nitrogen atom of the depicted ring or ring system;
x is 0, 1 or 2;
L is (CR$^{4a}$R$^{4b}$)$_n$;
J is J-40;
R$^{5a}$ is H;
each R$^2$ is independently halogen, cyano, —CH(=O), —C(=O)OH, —C(=O)NR$^{3a}$R$^{3b}$, —C(R$^6$)=NR$^7$ or —U—V—Q; or C$_1$-C$_6$ alkyl, C$_2$-C$_6$ alkenyl, C$_2$-C$_6$ alkynyl, C$_1$-C$_6$ alkoxy, C$_2$-C$_6$ alkoxycarbonyl, C$_3$-C$_6$ alkenyloxycarbonyl, C$_3$-C$_6$ alkynyloxycarbonyl or C$_4$-C$_7$ cycloalkoxycarbonyl, each optionally substituted with up to 1 substituent selected from R$^{10}$;
each R$^{3a}$ is independently H, cyano, hydroxy, C$_1$-C$_4$ alkyl, C$_1$-C$_4$ haloalkyl, C$_2$-C$_4$ alkenyl, C$_2$-C$_4$ alkynyl, C$_1$-C$_5$ alkoxy, C$_2$-C$_4$ alkoxyalkyl, C$_2$-C$_4$ alkylcarbonyl, C$_2$-C$_4$ haloalkylcarbonyl or C$_3$-C$_5$ alkoxycarbonylalkyl;
each R$^{3b}$ is independently H, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_2$-C$_6$ haloalkynyl, C$_3$-C$_8$ halocycloalkyl, C$_4$-C$_{10}$ cycloalkylalkyl, C$_4$-C$_{10}$ halocycloalkylalkyl, C$_2$-C$_6$ alkoxyalkyl, C$_2$-C$_6$ haloalkoxyalkyl, each optionally substituted with up to 1 substituent selected from cyano, C$_2$-C$_4$ alkylcarbonyl, C$_2$-C$_4$ alkoxycarbonyl and C$_3$-C$_{15}$ trialkylsilyl;

each R$^6$ is independently H;

each R$^7$ is independently C$_1$-C$_4$ alkoxy, C$_2$-C$_4$ alkenyloxy or C$_2$-C$_4$ alkynyloxy;

each R$^{10}$ is independently halogen, C$_1$-C$_4$ alkyl, C$_1$-C$_4$ haloalkyl, C$_1$-C$_4$ alkoxy, C$_1$-C$_4$ haloalkoxy, C$_2$-C$_4$ alkylcarbonyl, C$_2$-C$_4$ haloalkylcarbonyl, C$_2$-C$_5$ alkoxycarbonyl or —C(R$^{13}$)=NOR$^{14}$;

each U is independently a direct bond, C(=O)O or C(=O)NR$^{17}$;

each V is independently C$_1$-C$_3$ alkylene;

each Q is independently phenyl, each optionally substituted with up to 2 substituents independently selected from R$^{12}$; or pyridinyl, pyrazolyl, imidazolyl, triazolyl, thiazolyl or oxazolyl, each ring optionally substituted with up to 2 substituents independently selected from R$^{12}$;

each R$^{12}$ is independently halogen, cyano, C$_1$-C$_2$ alkyl, C$_1$-C$_2$ haloalkyl or C$_1$-C$_2$ alkoxy;

each R$^{13}$ is independently H, halogen, methyl or methoxy;

each R$^{14}$ is H, C$_1$-C$_5$ alkyl, C$_1$-C$_5$ haloalkyl, C$_2$-C$_5$ alkenyl, C$_2$-C$_5$ haloalkenyl, C$_2$-C$_5$ alkylcarbonyl or C$_2$-C$_5$ alkoxycarbonyl; and each R$^{17}$ is independently H, cyano, methyl or halomethyl.

Embodiment BG

A compound of Embodiment AG wherein
R$^1$ is U-2 or U-12;
each R$^2$ is independently —C(=O)NR$^{3a}$R$^{3b}$; or C$_2$-C$_6$ alkoxycarbonyl, optionally substituted with up to 1 substituent selected from R$^{10}$;
each R$^{3a}$ is independently H, C$_1$-C$_4$ alkyl, C$_1$-C$_4$ haloalkyl, C$_2$-C$_4$ alkenyl, C$_2$-C$_4$ alkynyl, C$_2$-C$_4$ alkoxyalkyl or C$_3$-C$_5$ alkoxycarbonylalkyl;
each R$^{3b}$ is independently H, C$_1$-C$_3$ alkyl, C$_1$-C$_3$ haloalkyl, C$_2$-C$_4$ alkenyl or C$_2$-C$_4$ haloalkenyl;
each R$^{10}$ is independently halogen, C$_1$-C$_4$ alkyl, C$_1$-C$_4$ alkoxy, C$_2$-C$_4$ alkylcarbonyl, C$_2$-C$_4$ haloalkylcarbonyl or C$_2$-C$_5$ alkoxycarbonyl; and
n is 1.

Also of note is a fungicidal composition comprising a fungicidally effective amount of a compound of Formula 1G (including all geometric and stereoisomers, N-oxides, and salts thereof) or any one of counterpart embodiments that are embodiment counterparts to Embodiments 1 through 158 and Embodiments A through F (e.g., Embodiment AG and BG), and at least one additional component selected from the group consisting of surfactants, solid diluents and liquid diluents. Also of note is a method for controlling plant diseases caused by fungal plant pathogens comprising applying to the plant or portion thereof, or to the plant seed, a fungicidally effective amount of a compound of Formula 1G (including all geometric and stereoisomers, N-oxides, and salts thereof) or any one of said counterpart embodiments. Of particular note are embodiments where the compounds of Formula 1G are applied as compositions of this invention.

Of further note are compounds of Formula 1 that are compounds of Formula 1P (including all geometric and stereoisomers), N-oxides, hydrates and salts thereof, and agricultural compositions containing them and their use as fungicides:

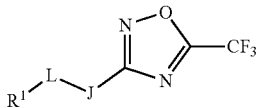

1P wherein
- $R^1$ is a phenyl ring optionally substituted with up to 3 substituents independently selected from $R^2$; or
- $R^1$ is a 5- to 6-membered heteroaromatic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 3 substituents independently selected from $R^2$; or; provided that $R^1$ is linked to L via a carbon atom ring member;
- L is O, $NR^3$, $NR^3CH_2$, $CH_2NR^3$, $NR^3CH_2CH_2$, $CH_2CH_2NR^3$, $(CR^{4a}R^{4b})_n$, $OCH_2$, $CH_2O$, $OCH_2CH_2$, $CH_2CH_2O$ or $CH_2OCH_2$, wherein the atom to the left is connected to $R^1$, and the atom to the right is connected to J, each carbon atom is optionally substituted with up to 2 substituents independently selected from halogen, cyano, hydroxy, nitro, $C_1$-$C_3$ alkyl, $C_1$-$C_3$ haloalkyl, $C_1$-$C_2$ alkoxy and $C_1$-$C_2$ haloalkoxy;
- J is

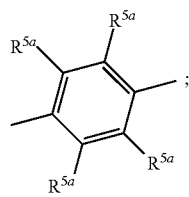

J-63 wherein the bond projecting to the left is bonded to L, and the bond projecting to the right is bonded to the oxadiazole ring in Formula 1;
- each $R^{5a}$ is independently H or $R^5$; provided that at most only two $R^{5a}$ substituents are other than H;
- each $R^2$ is independently —$NR^{3a}R^{3b}$, —C(=O)$NR^{3a}R^{3b}$, —C($R^6$)=$NR^7$ or —U—V-Q; or $C_3$-$C_6$ alkenyloxycarbonyl or $C_3$-$C_6$ alkynyloxycarbonyl, each optionally substituted with up to 3 substituents independently selected from $R^{10}$;
- each $R^3$ and $R^{3a}$ is independently $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_1$-$C_5$ alkoxy, $C_2$-$C_4$ alkoxyalkyl, $C_1$-$C_4$ alkylsulfonyl, $C_1$-$C_4$ haloalkylsulfonyl, $C_2$-$C_4$ alkylthioalkyl, $C_2$-$C_4$ alkylsulfinylalkyl, $C_2$-$C_4$ alkylsulfonylalkyl, $C_2$-$C_4$ alkylcarbonyl, $C_2$-$C_4$ haloalkylcarbonyl, $C_4$-$C_7$ cycloalkylcarbonyl, $C_2$-$C_5$ alkoxycarbonyl, $C_3$-$C_5$ alkoxycarbonylalkyl, $C_2$-$C_5$ alkylaminocarbonyl or $C_3$-$C_5$ dialkylaminocarbonyl;
- each $R^{3b}$ is independently $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_1$-$C_6$ hydroxyalkyl, $C_2$-$C_6$ cyanoalkyl, $C_3$-$C_8$ cycloalkyl, $C_3$-$C_8$ halocycloalkyl, $C_3$-$C_8$ cycloalkenyl, $C_3$-$C_8$ halocycloalkenyl, $C_4$-$C_{10}$ alkylcycloalkyl, $C_4$-$C_{10}$ cycloalkylalkyl, $C_4$-$C_{10}$ halocycloalkylalkyl, $C_6$-$C_{14}$ cycloalkylcycloalkyl, $C_5$-$C_{10}$ alkylcycloalkylalkyl, $C_2$-$C_6$ alkoxyalkyl, $C_2$-$C_6$ haloalkoxyalkyl, $C_4$-$C_{10}$ cycloalkoxyalkyl, $C_3$-$C_8$ alkoxyalkoxyalkyl, $C_2$-$C_6$ alkylthioalkyl, $C_2$-$C_6$ alkylsulfinylalkyl, $C_2$-$C_6$ alkylsulfonylalkyl, $C_2$-$C_6$ alkylaminoalkyl, $C_2$-$C_6$ haloalkylaminoalkyl, $C_3$-$C_8$ dialkylaminoalkyl or $C_4$-$C_{10}$ cycloalkylaminoalkyl, each optionally substituted with up to 1 substituent selected from cyano, hydroxy, nitro, $C_2$-$C_4$ alkylcarbonyl, $C_2$-$C_4$ alkoxycarbonyl, $C_3$-$C_{15}$ trialkylsilyl and $C_3$-$C_{15}$ halotrialkylsilyl; or
- a pair of $R^{3a}$ and $R^{3b}$ substituents are taken together with the nitrogen atom to which they are attached to form a 4- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 3 substituents independently selected from halogen and $C_1$-$C_3$ alkyl;
- each $R^{4a}$ and $R^{4b}$ is independently H, halogen, cyano, hydroxy, nitro, $C_1$-$C_3$ alkyl, $C_1$-$C_3$ haloalkyl, $C_1$-$C_2$ alkoxy or $C_1$-$C_2$ haloalkoxy; or
- a pair of $R^{4a}$ and $R^{4b}$ substituents attached to the same carbon atom are taken together to form a $C_3$-$C_5$ cycloalkyl ring optionally substituted with up to 2 substituents independently selected from halogen, methyl, methoxy and methylthio;
- each $R^5$ is independently hydroxy, cyano, nitro, halogen, $C_1$-$C_4$ alkyl, $C_1$-$C_4$ haloalkyl, $C_2$-$C_4$ alkenyl or $C_1$-$C_4$ alkoxy;
- each $R^6$ is independently H, cyano, halogen, methyl, methoxy, methylthio or methoxycarbonyl;
- each $R^7$ is independently hydroxy or $NR^{11a}R^{11b}$; or $C_1$-$C_4$ alkoxy, $C_2$-$C_4$ alkenyloxy, $C_2$-$C_4$ alkynyloxy, $C_2$-$C_4$ alkylcarbonyloxy, $C_2$-$C_5$ alkoxycarbonyloxy, $C_2$-$C_5$ alkylaminocarbonyloxy or $C_3$-$C_5$ dialkylaminocarbonyloxy, each optionally substituted with up to 1 substituent selected from halogen, cyano, hydroxy and —C(=O)OH;
- each $R^{10}$ is independently halogen, amino, cyano, hydroxy, nitro, thioyl, $C_1$-$C_4$ alkyl, $C_1$-$C_4$ haloalkyl, $C_3$-$C_6$ cycloalkyl, $C_3$-$C_6$ halocycloalkyl, $C_1$-$C_4$ alkoxy, $C_1$-$C_4$ haloalkoxy, $C_2$-$C_4$ alkoxyalkyl, $C_1$-$C_4$ alkylthio, $C_1$-$C_4$ alkylsulfinyl, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl, $C_1$-$C_6$ alkylamino, $C_2$-$C_6$ dialkylamino, $C_2$-$C_5$ alkylaminocarbonyl, $C_3$-$C_5$ dialkylaminocarbonyl, $C_3$-$C_5$ alkylthioalkylcarbonyl, $C_3$-$C_{15}$ trialkylsily, $C_3$-$C_{15}$ halotrialkylsilyl, —C($R^{13}$)=$NOR^{14}$ or —C($R^{15}$)=$NR^{16}$;
- each U is independently a direct bond, C(=O)O, C(=O)$NR^{17}$ or C(=S)$NR^{18}$, wherein the atom to the left is connected to $R^1$, and the atom to the right is connected to V;
- each V is independently a direct bond; or $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, each optionally substituted with up to 3 substituents independently selected from halogen, cyano, nitro, hydroxy, $C_1$-$C_2$ alkyl, $C_1$-$C_2$ haloalkyl, $C_1$-$C_2$ alkoxy and $C_1$-$C_2$ haloalkoxy;
- each Q is independently phenyl or phenoxy, each optionally substituted with up to 2 substituents independently selected from $R^{12}$; or
- each Q is independently a 5- to 6-membered heteroaromatic ring, each ring containing ring members selected from carbon atoms and 1 to 4 heteroatoms independently selected from up to 2 O, up to 2 S and up to 4

N atoms, wherein up to 2 ring members are independently selected from C(=O), C(=S), S(=O) and S(=O)$_2$, each ring optionally substituted with up to 2 substituents independently selected from R$^{12}$; or each Q is independently a 3- to 7-membered nonaromatic heterocyclic ring, each ring containing ring members selected from carbon atoms and 1 to 4 heteroatoms independently selected from up to 2 O, up to 2 S and up to 4 N atoms, wherein up to 2 ring members are independently selected from C(=O), C(=S), S(=O) and S(=O)$_2$, each ring optionally substituted with up to 2 substituents independently selected from R$^{12}$;

each R$^{11a}$ is independently H, C$_1$-C$_4$ alkyl or C$_2$-C$_4$ alkylcarbonyl;

each R$^{11b}$ is independently H, cyano, C$_1$-C$_5$ alkyl, C$_2$-C$_5$ alkylcarbonyl, C$_2$-C$_5$ haloalkylcarbonyl, C$_4$-C$_7$ cycloalkylcarbonyl, C$_2$-C$_5$ alkoxycarbonyl, C$_3$-C$_5$ alkoxycarbonylalkyl, C$_2$-C$_5$ alkylaminocarbonyl or C$_3$-C$_5$ dialkylaminocarbonyl; or a pair of R$^{11a}$ and R$^{11b}$ substituents are taken together with the nitrogen atom to which they are attached to form a 5- to 6-membered fully saturated heterocyclic ring, each ring containing ring members, in addition to the connecting nitrogen atom, selected from carbon atoms and up to 2 heteroatoms independently selected from up to 2 O, up to 2 S and up to 2 N atoms, each ring optionally substituted with up to 2 methyl;

each R$^{12}$ is independently halogen, cyano, hydroxy, nitro, C$_1$-C$_4$ alkyl, C$_1$-C$_4$ haloalkyl, C$_2$-C$_4$ alkenyl, C$_1$-C$_4$ alkoxy, C$_2$-C$_4$ alkylcarbonyl or C$_2$-C$_4$ alkoxycarbonyl;

each R$^{13}$ and R$^{15}$ is independently H, cyano, halogen, C$_1$-C$_3$ alkyl, C$_1$-C$_3$ haloalkyl, C$_3$-C$_6$ cycloalkyl or C$_1$-C$_3$ alkoxy; or a phenyl ring optionally substituted with up to 2 substituents independently selected from halogen and C$_1$-C$_3$ alkyl;

each R$^{14}$ is independently H, C$_1$-C$_5$ alkyl, C$_1$-C$_5$ haloalkyl, C$_2$-C$_5$ alkenyl, C$_2$-C$_5$ haloalkenyl, C$_2$-C$_5$ alkynyl, C$_3$-C$_6$ cycloalkyl, C$_3$-C$_6$ halocycloalkyl, C$_2$-C$_5$ alkylcarbonyl or C$_2$-C$_5$ alkoxycarbonyl; or each R$^{14}$ is a phenyl ring optionally substituted with up to 2 substituents independently selected from halogen and C$_1$-C$_3$ alkyl; or a 5- to 6-membered fully saturated heterocyclic ring, each ring containing ring members selected from carbon atoms and up to 2 heteroatoms independently selected from up to 2 O, up to 2 S and up to 2 N atoms, each ring optionally substituted with up to 2 substituents independently selected from halogen and C$_1$-C$_3$ alkyl;

each R$^{16}$ is independently H, cyano, C$_1$-C$_3$ alkyl, C$_1$-C$_3$ haloalkyl, C$_1$-C$_4$ alkoxy, C$_2$-C$_4$ alkylcarbonyl or C$_2$-C$_4$ alkoxycarbonyl;

each R$^{17}$ and R$^{18}$ is independently H, cyano, hydroxy, C$_1$-C$_4$ alkyl, C$_1$-C$_4$ haloalkyl, C$_2$-C$_4$ alkylcarbonyl, C$_2$-C$_4$ haloalkylcarbonyl, C$_2$-C$_4$ alkyloxycarbonyl or C$_2$-C$_4$ haloalkoxycarbonyl; and n is 1, 2 or 3.

Accordingly, of note is a compound selected from Formula 1P (including all geometric and stereoisomers), N-oxides, hydrates, and salts thereof, as defined above. Also of note are counterpart embodiments to Embodiments 1 through 158 and Embodiments A through F wherein in said counterpart embodiments "Formula 1" is replaced by "Formula 1P" and the scope of said counterpart embodiments does not exceed the scope defined above for Formula 1P. Examples of combinations of Embodiments 1 through 158, as well as any other embodiments described herein, as applied to Formula 1P are Embodiments AP and BP.

Embodiment AP

A compound of Formula 1P wherein
R$^1$ is

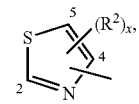
U-1

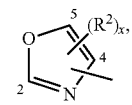
U-2

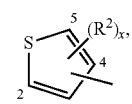
U-4

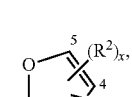
U-5

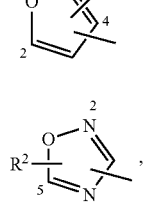
U-8

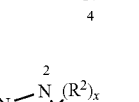
U-12

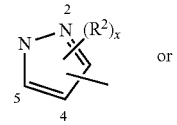
or

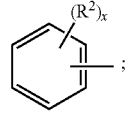
U-69 wherein the floating bond is connected to L in Formula 1 through any available carbon atom of the depicted ring or ring system;

x is 0, 1 or 2;

L is (CR$^{4a}$R$^{4b}$)$_n$, OCH$_2$, CH$_2$O, OCH$_2$CH$_2$, CH$_2$CH$_2$O or CH$_2$OCH$_2$, wherein the atom to the left is connected to R$^1$, and the atom to the right is connected to J, each carbon atom is optionally substituted with up to 2 substituents independently selected from halogen, cyano, hydroxy, nitro, C$_1$-C$_3$ alkyl, C$_1$-C$_3$ haloalkyl, C$_1$-C$_2$ alkoxy and C$_1$-C$_2$ haloalkoxy;

R$^{5a}$ is H; and each R$^2$ is independently —C(=O)NR$^{3a}$R$^{3b}$; or C$_3$-C$_6$ alkenyloxycarbonyl or C$_3$-C$_6$ alkynyloxycarbonyl, each optionally substituted with up to 3 substituents independently selected from R$^{10}$.

Embodiment BP

A compound of Embodiment AP wherein
R$^1$ is U-2 or U-12;
L is (CR$^{4a}$R$^{4b}$)$_n$;

each $R^2$ is independently —C(=O)NR$^{3a}$R$^{3b}$; or $C_2$-$C_6$ alkoxycarbonyl, optionally substituted with up to 1 substituent selected from $R^{10}$;

each $R^{3a}$ is independently $C_1$-$C_4$ haloalkyl, $C_2$-$C_4$ alkenyl, $C_2$-$C_4$ alkynyl, $C_2$-$C_4$ alkoxyalkyl or $C_3$-$C_5$ alkoxycarbonylalkyl;

each $R^{3b}$ is independently $C_1$-$C_3$ haloalkyl, $C_2$-$C_4$ alkenyl or $C_2$-$C_4$ haloalkenyl;

each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl or $C_2$-$C_5$ alkoxycarbonyl; and n is 1.

Also of note is a fungicidal composition comprising a fungicidally effective amount of a compound of Formula 1P (including all geometric and stereoisomers, N-oxides, and salts thereof) or any one of counterpart embodiments that are embodiment counterparts to Embodiments 1 through 158 and Embodiments A through E (e.g., Embodiment AP and BP), and at least one additional component selected from the group consisting of surfactants, solid diluents and liquid diluents. Also of note is a method for controlling plant diseases caused by fungal plant pathogens comprising applying to the plant or portion thereof, or to the plant seed, a fungicidally effective amount of a compound of Formula 1P (including all geometric and stereoisomers, N-oxides, and salts thereof) or any one of said counterpart embodiments. Of particular note are embodiments where the compounds of Formula 1P are applied as compositions of this invention.

One or more of the following methods and variations as described in Schemes 1-13 can be used to prepare the compounds of Formula 1. The definitions of $R^1$, $R^2$, L and J in the compounds of Formulae 1-21 below are as defined above in the Summary of the Invention unless otherwise noted. Compounds of Formulae 1a, 1b, 1c, 3a, 6a and 6b are various subsets of Formula 1, and all substituents for Formulae 1a, 1b, 1c, 3a, 6a and 6b are as defined above for Formula 1 unless otherwise noted.

As shown in Scheme 1, compounds of Formula 1 can be prepared by reaction of an amide oxime of Formula 2 with trifluoroacetic anhydride (TFAA) or an equivalent. The reaction can be carried out without solvent other than the compounds of Formula 2 and TFAA. Typically the reaction is conducted in a liquid phase with a solvent such as tetrahydrofuran, acetonitrile N,N-dimethylformamide or toluene at a temperature between about 0 to 100° C., optionally in the presence of a base such as pyridine or trimethylamine. Preparation of oxadiazole rings by this method and others are known in the art; see, for example, *Comprehensive Heterocyclic Chemistry*, Vol. 6, Part 4B, pages 365-391, Kevin T. Potts editor, Pergamon Press, New York, 1984. The method of Scheme 1 is also illustrated in present Example 10, Step C.

Scheme 1

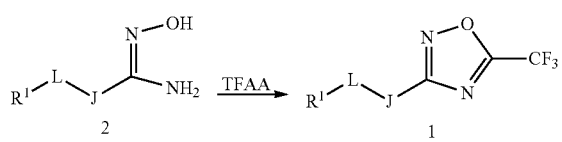

As shown in Scheme 2, oximes of Formula 2 can be prepared from corresponding nitriles of Formula 3 and hydroxylamine or a hydroxylamine salt (e.g., hydroxylamine hydrochloride) in a solvent such as ethanol, methanol or N,N-dimethylformamide at temperatures generally ranging from about 0 to 80° C. The hydroxylamine may be used in the form of a solution in water; alternatively, the hydroxylamine can be generated in situ by treating an acid salt of hydroxylamine with a base such as an alkali metal hydroxide or carbonate, preferably sodium hydroxide or sodium carbonate. Hydroxylamine salts include salts which hydroxylamine forms with inorganic acids such as sulfuric acid, hydrochloric acid, nitric acid and phosphoric acid or with organic acids such as formic acid, acetic acid, propionic acid and sulfonic acids. For reaction conditions see present Example 10, Step B.

Scheme 2

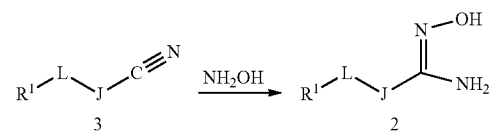

Compounds of Formula 1 wherein L is $(CR^{4a}R^{4b})_n$, and the like, and $R^1$ is a heterocyclic ring or ring system, such as pyrazole, indazole, imidazole, pyrrole and triazole, linked to L via a nitrogen atom, can be prepared by displacement of an appropriate leaving group $X^1$ of compounds of Formula 4 with nitrogen-containing heterocycles of Formula 5 in the presence of a base as depicted in Scheme 3. Suitable bases include inorganic bases such as alkali or alkaline earth metal (e.g., lithium, sodium, potassium and cesium) hydrides, alkoxides, carbonates, phosphates and hydroxides. A variety of solvents are suitable for the reaction including, for example, N,N-dimethylformamide, N,N-dimethylacetamide, N-methylpyrrolidinone, acetonitrile and acetone. Particularly useful reaction conditions include using cesium carbonate or potassium carbonate and N,N-dimethylformamide or acetonitrile as the solvent at temperatures ranging between about 0 to 80° C. Suitable leaving groups in the compounds of Formula 4 include bromide, chlorine, iodide, mesylate (OS(O)$_2$CH$_3$), triflate (OS(O)$_2$CF$_3$), and the like. The method of Scheme 3 is illustrated in present Example 1, Step C; Examples 2-9; and Example 11, Step C.

Scheme 3

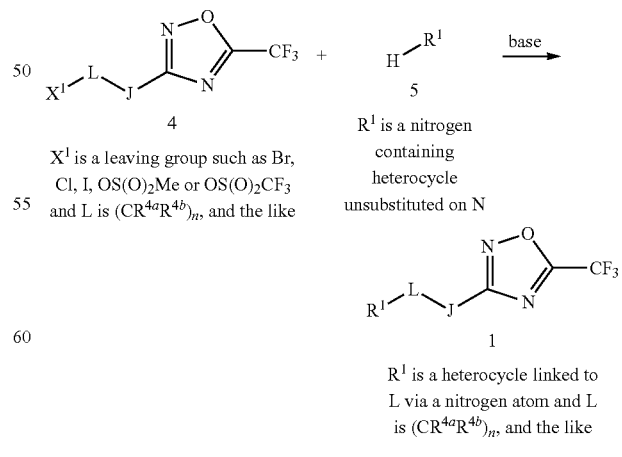

$X^1$ is a leaving group such as Br, Cl, I, OS(O)$_2$Me or OS(O)$_2$CF$_3$ and L is $(CR^{4a}R^{4b})_n$, and the like $R^1$ is a nitrogen containing heterocycle unsubstituted on N $R^1$ is a heterocycle linked to L via a nitrogen atom and L is $(CR^{4a}R^{4b})_n$, and the like Compounds of Formula 4 can be prepared by conversion of the corresponding alcohols of Formula 6 to an appropriate leaving group (i.e. $X^1$) as shown in Scheme 4. For example, alcohols of Formula 6 can be converted alkyl chlorides of Formula 4 by treatment with thionyl chloride, oxalyl chloride or phosphorus trichloride (for conditions, see Example 1, Step B). Alkyl bromides can be prepared in a similar reaction using phosphorus tribromide or phosphorus oxybromide. Sulfonates can be prepared by reaction of Formula 6 with a sulfonating agent such as methanesulfonyl chloride, typically in the presence of a base, under conditions well known to one skilled in the art of organic synthesis.

Scheme 4

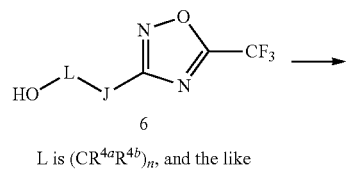

L is $(CR^{4a}R^{4b})_n$, and the like

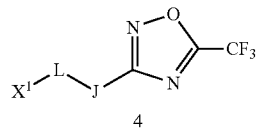

$X^1$ is a leaving group such as Br, Cl, I, $OS(O)_2Me$ or $OS(O)_2CF_3$ and L is $(CR^{4a}R^{4b})_n$, and the like Alternatively, compounds of Formula 1 wherein $R^1$ is an N-linked heterocycle can be prepared by reaction of primary or secondary alcohols of Formula 6 with nitrogen-containing heterocycles of Formula 5 using Mitsunobu coupling reaction conditions as shown in Scheme 5. Mitsunobu reactions are typically run in tetrahydrofuran with triphenylphosphine and diisopropyl azodicarboxylate (DIAD) or diethyl azodicarboxylate (DEAD) at room temperature. Polymer supported triphenylphosphine can be used to ease purification. For a review of the Mitsunobu reaction, see Mitsunobu, O. *Comprehensive Organic Synthesis*; Trost, B. M., Fleming, I., Eds.; Pergamon: Oxford, 1991; Vol. 6, pages 65-101. Also, Step C of Example 12 illustrates the preparation of a compound of Formula 1 using Mitsunobu conditions.

Scheme 5

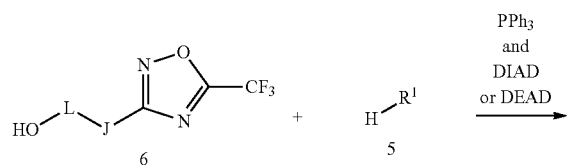

L is $(CR^{4a}R^{4b})_n$, and the like $R^1$ is a nitrogen containing heterocycle unsubsituted on N

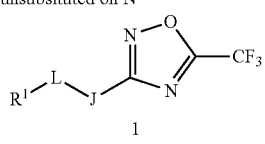

$R^1$ is a heterocycle linked to L via nitrogen atom

Compounds of Formula 6 can be prepared by treating corresponding nitriles with hydroxylamine or a hydroxylamine salt followed by TFAA analogous to the methods described in Schemes 1 and 2, and as illustrated in present Example 1, Step A. Additionally, secondary alcohols of Formula 6 can be prepared by oxidation of the corresponding alcohol to the aldehyde, and then reaction of the aldehyde with a Grignard reagent. The oxidation reaction can be performed by a variety of means, such as by treatment of the alcohol of Formula 6 with manganese dioxide, Dess-Martin periodinane, pyridinium chlorochromate or pyridinium dichromate. For example, as shown in Scheme 6, compounds of Formula 6b (i.e. Formula 6 wherein L in CHMe) can be synthesized by conversion of the alcohol of Formula 6a (i.e. Formula 6 wherein L is $CH_2$) to the aldehyde of Formula 7, and then treatment with methylmagnesium bromide. The method of Scheme 6 is illustrated in Example 12, Steps A-B.

Scheme 6

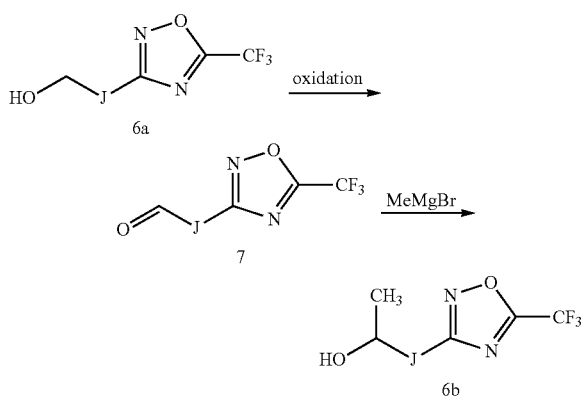

Compounds of Formula 1 can also be prepared by reaction of suitably functionalized compounds of Formula 8 with suitably functionalized compounds of Formula 9 as shown in Scheme 7. The functional groups $Y^1$ and $Y^2$ are selected from, but not limited to, moieties such as aldehydes, ketones, esters, acids, amides, thioamides, nitriles, amines, alcohols, thiols, hydrazines, oximes, amidines, amide oximes, olefins, acetylenes, halides, alkyl halides, methanesulfonates, trifluoromethanesulfonates (triflate), boronic acids, boronates, and the like, which under the appropriate reaction conditions, will allow for the construction of the various $R^1$ rings. As an example, reaction of a compound of Formula 8 where $Y^1$ is a chlorooxime moiety with a compound of Formula 9 where $Y^2$ is a vinyl or acetylene group in the presence of base will give a compound of Formula 1 where $R^1$ is an isoxazoline or isoxazole, respectively. Present Example 3, Step C illustrates the preparation of a compound of Formula 1 wherein $R^1$ is isoxazoline. The synthetic literature describes many general methods for forming heterocyclic rings and ring systems (e.g., U-1 through U-114); see, for example, *Comprehensive Heterocyclic Chemistry*, Volumes 4-6, A. R. Katritzky and C. W. Rees editors-in-chief, Pergamon Press, Oxford, 1984; *Comprehensive Heterocyclic Chemistry* II, Volumes 2-4, A. R. Katritzky, C. W. Rees and E. F. V. Scriven editors-in-chief, Pergamon Press, Oxford, 1996; and the series, *The Chemistry of Heterocyclic Compounds*, E. C. Taylor, editor, Wiley, New York. One skilled in the art knows how to select the appropriate functional groups to construct the desired ring R[1]. Compounds of Formula 8 are known or can be prepared by general methods known in the art. Compounds of Formula 9 can be prepared by treating corresponding nitriles with hydroxylamine or a hydroxylamine salt followed by TFAA analogous to the reactions described in Schemes 1 and 2, and as illustrated in present Example 12, Steps A-B.

Scheme 7

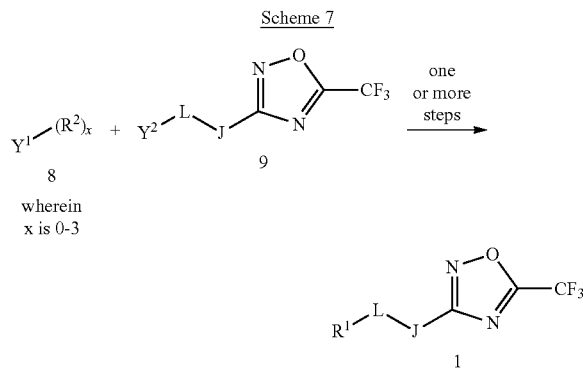

wherein x is 0-3 wherein Y[1] and Y[2] are suitable functional groups capable of undergoing transformation to form the desired R[1] ring Compounds of Formula 1a (i.e. Formula 1 wherein R[1] is oxazoline) can also be prepared as outlined in Scheme 8. In this method, an amine of Formula 11 is contacted with a compound of Formula 10 in the presence of O-(7-azabenzotriazol-1-yl)-N,N,N',N'-tetramethyluronium hexafluorophosphate (HATU) or 2-chloro-1-methylpyridinium iodide and a base such as triethylamine, N,N-diisopropylethylamine or 4-methylmorpholine at a temperature ranging from 0 to 100° C. to provide an amide of Formula 12. In a subsequent step, the amide of Formula 12 is dehydrated using a dehydrating agent such as diethylaminosulfur trifluoride (DAST) in a suitable solvent. The reaction is typically carried out by adding 0.9 to 2 equivalents, preferably 1.5 equivalents, of diethylaminosulfur trifluoride to a mixture of a compound of Formula 12 in a solvent such as dichloromethane, at a temperature ranging from −78 to 0° C. The method of Scheme 8 is illustrated by Steps B-C of Example 15. Compounds of Formula 11 are commercially available or their preparation is known in the art. Compounds of Formula 10 can be prepared by treating corresponding nitriles with hydroxylamine or a hydroxylamine salt followed by TFAA analogous to the reactions described in Schemes 1 and 2 (illustrated in Example 15, Step A).

Scheme 8

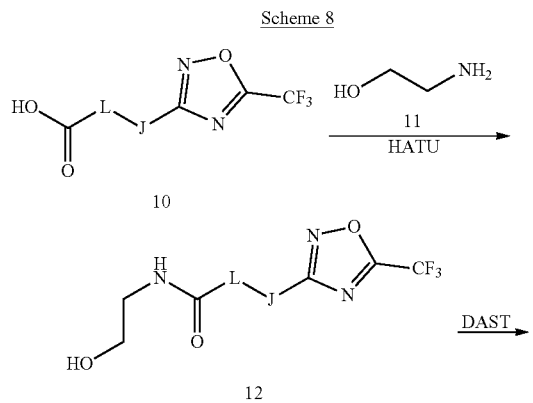

-continued

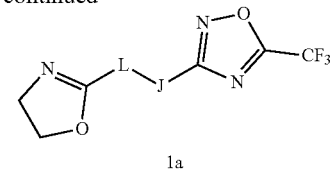

1a

As shown in Scheme 9, compounds of Formula 1b (i.e. Formula 1 wherein L is an amino nitrile) can be prepared from amines of Formula 14, aldehydes of Formula 13 and a cyanide source by means of the Strecker reaction. A variety of solvents and cyanide sources can be employed in the method of Scheme 9. The presence of a Lewis acid such as titanium(IV) isopropoxide can be advantageous. For conditions and variations of this reaction see the following references and references cited therein: D. T. Mowry, *Chemical Reviews* 1948, 42, 236, H. Groeger, *Chemical Reviews* 2003, 103, 2795-2827, and M. North in *Comprehensive Organic Functional Group Transformations* A. R. Katritsky, O. Meth-Cohn and C. W. Rees Editors, Volume 3, 615-617; Pergamon, Oxford, 1995. The method of Scheme 9 is also illustrated in Step E of Example 14. For less reactive amines of Formula 14, such as aryl amines containing ortho electron withdrawing groups, the use of trimethylsilyl cyanide in combination with a catalyst such a guanidine hydrochloride can be advantageous. For a reference see, for example, Heydari et al., *Journal of Molecular Catalysis A: Chemical* 2007, 271(1-2), 142-144.

Scheme 9

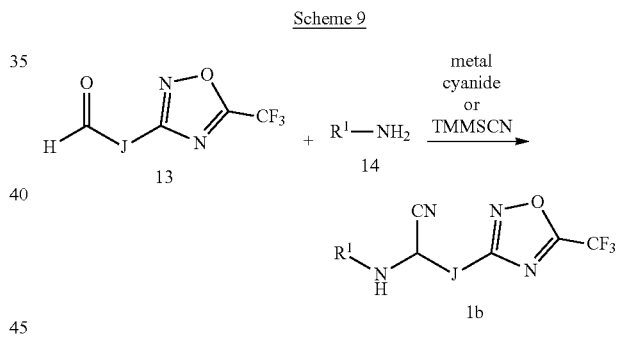

As shown in Scheme 2 above, nitriles of Formula 3 are useful intermediates for preparing compounds of Formula 2 which can be reacted with TFAA to provide compounds of Formula 1. Compounds of Formula 3 can be prepared as shown in Scheme 10 below from compounds of Formulae 15 and 16 wherein Y[3] and Y[4] are suitable functional groups which under the appropriate reaction conditions will allow for the construction of the various L groups. Suitable functional groups include, but are not limited to, ionizable hydrogen (e.g., a hydrogen attached to a nitrogen atom of a heterocyclic ring or a hydrogen attached to a carbon atom adjacent to a C(═O) moiety), carbonyl, aldehyde, ketone, ester, acid, acid chloride, amine, alcohol, thiol, hydrazine, oxime, olefin, acetylene, halide, alkyl halide, boronic acid, boronate, and the like. For example, compounds of Formula 3 wherein L is $CH_2$ can be prepared by reacting a compound of Formula 15 wherein Y[3] is hydrogen (i.e. an ionizable hydrogen attached to a nitrogen atom ring member of an R[1] ring) with a base such as potassium carbonate or sodium hydride, followed by treatment with a compound of Formula 16 wherein Y[4] is an methyl halide (e.g., $BrCH_2$—); while treatment with a compound of Formula 16 wherein $Y^4$ is CH(=O)— will give a compound of Formula 3 wherein L is CH(OH). Compounds of Formula 3 wherein L is O can be prepared by reacting a compound of Formula 15 wherein $Y^3$ is Br with a compound of Formula 16 wherein $Y^4$ is OH in the presence of a base such as sodium hydride. Compounds of Formula 3 wherein L is $CH_2O$ can be prepared by reacting a compound of Formula 15 wherein $Y^3$ is $BrCH_2$— with a compound of Formula 16 wherein $Y^4$ is OH in the presence of a base. Compounds of Formula 3 wherein L is $OCH_2CH_2$ can be prepared by reacting a compound of Formula 15 wherein $Y^3$ is OH with a compound of Formula 16 wherein $Y^4$ is ethyl halide (e.g., $ICH_2CH_2$—) in the presence of a base. The synthetic literature describes many general methods for forming a saturated chain containing 1- to 3-atoms consisting of carbon and heteroatoms such as the L groups of the present invention; see, for example, *Comprehensive Organic Functional Group Transformations*, Vol. 1, 2, 3 and 5, A. R. Katritzky editor, Pergamon Press, New York, 1995; *Vogel's Textbook of Practical Organic Chemistry*, 5th Ed., pp 470-823, Longman Group, London, 1989; and *Advanced Organic Chemistry*, 4th Ed. Jerry March, Wiley, New York 1992. One skilled in the art can easily determine how to select an appropriate compound of Formula 15 and Formula 16 to construction a desired L group.

Scheme 10

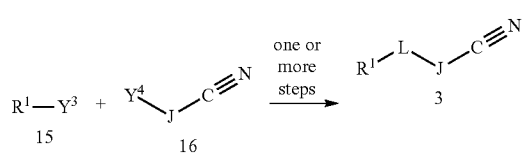

wherin $Y^3$ and $Y^4$ are a suitable functional groups for construction of the desired L group Scheme 11 illustrates a specific example of the general method of Scheme 10 for the preparation of a compound of Formula 3a (i.e. Formula 3 wherein $R^1$ is pyrazole and L is $CH_2$). In this method a pyrazole of Formula 17 is reacted with a methyl bromide of Formula 18 in the presence of a base such as sodium or potassium hydroxide, sodium hydride or potassium carbonate in a solvent such as tetrahydrofuran, N,N-dimethylformamide, ethanol or acetonitrile typically at a temperature between about 0 to 80° C. Present Example 10, Step A illustrates the method of Scheme 11.

Scheme 11

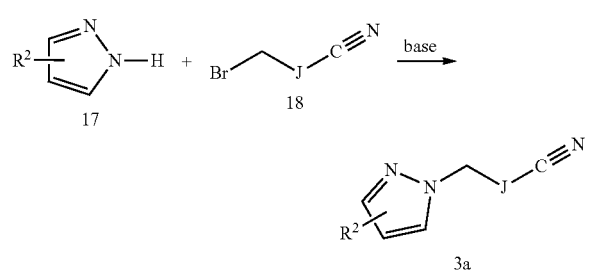

One skilled in the art will recognize that the method of Scheme 10 can also be performed when the substituent —C≡N in Formula 16 is replaced with 5-(trifluoromethyl)-1,2,4-oxadiazol-3-yl (i.e. Formula 19) thus providing a compound of Formula 1 as shown below in Scheme 12.

Scheme 12

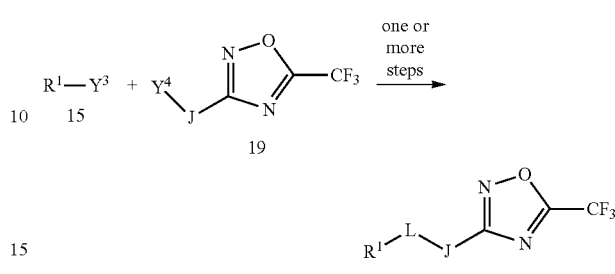

wherein $Y^2$ and $Y^3$ are a suitable functional groups for construction of the desired L group Scheme 13 illustrates a specific example of the general method of Scheme 12 for the preparation of a compound of Formula 1c (i.e. Formula 1 wherein $R^1$ is oxazole and L is $CH_2O$). In this method a methyl chloride of Formula 20 is reacted with an alcohol of Formula 21 in the presence of a base such as sodium or potassium hydroxide, sodium hydride or potassium carbonate in a solvent such as tetrahydrofuran, N,N-dimethylformamide, ethanol or acetonitrile typically at a temperature between about 0 to 80° C. Present Examples 17 and 18 illustrate the method of Scheme 19.

Scheme 13

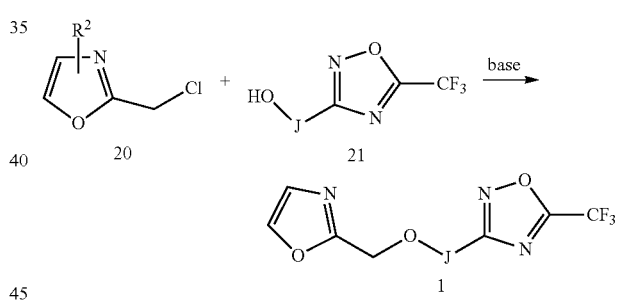

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, Protective Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet and "br d" means broad doublet. $^{19}$F NMR spectra are reported in ppm using trichlorofluoromethane as the reference.

Example 1

Preparation 1-[[4-[5-(trifluoromethyl)-1,2,4-oxadiazol-3-yl]phenyl]methyl]-1H-pyrazolo[3,4-b]pyridine (Compound 147)

Step A: Preparation of 4-[5-(trifluoromethyl)-1,2,4-oxadiazol-3-yl]benzenemethanol A mixture of 4-(hydroxymethyl)benzonitrile (52.8 g, 397 mmol), hydroxylamine hydrochloride (33.1 g, 476 mmol), N,N-diisopropylethylamine (107 mL, 595 mmol) and 8-quinolinol (0.3 g) in ethanol (400 mL) was heated at reflux for 5 h. The reaction mixture was concentrated under reduced pressure to provide the intermediate compound N-hydroxy-4-(hydroxymethyl)benzenecarboximidamide.

To a mixture of N-hydroxy-4-(hydroxymethyl)benzenecarboximidamide in acetonitrile and tetrahydrofuran (1:1, 400 mL) was added pyridine (70 mL, 873 mmol) and trifluoroacetic anhydride (121 mL, 873 mmol) dropwise at room temperature. The reaction mixture was heated at reflux for 15 h, allowed to cool to room temperature, and then saturated aqueous sodium bicarbonate solution (300 mL) was slowly added, followed by ethyl acetate (400 mL) and water. The resulting mixture was separated and the organic layer was washed with saturated aqueous sodium chloride solution (100 mL), dried over sodium sulfate, filtered and concentrated under reduce pressure to provide the title compound.

$^1$H NMR (CDCl$_3$): δ 4.77 (s, 2H), 7.50 (d, 2H), 8.08 (d, 2H).
$^{19}$F NMR (CDCl$_3$): δ −65.47.

Step B: Preparation of 3-[4-(chloromethyl)phenyl]-5-(trifluoromethyl)-1,2,4-oxadiazole To a mixture of 4-[5-(trifluoromethyl)-1,2,4-oxadiazol-3-yl]benzenemethanol (i.e. the product of Step A) (98.0 g, 397 mmol) and N,N-dimethylformamide (4 drops) in dichloromethane (500 mL) at 5° C. was added thionyl chloride (57 mL). The reaction mixture was heated at approximately 42° C. for 30 minutes, and then concentrated under reduced pressure removing the dichloromethane. The resulting mixture was diluted with acetonitrile (80 mL) and poured into ice water (700 mL). The resulting solid precipitate was collected by filtration, rinsed with water, and dried in a vacuum oven under nitrogen to provide the title compound as a solid (55 g).

$^1$H NMR (CDCl$_3$): δ 4.64 (s, 2H), 7.54-7.55 (d, 2H), 8.10-8.12 (d, 2H).
$^{19}$F NMR (CDCl$_3$): δ −65.45.

Step C: Preparation of 1-[[4-[5-(trifluoromethyl)-1,2,4-oxadiazol-3-yl]phenyl]methyl]-1H-pyrazolo[3,4-b]pyridine A mixture of 3-[4-(chloromethyl)phenyl]-5-(trifluoromethyl)-1,2,4-oxadiazole (i.e. the product of Step B) (0.3 g, 1.1 mmol), 1H-pyrazolo[3,4-b]pyridine (0.136 g, 1.1 mmol) and cesium carbonate (0.38 g, 1.1 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound, a compound of the present invention, as a solid (0.090 g).

$^1$H NMR (CDCl$_3$): δ 5.80 (s, 2H), 7.13-7.21 (m, 1H), 7.42-7.51 (m, 2H), 8.01-8.13 (m, 4H), 8.58 (dd, 1H).
$^{19}$F NMR (CDCl$_3$): δ −65.43.

Example 2

Preparation of 1-[[4-[5-(trifluoromethyl)-1,2,4-oxadiazol-3-yl]phenyl]methyl]-1H-pyrazole-4-carbonitrile (Compound 95)

A mixture of 3-[4-(chloromethyl)phenyl]-5-(trifluoromethyl)-1,2,4-oxadiazole (i.e. product of Example 1, Step B) (3.60 g, 13.7 mmol), 1H-pyrazole-4-carbonitrile (1.91 g, 20.6 mmol), potassium carbonate (3.41 g, 24.7 mmol) and sodium bromide (1.62 g, 15.8 mmol) in acetonitrile (100 mL) was heated at reflux for 18 h. The reaction mixture was allowed to cool to room temperature, filtered, and the filtrate was concentrated under reduced pressure. The resulting material was purified by silica gel chromatography (eluting with a gradient of 0 to 100% ethyl acetate in hexanes) to provide a white solid (4.38 g). The solid was crystallized from ethanol to provide the title compound, a compound of the present invention, as a white solid (3.29 g) melting at 106-108° C.

$^1$H NMR (CDCl$_3$): δ 5.42 (s, 2H), 7.38-7.39 (d, 2H), 7.86-7.87 (m, 2H), 8.13-8.15 (d, 2H).
$^{19}$F NMR (CDCl$_3$): δ −65.33.

Example 3

Preparation of 6-chloro-2-[[4-[5-(trifluoromethyl)-1,2,4-oxadiazol-3-yl]phenyl]methyl]-3(2H)-pyridazinone (Compound 4)

A mixture of 3-[4-(chloromethyl)phenyl]-5-(trifluoromethyl)-1,2,4-oxadiazole (i.e. product of Example 1, Step B) (0.2 g, 0.76 mmol), 6-chloro-3(2H)-pyridazinone (0.099 g, 0.76 mmol) and potassium carbonate (0.21 g, 1.52 mmol) in N,N-dimethylformamide (5 mL) was stirred at room temperature overnight. The reaction mixture was diluted with water and extracted with diethyl ether (2×). The combined extracts were washed with saturated aqueous sodium chloride solution, dried over sodium sulfate, filtered and concentrated under reduced pressure. The resulting material was and purified by silica gel chromatography (eluting with 1:1 ethyl acetate in hexanes) to provide the title compound, a compound of the present invention, as a white solid (0.18 g).
$^1$H NMR (CDCl$_3$): δ 8.10 (d, 2H), 7.58 (d, 2H), 7.19 (d, 1H), 6.95 (d, 1H), 5.32 (s, 2H).

Example 4

Preparation of methyl 2-[[4-[5-(trifluoromethyl)-1,2,4-oxadiazol-3-yl]phenyl]methyl]-2H-indazole-4-carboxylate (Compound 36) and methyl 1-[[4-[5-(trifluoromethyl)-1,2,4-oxadiazol-3-yl]phenyl]methyl]-1H-indazole-4-carboxylate (Compound 49)

A mixture of 3-[4-(chloromethyl)phenyl]-5-(trifluoromethyl)-1,2,4-oxadiazole (i.e. the product of Example 1, Step B) (0.3 g, 1.1 mmol), methyl 1H-indazole-4-carboxylate (0.2 g, 1.1 mmol) and cesium carbonate (0.56 g, 1.7 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title Compound 49 (faster eluting product) as a solid (0.11 g). Also obtained was the title Compound 36, (slower eluting product) as a solid (0.04 g).
$^1$H NMR (CDCl$_3$): δ 3.97 (s, 3H), 5.73 (s, 2H), 7.33-7.42 (m, 1H), 7.42-7.49 (m, 2H), 7.90-8.02 (m, 2H), 8.07-8.16 (m, 2H), 8.53 (s, 1H) (Compound 36).
$^{19}$F NMR (CDCl$_3$): δ −65.39 (Compound 36).
$^1$H NMR (CDCl$_3$): δ 3.98-4.08 (m, 3H), 5.67-5.76 (m, 2H), 7.28-7.35 (m, 2H), 7.37-7.48 (m, 1H), 7.50-7.59 (m, 1H), 7.89-7.98 (m, 1H), 8.01-8.10 (m, 2H), 8.59 (s, 1H) (Compound 49).
$^{19}$F NMR (CDCl$_3$): δ −65.42 (Compound 49).

Example 5

Preparation of 1-[[4-[5-(trifluoromethyl)-1,2,4-oxadiazol-3-yl]phenyl]methyl]-1H-pyrrolo[3,2-b]pyridine (Compound 136)

A mixture of 3-[4-(chloromethyl)phenyl]-5-(trifluoromethyl)-1,2,4-oxadiazole (i.e. the product of Example 1, Step B) (0.3 g, 1.1 mmol), 1H-pyrrolo[3,2-b]pyridine (0.14 g, 1.1 mmol) and cesium carbonate (0.56 g, 1.7 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound, a compound of the present invention, as a solid (0.045 g).

$^1$H NMR (CDCl$_3$): δ 5.42 (m, 2H), 6.79-6.88 (m, 1H), 7.06-7.15 (m, 1H), 7.23 (m, 2H), 7.41 (d, 1H), 7.54 (d, 1H), 8.07 (d, 2H), 8.49 (br d, 1H).
$^{19}$F NMR (CDCl$_3$): δ −65.40.

Example 6

Preparation of 1-[[4-[5-(trifluoromethyl)-1,2,4-oxadiazol-3-yl]phenyl]methyl]-2(1H)-quinoxalinone (Compound 158)

A mixture of 3-[4-(chloromethyl)phenyl]-5-(trifluoromethyl)-1,2,4-oxadiazole (i.e. the product of Example 1, Step B) (0.3 g, 1.1 mmol), 2(1H)-quinoxalinone (0.17 g, 1.1 mmol) and cesium carbonate (0.56 g, 1.7 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound, a compound of the present invention, as a solid (0.08 g).
$^1$H NMR (CDCl$_3$): δ 5.57 (s, 2H), 7.19-7.24 (m, 1H), 7.32-7.38 (m, 1H), 7.40 (d, 2H), 7.45-7.53 (m, 1H), 7.90-7.97 (m, 1H), 8.08 (d, 2H), 8.44 (s, 1H).
$^{19}$F NMR (CDCl$_3$): δ −65.40.

Example 7

Preparation of 1,3-dihydro-1-methyl-3-[[4-[5-(trifluoromethyl)-1,2,4-oxadiazol-3-yl]phenyl]methyl]-2H-benzimidazol-2-one (Compound 159)

A mixture of 3-[4-(chloromethyl)phenyl]-5-(trifluoromethyl)-1,2,4-oxadiazole (i.e. the product of Example 1, Step B) (0.3 g, 1.1 mmol), 1,3-dihydro-1-methyl-2H-benzimidazol-2-one (0.17 g, 1.1 mmol) and cesium carbonate (0.56 g, 1.7 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 0 to 50% ethyl acetate in hexanes) to provide the title compound, a compound of the present invention, as a solid (0.095 g).
$^1$H NMR (CDCl$_3$): δ 3.49 (s, 3H), 5.16 (s, 2H), 6.81-6.90 (m, 1H), 6.97-7.06 (m, 2H), 7.06-7.18 (m, 1H), 7.47 (d, 2H), 8.07 (d, 2H).

Example 8

Preparation of methyl 1,2-dihydro-2-oxo-1-[[4-[5-(trifluoromethyl)-1,2,4-oxadiazol-3-yl]phenyl]methyl]-4-pyridinecarboxylate (Compound 24)

A mixture of 3-[4-(chloromethyl)phenyl]-5-(trifluoromethyl)-1,2,4-oxadiazole (i.e. the product of Example 1, Step B) (1.0 g, 3.8 mmol), methyl 1,2-dihydro-2-oxo-4-pyridinecarboxylate (0.59 g, 3.81 mmol) and cesium carbonate (1.90 g, 5.72 mmol) in N,N-dimethylformamide (5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound, a compound of the present invention, as a solid (0.35 g).

$^1$H NMR (CDCl$_3$): δ 3.92 (s, 3H), 5.23 (s, 2H), 6.64-6.73 (m, 1H), 7.27 (d, 1H), 7.33-7.40 (m, 1H), 7.40-7.49 (m, 2H), 8.04-8.17 (m, 2H).

$^{19}$F NMR (CDCl$_3$): δ −65.39.

Example 9

Preparation of 2-[[4-[5-(trifluoromethyl)-1,2,4-oxadiazol-3-yl]phenyl]methyl]-1H-isoindole-1,3(2H)-dione (Compound 90)

A mixture of 3-[4-(chloromethyl)phenyl]-5-(trifluoromethyl)-1,2,4-oxadiazole (i.e. the product of Example 1, Step B) (0.25 g, 0.95 mmol) and potassium phthalimide (0.17 g, 0.95 mmol) in N,N-dimethylformamide (2.5 ml) was stirred at room temperature for 12 h. The reaction mixture was partitioned between ethyl acetate (25 ml) and water (5 ml). The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound, a compound of the present invention, as a solid (0.21 g).

$^1$H NMR (CDCl$_3$): δ 4.92 (s, 2H), 7.50-7.63 (m, 2H), 7.68-7.79 (m, 2H), 7.82-7.93 (m, 2H), 8.01-8.13 (m, 2H).

$^{19}$F NMR (CDCl$_3$): δ −65.39.

Example 10

Preparation of ethyl 1-[[4-[5-(trifluoromethyl)-1,2,4-oxadiazol-3-yl]phenyl]methyl]-1H-pyrazole-4-carboxylate (Compound 83)

Step A: Preparation of ethyl 1-[(4-cyanophenyl)methyl]-1H-pyrazole-4-carboxylate A mixture of ethyl 1H-pyrazole-4-carboxylate (4.96 g, 35.4 mmol), 4-(bromomethyl)benzonitrile (6.92 g, 35.3 mmol) and potassium carbonate (6.0 g, 43.5 mmol) in acetonitrile (100 mL) was heated at 60° C. for 6 h, and then stirred at room temperature overnight. The reaction mixture was diluted with water and the resulting solid precipitate was filtered, washed with water and air dried to provide the title compound as a white solid (8.65 g).

$^1$H NMR (CDCl$_3$): δ 1.34 (t, 3H), 4.30 (q, 2H), 5.37 (s, 2H), 7.29-7.31 (m, 2H), 7.65-7.66 (m, 2H), 7.93 (s, 1H), 7.96 (s, 1H).

Step B: Preparation of ethyl 1-[[4-[(hydroxyamino)iminomethyl]phenyl]methyl]-1H-pyrazole-4-carboxylate A mixture ethyl 1-[(4-cyanophenyl)methyl]-1H-pyrazole-4-carboxylate (i.e. the product of Step A) (29.1 g, 114 mmol) and hydroxylamine (50% aqueous solution, 12 mL, 194 mmol) in N,N-dimethylformamide (200 mL) was stirred at room temperature for 3 days. The reaction mixture was poured into ice water and the resulting solid precipitate was filtered and washed with water. The wet solid was mixed with acetonitrile (500 mL) and concentrated under reduced pressure to provide the title compound as a white solid (31.32 g).

$^1$H NMR (DMSO-d$_6$): δ 1.26 (t, 3H), 4.21 (q, 2H), 5.38 (s, 2H), 5.79 (s, 2H), 7.25-7.27 (m, 2H), 7.63-7.65 (m, 2H), 7.87 (s, 1H), 8.47 (s, 1H), 9.63 (s, 1H).

Step C: Preparation of ethyl 1-[[4-[5-(trifluoromethyl)-1,2,4-oxadiazol-3-yl]phenyl]methyl]-1H-pyrazole-4-carboxylate To a mixture of ethyl 1-[[4-[(hydroxyamino)iminomethyl]phenyl]methyl]-1H-pyrazole-4-carboxylate (i.e. the product of Step B) (33.65 g, 117 mmol) and pyridine (13 mL, 160 mmol) in N,N-dimethylformamide (100 mL) at 0° C. was added trifluoroacetic anhydride (19 mL, 140 mmol) dropwise over 20 minutes. The reaction mixture was heated at 70° C. for 2 h, cooled and allowed to stir at room temperature overnight. The reaction mixture was poured into ice water and the resulting solid precipitate was filtered and washed with water. The solid was crystallized from ethanol (250 mL) to provide the title compound, a compound of the present invention, as solid needles (35.1 g) melting at 127-129° C.

$^1$H NMR (CDCl$_3$): δ 1.34 (t, 3H), 4.30 (q, 2H), 5.39 (s, 2H), 7.37-7.39 (m, 2H), 7.93 (s, 1H), 7.97 (s, 1H), 8.11-8.13 (m, 2H).

$^{19}$F NMR (CDCl$_3$): δ −65.34.

Example 11

Preparation of 3-[5-[(4-bromo-1H-pyrazol-1-yl)methyl]-2-thienyl]-5-(trifluoromethyl)-1,2,4-oxadiazole (Compound 71)

Step A: Preparation of 3-(5-methyl-2-thienyl)-5-(trifluoromethyl)-1,2,4-oxadiazole A mixture of 5-methyl-2-thiophenecarbonitrile (4.0 g, 32 mmol), hydroxylamine hydrochloride (3.3 g, 48 mmol), diisopropylethylamine (10 ml, 56 mmol) and 8-quinolinol (0.074 g) in ethanol (65 ml) was refluxed for 5 h. The reaction mixture was concentrated under reduced pressure to provide the intermediate compound N-hydroxy-5-methyl-2-thiophenecarboximidamide.

N-hydroxy-5-methyl-2-thiophenecarboximidamide in tetrahydrofuran (65 ml) was added dropwise to a mixture of trifluoroacetic anhydride (13 mL, 96 mmol), diisopropylethylamine (20 mL, 112 mmol) and 4-dimethylaminopyridine (1.0 g, 8 mmol). The reaction mixture was stirred at room temperature 15 h, and then diluted with saturated aqueous sodium bicarbonate solution (30 mL). The aqueous mixture was extracted with ethyl acetate (80 ml) and the organic layer was washed with saturated aqueous sodium chloride solution, dried over sodium sulfate, filtered and concentrated under reduced pressure. The resulting material was purified by silica gel chromatography (eluting with 1:10 ethyl acetate in hexanes) to provide the title compound as a solid (3.2 g).

$^1$H NMR (CDCl$_3$): δ 2.57 (s, 3H), 6.85 (d, 1H), 7.68 (d, 1H).

$^{19}$F NMR (CDCl$_3$): δ −65.46.

Step B: Preparation of 3-[5-(bromomethyl)-2-thienyl]-5-(trifluoromethyl)-1,2,4-oxadiazole To a mixture of 3-(5-methyl-2-thienyl)-5-(trifluoromethyl)-1,2,4-oxadiazole (i.e. the product of Step A) (3.1 g, 13.2 mmol) in dichloromethane (30 mL) was added N-bromosuccinimide (2.6 g, 14.8 mmol) and 2,2'-azodiisobutyronitrile (0.2 g, 1.3 mmol). The reaction mixture was heated at reflux for 6 h, cool to room temperature, and concentrated under reduced pressure. The resulting material was purified by silica gel chromatography (eluting with 1:10 ethyl acetate in hexanes) to provide the title compound as a white solid (2.8 g).

$^1$H NMR (CDCl$_3$): δ 4.73 (s, 2H), 7.18 (m, 1H), 7.73 (m, 1H).

$^{19}$F NMR (CDCl$_3$): δ −65.40.

Step C: Preparation of 3-[5-[(4-bromo-1H-pyrazol-1-yl)methyl]-2-thienyl]-5-(trifluoromethyl)-1,2,4-oxadiazole A mixture of 3-[5-(bromomethyl)-2-thienyl]-5-(trifluoromethyl)-1,2,4-oxadiazole (i.e. the product of Step B) (0.16 g, 0.5 mmol), 4-bromo-1H-pyrazole (0.080 g, 0.55 mmol) and potassium carbonate (0.152 g, 1.1 mmol) in acetonitrile (4 mL) was heated at refluxed for 2 h. After cooling to room temperature, the reaction mixture was concentrated under reduced pressure. The resulting material was purified by silica gel chromatography (eluting with 3:1 hexanes in ethyl acetate) to provide the title compound, a compound of the present invention, as an oil (0.088 g).

$^1$H NMR (CDCl$_3$): δ 5.47 (s, 2H), 7.09 (m, 1H), 7.48 (s, 1H), 7.50 (s, 1H), 7.74 (m, 1H).

$^{19}$F NMR (CDCl$_3$): δ −65.41.

Example 12

Preparation of ethyl 1-[1-[4-[5-(trifluoromethyl)-1,2,4-oxadiazol-3-yl]phenyl]ethyl]-1H-pyrazole-4-carboxylate (Compound 2)

Step A: Preparation of 4-[5-(trifluoromethyl)-1,2,4-oxadiazol-3-yl]benzaldehyde

To a mixture of 4-[5-(trifluoromethyl)-1,2,4-oxadiazol-3-yl]benzenemethanol (2.00 g, 8.19 mmol) in dichloromethane (20 ml) was added 1,1,1-tris(acetoxy)-1,1-dihydro-1,2-benziodoxol-3(1H)-one (Dess-Martin periodinane) (3.47 g, 8.19 mmol) portionwise at room temperature. After stirring for 3 h, the reaction mixture was diluted with dichloromethane and saturated aqueous sodium bicarbonate solution. The organic layer was separated and washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound as an oil (1.53 g).

$^1$H NMR (CDCl$_3$): δ 8.05 (d, 2H), 8.32 (d, 2H), 10.12 (s, 1H).

$^{19}$F NMR (CDCl$_3$): δ −65.32.

Step B: Preparation of α-methyl-4-[5-(trifluoromethyl)-1,2,4-oxadiazol-3-yl]benzenemethanol To a mixture of 4-[5-(trifluoromethyl)-1,2,4-oxadiazol-3-yl]benzaldehyde (i.e. the product of Step A) (1.53 g, 6.3 mmol) in tetrahydrofuran (20 ml) at −12° C. was added a solution of methylmagnesium bromide (3M in diethyl ether; 2.1 mL, 6.3 mmol) dropwise. The reaction mixture was stirred for 2 h at −12° C., and then quenched with saturated aqueous ammonium chloride solution. The resulting mixture was poured into water and extracted with ethyl acetate. The combined organic extracts were washed with saturated aqueous sodium chloride solution, dried over sodium sulfate, filtered and concentrated under reduced pressure. The resulting material was purified by silica gel chromatography (eluting with a gradient of 5 to 50% ethyl acetate in hexanes) to provide the title compound as a solid (1.63 g).

$^1$H NMR (CDCl$_3$): δ 1.40-1.61 (m, 3H), 4.84-5.06 (m, 1H), 7.50 (d, 2H), 8.06 (d, 2H).

$^{19}$F NMR (CDCl$_3$): δ −65.49.

Step C: Preparation of ethyl 1-[1-[4-[5-(trifluoromethyl)-1,2,4-oxadiazol-3-yl]phenyl]ethyl]-1H-pyrazole-4-carboxylate A mixture of α-methyl-4-[5-(trifluoromethyl)-1,2,4-oxadiazol-3-yl]benzenemethanol (i.e. the product of Step B) (0.372 g, 0.95 mmol), ethyl 1H-pyrazole-4-carboxylate (0.202 g, 0.95 mmol) and triphenylphosphine (0.377 g, 0.95 mmol) in tetrahydrofuran (10 mL) was stirred at room temperature for 10 minutes, and then 1,2-bis(1-methylethyl) 1,2-diazene-dicarboxylate (DIAD) (0.285 mL, 0.95 mmol) was added. After 12 h, the reaction mixture was concentrated under reduced pressure. The resulting material was purified by silica gel flash chromatography (eluting with a gradient of 5 to 50% ethyl acetate in hexanes) to provide the title compound, a compound of the present invention, as a solid (0.11 g).

$^1$H NMR (CDCl$_3$): δ 1.25-1.38 (m, 3H), 1.88-2.00 (m, 3H), 4.28 (q, 2H), 5.49-5.67 (m, 1H), 7.29-7.41 (m, 2H), 7.89-8.02 (m, 2H), 8.03-8.16 (m, 2H).

$^{19}$F NMR (CDCl$_3$): δ −65.44.

Example 13

Preparation of 4,5-dihydro-N,N-dimethyl-5-[[4-[5-(trifluoromethyl)-1,2,4-oxadiazol-3-yl]phenyl]methyl]-3-isoxazolecarboxamide (Compound 12)

Step A: Preparation of N-hydroxy-4-(2-propen-1-yl)benzenecarboximidamide

A mixture of 4-(2-propen-1-yl)benzonitrile (5.0 g, 35 mmol) and hydroxylamine (50% aqueous solution, 4.5 mL, 73 mmol) in absolute ethanol (50 mL) was stirred at room temperature for 16 h. The reaction mixture was concentrated under reduced pressure, diluted with acetonitrile (50 mL), concentrated under reduced pressure, and again diluted with acetonitrile (50 mL) and concentrated under reduced pressure to provide the title compound as a colorless oil which crystallized on standing (6.1 g).

$^1$H NMR (CDCl$_3$): δ 3.39-3.41 (m, 2H), 4.90 (br s, 2H), 5.07-5.10 (m, 2H), 5.90-6.00 (m, 1H), 7.20-7.22 (m, 2H), 7.54-7.56 (m, 2H), 8.5-9.5 (br s, 1H).

Step B: Preparation of 3-[4-(2-propen-1-yl)phenyl]-5-(trifluoromethyl)-1,2,4-oxadiazole To a mixture of N-hydroxy-4-(2-propen-1-yl)benzenecarboximidamide (i.e. the product of Step A) (6.0 g, 34 mmol) and pyridine (3.5 mL, 43 mmol) in acetonitrile (25 mL) at 0° C. was added trifluoroacetic anhydride (5.5 mL, 40 mmol) dropwise over 20 minutes. The reaction mixture was heated at 60° C. for 4 h, cooled, and then poured into ice water and extracted with diethyl ether (3×100 mL). The combined organic extracts were washed with aqueous hydrochloric acid solution (1N), saturated aqueous sodium bicarbonate solution, saturated aqueous sodium chloride solution, dried over magnesium sulfate, filtered and concentrated under reduced pressure to provide the title compound as a light-yellow oil (8.0 g).

$^1$H NMR (CDCl$_3$): δ 3.46-3.48 (m, 2H), 5.10-5.15 (m, 2H), 5.90-6.05 (m, 1H), 7.34-7.36 (m, 2H), 8.03-8.05 (m, 2H).

$^{19}$F NMR (CDCl$_3$): δ −65.40.

Step C: Preparation of 4,5-dihydro-N,N-dimethyl-5-[[4-[5-(trifluoromethyl)-1,2,4-oxadiazol-3-yl]phenyl]methyl]-3-isoxazolecarboxamide A mixture of 3-[4-(2-propen-1-yl)phenyl]-5-(trifluoromethyl)-1,2,4-oxadiazole (i.e. the product of Step B) (0.254 g, 1.0 mmol), 2-(dimethylamino)-N-hydroxy-2-oxo-acetimidoyl chloride (0.152 g, 1.0 mmol) and sodium bicarbonate (0.3 g, 3.5 mmol) in ethyl acetate (20 mL) was stirred at room temperature for 24 h. The reaction mixture was filtered washing with a small amount of ethyl acetate and the filtrate was concentrated under reduced pressure. The resulting material was purified by silica gel flash chromatography (eluting with a gradient of 0-100% ethyl acetate in hexanes) to provide the title compound, a compound of the present invention, as a white solid (0.27 g).

$^1$H NMR (CDCl$_3$): δ 3.00-3.15 (m, 2H), 3.03 (s, 3H), 3.17 (s, 3H), 3.33-3.40 (m, 1H), 4.92-5.00 (m, 1H), 7.40-7.44 (m, 2H), 8.06-8.10 (m, 2H).

$^{19}$F NMR (CDCl$_3$): δ −65.36.

Example 14

Preparation of α-(phenylamino)-4-[5-(trifluoromethyl)-1,2,4-oxadiazol-3-yl]benzeneacetonitrile (Compound 13)

Step A: Preparation of 4-(1,3-dioxolan-2-yl)benzonitrile

To a mixture of 4-formylbenzonitrile (25.16 g, 191.9 mmol) in toluene (250 mL) was added ethylene glycol (35.73 g, 576 mmol) and p-toluenesulfonic acid monohydrate (2.92 g, 15.3 mmol). The reaction mixture was heated at reflux for 18 h with use of a Dean-Stark trap for the azeotropic removal of water. After cooling to room temperature, the reaction mixture was washed with saturated aqueous sodium bicarbonate solution, saturated aqueous sodium chloride solution, dried over magnesium sulfate, filtered and concentrated under reduced pressure to provide the title compound as a white solid (33.6 g).

$^1$H NMR (CDCl$_3$): δ 4.04-4.13 (m, 4H), 5.85 (s, 1H), 7.57-7.62 (m, 2H), 7.66-7.70 (m, 2H).

Step B: Preparation of 4-(1,3-dioxolan-2-yl)-N-hydroxybenzenecarboximidamide

A mixture of 4-(1,3-dioxolan-2-yl)benzonitrile (i.e. the product of Step A) (33.6 g, 192 mmol) and hydroxylamine (50% aqueous solution, 14 mL, 228 mmol) in ethanol (200 mL) was heated at 70° C. for 1 h. After cooling to room temperature, the reaction mixture was concentrated under reduced pressure. The resulting material was diluted with acetonitrile and concentrated under reduced pressure to provide the title compound as a white solid (40.2 g).

$^1$H NMR (DMSO-d$_6$): δ 3.91-4.09 (m, 4H), 5.74 (s, 1H), 5.77-5.88 (m, 2H), 7.42-7.44 (m, 2H), 7.68-7.71 (m, 2H), 9.67 (s, 1H).

Step C: Preparation of 3-[4-(1,3-dioxolan-2-yl)phenyl]-5-(trifluoromethyl)-1,2,4-oxadiazole To a mixture of 4-(1,3-dioxolan-2-yl)-N-hydroxybenzenecarboximidamide (i.e. the product of Step B) (40.2 g, 192 mmol) and pyridine (18.3 mL, 226 mmol) in acetonitrile (350 mL) at 0° C. was added trifluoroacetic anhydride (28.8 mL, 207 mmol) dropwise over 10 minutes. The reaction mixture was allowed to warm to room temperature and stirred overnight. The reaction mixture was concentrated under reduced pressure and the resulting material was partitioned between dichloromethane and water. The organic layer was separated and washed with saturated aqueous sodium chloride solution, dried over magnesium sulfate, filtered and concentrated under reduced pressure. The resulting material was purified by silica gel chromatography (eluting with a gradient of 0 to 100% ethyl acetate in hexanes) to provide the title compound as a white solid melting at 53-55° C.

$^1$H NMR (CDCl$_3$): δ 4.05-4.23 (m, 4H), 5.88 (s, 1H), 7.65 (d, 2H), 8.14 (d, 2H).

$^{19}$F NMR (CDCl$_3$): δ −65.36.

Step D: Preparation of 4-[5-(trifluoromethyl)-1,2,4-oxadiazol-3-yl)]benzaldehyde A mixture of 3-[4-(1,3-dioxolan-2-yl)phenyl]-5-(trifluoromethyl)-1,2,4-oxadiazole (i.e. the product of Step C) (2.48 g 8.67 mmol), tetrahydrofuran (25 mL), water (25 mL) and concentrated hydrochloric acid (25 mL) was stirred for 30 minutes at room temperature. The reaction mixture was diluted with ethyl acetate (100 mL) and the layers were separated. The organic layer was washed with water and saturated aqueous sodium chloride solution, dried over magnesium sulfate, filtered and concentrated under reduced pressure to provide the title compound as a white solid (2.09 g) melting at 50-52° C.

$^1$H NMR (CDCl$_3$): δ 8.04-8.06 (m, 2H) 8.31-8.33 (m, 2H) 10.12 (s, 1H).

Step E: Preparation of α-(phenylamino)-4-[5-(trifluoromethyl)-1,2,4-oxadiazol-3-yl]benzeneacetonitrile A mixture of 4-[5-(trifluoromethyl)-1,2,4-oxadiazol-3-yl)benzaldehyde (i.e. the product of Step D) (2.59 g, 10.7 mmol), benzenamine (95 uL, 1.0 mmol) and titanium(IV) isopropoxide (500 uL, 170 mmol) in tetrahydrofuran (5 mL) was stirred at room temperature for 2 h, and then trimethylsilyl cyanide (500 uL, 3.9 mol) was added. The reaction mixture was stirred at room temperature overnight, and then added to a vigorously stirred mixture of ice and ethyl acetate. After 1 h, the mixture was filtered and the filtrate was washed with water and saturated aqueous sodium chloride solution, dried over magnesium sulfate, filtered and concentrated under reduced pressure to provide a yellow solid. The solid was crystalized from diethyl ether (4 mL) and hexanes (10 mL) to provide the title compound, a compound of the present invention, as a colorless solid (163 mg).

$^1$H NMR (CDCl$_3$): δ 4.12 (d, 1H), 5.55 (d, 1H), 6.80 (m, 2H), 6.95 (m, 1H), 7.27-7.32 (m, 2H), 7.79-7.81 (m, 2H), 8.20-8.24 (m, 2H).

$^{19}$F NMR (CDCl$_3$): δ −65.31.

Example 15

Preparation of methyl 4,5-dihydro-2-[[4-[5-(trifluoromethyl)-1,2,4-oxadiazol-3-yl]phenyl]methyl]-4-oxazolecarboxylate (Compound 74)

Step A: Preparation of 4-[5-(trifluoromethyl)-1,2,4-oxadiazol-3-yl]benzeneacetic acid A mixture of 4-cyanobenzeneacetic acid (25.0 g, 155 mmol) and hydroxylamine (50% aqueous solution, 23.8 mL, 780 mmol) in ethanol (500 mL) was heated at reflux overnight. The reaction mixture was concentrated under reduced pressure and the resulting solid was dried in a vacuum oven overnight. The solid (i.e. the intermediate compound 4-[(hydroxyamino)iminomethyl]benzeneacetic acid) was suspended in tetrahydrofuran (500 mL) and cooled to 0° C., and then trifluoroacetic anhydride (48 mL, 340 mmol) and triethylamine (47 mL, 340 mmol) were added. The reaction mixture was stirred at room temperature overnight, and then concentrated under reduced. The resulting material was partitioned between water and dichloromethane. The organic layer was separated, dried over sodium sulfate, filtered, and concentrated onto Celite® (diatomaceous filter aid). The Celite® mixture was purified by medium pressure silica gel chromatography (eluting with a gradient of 0 to 100% of ethyl acetate in hexanes) to provide the title compound as a white solid (17.8 g).

$^1$H NMR (CDCl$_3$): δ 8.10 (d, 2H), 7.46 (d, 2H), 3.76 (s, 2H).
$^{19}$F NMR (CDCl$_3$): δ −65.35.

Step B: Preparation of N-[2-[4-[5-(trifluoromethyl)-1,2,4-oxadiazol-3-yl]phenyl]acetyl]serine methyl ester To 4-[5-(trifluoromethyl)-1,2,4-oxadiazol-3-yl]benzeneacetic acid (i.e. the product of Step A) (17.8 g, 65.3 mmol) in N,N-dimethylformamide (220 mL) was added DL-serine methyl ester hydrochloride (1:1) (12.2 g, 78.4 mmol), 1-[bis(dimethylamino)methylene]-1H-1,2,3-triazolo[4,5-b]pyridinium 3-oxide hexafluorophosphate (HATU) (29.8 g, 78.4 mmol) and 4-methylmorpholine (14.4 mL, 131 mmol). The reaction was stirred at room temperature overnight, and then diluted with water and extracted with ethyl acetate (3×). The combined organic layers were washed with water and saturated aqueous sodium chloride solution, dried over magnesium sulfate, filtered, and concentrated onto Celite® (diatomaceous filter aid). The Celite® mixture was purified by medium pressure silica gel chromatography (eluting with a gradient of 0% to 100% ethyl acetate in hexanes) to provide the title compound.

$^1$H NMR (CDCl$_3$): δ 8.12 (d, 2H), 7.48 (d, 2H), 6.47, (br s, 1H), 4.68 (dt, 1H), 4.00 (dd, 1H), 3.92 (m, 1H), 3.78 (s, 3H), 3.72 (s, 2H).
$^{19}$F NMR (CDCl$_3$): δ −65.34.

Step C: Preparation of methyl 4,5-dihydro-2-[[4-[5-(trifluoromethyl)-1,2,4-oxadiazol-3-yl]phenyl]methyl]-4-oxazolecarboxylate To N-[2-[4-[5-(trifluoromethyl)-1,2,4-oxadiazol-3-yl]phenyl]acetyl]serine methyl ester (i.e. the product of Step B) (65.3 mmol) in dichloromethane (650 mL) at −78° C. was added diethylaminosulfur trifluoride (DAST) (13 mL, 98 mmol). The reaction was stirred for 1.5 h at −78° C., and then quenched with saturated aqueous sodium bicarbonate solution and the layers were separated. The aqueous layer was further extracted with dichloromethane and the combined organic layers were washed with saturated aqueous sodium bicarbonate solution, dried over magnesium sulfate, filtered, concentrated onto Celite® (diatomaceous filter aid). The Celite® mixture was purified by medium pressure silica gel chromatography (eluting with a gradient of 0% to 100% ethyl acetate in hexanes) to provide the title compound, a compound of the present invention, as a solid (8.17 g).

$^1$H NMR (CDCl$_3$): δ 8.08 (d, 2H), 7.48 (d, 2H), 4.78 (m, 1H), 4.53 (m, 1H), 4.43 (m, 1H), 3.80 (s, 3H), 3.76 (m, 2H).
$^{19}$F NMR (CDCl$_3$): δ −65.33.

Example 16

Preparation of 4,5-dihydro-N,N-dimethyl-2-[[4-[5-(trifluoromethyl)-1,2,4-oxadiazol-3-yl]phenyl]methyl]-4-oxazolecarboxamide (Compound 178)

To a mixture of methyl 4,5-dihydro-2-[[4-[5-(trifluoromethyl)-1,2,4-oxadiazol-3-yl]phenyl]methyl]-4-oxazolecarboxylate (i.e. the product of Example 15, Step C) (0.25 g, 0.7 mmol) in methanol (7 mL) was added N,N-dimethylamine (5.6 N in ethanol, 0.63 mL) The reaction mixture was stirred overnight at 65° C., and then cooled to room temperature and concentrated onto Celite® (diatomaceous filter aid). The Celite® mixture was purified by medium pressure silica gel chromatography (eluting with a gradient of 0% to 100% ethyl acetate in hexanes) to provide the title compound, a compound of the present invention, as a solid (0.009 g).

$^1$H NMR (CDCl$_3$): δ 8.06 (d, 2H), 7.46 (d, 2H), 4.95 (m, 2H), 4.29 (dd, 1H), 3.71 (m, 2H), 3.26 (s, 3H), 3.00 (s, 3H).
$^{19}$F NMR (CDCl$_3$): δ −65.36.

Example 17

Preparation of 4,5-dihydro-2-[[4-[5-(trifluoromethyl)-1,2,4-oxadiazol-3-yl]phenyl]methyl]-4-oxazolecarboxamide (Compound 75)

A mixture of methyl 4,5-dihydro-2-[[4-[5-(trifluoromethyl)-1,2,4-oxadiazol-3-yl]phenyl]methyl]-4-oxazolecarboxylate (i.e. the product of Example 15, Step C) (0.5 g, 1.4 mmol) and ammonia (7 N in methanol, 14 mL) was stirred at room temperature overnight. The reaction mixture was concentrated under reduced pressure to provide the title compound, a compound of the present invention, as a solid (0.134 g).

$^1$H NMR (CDCl$_3$): δ 8.10 (d, 2H), 7.46 (d, 2H), 4.68 (m, 2H), 4.52, m, 2H), 3.73 (m, 2H).
$^{19}$F NMR (CDCl$_3$): δ −65.32.

Example 18

Preparation of methyl 2-[[4-[5-(trifluoromethyl)-1,2,4-oxadiazol-3-yl]-phenoxy]-methyl]oxazole-4-carboxylate (Compound 403)

Step A: Preparation of 4-[5-(trifluoromethyl)-1,2,4-oxadiazol-3-yl]phenol

To a mixture of 4-hydroxybenzonitrile (20 g, 168 mmol) in ethanol (177 mL) was added hydroxylamine (50% aqueous solution, 13.4 mL, 440 mmol). The reaction mixture was stirred for 18 h, and then concentrated under reduced pressure. The solid (i.e. the intermediate compound N,4-dihydroxybenzenecarboximidamide) was dissolved in dichloromethane (336 mL) and trifluoroacetic anhydride (47 mL, 336 mmol) was added. The reaction mixture was heated to reflux for 18 h, and then cooled to room temperature and quenched with water. The layers were separated and the aqueous layer further extracted with dichloromethane two times. The combined organics were washed with saturated aqueous sodium bicarbonate solution and aqueous sodium chloride solution, dried over magnesium sulfate and filtered, and concentrated onto Celite® (diatomaceous filter aid). The Celite® mixture was purified by medium pressure liquid chromatography (0% to 100% ethyl acetate in hexanes as eluent) to provide the title compound (16.3 g).

$^1$H NMR (CDCl$_3$): δ 8.10 (d, 2H), 6.96 (d, 2H).
$^{19}$F NMR (CDCl$_3$): δ −65.45.

Step B: Preparation of Methyl 2-[[4-[5-(trifluoromethyl)-1,2,4-oxadiazol-3-yl]-phenoxy]-methyl]oxazole-4-carboxylate To 4-[5-(trifluoromethyl)-1,2,4-oxadiazol-3-yl]phenol (i.e. the product of Step A) (1.13 g, 5 mmol) in acetonitrile (50 mL) was added methyl 2-(chloromethyl)oxazole-4-carboxylate (0.95 g, 5.4 mmol), potassium carbonate (1.52 g, 11 mmol) and tetrabutylammonium iodide (0.18 g, 0.5 mmol). The reaction mixture was heated to 80° C. for 18 h, and then cooled to room temperature and concentrated onto Celite® (diatomaceous filter aid). The Celite® mixture was purified by medium pressure liquid chromatography (0% to 100% ethyl acetate in hexanes as eluent) to provide the title compound, a compound of the present invention, as a solid (1.14 g).

$^1$H NMR (CDCl$_3$): δ 8.29 (s, 1H), 8.07 (d, 2H), 7.13 (d, 2H), 5.27 (s, 2H), 3.94 (s, 3H).
$^{19}$F NMR (CDCl$_3$): δ −65.38.

By the procedures described herein, together with methods known in the art, the following compounds of Tables 1, 1A-92A, 2 and 1B-92B can be prepared. The following abbreviations are used in the Tables: t means tertiary, s means secondary, n means normal, i means iso, c means cyclo, Me means methyl, Et means ethyl, Pr means propyl, i-Pr means isopropyl, c-Pr means cyclopropyl, Bu means butyl, i-Bu means isobutyl, t-Bu means tert-butyl, and Ph means phenyl.

TABLE 1

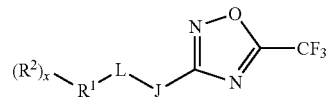

The definitions of R$^1$ and J in Table 1 are as defined Exhibits A and B in the above Embodiments. In the column R$^1$, the number in parentheses following the U-ring number refers to the attachment point of the ring to L. The (R$^2$)$_x$ column refers to the substituent(s) attached to the U-ring as shown in Exhibit A above. A dash "—" in the (R$^2$)$_x$ column means that no R$^2$ substituent is present and the remaining valences are occupied by hydrogen atoms.

| L is CH$_2$ and J is J-40. | | L is CH$_2$ and J is J-40. | |
|---|---|---|---|
| R$^1$ | (R$^2$)$_x$ | R$^1$ | R$^1$ |
| U-1 (4) | — | U-8 (5) | — |
| U-1 (4) | 2-Me | U-8 (5) | 3-Me |
| U-1 (4) | 2-Et | U-8 (5) | 3-Et |
| U-1 (4) | 2-n-Pr | U-8 (5) | 3-n-Pr |
| U-1 (4) | 2-i-Pr | U-8 (5) | 3-i-Pr |
| U-1 (4) | 2-c-Pr | U-8 (5) | 3-c-Pr |
| U-1 (4) | 2-n-Bu | U-8 (5) | 3-n-Bu |
| U-1 (4) | 2-i-Bu | U-8 (5) | 3-i-Bu |
| U-1 (4) | 2-t-Bu | U-8 (5) | 3-t-Bu |
| U-1 (4) | 2-F | U-8 (5) | 3-F |
| U-1 (4) | 2-Cl | U-8 (5) | 3-Cl |
| U-1 (4) | 2-Br | U-8 (5) | 3-Br |
| U-1 (4) | 2-CF$_3$ | U-8 (5) | 3-CF$_3$ |
| U-1 (4) | 2-HO | U-8 (5) | 3-HO |
| U-1 (4) | 2-N≡C | U-8 (5) | 3-N≡C |
| U-1 (4) | 2-N═CCH$_2$ | U-8 (5) | 3-N═CCH$_2$ |
| U-1 (4) | 2-(MeO) | U-8 (5) | 3-(MeO) |
| U-1 (4) | 2-(MeOCH$_2$) | U-8 (5) | 3-(MeOCH$_2$) |
| U-1 (4) | 2-(EtOCH$_2$) | U-8 (5) | 3-(EtOCH$_2$) |
| U-1 (4) | 2-(CH(═O)) | U-8 (5) | 3-(CH(═O)) |
| U-1 (4) | 2-(HOC(═O)) | U-8 (5) | 3-(HOC(═O)) |
| U-1 (4) | 2-(MeOC(═O)) | U-8 (5) | 3-(MeOC(═O)) |
| U-1 (4) | 2-(EtOC(═O)) | U-8 (5) | 3-(EtOC(═O)) |
| U-1 (4) | 2-(i-PrOC(═O)) | U-8 (5) | 3-(i-PrOC(═O)) |
| U-1 (4) | 2-(n-PrOC(═O)) | U-8 (5) | 3-(n-PrOC(═O)) |
| U-1 (4) | 2-(BuOC(═O)) | U-8 (5) | 4-(BuOC(═O)) |
| U-1 (4) | 2-(i-BuOC(═O)) | U-8 (5) | 3-(i-BuOC(═O)) |
| U-1 (4) | 2-(t-BuOC(═O)) | U-8 (5) | 3-(t-BuOC(═O)) |
| U-1 (4) | 2-(CF$_3$CH$_2$OC(═O) | U-8 (5) | 3-(CF$_3$CH$_2$OC(═O) |
| U-1 (4) | 2-(CH$_2$═CHOC(═O)) | U-8 (5) | 3-(CH$_2$═CHOC(═O)) |
| U-1 (4) | 2-(CH$_2$═CHCH$_2$OC(═O)) | U-8 (5) | 3-(CH$_2$═CHCH$_2$OC(═O)) |
| U-1 (4) | 2-(CH$_2$═CBrCH$_2$OC(═O)) | U-8 (5) | 3-(CH$_2$═CBrCH2OC(═O)) |
| U-1 (4) | 2-(CH$_2$═CHCF$_2$OC(═O)) | U-8 (5) | 3-(CH$_2$═CHCF$_2$OC(═O)) |
| U-1 (4) | 2-(Me$_2$C═CHCH$_2$OC(═O)) | U-8 (5) | 3-(Me$_2$C═CHCH$_2$OC(═O)) |
| U-1 (4) | 2-(CH$_2$═C(Me)CH$_2$OC(═O)) | U-8 (5) | 3-(CH$_2$═C(Me)CH$_2$OC(═O)) |
| U-1 (4) | 2-(CH≡CCH$_2$OC(═O)) | U-8 (5) | 3-(CH≡CCH2OC(═O)) |

TABLE 1-continued

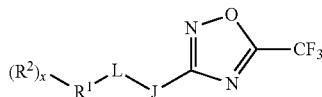

The definitions of $R^1$ and J in Table 1 are as defined Exhibits A and B in the above Embodiments. In the column $R^1$, the number in parentheses following the U-ring number refers to the attachment point of the ring to L. The $(R^2)_x$ column refers to the substituent(s) attached to the U-ring as shown in Exhibit A above. A dash "—" in the $(R^2)_x$ column means that no $R^2$ substituent is present and the remaining valences are occupied by hydrogen atoms.

| L is CH₂ and J is J-40. | | L is CH₂ and J is J-40. | |
|---|---|---|---|
| $R^1$ | $(R^2)_x$ | $R^1$ | $R^1$ |
| U-1 (4) | 2-(N=CCH₂OC(=O)) | U-8 (5) | 3-(N=CCH₂OC(=O)) |
| U-1 (4) | 2-(MeNHC(=O)) | U-8 (5) | 3-(MeNHC(=O)) |
| U-1 (4) | 2-(Me₂NC(=O)) | U-8 (5) | 3-(Me₂NC(=O)) |
| U-1 (4) | 2-(MeNHC(=O)) | U-8 (5) | 3-(MeNHC(=O)) |
| U-1 (4) | 2-(EtNHC(=O)) | U-8 (5) | 3-(EtNHC(=O)) |
| U-1 (4) | 2-(PrNHC(=O)) | U-8 (5) | 3-(PrNHC(=O)) |
| U-1 (4) | 2-(i-PrNHC(=O)) | U-8 (5) | 3-(i-PrNHC(=O)) |
| U-1 (4) | 2-(BuNHC(=O)) | U-8 (5) | 3-(BuNHC(=O)) |
| U-1 (4) | 2-(t-BuNHC(=O)) | U-8 (5) | 3-(t-BuNHC(=O)) |
| U-1 (4) | 2-(i-BuNHC(=O)) | U-8 (5) | 3-(i-BuNHC(=O)) |
| U-1 (4) | 2-(CF₃CH₂NHC(=O)) | U-8 (5) | 3-(CF₃CH₂NHC(=O)) |
| U-1 (4) | 2-(c-PrCH₂NHC(=O)) | U-8 (5) | 3-(c-PrCH₂NHC(=O)) |
| U-1 (4) | 2-(MeOCH₂NHC(=O)) | U-8 (5) | 3-(MeOCH₂NHC(=O)) |
| U-1 (4) | 2-(MeOCH₂CH₂NHC(=O)) | U-8 (5) | 3-(MeOCH₂CH₂NHC(=O)) |
| U-1 (4) | 2-(CH₂=CHCH₂NHC(=O)) | U-8 (5) | 3-(CH₂=CHCH₂NHC(=O)) |
| U-1 (4) | 2-(N=CCH₂NHC(=O)) | U-8 (5) | 3-(N=CCH₂NHC(=O)) |
| U-1 (4) | 2-(OH—N=CH) | U-8 (5) | 3-(OH—N=CH) |
| U-1 (4) | 2-(Me₂NN=CH) | U-8 (5) | 3-(Me₂NN=CH) |
| U-1 (4) | 2-(MeOC(=O)NHN=CH) | U-8 (5) | 3-(MeOC(=O)NHN=CH) |
| U-1 (4) | 2-(OHC(=O)CH₂ON=CH) | U-8 (5) | 3-(OHC(=O)CH₂ON=CH) |
| U-1 (2) | — | U-12 (3) | 1-Me |
| U-1 (2) | 4-Me | U-12 (3) | 1,5-di-Me |
| U-1 (2) | 4-Et | U-12 (3) | 1-Me, 5-Et |
| U-1 (2) | 4-n-Pr | U-12 (3) | 1-Me, 5-n-Pr |
| U-1 (2) | 4-i-Pr | U-12 (3) | 1-Me, 5-i-Pr |
| U-1 (2) | 4-c-Pr | U-12 (3) | 1-Me, 5-c-Pr |
| U-1 (2) | 4-n-Bu | U-12 (3) | 1-Me, 5-n-Bu |
| U-1 (2) | 4-i-Bu | U-12 (3) | 1-Me, 5-i-Bu |
| U-1 (2) | 4-t-Bu | U-12 (3) | 1-Me, 5-t-Bu |
| U-1 (2) | 4-F | U-12 (3) | 1-Me, 5-F |
| U-1 (2) | 4-Cl | U-12 (3) | 1-Me, 5-Cl |
| U-1 (2) | 4-Br | U-12 (3) | 1-Me, 5-Br |
| U-1 (2) | 4-CF₃ | U-12 (3) | 1-Me, 5-CF₃ |
| U-1 (2) | 4-HO | U-12 (3) | 1-Me, 5-HO |
| U-1 (2) | 4-N=C | U-12 (3) | 1-Me, 5-N=C |
| U-1 (2) | 4-N=CCH₂ | U-12 (3) | 1-Me, 5-N=CCH₂ |
| U-1 (2) | 4-(MeO) | U-12 (3) | 1-Me, 5-(MeO) |
| U-1 (2) | 4-(MeOCH₂) | U-12 (3) | 1-Me, 5-(MeOCH₂) |
| U-1 (2) | 4-(EtOCH₂) | U-12 (3) | 1-Me, 5-(EtOCH₂) |
| U-1 (2) | 4-(CH(=O)) | U-12 (3) | 1-Me, 5-(CH(=O)) |
| U-1 (2) | 4-(HOC(=O)) | U-12 (3) | 1-Me, 5-(HOC(=O)) |
| U-1 (2) | 4-(MeOC(=O)) | U-12 (3) | 1-Me, 5-(MeOC(=O)) |
| U-1 (2) | 4-(EtOC(=O)) | U-12 (3) | 1-Me, 5-(EtOC(=O)) |
| U-1 (2) | 4-(i-PrOC(=O)) | U-12 (3) | 1-Me, 5-(i-PrOC(=O)) |
| U-1 (2) | 4-(n-PrOC(=O)) | U-12 (3) | 1-Me, 5-(n-PrOC(=O)) |
| U-1 (2) | 4-(BuOC(=O)) | U-12 (3) | 1-Me, 5-(BuOC(=O)) |
| U-1 (2) | 4-(i-BuOC(=O)) | U-12 (3) | 1-Me, 5-(i-BuOC(=O)) |
| U-1 (2) | 4-(t-BuOC(=O)) | U-12 (3) | 1-Me, 5-(t-BuOC(=O)) |
| U-1 (2) | 4-(CF₃CH₂OC(=O) | U-12 (3) | 1-Me, 5-(CF₃CH₂OC(=O) |
| U-1 (2) | 4-(CH₂=CHOC(=O)) | U-12 (3) | 1-Me, 5-(CH₂=CHOC(=O)) |
| U-1 (2) | 4-(CH₂=CHCH₂OC(=O)) | U-12 (3) | 1-Me, 5-(CH₂=CHCH₂OC(=O)) |
| U-1 (2) | 4-(CH₂=CBrCH₂OC(=O)) | U-12 (3) | 1-Me, 5-(CH₂=CBrCH₂OC(=O)) |
| U-1 (2) | 4-(CH₂=CHCF₂OC(=O)) | U-12 (3) | 1-Me, 5-(CH₂=CHCF₂OC(=O)) |
| U-1 (2) | 4-(Me₂C=CHCH₂OC(=O)) | U-12 (3) | 1-Me, 5-(Me₂C=CHCH₂OC(=O)) |
| U-1 (2) | 4-(CH₂=C(Me)CH₂OC(=O)) | U-12 (3) | 1-Me, 5-(CH₂=C(Me)CH₂OC(=O)) |
| U-1 (2) | 4-(CH=CCH₂OC(=O)) | U-12 (3) | 1-Me, 5-(CH=CCH₂OC(=O)) |
| U-1 (2) | 4-(N=CCH₂OC(=O)) | U-12 (3) | 1-Me, 5-(N=CCH₂OC(=O)) |
| U-1 (2) | 4-(MeNHC(=O)) | U-12 (3) | 1-Me, 5-(MeNHC(=O)) |
| U-1 (2) | 4-(Me₂NC(=O)) | U-12 (3) | 1-Me, 5-(Me₂NC(=O)) |
| U-1 (2) | 4-(MeNHC(=O)) | U-12 (3) | 1-Me, 5-(MeNHC(=O)) |
| U-1 (2) | 4-(EtNHC(=O)) | U-12 (3) | 1-Me, 5-(EtNHC(=O)) |
| U-1 (2) | 4-(PrNHC(=O)) | U-12 (3) | 1-Me, 5-(PrNHC(=O)) |
| U-1 (2) | 4-(i-PrNHC(=O)) | U-12 (3) | 1-Me, 5-(i-PrNHC(=O)) |
| U-1 (2) | 4-(BuNHC(=O)) | U-12 (3) | 1-Me, 5-(BuNHC(=O)) |

TABLE 1-continued

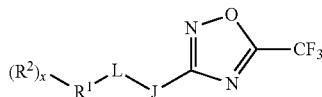

The definitions of $R^1$ and J in Table 1 are as defined Exhibits A and B in the above Embodiments. In the column $R^1$, the number in parentheses following the U-ring number refers to the attachment point of the ring to L. The $(R^2)_x$ column refers to the substituent(s) attached to the U-ring as shown in Exhibit A above. A dash "—" in the $(R^2)_x$ column means that no $R^2$ substituent is present and the remaining valences are occupied by hydrogen atoms.

| L is CH$_2$ and J is J-40. | | L is CH$_2$ and J is J-40. | |
|---|---|---|---|
| $R^1$ | $(R^2)_x$ | $R^1$ | $R^1$ |
| U-1 (2) | 4-(t-BuNHC(=O)) | U-12 (3) | 1-Me, 5-(t-BuNHC(=O)) |
| U-1 (2) | 4-(i-BuNHC(=O)) | U-12 (3) | 1-Me, 5-(i-BuNHC(=O)) |
| U-1 (2) | 4-(CF$_3$CH$_2$NHC(=O)) | U-12 (3) | 1-Me, 5-(CF$_3$CH$_2$NHC(=O)) |
| U-1 (2) | 4-(c-PrCH$_2$NHC(=O)) | U-12 (3) | 1-Me, 5-(c-PrCH$_2$NHC(=O)) |
| U-1 (2) | 4-(MeOCH$_2$NHC(=O)) | U-12 (3) | 1-Me, 5-(MeOCH$_2$NHC(=O)) |
| U-1 (2) | 4-(MeOCH$_2$CH$_2$NHC(=O)) | U-12 (3) | 1-Me, 5-(MeOCH$_2$CH$_2$NHC(=O)) |
| U-1 (2) | 4-(CH$_2$=CHCH$_2$NHC(=O)) | U-12 (3) | 1-Me, 5-(CH$_2$=CHCH$_2$NHC(=O)) |
| U-1 (2) | 4-(N≡CCH$_2$NHC(=O)) | U-12 (3) | 1-Me, 5-(N≡CCH$_2$NHC(=O)) |
| U-1 (2) | 4-(OH—N=CH) | U-12 (3) | 1-Me, 5-(OH—N=CH) |
| U-1 (2) | 4-(Me$_2$NN=CH) | U-12 (3) | 1-Me, 5-(Me$_2$NN=CH) |
| U-1 (2) | 4-(MeOC(=O)NHN=CH) | U-12 (3) | 1-Me, 5-(MeOC(=O)NHN=CH) |
| U-1 (2) | 4-(OHC(=O)CH$_2$ON=CH) | U-12 (3) | 1-Me, 5-(OHC(=O)CH$_2$ON=CH) |
| U-2 (2) | — | U-12 (1) | — |
| U-2 (2) | 4-Me | U-12 (1) | 4-Me |
| U-2 (2) | 4-Et | U-12 (1) | 4-Et |
| U-2 (2) | 4-n-Pr | U-12 (1) | 4-n-Pr |
| U-2 (2) | 4-i-Pr | U-12 (1) | 4-i-Pr |
| U-2 (2) | 4-c-Pr | U-12 (1) | 4-c-Pr |
| U-2 (2) | 4-n-Bu | U-12 (1) | 4-n-Bu |
| U-2 (2) | 4-i-Bu | U-12 (1) | 4-i-Bu |
| U-2 (2) | 4-t-Bu | U-12 (1) | 4-t-Bu |
| U-2 (2) | 4-F | U-12 (1) | 4-F |
| U-2 (2) | 4-Cl | U-12 (1) | 4-Cl |
| U-2 (2) | 4-Br | U-12 (1) | 4-Br |
| U-2 (2) | 4-CF$_3$ | U-12 (1) | 4-CF$_3$ |
| U-2 (2) | 4-HO | U-12 (1) | 4-HO |
| U-2 (2) | 4-N≡C | U-12 (1) | 4-N≡C |
| U-2 (2) | 4-N=CCH$_2$ | U-12 (1) | 4-N=CCH$_2$ |
| U-2 (2) | 4-(MeO) | U-12 (1) | 4-(MeO) |
| U-2 (2) | 4-(MeOCH$_2$) | U-12 (1) | 4-(MeOCH$_2$) |
| U-2 (2) | 4-(EtOCH$_2$) | U-12 (1) | 4-(EtOCH$_2$) |
| U-2 (2) | 4-(CH(=O)) | U-12 (1) | 4-(CH(=O)) |
| U-2 (2) | 4-(HOC(=O)) | U-12 (1) | 4-(HOC(=O)) |
| U-2 (2) | 4-(MeOC(=O)) | U-12 (1) | 4-(MeOC(=O)) |
| U-2 (2) | 4-(EtOC(=O)) | U-12 (1) | 4-(EtOC(=O)) |
| U-2 (2) | 4-(i-PrOC(=O)) | U-12 (1) | 4-(i-PrOC(=O)) |
| U-2 (2) | 4-(n-PrOC(=O)) | U-12 (1) | 4-(n-PrOC(=O)) |
| U-2 (2) | 4-(BuOC(=O)) | U-12 (1) | 4-(BuOC(=O)) |
| U-2 (2) | 4-(i-BuOC(=O)) | U-12 (1) | 4-(i-BuOC(=O)) |
| U-2 (2) | 4-(t-BuOC(=O)) | U-12 (1) | 4-(t-BuOC(=O)) |
| U-2 (2) | 4-(CF$_3$CH$_2$OC(=O) | U-12 (1) | 4-(CF$_3$CH$_2$OC(=O) |
| U-2 (2) | 4-(CH$_2$=CHOC(=O)) | U-12 (1) | 4-(CH$_2$=CHOC(=O)) |
| U-2 (2) | 4-(CH$_2$=CHCH$_2$OC(=O)) | U-12 (1) | 4-(CH$_2$=CHCH$_2$OC(=O)) |
| U-2 (2) | 4-(CH$_2$=CBrCH$_2$OC(=O)) | U-12 (1) | 4-(CH$_2$=CBrCH$_2$OC(=O)) |
| U-2 (2) | 4-(CH$_2$=CHCF$_2$OC(=O)) | U-12 (1) | 4-(CH$_2$=CHCF$_2$OC(=O)) |
| U-2 (2) | 4-(Me$_2$C=CHCH$_2$OC(=O)) | U-12 (1) | 4-(Me$_2$C=CHCH$_2$OC(=O)) |
| U-2 (2) | 4-(CH$_2$=C(Me)CH$_2$OC(=O)) | U-12 (1) | 4-(CH$_2$=C(Me)CH$_2$OC(=O)) |
| U-2 (2) | 4-(CH≡CCH$_2$OC(=O)) | U-12 (1) | 4-(CH≡CCH$_2$OC(=O)) |
| U-2 (2) | 4-(N≡CCH$_2$OC(=O)) | U-12 (1) | 4-(N≡CCH$_2$OC(=O)) |
| U-2 (2) | 4-(MeNHC(=O)) | U-12 (1) | 4-(MeNHC(=O)) |
| U-2 (2) | 4-(Me$_2$NC(=O)) | U-12 (1) | 4-(Me$_2$NC(=O)) |
| U-2 (2) | 4-(MeNHC(=O)) | U-12 (1) | 4-(MeNHC(=O)) |
| U-2 (2) | 4-(EtNHC(=O)) | U-12 (1) | 4-(EtNHC(=O)) |
| U-2 (2) | 4-(PrNHC(=O)) | U-12 (1) | 4-(PrNHC(=O)) |
| U-2 (2) | 4-(i-PrNHC(=O)) | U-12 (1) | 4-(i-PrNHC(=O)) |
| U-2 (2) | 4-(BuNHC(=O)) | U-12 (1) | 4-(BuNHC(=O)) |
| U-2 (2) | 4-(t-BuNHC(=O)) | U-12 (1) | 4-(t-BuNHC(=O)) |
| U-2 (2) | 4-(i-BuNHC(=O)) | U-12 (1) | 4-(i-BuNHC(=O)) |
| U-2 (2) | 4-(CF$_3$CH$_2$NHC(=O)) | U-12 (1) | 4-(CF$_3$CH$_2$NHC(=O)) |
| U-2 (2) | 4-(c-PrCH$_2$NHC(=O)) | U-12 (1) | 4-(c-PrCH$_2$NHC(=O)) |
| U-2 (2) | 4-(MeOCH$_2$NHC(=O)) | U-12 (1) | 4-(MeOCH$_2$NHC(=O)) |
| U-2 (2) | 4-(MeOCH$_2$CH$_2$NHC(=O)) | U-12 (1) | 4-(MeOCH$_2$CH$_2$NHC(=O)) |
| U-2 (2) | 4-(CH$_2$=CHCH$_2$NHC(=O)) | U-12 (1) | 4-(CH$_2$=CHCH$_2$NHC(=O)) |
| U-2 (2) | 4-(N≡CCH$_2$NHC(=O)) | U-12 (1) | 4-(N≡CCH$_2$NHC(=O)) |

TABLE 1-continued

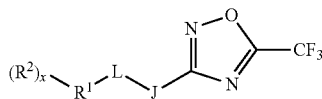

The definitions of $R^1$ and J in Table 1 are as defined Exhibits A and B in the above Embodiments. In the column $R^1$, the number in parentheses following the U-ring number refers to the attachment point of the ring to L. The $(R^2)_x$ column refers to the substituent(s) attached to the U-ring as shown in Exhibit A above. A dash "—" in the $(R^2)_x$ column means that no $R^2$ substituent is present and the remaining valences are occupied by hydrogen atoms.

| L is CH$_2$ and J is J-40. | | L is CH$_2$ and J is J-40. | |
|---|---|---|---|
| $R^1$ | $(R^2)_x$ | $R^1$ | $R^1$ |
| U-2 (2) | 4-(OH—N=CH) | U-12 (1) | 4-(OH—N=CH) |
| U-2 (2) | 4-(Me$_2$NN=CH) | U-12 (1) | 4-(Me$_2$NN=CH) |
| U-2 (2) | 4-(MeOC(=O)NHN=CH) | U-12 (1) | 4-(MeOC(=O)NHN=CH) |
| U-2 (2) | 4-(OHC(=O)CH$_2$ON=CH) | U-12 (1) | 4-(OHC(=O)CH$_2$ON=CH) |
| U-2 (4) | — | U-69 (1) | — |
| U-2 (4) | 2-Me | U-69 (1) | 4-Me |
| U-2 (4) | 2-Et | U-69 (1) | 4-Et |
| U-2 (4) | 2-n-Pr | U-69 (1) | 4-n-Pr |
| U-2 (4) | 2-i-Pr | U-69 (1) | 4-i-Pr |
| U-2 (4) | 2-c-Pr | U-69 (1) | 4-c-Pr |
| U-2 (4) | 2-n-Bu | U-69 (1) | 4-n-Bu |
| U-2 (4) | 2-i-Bu | U-69 (1) | 4-i-Bu |
| U-2 (4) | 2-t-Bu | U-69 (1) | 4-t-Bu |
| U-2 (4) | 2-F | U-69 (1) | 4-F |
| U-2 (4) | 2-Cl | U-69 (1) | 4-Cl |
| U-2 (4) | 2-Br | U-69 (1) | 4-Br |
| U-2 (4) | 2-CF$_3$ | U-69 (1) | 4-CF$_3$ |
| U-2 (4) | 2-HO | U-69 (1) | 4-HO |
| U-2 (4) | 2-N≡C | U-69 (1) | 4-N≡C |
| U-2 (4) | 2-N=CCH$_2$ | U-69 (1) | 4-N=CCH$_2$ |
| U-2 (4) | 2-(MeO) | U-69 (1) | 4-(MeO) |
| U-2 (4) | 2-(MeOCH$_2$) | U-69 (1) | 4-(MeOCH$_2$) |
| U-2 (4) | 2-(EtOCH$_2$) | U-69 (1) | 4-(EtOCH$_2$) |
| U-2 (4) | 2-(CH(=O)) | U-69 (1) | 4-(CH(=O)) |
| U-2 (4) | 2-(HOC(=O)) | U-69 (1) | 4-(HOC(=O)) |
| U-2 (4) | 2-(MeOC(=O)) | U-69 (1) | 4-(MeOC(=O)) |
| U-2 (4) | 2-(EtOC(=O)) | U-69 (1) | 4-(EtOC(=O)) |
| U-2 (4) | 2-(i-PrOC(=O)) | U-69 (1) | 4-(i-PrOC(=O)) |
| U-2 (4) | 2-(n-PrOC(=O)) | U-69 (1) | 4-(n-PrOC(=O)) |
| U-2 (4) | 2-(BuOC(=O)) | U-69 (1) | 4-(BuOC(=O)) |
| U-2 (4) | 2-(i-BuOC(=O)) | U-69 (1) | 4-(i-BuOC(=O)) |
| U-2 (4) | 2-(t-BuOC(=O)) | U-69 (1) | 4-(t-BuOC(=O)) |
| U-2 (4) | 2-(CF$_3$CH$_2$OC(=O) | U-69 (1) | 4-(CF$_3$CH$_2$OC(=O) |
| U-2 (4) | 2-(CH$_2$=CHOC(=O)) | U-69 (1) | 4-(CH$_2$=CHOC(=O)) |
| U-2 (4) | 2-(CH$_2$=CHCH$_2$OC(=O)) | U-69 (1) | 4-(CH$_2$=CHCH$_2$OC(=O)) |
| U-2 (4) | 2-(CH$_2$=CBrCH$_2$OC(=O)) | U-69 (1) | 4-(CH$_2$=CBrCH$_2$OC(=O)) |
| U-2 (4) | 2-(CH$_2$=CHCF$_2$OC(=O)) | U-69 (1) | 4-(CH$_2$=CHCF$_2$OC(=O)) |
| U-2 (4) | 2-(Me$_2$C=CHCH$_2$OC(=O)) | U-69 (1) | 4-(Me$_2$C=CHCH$_2$OC(=O)) |
| U-2 (4) | 2-(CH$_2$=C(Me)CH$_2$OC(=O)) | U-69 (1) | 4-(CH$_2$=C(Me)CH$_2$OC(=O)) |
| U-2 (4) | 2-(CH≡CCH$_2$OC(=O)) | U-69 (1) | 4-(CH≡CCH$_2$OC(=O)) |
| U-2 (4) | 2-(N≡CCH$_2$OC(=O)) | U-69 (1) | 4-(N≡CCH$_2$OC(=O)) |
| U-2 (4) | 2-(MeNHC(=O)) | U-69 (1) | 4-(MeNHC(=O)) |
| U-2 (4) | 2-(Me$_2$NC(=O)) | U-69 (1) | 4-(Me$_2$NC(=O)) |
| U-2 (4) | 2-(MeNHC(=O)) | U-69 (1) | 4-(MeNHC(=O)) |
| U-2 (4) | 2-(EtNHC(=O)) | U-69 (1) | 4-(EtNHC(=O)) |
| U-2 (4) | 2-(PrNHC(=O)) | U-69 (1) | 4-(PrNHC(=O)) |
| U-2 (4) | 2-(i-PrNHC(=O)) | U-69 (1) | 4-(i-PrNHC(=O)) |
| U-2 (4) | 2-(BuNHC(=O)) | U-69 (1) | 4-(BuNHC(=O)) |
| U-2 (4) | 2-(t-BuNHC(=O)) | U-69 (1) | 4-(t-BuNHC(=O)) |
| U-2 (4) | 2-(i-BuNHC(=O)) | U-69 (1) | 4-(i-BuNHC(=O)) |
| U-2 (4) | 2-(CF$_3$CH$_2$NHC(=O)) | U-69 (1) | 4-(CF$_3$CH$_2$NHC(=O)) |
| U-2 (4) | 2-(c-PrCH$_2$NHC(=O)) | U-69 (1) | 4-(c-PrCH$_2$NHC(=O)) |
| U-2 (4) | 2-(MeOCH$_2$NHC(=O)) | U-69 (1) | 4-(MeOCH$_2$NHC(=O)) |
| U-2 (4) | 2-(MeOCH$_2$CH$_2$NHC(=O)) | U-69 (1) | 4-(MeOCH$_2$CH$_2$NHC(=O)) |
| U-2 (4) | 2-(CH$_2$=CHCH$_2$NHC(=O)) | U-69 (1) | 4-(CH$_2$=CHCH$_2$NHC(=O)) |
| U-2 (4) | 2-(N≡CCH$_2$NHC(=O)) | U-69 (1) | 4-(N≡CCH$_2$NHC(=O)) |
| U-2 (4) | 2-(OH—N=CH) | U-69 (1) | 4-(OH—N=CH) |
| U-2 (4) | 2-(Me$_2$NN=CH) | U-69 (1) | 4-(Me$_2$NN=CH) |

TABLE 1-continued

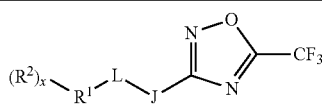

The definitions of $R^1$ and J in Table 1 are as defined Exhibits A and B in the above Embodiments. In the column $R^1$, the number in parentheses following the U-ring number refers to the attachment point of the ring to L. The $(R^2)_x$ column refers to the substituent(s) attached to the U-ring as shown in Exhibit A above. A dash "—" in the $(R^2)_x$ column means that no $R^2$ substituent is present and the remaining valences are occupied by hydrogen atoms.

| L is CH$_2$ and J is J-40. | | L is CH$_2$ and J is J-40. | |
|---|---|---|---|
| $R^1$ | $(R^2)_x$ | $R^1$ | $R^1$ |
| U-2 (4) | 2-(MeOC(=O)NHN=CH) | U-69 (1) | 4-(MeOC(=O)NHN=CH) |
| U-2 (4) | 2-(OHC(=O)CH$_2$ON=CH) | U-69 (1) | 4-(OHC(=O)CH$_2$ON=CH) |

The present disclosure also includes Tables 1A through 47A, each of which is constructed the same as Table 1 above, except that the row heading in Table 1 (i.e. "L is CH$_2$ and J is J-40") is replaced with the respective row heading shown below.

| Table | Row Heading |
|---|---|
| 1A | L is CH$_2$CH$_2$ and J is J-40. |
| 2A | L is CH$_2$(Me) and J is J-40. |
| 3A | L is CH$_2$CH$_2$CH$_2$ and J is J-40. |
| 4A | L is OCH$_2$ and J is J-40. |
| 5A | L is CH$_2$O and J is J-40. |
| 6A | L is CH$_2$OCH$_2$ and J is J-40. |
| 7A | L is CH$_2$ and J is J-4. |
| 8A | L is CH$_2$CH$_2$ and J is J-4. |
| 9A | L is CH$_2$(Me) and J is J-4. |
| 10A | L is CH$_2$CH$_2$CH$_2$ and J is J-4. |
| 11A | L is OCH$_2$ and J is J-4. |
| 12A | L is CH$_2$O and J is J-4. |
| 13A | L is CH$_2$OCH$_2$ and J is J-4. |
| 14A | L is CH$_2$ and J is J-18. |
| 15A | L is CH$_2$CH$_2$ and J is J-18. |
| 16A | L is CH$_2$(Me) and J is J-18. |
| 17A | L is CH$_2$CH$_2$CH$_2$ and J is J-18. |
| 18A | L is OCH$_2$ and J is J-18. |
| 19A | L is CH$_2$O and J is J-18. |
| 20A | L is CH$_2$OCH$_2$ and J is J-18. |
| 21A | L is CH$_2$ and J is J-27. |
| 22A | L is CH$_2$CH$_2$ and J is J-27. |
| 23A | L is CH$_2$(Me) and J is J-27. |
| 24A | L is CH$_2$CH$_2$CH$_2$ and J is J-27. |
| 25A | L is OCH$_2$ and J is J-27. |
| 26A | L is CH$_2$O and J is J-27. |
| 27A | L is CH$_2$OCH$_2$ and J is J-27. |
| 28A | L is CH$_2$ and J is J-63. |
| 29A | L is CH$_2$CH$_2$ and J is J-63. |
| 30A | L is CH$_2$(Me) and J is J-63. |
| 31A | L is CH$_2$CH$_2$CH$_2$ and J is J-63. |
| 32A | L is OCH$_2$ and J is J-63. |
| 33A | L is CH$_2$O and J is J-63. |
| 34A | L is CH$_2$OCH$_2$ and J is J-63. |
| 35A | L is CH$_2$ and J is J-73. |
| 36A | L is CH$_2$CH$_2$ and J is J-73. |
| 37A | L is CH$_2$(Me) and J is J-73. |
| 38A | L is CH$_2$CH$_2$CH$_2$ and J is J-73. |
| 39A | L is OCH$_2$ and J is J-73. |
| 40A | L is CH$_2$O and J is J-73. |
| 41A | L is CH$_2$OCH$_2$ and J is J-73. |
| 42A | L is CH$_2$ and J is J-93. |
| 43A | L is CH$_2$CH$_2$ and J is J-93. |
| 44A | L is CH$_2$(Me) and J is J-93. |
| 45A | L is CH$_2$CH$_2$CH$_2$ and J is J-93. |
| 46A | L is OCH$_2$ and J is J-93. |
| 47A | L is CH$_2$O and J is J-93. |
| 48A | L is CH$_2$OCH$_2$ and J is J-93. |

Table 2 discloses specific compounds Formula 3 which are useful as process intermediates for preparing compounds of Formula 1, as described in Schemes 2 and 10 above.

TABLE 2

3

$R^1\text{—}L\text{—}J\text{—}C{\equiv}N$

| L is CH$_2$ and J is J-40. | | L is CH$_2$ and J is J-40. | |
|---|---|---|---|
| $R^1$ | $(R^2)_x$ | $R^1$ | $R^1$ |
| U-1 (4) | — | U-8 (5) | — |
| U-1 (4) | 2-Me | U-8 (5) | 3-Me |
| U-1 (4) | 2-Et | U-8 (5) | 3-Et |
| U-1 (4) | 2-n-Pr | U-8 (5) | 3-n-Pr |
| U-1 (4) | 2-i-Pr | U-8 (5) | 3-i-Pr |
| U-1 (4) | 2-c-Pr | U-8 (5) | 3-c-Pr |
| U-1 (4) | 2-n-Bu | U-8 (5) | 3-n-Bu |
| U-1 (4) | 2-i-Bu | U-8 (5) | 3-i-Bu |
| U-1 (4) | 2-t-Bu | U-8 (5) | 3-t-Bu |
| U-1 (4) | 2-F | U-8 (5) | 3-F |
| U-1 (4) | 2-Cl | U-8 (5) | 3-Cl |
| U-1 (4) | 2-Br | U-8 (5) | 3-Br |

TABLE 2-continued

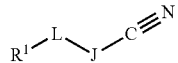

| L is CH$_2$ and J is J-40. | | L is CH$_2$ and J is J-40. | |
|---|---|---|---|
| R$^1$ | (R$^2$)$_x$ | R$^1$ | R$^1$ |
| U-1 (4) | 2-CF$_3$ | U-8 (5) | 3-CF$_3$ |
| U-1 (4) | 2-HO | U-8 (5) | 3-HO |
| U-1 (4) | 2-N≡C | U-8 (5) | 3-N≡C |
| U-1 (4) | 2-N═CCH$_2$ | U-8 (5) | 3-N═CCH$_2$ |
| U-1 (4) | 2-(MeO) | U-8 (5) | 3-(MeO) |
| U-1 (4) | 2-(MeOCH$_2$) | U-8 (5) | 3-(MeOCH$_2$) |
| U-1 (4) | 2-(EtOCH$_2$) | U-8 (5) | 3-(EtOCH$_2$) |
| U-1 (4) | 2-(CH(═O)) | U-8 (5) | 3-(CH(═O)) |
| U-1 (4) | 2-(HOC(═O)) | U-8 (5) | 3-(HOC(═O)) |
| U-1 (4) | 2-(MeOC(═O)) | U-8 (5) | 3-(MeOC(═O)) |
| U-1 (4) | 2-(EtOC(═O)) | U-8 (5) | 3-(EtOC(═O)) |
| U-1 (4) | 2-(i-PrOC(═O)) | U-8 (5) | 3-(i-PrOC(═O)) |
| U-1 (4) | 2-(n-PrOC(═O)) | U-8 (5) | 3-(n-PrOC(═O)) |
| U-1 (4) | 2-(BuOC(═O)) | U-8 (5) | 4-(BuOC(═O)) |
| U-1 (4) | 2-(i-BuOC(═O)) | U-8 (5) | 3-(i-BuOC(═O)) |
| U-1 (4) | 2-(t-BuOC(═O)) | U-8 (5) | 3-(t-BuOC(═O)) |
| U-1 (4) | 2-(CF$_3$CH$_2$OC(═O) | U-8 (5) | 3-(CF$_3$CH$_2$OC(═O) |
| U-1 (4) | 2-(CH$_2$═CHOC(═O)) | U-8 (5) | 3-(CH$_2$═CHOC(═O)) |
| U-1 (4) | 2-(CH$_2$═CHCH$_2$OC(═O)) | U-8 (5) | 3-(CH$_2$═CHCH$_2$OC(═O)) |
| U-1 (4) | 2-(CH$_2$═CBrCH$_2$OC(═O)) | U-8 (5) | 3-(CH$_2$═CBrCH$_2$OC(═O)) |
| U-1 (4) | 2-(CH$_2$═CHCF$_2$OC(═O)) | U-8 (5) | 3-(CH$_2$═CHCF$_2$OC(═O)) |
| U-1 (4) | 2-(Me$_2$C═CHCH$_2$OC(═O)) | U-8 (5) | 3-(Me$_2$C═CHCH$_2$OC(═O)) |
| U-1 (4) | 2-(CH$_2$═C(Me)CH$_2$OC(═O)) | U-8 (5) | 3-(CH$_2$═C(Me)CH$_2$OC(═O)) |
| U-1 (4) | 2-(CH≡CCH$_2$OC(═O)) | U-8 (5) | 3-(CH≡CCH$_2$OC(═O)) |
| U-1 (4) | 2-(N≡CCH$_2$OC(═O)) | U-8 (5) | 3-(N≡CCH$_2$OC(═O)) |
| U-1 (4) | 2-(MeNHC(═O)) | U-8 (5) | 3-(MeNHC(═O)) |
| U-1 (4) | 2-(Me$_2$NC(═O)) | U-8 (5) | 3-(Me$_2$NC(═O)) |
| U-1 (4) | 2-(MeNHC(═O)) | U-8 (5) | 3-(MeNHC(═O)) |
| U-1 (4) | 2-(EtNHC(═O)) | U-8 (5) | 3-(EtNHC(═O)) |
| U-1 (4) | 2-(PrNHC(═O)) | U-8 (5) | 3-(PrNHC(═O)) |
| U-1 (4) | 2-(i-PrNHC(═O)) | U-8 (5) | 3-(i-PrNHC(═O)) |
| U-1 (4) | 2-(BuNHC(═O)) | U-8 (5) | 3-(BuNHC(═O)) |
| U-1 (4) | 2-(t-BuNHC(═O)) | U-8 (5) | 3-(t-BuNHC(═O)) |
| U-1 (4) | 2-(i-BuNHC(═O)) | U-8 (5) | 3-(i-BuNHC(═O)) |
| U-1 (4) | 2-(CF$_3$CH$_2$NHC(═O)) | U-8 (5) | 3-(CF$_3$CH$_2$NHC(═O)) |
| U-1 (4) | 2-(c-PrCH$_2$NHC(═O)) | U-8 (5) | 3-(c-PrCH$_2$NHC(═O)) |
| U-1 (4) | 2-(MeOCH$_2$NHC(═O)) | U-8 (5) | 3-(MeOCH$_2$NHC(═O)) |
| U-1 (4) | 2-(MeOCH$_2$CH$_2$NHC(═O)) | U-8 (5) | 3-(MeOCH$_2$CH$_2$NHC(═O)) |
| U-1 (4) | 2-(CH$_2$═CHCH$_2$NHC(═O)) | U-8 (5) | 3-(CH$_2$═CHCH$_2$NHC(═O)) |
| U-1 (4) | 2-(N≡CCH$_2$NHC(═O)) | U-8 (5) | 3-(N≡CCH$_2$NHC(═O)) |
| U-1 (4) | 2-(OH—N═CH) | U-8 (5) | 3-(OH—N═CH) |
| U-1 (4) | 2-(Me$_2$NN═CH) | U-8 (5) | 3-(Me$_2$NN═CH) |
| U-1 (4) | 2-(MeOC(═O)NHN═CH) | U-8 (5) | 3-(MeOC(═O)NHN═CH) |
| U-1 (4) | 2-(OHC(═O)CH$_2$ON═CH) | U-8 (5) | 3-(OHC(═O)CH$_2$ON═CH) |
| U-1 (2) | — | U-12 (3) | 1-Me |
| U-1 (2) | 4-Me | U-12 (3) | 1,5-di-Me |
| U-1 (2) | 4-Et | U-12 (3) | 1-Me, 5-Et |
| U-1 (2) | 4-n-Pr | U-12 (3) | 1-Me, 5-n-Pr |
| U-1 (2) | 4-i-Pr | U-12 (3) | 1-Me, 5-i-Pr |
| U-1 (2) | 4-c-Pr | U-12 (3) | 1-Me, 5-c-Pr |
| U-1 (2) | 4-n-Bu | U-12 (3) | 1-Me, 5-n-Bu |
| U-1 (2) | 4-i-Bu | U-12 (3) | 1-Me, 5-i-Bu |
| U-1 (2) | 4-t-Bu | U-12 (3) | 1-Me, 5-t-Bu |
| U-1 (2) | 4-F | U-12 (3) | 1-Me, 5-F |
| U-1 (2) | 4-Cl | U-12 (3) | 1-Me, 5-Cl |
| U-1 (2) | 4-Br | U-12 (3) | 1-Me, 5-Br |
| U-1 (2) | 4-CF$_3$ | U-12 (3) | 1-Me, 5-CF$_3$ |
| U-1 (2) | 4-HO | U-12 (3) | 1-Me, 5-HO |
| U-1 (2) | 4-N≡C | U-12 (3) | 1-Me, 5-N≡C |
| U-1 (2) | 4-N═CCH$_2$ | U-12 (3) | 1-Me, 5-N═CCH$_2$ |
| U-1 (2) | 4-(MeO) | U-12 (3) | 1-Me, 5-(MeO) |
| U-1 (2) | 4-(MeOCH$_2$) | U-12 (3) | 1-Me, 5-(MeOCH$_2$) |
| U-1 (2) | 4-(EtOCH$_2$) | U-12 (3) | 1-Me, 5-(EtOCH$_2$) |
| U-1 (2) | 4-(CH(═O)) | U-12 (3) | 1-Me, 5-(CH(═O)) |
| U-1 (2) | 4-(HOC(═O)) | U-12 (3) | 1-Me, 5-(HOC(═O)) |
| U-1 (2) | 4-(MeOC(═O)) | U-12 (3) | 1-Me, 5-(MeOC(═O)) |
| U-1 (2) | 4-(EtOC(═O)) | U-12 (3) | 1-Me, 5-(EtOC(═O)) |
| U-1 (2) | 4-(i-PrOC(═O)) | U-12 (3) | 1-Me, 5-(i-PrOC(═O)) |
| U-1 (2) | 4-(n-PrOC(═O)) | U-12 (3) | 1-Me, 5-(n-PrOC(═O)) |
| U-1 (2) | 4-(BuOC(═O) | U-12 (3) | 1-Me, 5-(BuOC(═O)) |
| U-1 (2) | 4-(i-BuOC(═O)) | U-12 (3) | 1-Me, 5-(i-BuOC(═O)) |

TABLE 2-continued

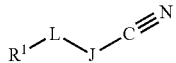

| L is CH₂ and J is J-40. | | L is CH₂ and J is J-40. | |
|---|---|---|---|
| R¹ | (R²)ₓ | R¹ | R¹ |
| U-1 (2) | 4-(t-BuOC(=O)) | U-12 (3) | 1-Me, 5-(t-BuOC(=O)) |
| U-1 (2) | 4-(CF₃CH₂OC(=O)) | U-12 (3) | 1-Me, 5-(CF₃CH₂OC(=O) |
| U-1 (2) | 4-(CH₂=CHOC(=O)) | U-12 (3) | 1-Me, 5-(CH₂=CHOC(=O)) |
| U-1 (2) | 4-(CH₂=CHCH₂OC(=O)) | U-12 (3) | 1-Me, 5-(CH₂=CHCH₂OC(=O)) |
| U-1 (2) | 4-(CH₂=CBrCH₂OC(=O)) | U-12 (3) | 1-Me, 5-(CH₂=CBrCH₂OC(=O)) |
| U-1 (2) | 4-(CH₂=CHCF₂OC(=O)) | U-12 (3) | 1-Me, 5-(CH₂=CHCF₂OC(=O)) |
| U-1 (2) | 4-(Me₂C=CHCH₂OC(=O)) | U-12 (3) | 1-Me, 5-(Me₂C=CHCH₂OC(=O)) |
| U-1 (2) | 4-(CH₂=C(Me)CH₂OC(=O)) | U-12 (3) | 1-Me, 5-(CH₂=C(Me)CH₂OC(=O)) |
| U-1 (2) | 4-(CH≡CCH₂OC(=O)) | U-12 (3) | 1-Me, 5-(CH≡CCH₂OC(=O)) |
| U-1 (2) | 4-(N≡CCH₂OC(=O)) | U-12 (3) | 1-Me, 5-(N≡CCH₂OC(=O)) |
| U-1 (2) | 4-(MeNHC(=O)) | U-12 (3) | 1-Me, 5-(MeNHC(=O)) |
| U-1 (2) | 4-(Me₂NC(=O)) | U-12 (3) | 1-Me, 5-(Me₂NC(=O)) |
| U-1 (2) | 4-(MeNHC(=O)) | U-12 (3) | 1-Me, 5-(MeNHC(=O)) |
| U-1 (2) | 4-(EtNHC(=O)) | U-12 (3) | 1-Me, 5-(EtNHC(=O)) |
| U-1 (2) | 4-(PrNHC(=O)) | U-12 (3) | 1-Me, 5-(PrNHC(=O)) |
| U-1 (2) | 4-(i-PrNHC(=O)) | U-12 (3) | 1-Me, 5-(i-PrNHC(=O)) |
| U-1 (2) | 4-(BuNHC(=O)) | U-12 (3) | 1-Me, 5-(BuNHC(=O)) |
| U-1 (2) | 4-(t-BuNHC(=O)) | U-12 (3) | 1-Me, 5-(t-BuNHC(=O)) |
| U-1 (2) | 4-(i-BuNHC(=O)) | U-12 (3) | 1-Me, 5-(i-BuNHC(=O)) |
| U-1 (2) | 4-(CF₃CH₂NHC(=O)) | U-12 (3) | 1-Me, 5-(CF₃CH₂NHC(=O)) |
| U-1 (2) | 4-(c-PrCH₂NHC(=O)) | U-12 (3) | 1-Me, 5-(c-PrCH₂NHC(=O)) |
| U-1 (2) | 4-(MeOCH₂NHC(=O)) | U-12 (3) | 1-Me, 5-(MeOCH₂NHC(=O)) |
| U-1 (2) | 4-(MeOCH₂CH₂NHC(=O)) | U-12 (3) | 1-Me, 5-(MeOCH₂CH₂NHC(=O)) |
| U-1 (2) | 4-(CH₂=CHCH₂NHC(=O)) | U-12 (3) | 1-Me, 5-(CH₂=CHCH₂NHC(=O)) |
| U-1 (2) | 4-(N≡CCH₂NHC(=O)) | U-12 (3) | 1-Me, 5-(N≡CCH₂NHC(=O)) |
| U-1 (2) | 4-(OH—N=CH) | U-12 (3) | 1-Me, 5-(OH—N=CH) |
| U-1 (2) | 4-(Me₂NN=CH) | U-12 (3) | 1-Me, 5-(Me₂NN=CH) |
| U-1 (2) | 4-(MeOC(=O)NHN=CH) | U-12 (3) | 1-Me, 5-(MeOC(=O)NHN=CH) |
| U-1 (2) | 4-(OHC(=O)CH₂ON=CH) | U-12 (3) | 1-Me, 5-(OHC(=O)CH₂ON=CH) |
| U-2 (2) | — | U-12 (1) | — |
| U-2 (2) | 4-Me | U-12 (1) | 4-Me |
| U-2 (2) | 4-Et | U-12 (1) | 4-Et |
| U-2 (2) | 4-n-Pr | U-12 (1) | 4-n-Pr |
| U-2 (2) | 4-i-Pr | U-12 (1) | 4-i-Pr |
| U-2 (2) | 4-c-Pr | U-12 (1) | 4-c-Pr |
| U-2 (2) | 4-n-Bu | U-12 (1) | 4-n-Bu |
| U-2 (2) | 4-i-Bu | U-12 (1) | 4-i-Bu |
| U-2 (2) | 4-t-Bu | U-12 (1) | 4-t-Bu |
| U-2 (2) | 4-F | U-12 (1) | 4-F |
| U-2 (2) | 4-Cl | U-12 (1) | 4-Cl |
| U-2 (2) | 4-Br | U-12 (1) | 4-Br |
| U-2 (2) | 4-CF₃ | U-12 (1) | 4-CF₃ |
| U-2 (2) | 4-HO | U-12 (1) | 4-HO |
| U-2 (2) | 4-N≡C | U-12 (1) | 4-N≡C |
| U-2 (2) | 4-N=CCH₂ | U-12 (1) | 4-N=CCH₂ |
| U-2 (2) | 4-(MeO) | U-12 (1) | 4-(MeO) |
| U-2 (2) | 4-(MeOCH₂) | U-12 (1) | 4-(MeOCH₂) |
| U-2 (2) | 4-(EtOCH₂) | U-12 (1) | 4-(EtOCH₂) |
| U-2 (2) | 4-(CH(=O)) | U-12 (1) | 4-(CH(=O)) |
| U-2 (2) | 4-(HOC(=O)) | U-12 (1) | 4-(HOC(=O)) |
| U-2 (2) | 4-(MeOC(=O)) | U-12 (1) | 4-(MeOC(=O)) |
| U-2 (2) | 4-(EtOC(=O)) | U-12 (1) | 4-(EtOC(=O)) |
| U-2 (2) | 4-(i-PrOC(=O)) | U-12 (1) | 4-(i-PrOC(=O)) |
| U-2 (2) | 4-(n-PrOC(=O)) | U-12 (1) | 4-(n-PrOC(=O)) |
| U-2 (2) | 4-(BuOC(=O)) | U-12 (1) | 4-(BuOC(=O)) |
| U-2 (2) | 4-(i-BuOC(=O)) | U-12 (1) | 4-(i-BuOC(=O)) |
| U-2 (2) | 4-(t-BuOC(=O)) | U-12 (1) | 4-(t-BuOC(=O)) |
| U-2 (2) | 4-(CF₃CH₂OC(=O) | U-12 (1) | 4-(CF₃CH₂OC(=O) |
| U-2 (2) | 4-(CH₂=CHOC(=O)) | U-12 (1) | 4-(CH₂=CHOC(=O)) |
| U-2 (2) | 4-(CH₂=CHCH₂OC(=O)) | U-12 (1) | 4-(CH₂=CHCH₂OC(=O)) |
| U-2 (2) | 4-(CH₂=CBrCH₂OC(=O)) | U-12 (1) | 4-(CH₂=CBrCH₂OC(=O)) |
| U-2 (2) | 4-(CH₂=CHCF₂OC(=O)) | U-12 (1) | 4-(CH₂=CHCF₂OC(=O)) |
| U-2 (2) | 4-(Me₂C=CHCH₂OC(=O)) | U-12 (1) | 4-(Me₂C=CHCH₂OC(=O)) |
| U-2 (2) | 4-(CH₂=C(Me)CH₂OC(=O)) | U-12 (1) | 4-(CH₂=C(Me)CH₂OC(=O)) |
| U-2 (2) | 4-(CH≡CCH₂OC(=O)) | U-12 (1) | 4-(CH≡CCH₂OC(=O)) |
| U-2 (2) | 4-(N≡CCH₂OC(=O)) | U-12 (1) | 4-(N≡CCH₂OC(=O)) |
| U-2 (2) | 4-(MeNHC(=O)) | U-12 (1) | 4-(MeNHC(=O)) |
| U-2 (2) | 4-(Me₂NC(=O)) | U-12 (1) | 4-(Me₂NC(=O)) |
| U-2 (2) | 4-(MeNHC(=O)) | U-12 (1) | 4-(MeNHC(=O)) |
| U-2 (2) | 4-(EtNHC(=O)) | U-12 (1) | 4-(EtNHC(=O)) |
| U-2 (2) | 4-(PrNHC(=O)) | U-12 (1) | 4-(PrNHC(=O)) |

TABLE 2-continued

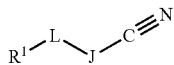

| L is CH₂ and J is J-40. | | L is CH₂ and J is J-40. | |
|---|---|---|---|
| R¹ | (R²)ₓ | R¹ | R¹ |
| U-2 (2) | 4-(i-PrNHC(=O)) | U-12 (1) | 4-(i-PrNHC(=O)) |
| U-2 (2) | 4-(BuNHC(=O)) | U-12 (1) | 4-(BuNHC(=O)) |
| U-2 (2) | 4-(t-BuNHC(=O)) | U-12 (1) | 4-(t-BuNHC(=O)) |
| U-2 (2) | 4-(i-BuNHC(=O)) | U-12 (1) | 4-(i-BuNHC(=O)) |
| U-2 (2) | 4-(CF₃CH₂NHC(=O)) | U-12 (1) | 4-(CF₃CH₂NHC(=O)) |
| U-2 (2) | 4-(c-PrCH₂NHC(=O)) | U-12 (1) | 4-(c-PrCH₂NHC(=O)) |
| U-2 (2) | 4-(MeOCH₂NHC(=O)) | U-12 (1) | 4-(MeOCH₂NHC(=O)) |
| U-2 (2) | 4-(MeOCH₂CH₂NHC(=O)) | U-12 (1) | 4-(MeOCH₂CH₂NHC(=O)) |
| U-2 (2) | 4-(CH₂=CHCH₂NHC(=O)) | U-12 (1) | 4-(CH₂=CHCH₂NHC(=O)) |
| U-2 (2) | 4-(N≡CCH₂NHC(=O)) | U-12 (1) | 4-(N≡CCH₂NHC(=O)) |
| U-2 (2) | 4-(OH—N=CH) | U-12 (1) | 4-(OH—N=CH) |
| U-2 (2) | 4-(Me₂NN=CH) | U-12 (1) | 4-(Me₂NN=CH) |
| U-2 (2) | 4-(MeOC(=O)NHN=CH) | U-12 (1) | 4-(MeOC(=O)NHN=CH) |
| U-2 (2) | 4-(OHC(=O)CH₂ON=CH) | U-12 (1) | 4-(OHC(=O)CH₂ON=CH) |
| U-2 (4) | — | U-69 (1) | — |
| U-2 (4) | 2-Me | U-69 (1) | 4-Me |
| U-2 (4) | 2-Et | U-69 (1) | 4-Et |
| U-2 (4) | 2-n-Pr | U-69 (1) | 4-n-Pr |
| U-2 (4) | 2-i-Pr | U-69 (1) | 4-i-Pr |
| U-2 (4) | 2-c-Pr | U-69 (1) | 4-c-Pr |
| U-2 (4) | 2-n-Bu | U-69 (1) | 4-n-Bu |
| U-2 (4) | 2-i-Bu | U-69 (1) | 4-i-Bu |
| U-2 (4) | 2-t-Bu | U-69 (1) | 4-t-Bu |
| U-2 (4) | 2-F | U-69 (1) | 4-F |
| U-2 (4) | 2-Cl | U-69 (1) | 4-Cl |
| U-2 (4) | 2-Br | U-69 (1) | 4-Br |
| U-2 (4) | 2-CF₃ | U-69 (1) | 4-CF₃ |
| U-2 (4) | 2-HO | U-69 (1) | 4-HO |
| U-2 (4) | 2-N≡C | U-69 (1) | 4-N≡C |
| U-2 (4) | 2-N=CCH₂ | U-69 (1) | 4-N=CCH₂ |
| U-2 (4) | 2-(MeO) | U-69 (1) | 4-(MeO) |
| U-2 (4) | 2-(MeOCH₂) | U-69 (1) | 4-(MeOCH₂) |
| U-2 (4) | 2-(EtOCH₂) | U-69 (1) | 4-(EtOCH₂) |
| U-2 (4) | 2-(CH(=O)) | U-69 (1) | 4-(CH(=O)) |
| U-2 (4) | 2-(HOC(=O)) | U-69 (1) | 4-(HOC(=O)) |
| U-2 (4) | 2-(MeOC(=O)) | U-69 (1) | 4-(MeOC(=O)) |
| U-2 (4) | 2-(EtOC(=O)) | U-69 (1) | 4-(EtOC(=O)) |
| U-2 (4) | 2-(i-PrOC(=O)) | U-69 (1) | 4-(i-PrOC(=O)) |
| U-2 (4) | 2-(n-PrOC(=O)) | U-69 (1) | 4-(n-PrOC(=O)) |
| U-2 (4) | 2-(BuOC(=O)) | U-69 (1) | 4-(BuOC(=O)) |
| U-2 (4) | 2-(i-BuOC(=O)) | U-69 (1) | 4-(i-BuOC(=O)) |
| U-2 (4) | 2-(t-BuOC(=O)) | U-69 (1) | 4-(t-BuOC(=O)) |
| U-2 (4) | 2-(CF₃CH₂OC(=O) | U-69 (1) | 4-(CF₃CH₂OC(=O) |
| U-2 (4) | 2-(CH₂=CHOC(=O)) | U-69 (1) | 4-(CH₂=CHOC(=O)) |
| U-2 (4) | 2-(CH₂=CHCH₂OC(=O)) | U-69 (1) | 4-(CH₂=CHCH₂OC(=O)) |
| U-2 (4) | 2-(CH₂=CBrCH₂OC(=O)) | U-69 (1) | 4-(CH₂=CBrCH₂OC(=O)) |
| U-2 (4) | 2-(CH₂=CHCF₂OC(=O)) | U-69 (1) | 4-(CH₂=CHCF₂OC(=O)) |
| U-2 (4) | 2-(Me₂C=CHCH₂OC(=O)) | U-69 (1) | 4-(Me₂C=CHCH₂OC(=O)) |
| U-2 (4) | 2-(CH₂=C(Me)CH₂OC(=O)) | U-69 (1) | 4-(CH₂=C(Me)CH₂OC(=O)) |
| U-2 (4) | 2-(CH≡CCH₂OC(=O)) | U-69 (1) | 4-(CH≡CCH₂OC(=O)) |
| U-2 (4) | 2-N(≡CCH₂OC(=O)) | U-69 (1) | 4-(N≡CCH₂OC(=O)) |
| U-2 (4) | 2-(MeNHC(=O)) | U-69 (1) | 4-(MeNHC(=O)) |
| U-2 (4) | 2-(Me₂NC(=O)) | U-69 (1) | 4-(Me₂NC(=O)) |
| U-2 (4) | 2-(MeNHC(=O)) | U-69 (1) | 4-(MeNHC(=O)) |
| U-2 (4) | 2-(EtNHC(=O)) | U-69 (1) | 4-(EtNHC(=O)) |
| U-2 (4) | 2-(PrNHC(=O)) | U-69 (1) | 4-(PrNHC(=O)) |
| U-2 (4) | 2-(i-PrNHC(=O)) | U-69 (1) | 4-(i-PrNHC(=O)) |
| U-2 (4) | 2-(BuNHC(=O)) | U-69 (1) | 4-(BuNHC(=O)) |
| U-2 (4) | 2-(t-BuNHC(=O)) | U-69 (1) | 4-(t-BuNHC(=O)) |
| U-2 (4) | 2-(i-BuNHC(=O)) | U-69 (1) | 4-(i-BuNHC(=O)) |
| U-2 (4) | 2-(CF₃CH₂NHC(=O)) | U-69 (1) | 4-(CF₃CH₂NHC(=O)) |
| U-2 (4) | 2-(c-PrCH₂NHC(=O)) | U-69 (1) | 4-(c-PrCH₂NHC(=O)) |
| U-2 (4) | 2-(MeOCH₂NHC(=O)) | U-69 (1) | 4-(MeOCH₂NHC(=O)) |
| U-2 (4) | 2-(MeOCH₂CH₂NHC(=O)) | U-69 (1) | 4-(MeOCH₂CH₂NHC(=O)) |
| U-2 (4) | 2-(CH₂=CHCH₂NHC(=O)) | U-69 (1) | 4-(CH₂=CHCH₂NHC(=O)) |
| U-2 (4) | 2-(N≡CCH₂NHC(=O)) | U-69 (1) | 4-(N≡CCH₂NHC(=O)) |

TABLE 2-continued $$R^1 \text{—} L \text{—} J \text{—} C \equiv N \qquad 3$$

| R¹ (L is CH₂ and J is J-40.) | (R²)ₓ | R¹ (L is CH₂ and J is J-40.) | R¹ |
|---|---|---|---|
| U-2 (4) | 2-(OH—N=CH) | U-69 (1) | 4-(OH—N=CH) |
| U-2 (4) | 2-(Me₂NN=CH) | U-69 (1) | 4-(Me₂NN=CH) |
| U-2 (4) PA105 | 2-(MeOC(=O)NHN=CH) | U-69 (1) | 4-(MeOC(=O)NHN=CH) |
| U-2 (4) | 2-(OHC(=O)CH₂ON=CH) | U-69 (1) | 4-(OHC(=O)CH₂OH=CH) |

The definitions of R¹ and J in Table 2 are as defined Exhibits A and B in the above Embodiments. In the column R¹, the number in parentheses following the U-ring refers to the attachment point of the ring to L. The (R²)ₓ column refers to the substituent(s) attached to the U-ring as shown in Exhibit A above. A dash "—" in the (R²)ₓ column means that no R² substituent is present and the remaining valences are occupied by hydrogen atoms.

The present disclosure also includes Tables 1B through 47B, each of which is constructed the same as Table 2 above, except that the row heading in Table 2 (i.e. "L is CH₂ and J is J-40") is replaced with the respective row heading shown below.

| Table | Row Heading |
|---|---|
| 1B | L is CH₂CH₂ and J is J-40. |
| 2B | L is CH₂(Me) and J is J-40. |
| 3B | L is CH₂CH₂CH₂ and J is J-40. |
| 4B | L is OCH₂ and J is J-40. |
| 5B | L is CH₂O and J is J-40. |
| 6B | L is CH₂OCH₂ and J is J-40. |
| 7B | L is CH₂ and J is J-4. |
| 8B | L is CH₂CH₂ and J is J-4. |
| 9B | L is CH₂(Me) and J is J-4. |
| 10B | L is CH₂CH₂CH₂ and J is J-4. |
| 11B | L is OCH₂ and J is J-4. |
| 12B | L is CH₂O and J is J-4. |
| 13B | L is CH₂OCH₂ and J is J-4. |
| 14B | L is CH₂ and J is J-18. |
| 15B | L is CH₂CH₂ and J is J-18. |
| 16B | L is CH₂(Me) and J is J-18. |
| 17B | L is CH₂CH₂CH₂ and J is J-18. |
| 18B | L is OCH₂ and J is J-18. |
| 19B | L is CH₂O and J is J-18. |
| 20B | L is CH₂OCH₂ and J is J-18. |
| 21B | L is CH₂ and J is J-27. |
| 22B | L is CH₂CH₂ and J is J-27. |
| 23B | L is CH₂(Me) and J is J-27. |
| 24B | L is CH₂CH₂CH₂ and J is J-27. |
| 25B | L is OCH₂ and J is J-27. |
| 26B | L is CH₂O and J is J-27. |
| 27B | L is CH₂OCH₂ and J is J-27. |
| 28B | L is CH₂ and J is J-63. |
| 29B | L is CH₂CH₂ and J is J-63. |
| 30B | L is CH₂(Me) and J is J-63. |
| 31B | L is CH₂CH₂CH₂ and J is J-63. |
| 32B | L is OCH₂ and J is J-63. |
| 33B | L is CH₂O and J is J-63. |
| 34B | L is CH₂OCH₂ and J is J-63. |
| 35B | L is CH₂ and J is J-73. |
| 36B | L is CH₂CH₂ and J is J-73. |
| 37B | L is CH₂(Me) and J is J-73. |
| 38B | L is CH₂CH₂CH₂ and J is J-73. |
| 39B | L is OCH₂ and J is J-73. |
| 40B | L is CH₂O and J is J-73. |
| 41B | L is CH₂OCH₂ and J is J-73. |
| 42B | L is CH₂ and J is J-93. |
| 43B | L is CH₂CH₂ and J is J-93. |
| 44B | L is CH₂(Me) and J is J-93. |
| 45B | L is CH₂CH₂CH₂ and J is J-93. |
| 46B | L is OCH₂ and J is J-93. |
| 47B | L is CH₂O and J is J-93. |
| 48B | L is CH₂OCH₂ and J is J-93. |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pp 8-57 and following, and WO 91/13546. Pellets can be prepared as described in U.S. Pat. No. 4,172,714. Water-dispersible and water-soluble granules can be prepared as taught in U.S. Pat. Nos. 4,144,050, 3,920,442 and DE 3,246,493. Tablets can be prepared as taught in U.S. Pat. Nos. 5,180,587, 5,232,701 and 5,208,030. Films can be prepared as taught in GB 2,095,558 and U.S. Pat. No. 3,299,566.

One embodiment of the present invention relates to a method for controlling fungal pathogens, comprising diluting the fungicidal composition of the present invention (a compound of Formula 1 formulated with surfactants, solid diluents and liquid diluents or a formulated mixture of a compound of Formula 1 and at least one other fungicide) with water, and optionally adding an adjuvant to form a diluted composition, and contacting the fungal pathogen or its environment with an effective amount of said diluted composition.

Although a spray composition formed by diluting with water a sufficient concentration of the present fungicidal composition can provide sufficient efficacy for controlling fungal pathogens, separately formulated adjuvant products can also be added to spray tank mixtures. These additional adjuvants are commonly known as "spray adjuvants" or "tank-mix adjuvants", and include any substance mixed in a spray tank to improve the performance of a pesticide or alter the physical properties of the spray mixture. Adjuvants can be anionic or nonionic surfactants, emulsifying agents, petroleum-based crop oils, crop-derived seed oils, acidifiers, buffers, thickeners or defoaming agents. Adjuvants are used to enhancing efficacy (e.g., biological availability, adhesion, penetration, uniformity of coverage and durability of protection), or minimizing or eliminating spray application problems associated with incompatibility, foaming, drift, evaporation, volatilization and degradation. To obtain optimal performance, adjuvants are selected with regard to the properties of the active ingredient, formulation and target (e.g., crops, insect pests).

The amount of adjuvants added to spray mixtures is generally in the range of about 2.5% to 0.1% by volume. The application rates of adjuvants added to spray mixtures are typically between about 1 to 5 L per hectare. Representative examples of spray adjuvants include: Adigor® (Syngenta) 47% methylated rapeseed oil in liquid hydrocarbons, Silwet® (Helena Chemical Company) polyalkyleneoxide modified heptamethyltrisiloxane and Assist® (BASF) 17% surfactant blend in 83% paraffin based mineral oil.

One method of seed treatment is by spraying or dusting the seed with a compound of the invention (i.e. as a formulated composition) before sowing the seeds. Compositions formulated for seed treatment generally comprise a film former or adhesive agent. Therefore typically a seed coating composition of the present invention comprises a biologically effective amount of a compound of Formula 1 and a film former or adhesive agent. Seeds can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treatment: Progress and Prospects*, 1994 BCPC Mongraph No. 57, and references listed therein.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. Also see U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, U K, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be constructed as merely illustrative, and not limiting of the disclosure in any way whatsoever.

Example A

| High Strength Concentrate | |
|---|---|
| Compound 21 | 98.5% |
| silica aerogel | 0.5% |
| synthetic amorphous fine silica | 1.0% |

Example B

| Wettable Powder | |
|---|---|
| Compound 198 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 316 | 10.0% |
| attapulgite granules (low volatile matter, 0.71/0.30 mm; U.S.S. No. 25-50 sieves) | 90.0% |

Example D

| Extruded Pellet | |
|---|---|
| Compound 198 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example D

| Emulsifiable Concentrate | |
|---|---|
| Compound 56 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 57 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 58 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Fertilizer Stick | |
|---|---|
| Compound 147 | 2.50% |
| pyrrolidone-styrene copolymer | 4.80% |
| tristyrylphenyl 16-ethoxylate | 2.30% |
| talc | 0.80% |
| corn starch | 5.00% |
| slow-release fertilizer | 36.00% |
| kaolin | 38.00% |
| water | 10.60% |

Example I

| Suspension Concentrate | |
|---|---|
| Compound 152 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| water | 53.7% |

Example J

| Emulsion in Water | |
|---|---|
| Compound 157 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example K

| Oil Dispersion | |
|---|---|
| Compound 83 | 25% |
| polyoxyethylene sorbitol hexaoleate | 15% |
| organically modified bentonite clay | 2.5% |
| fatty acid methyl ester | 57.5% |

Example L

| Suspoemulsion | |
|---|---|
| Compound 110 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Water-soluble and water-dispersible formulations are typically diluted with water to form aqueous compositions before application. Aqueous compositions for direct applications to the plant or portion thereof (e.g., spray tank compositions) typically contain at least about 1 ppm or more (e.g., from 1 ppm to 100 ppm) of the compound(s) of this invention.

Seed is normally treated at a rate of from about 0.001 g (more typically about 0.1 g) to about 10 g per kilogram of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Ascomycota, Basidiomycota, Zygomycota phyla, and the fungal-like Oomycata class. They are effective in controlling a broad spectrum of plant diseases, particularly foliar pathogens of ornamental, turf, vegetable, field, cereal, and fruit crops. These pathogens include but are not limited to those listed in Table 1-1. For Ascomycetes and Basidiomycetes, names for both the sexual/teleomorph/perfect stage as well as names for the asexual/anamorph/imperfect stage (in parentheses) are listed where known. Synonymous names for pathogens are indicated by an equal sign. For example, the sexual/teleomorph/perfect stage name *Phaeosphaeria nodorum* is followed by the corresponding asexual/anamorph/imperfect stage name *Stagnospora nodorum* and the synonymous older name *Septoria nodorum*.

TABLE 1-1

Ascomycetes in the order Pleosporales including *Alternaria solani*, *A. alternata* and *A. brassicae*, *Guignardia bidwellii*, *Venturia inaequalis*, *Pyrenophora tritici-repentis* (*Dreschlera tritici-repentis* = *Helminthosporium tritici-repentis*) and *Pyrenophora teres* (*Dreschlera teres* = *Helminthosporium teres*), *Corynespora cassiicola*, *Phaeosphaeria nodorum* (*Stagonospora nodorum* = *Septoria nodorum*), *Cochliobolus carbonum* and *C. heterostrophus*, *Leptosphaeria biglobosa* and *L. maculans*;
Ascomycetes in the order Mycosphaerellales including *Mycosphaerella graminicola* (*Zymoseptoria tritici* = *Septoria tritici*), *M. berkeleyi* (*Cercosporidium personatum*), *M. arachidis* (*Cercospora arachidicola*), *Passalora sojina* (*Cercospora sojina*), *Cercospora zeae-maydis* and *C. beticola*;
Ascomycetes in the order Erysiphales (the powdery mildews) such as *Blumeria graminis* f. sp. *tritici* and *Blumeria graminis* f. sp. *hordei*, *Erysiphe polygoni*, *E. necator* (=*Uncinula necator*), *Podosphaera fuliginea* (=*Sphaerotheca fuliginea*), and *Podosphaera leucotricha* (=*Sphaerotheca fuliginea*);

TABLE 1-1-continued

Ascomycetes in the order Helotiales such as *Botryotinia fuckeliana* (*Botrytis cinerea*), *Oculimacula yallundae* (=*Tapesia yallundae*; anamorph *Helgardia herpotrichoides* = *Pseudocercosporella herpetrichoides*), *Monilinia fructicola*, *Sclerotinia sclerotiorum*, *Sclerotinia minor*, and *Sclerotinia homoeocarpa*;
Ascomycetes in the order Hypocreales such as *Giberella zeae* (*Fusarium graminearum*), *G. monoliformis* (*Fusarium moniliforme*), *Fusarium solani* and *Verticillium dahliae*;
Ascomycetes in the order Eurotiales such as *Aspergillus flavus* and *A. parasiticus*;
Ascomycetes in the order Diaporthales such as *Cryptosphorella viticola* (=*Phomopsis viticola*), *Phomopsis longicolla*, and *Diaporthe phaseolorum*;
Other Ascomycete pathogens including *Magnaporthe grisea*, *Gaeumannomyces graminis*, *Rhynchosporium secalis*, and anthracnose pathogens such as *Glomerella acutata* (*Colletotrichum acutatum*), *G. graminicola* (*C. graminicola*) and *G. lagenaria* (*C. orbiculare*);
Basidiomycetes in the order Urediniales (the rusts) including *Puccinia recondita*, *P. striiformis*, *Puccinia hordei*, *P. graminis* and *P. arachidis*), *Hemileia vastatrix* and *Phakopsora pachyrhizi*;
Basidiomycetes in the order Ceratobasidiales such as *Thanatophorum cucumeris* (*Rhizoctonia solani*) and *Ceratobasidium oryzae-sativae* (*Rhizoctonia oryzae*);
Basidiomycetes in the order Polyporales such as *Athelia rolfsii* (*Sclerotium rolfsii*);
Basidiomycetes in the order Ustilaginales such as *Ustilago maydis*;
Zygomycetes in the order Mucorales such as *Rhizopus stolonifer*;
Oomycetes in the order Pythiales, including *Phytophthora infestans*, *P. megasperma*, *P. parasitica*, *P. sojae*, *P. cinnamomi* and *P. capsici*, and *Pythium* pathogens such as *Pythium aphanidermatum*, *P. graminicola*, *P. irregulare*, *P. ultimum* and *P. dissoticum*;
Oomycetes in the order Peronosporales such as *Plasmopara viticola*, *P. halstedii*, *Peronospora hyoscyami* (=*Peronospora tabacina*), *P. manshurica*, *Hyaloperonospora parasitica* (=*Peronospora parasitica*), *Pseudoperonospora cubensis* and *Bremia lactucae*;
and other genera and species closely related to all of the above pathogens.

In addition to their fungicidal activity, the compositions or combinations also have activity against bacteria such as *Erwinia amylovora, Xanthomonas campestris, Pseudomonas syringae*, and other related species. By controlling harmful microorganisms, the compounds of the invention are useful for improving (i.e. increasing) the ratio of beneficial to harmful microorganisms in contact with crop plants or their propagules (e.g., seeds, corms, bulbs, tubers, cuttings) or in the agronomic environment of the crop plants or their propagules.

Compounds of the invention are useful in treating all plants, plant parts and seeds. Plant and seed varieties and cultivars can be obtained by conventional propagation and breeding methods or by genetic engineering methods. Genetically modified plants or seeds (transgenic plants or seeds) are those in which a heterologous gene (transgene) has been stably integrated into the plant's or seed's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance.

Treatment of genetically modified plants and seeds with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants and seeds.

Compounds of this invention are useful in seed treatments for protecting seeds from plant diseases. In the context of the present disclosure and claims, treating a seed means contacting the seed with a biologically effective amount of a compound of this invention, which is typically formulated as a composition of the invention. This seed treatment protects the seed from soil-borne disease pathogens and generally can also protect roots and other plant parts in contact with the soil of the seedling developing from the germinating seed. The seed treatment may also provide protection of foliage by translocation of the compound of this invention or a second active ingredient within the developing plant. Seed treatments can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance such as glyphosate acetyltransferase, which provides resistance to glyphosate. Seed treatments with compounds of this invention can also increase vigor of plants growing from the seed.

Compounds of this invention and their compositions, both alone and in combination with other fungicides, nematicides and insecticides, are particularly useful in seed treatment for crops including, but not limited to, maize or corn, soybeans, cotton, cereal (e.g., wheat, oats, barley, rye and rice), potatoes, vegetables and oilseed rape.

Furthermore, the compounds of this invention are useful in treating postharvest diseases of fruits and vegetables caused by fungi and bacteria. These infections can occur before, during and after harvest. For example, infections can occur before harvest and then remain dormant until some point during ripening (e.g., host begins tissue changes in such a way that infection can progress); also infections can arise from surface wounds created by mechanical or insect injury. In this respect, the compounds of this invention can reduce losses (i.e. losses resulting from quantity and quality) due to postharvest diseases which may occur at any time from harvest to consumption. Treatment of postharvest diseases with compounds of the invention can increase the period of time during which perishable edible plant parts (e.g, fruits, seeds, foliage, stems, bulbs, tubers) can be stored refrigerated or un-refrigerated after harvest, and remain edible and free from noticeable or harmful degradation or contamination by fungi or other microorganisms. Treatment of edible plant parts before or after harvest with compounds of the invention can also decrease the formation of toxic metabolites of fungi or other microorganisms, for example, mycotoxins such as aflatoxins.

Plant disease control is ordinarily accomplished by applying an effective amount of a compound of this invention either pre- or post-infection, to the portion of the plant to be protected such as the roots, stems, foliage, fruits, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants. Control of postharvest pathogens which infect the produce before harvest is typically accomplished by field application of a compound of this invention, and in cases where infection occurs after harvest the compounds can be applied to the harvested crop as dips, sprays, fumigants, treated wraps and box liners.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.001 g (more typically about 0.1 g) to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

As mentioned in the Summary of the Invention, one aspect of the present invention is a fungicidal composition comprising (i.e. a mixture or combination of) a compound of Formula 1, an N-oxide, or a salt thereof (i.e. component a), and at least one other fungicide (i.e. component b). Of note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a fungicidally effective amount of at least one additional fungicidal active ingredient having a similar spectrum of control but a different site of action.

Of note is a composition which in addition to the Formula 1 compound of component (a), includes as component (b) at least one fungicidal compound selected from the group consisting of the FRAC-defined mode of action (MOA) classes (A) nucleic acid synthesis, (B) mitosis and cell division, (C) respiration, (D) amino acid and protein synthesis, (E) signal transduction, (F) lipid synthesis and membrane integrity, (G) sterol biosynthesis in membranes, (H) cell wall biosynthesis in membranes, (I) melanin synthesis in cell wall, (P) host plant defense induction, multi-site contact activity and unknown mode of action.

FRAC-recognized or proposed target sites of action along with their FRAC target site codes belonging to the above MOA classes are (A1) RNA polymerase I, (A2) adenosine deaminase, (A3) DNA/RNA synthesis (proposed), (A4) DNA topoisomerase, (B1-B3) β-tubulin assembly in mitosis, (B4) cell division (proposed), (B5) delocalization of spectrin-like proteins, (C1) complex I NADH odxido-reductase, (C2) complex II: succinate dehydrogenase, (C3) complex III: cytochrome bc1 (ubiquinol oxidase) at Qo site, (C4) complex III: cytochrome bc1 (ubiquinone reductase) at Qi site, (C5) uncouplers of oxidative phosphorylation, (C6) inhibitors of oxidative phosphorylation, ATP synthase, (C7) ATP production (proposed), (C8) complex III: cytochrome bc1 (ubiquinone reductase) at Qx (unknown) site, (D1) methionine biosynthesis (proposed), (D2-D5) protein synthesis, (E1) signal transduction (mechanism unknown), (E2-E3) MAP/histidine kinase in osmotic signal transduction, (F2) phospholipid biosynthesis, methyl transferase, (F3) lipid peroxidation (proposed), (F4) cell membrane permeability, fatty acids (proposed), (F6) microbial disrupters of pathogen cell membranes, (F7) cell membrane disruption (proposed), (G1) C14-demethylase in sterol biosynthesis, (G2) Δ14-reductase and Δ8→Δ7-isomerase in sterol biosynthesis, (G3) 3-keto reductase, C4-demethylation, (G4) squalene epoxidase in sterol biosynthesis, (H3) trehalase and inositol biosynthesis, (H4) chitin synthase, (H5) cellulose synthase, (I1) reductase in melanin biosynthesis and (I2) dehydratase in melanin biosynthesis.

Of particular note is a composition which in addition to the Formula 1 compound of component (a), includes as component (b) at least one fungicidal compound selected from the group consisting of the classes (b1) methyl benzimidazole carbamate (MBC) fungicides; (b2) dicarboximide fungicides; (b3) demethylation inhibitor (DMI) fungicides; (b4) phenylamide fungicides; (b5) amine/morpholine fungicides; (b6) phospholipid biosynthesis inhibitor fungicides; (b7) succinate dehydrogenase inhibitor fungicides; (b8) hydroxy(2-amino-)pyrimidine fungicides; (b9) anilinopyrimidine fungicides; (b10) N-phenyl carbamate fungicides; (b11) quinone outside inhibitor (QoI) fungicides; (b12) phenylpyrrole fungicides; (b13) azanaphthalene fungicides; (b14) lipid peroxidation inhibitor fungicides; (b15) melanin biosynthesis inhibitor-reductase (MBI-R) fungicides; (b16) melanin biosynthesis inhibitor-dehydratase (MBI-D) fungicides; (b17) sterol biosynthesis inhibitor (SBI): Class III fungicides; (b18) squalene-epoxidase inhibitor fungicides; (b19) polyoxin fungicides; (b20) phenylurea fungicides; (b21) quinone inside inhibitor (QiI) fungicides; (b22) benzamide and thiazole carboxamide fungicides; (b23) enopyranuronic acid antibiotic fungicides; (b24) hexopyranosyl antibiotic fungicides; (b25) glucopyranosyl antibiotic: protein synthesis fungicides; (b26) glucopyranosyl antibiotic: trehalase and inositol biosynthesis fungicides; (b27) cyanoacetamideoxime fungicides; (b28) carbamate fungicides; (b29) oxidative phosphorylation uncoupling fungicides; (b30) organo tin fungicides; (b31) carboxylic acid fungicides; (b32) heteroaromatic fungicides; (b33) phosphonate fungicides; (b34) phthalamic acid fungicides; (b35) benzotriazine fungicides; (b36) benzene-sulfonamide fungicides; (b37) pyridazinone fungicides; (b38) thiophene-carboxamide fungicides; (b39) complex I NADH oxidoreductase inhibitor fungicides; (b40) carboxylic acid amide (CAA) fungicides; (b41) tetracycline antibiotic fungicides; (b42) thiocarbamate fungicides; (b43) benzamide fungicides; (b44) microbial fungicides; (b45) $Q_xI$ fungicides; (b46) plant extract fungicides; (b47) host plant defense induction fungicides; (b48) multi-site contact activity fungicides; (b49) fungicides other than fungicides of classes (b1) through (b48); and salts of compounds of classes (b1) through (b48).

Further descriptions of these classes of fungicidal compounds are provided below.

(b1) "Methyl benzimidazole carbamate (MBC) fungicides" (FRAC code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(b2) "Dicarboximide fungicides" (FRAC code 2) inhibit a MAP/histidine kinase in osmotic signal transduction. Examples include chlozolinate, iprodione, procymidone and vinclozolin.

(b3) "Demethylation inhibitor (DMI) fungicides" (FRAC code 3) (Sterol Biosynthesis Inhibitors (SBI): Class I) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines, pyridines and triazolinthiones. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, quinconazole, simeconazole, tebuconazole, tetraconazole, triadimefon, triadimenol, triticonazole, uniconazole, uniconazole-P, α-(1-chlorocyclopropyl)-α-[2-(2,2-dichlorocyclopropyl)ethyl]-1H-1,2,4-triazole-1-ethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chlorophenyl)-2-(2,4-difluorophenyl)-2-oxiranyl]methyl]-1,2-dihydro-3H-1,2,4-triazole-3-thione, and rel-1-[[(2R,3S)-3-(2-chlorophenyl)-2-(2,4-difluorophenyl)-2-oxiranyl]methyl]-5-(2-propen-1-ylthio)-1H-1,2,4-triazole. The imidazoles include econazole, imazalil, oxpoconazole, prochloraz, pefurazoate and triflumizole. The pyrimidines include fenarimol, nuarimol and triarimol. The piperazines include triforine. The pyridines include buthiobate, pyrifenox, pyrisoxazole (3-[(3R)-5-(4-chlorophenyl)-2,3-dimethyl 3-isoxazolidinyl]pyridine, mixture of 3R,5R- and 3R,5S-isomers) and (αS)-[3-(4-chloro-2-fluorophenyl)5-(2,4-difluorophenyl)-4-isoxazolyl]-3-pyridinemethanol. The triazolinthiones include prothioconazole and 2-[2-(1-chlorocyclopropyl)-4-(2,2-dichloro-cyclopropyl)-2-hydroxybutyl]-1,2-dihydro-3H-1,2,4-triazole-3-thione. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(b4) "Phenylamide fungicides" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M (also known as kiralaxyl), furalaxyl, metalaxyl and metalaxyl-M (also known as mefenoxam). The oxazolidinones include oxadixyl. The butyrolactones include ofurace.

(b5) "Amine/morpholine fungicides" (FRAC code 5) (SBI: Class II) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(b6) "Phospholipid biosynthesis inhibitor fungicides" (FRAC code 6) inhibit growth of fungi by affecting phospholipid biosynthesis. Phospholipid biosynthesis fungicides include phophorothiolate and dithiolane fungicides. The phosphorothiolates include edifenphos, iprobenfos and pyrazophos. The dithiolanes include isoprothiolane.

(b7) "Succinate dehydrogenase inhibitor (SDHI) fungicides"" (FRAC code 7) inhibit Complex II fungal respiration by disrupting a key enzyme in the Krebs Cycle (TCA cycle) named succinate dehydrogenase. Inhibiting respiration prevents the fungus from making ATP, and thus inhibits growth and reproduction. SDHI fungicides include phenylbenzamide, furan carboxamide, oxathiin carboxamide, thiazole carboxamide, pyrazole-4-carboxamide, pyridine carboxamide, phenyl oxoethyl thiophene amides and pyridinylethyl benzamides The benzamides include benodanil, flutolanil and mepronil. The furan carboxamides include fenfuram. The oxathiin carboxamides include carboxin and oxycarboxin. The thiazole carboxamides include thifluzamide. The pyrazole-4-carboxamides include benzovindiflupyr (N-[9-(dichloromethylene)-1,2,3,4-tetrahydro-1,4-methanonaphthalen-5-yl]-3-(difluoromethyl)-1-methyl-1H-pyrazole-4-carboxamide), bixafen, fluindapyr, fluxapyroxad (3-(difluoromethyl)-1-methyl-N-(3',4',5'-trifluoro[1,1'-biphenyl]-2-yl)-1H-pyrazole-4-carboxamide), furametpyr, isopyrazam (3-(difluoromethyl)-1-methyl-N-[1,2,3,4-tetrahydro9-(1-methylethyl)-1,4-methanonaphthalen-5-yl]-1H-pyrazole-4-carboxamide), penflufen (N-[2-(1,3-dimethylbutyl)phenyl]-5-fluoro-1,3-dimethyl-1H-pyrazole-4-carboxamide), penthiopyrad, sedaxane (N-[2-[1,1'-bicyclopropyl]-2-ylphenyl]-3-(difluoromethyl)-1-methyl-1H-pyrazole-4-carboxamide), N-[2-(1S,2R)-[1,1'- bicyclopropyl]-2-ylphenyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, N-[2-(2,4-dichlorophenyl)2-methoxy-1-methylethyl]-3-(difluoromethyl)-1-methyl-1H-pyrazole-4-carboxamide and N-cyclopropyl-3-(difluoromethyl)-5-fluoro-1-methyl-N-[[2-(1-methylethyl)phenyl]methyl]-1H-pyrazole-4-carboxamide. The pyridine carboxamides include boscalid. The phenyl oxoethyl thiophene amides include isofetamid (N-[1,1-dimethyl-2-[2-methyl-4-(1-methylethoxy)phenyl]-2-oxoethyl]-3-methyl-2-thiophenecarboxamide). The pyridinylethyl benzamides include fluopyram.

(b8) "Hydroxy-(2-amino-)pyrimidine fungicides" (FRAC code 8) inhibit nucleic acid synthesis by interfering with adenosine deaminase. Examples include bupirimate, dimethirimol and ethirimol.

(b9) "Anilinopyrimidine fungicides" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(b10) "N-Phenyl carbamate fungicides" (FRAC code 10) inhibit mitosis by binding to β-tubulin and disrupting microtubule assembly. Inhibition of microtubule assembly can disrupt cell division, transport within the cell and cell structure. Examples include diethofencarb.

(b11) "Quinone outside inhibitor (QoI) fungicides" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, coumoxystrobin (methyl (αE)-2-[[(3-butyl-4-methyl-2-oxo-2H-1-benzopyran-7-yl)oxy]methyl]-α-(methoxymethylene)benzeneacetate), enoxastrobin (methyl (αE)-2-[[[(E)-[(2E)-3-(4-chlorophenyl)-1-methyl-2-propen-1-ylidene]amino]oxy]methyl]-α-(methoxymethylene)benzeneaceate) (also known as enestroburin), flufenoxystrobin (methyl (αE)-2-[[2-chloro-4-(trifluoromethyl)phenoxy]methyl]-α-(methoxymethylene)benzeneacetate), picoxystrobin, and pyraoxystrobin (methyl (αE)-2-[[[3-(4-chlorophenyl)-1-methyl-1H-pyrazol-5-yl]oxy]methyl]-α-(methoxymethylene)benzeneacetate). The methoxy-carbamates include pyraclostrobin, pyrametostrobin (methyl N-[2-[[[(1,4-dimethyl-3-phenyl-1H-pyrazol-5-yl)oxy]methyl]phenyl]-N-methoxycarbamate) and triclopyricarb (methyl N-methoxy-N-[2-[[(3,5,6-trichloro-2-pyridinyl)oxy]methyl]phenyl]carbamate). The oximino-acetates include kresoxim-methyl, and trifloxystrobin. The oximinoacetamides include dimoxystrobin, fenaminstrobin ((αE)-2-[[[(E)-[(2E)-3-(2,6-dichlorophenyl)-1-methyl-2-propen-1-ylidene]amino]oxy]methyl]-α-(methoxyimino)-N-methylbenzeneacetamide), metominostrobin, orysastrobin and α-[methoxyimino]-N-methyl-2-[[[1-[3-(trifluoro-methyl)phenyl]ethoxy]imino]methyl]benzeneacetamide. The dihydrodioxazines include fluoxastrobin. The oxazolidinediones include famoxadone. The imidazolinones include fenamidone. The benzylcarbamates include pyribencarb. Class (b11) also includes mandestrobin (2-[(2,5-dimethylphenoxy)methyl]-α-methoxy-N-benzeneacetamide).

(b12) "Phenylpyrrole fungicides" (FRAC code 12) inhibit a MAP/histidine kinase associated with osmotic signal transduction in fungi. Fenpiclonil and fludioxonil are examples of this fungicide class.

(b13) "Azanaphthalene fungicides" (FRAC code 13) are proposed to inhibit signal transduction by a mechanism which is as yet unknown. They have been shown to interfere with germination and/or appressorium formation in fungi that cause powdery mildew diseases. Azanaphthalene fungicides include aryloxyquinolines and quinazolinones. The aryloxyquinolines include quinoxyfen. The quinazolinones include proquinazid.

(b14) "Lipid peroxidation inhibitor fungicides" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic hydrocarbon and 1,2,4-thiadiazole fungicides. The aromatic hydrocarboncarbon fungicides include biphenyl, chloroneb, dicloran, quintozene, tecnazene and tolclofos-methyl. The 1,2,4-thiadiazoles include etridiazole.

(b15) "Melanin biosynthesis inhibitors-reductase (MBI-R) fungicides" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(b16) "Melanin biosynthesis inhibitors-dehydratase (MBI-D) fungicides" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(b17) "Sterol Biosynthesis Inhibitor (SBI): Class III fungicides (FRAC code 17) inhibit 3-ketoreductase during C4-demethylation in sterol production. SBI: Class III inhibitors include hydroxyanilide fungicides and amino-pyrazolinone fungicides. Hydroxyanilides include fenhexamid. Amino-pyrazolinones include fenpyrazamine (S-2-propen-1-yl 5-amino-2,3-dihydro-2-(1-methylethyl)-4-(2-methylphenyl)-3-oxo-1H-pyrazole-1-carbothioate).

(b18) "Squalene-epoxidase inhibitor fungicides" (FRAC code 18) (SBI: Class IV) inhibit squalene-epoxidase in the sterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(b19) "Polyoxin fungicides" (FRAC code 19) inhibit chitin synthase. Examples include polyoxin.

(b20) "Phenylurea fungicides" (FRAC code 20) are proposed to affect cell division. Examples include pencycuron.

(b21) "Quinone inside inhibitor (QiI) fungicides" (FRAC code 21) inhibit Complex III mitochondrial respiration in fungi by affecting ubiquinone reductase. Reduction of ubiquinone is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(b22) "Benzamide and thiazole carboxamide fungicides" (FRAC code 22) inhibit mitosis by binding to β-tubulin and disrupting microtubule assembly. Inhibition of microtubule assembly can disrupt cell division, transport within the cell and cell structure. The benzamides include zoxamide. The thiazole carboxamides include ethaboxam.

(b23) "Enopyranuronic acid antibiotic fungicides" (FRAC code 23) inhibit growth of fungi by affecting protein biosynthesis. Examples include blasticidin-S.

(b24) "Hexopyranosyl antibiotic fungicides" (FRAC code 24) inhibit growth of fungi by affecting protein biosynthesis. Examples include kasugamycin.

(b25) "Glucopyranosyl antibiotic: protein synthesis fungicides" (FRAC code 25) inhibit growth of fungi by affecting protein biosynthesis. Examples include streptomycin.

(b26) "Glucopyranosyl antibiotic: trehalase and inositol biosynthesis fungicides" (FRAC code 26) inhibit trehalase and inositol biosynthesis. Examples include validamycin.

(b27) "Cyanoacetamideoxime fungicides (FRAC code 27) include cymoxanil.

(b28) "Carbamate fungicides" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

(b29) "Oxidative phosphorylation uncoupling fungicides" (FRAC code 29) inhibit fungal respiration by uncoupling oxidative phosphorylation. Inhibiting respiration prevents normal fungal growth and development. This class includes 2,6-dinitroanilines such as fluazinam, and dinitrophenyl crotonates such as dinocap, meptyldinocap and binapacryl.

(b30) "Organo tin fungicides" (FRAC code 30) inhibit adenosine triphosphate (ATP) synthase in oxidative phosphorylation pathway. Examples include fentin acetate, fentin chloride and fentin hydroxide.

(b31) "Carboxylic acid fungicides" (FRAC code 31) inhibit growth of fungi by affecting deoxyribonucleic acid (DNA) topoisomerase type II (gyrase). Examples include oxolinic acid.

(b32) "Heteroaromatic fungicides" (Fungicide Resistance Action Committee (FRAC) code 32) are proposed to affect DNA/ribonucleic acid (RNA) synthesis. Heteroaromatic fungicides include isoxazoles and isothiazolones. The isoxazoles include hymexazole and the isothiazolones include octhilinone.

(b33) "Phosphonate fungicides" (FRAC code 33) include phosphorous acid and its various salts, including fosetyl-aluminum.

(b34) "Phthalamic acid fungicides" (FRAC code 34) include teclofthalam.

(b35) "Benzotriazine fungicides" (FRAC code 35) include triazoxide.

(b36) "Benzene-sulfonamide fungicides" (FRAC code 36) include flusulfamide.

(b37) "Pyridazinone fungicides" (FRAC code 37) include diclomezine.

(b38) "Thiophene-carboxamide fungicides" (FRAC code 38) are proposed to affect ATP production. Examples include silthiofam.

(b39) "Complex I NADH oxidoreductase inhibitor fungicides" (FRAC code 39) inhibit electron transport in mitochondria and include pyrimidinamines such as diflumetorim, and pyrazole-5-carboxamides such as tolfenpyrad.

(b40) "Carboxylic acid amide (CAA) fungicides" (FRAC code 40) inhibit cellulose synthase which prevents growth and leads to death of the target fungus. Carboxylic acid amide fungicides include cinnamic acid amide, valinamide and other carbamate, and mandelic acid amide fungicides. The cinnamic acid amides include dimethomorph, flumorph and pyrimorph (3-(2-chloro-4-pyridinyl)-3-[4-(1,1-dimethylethyl)phenyl]-1-(4-morpholinyl)-2-propene-1-one). The valinamide and other carbamates include benthiavalicarb, benthiavalicarb-isopropyl, iprovalicarb, tolprocarb (2,2,2-trifluoroethyl N-[(1S)-2-methyl-1-[[(4-methylbenzoyl)amino]methyl]propyl]carbamate) and valifenalate (methyl N-[(1-methylethoxy)carbonyl]-L-valyl-3-(4-chlorophenyl)-β-alaninate) (also known as valiphenal). The mandelic acid amides include mandipropamid, N-[2-[4-[[3-(4-chloro-phenyl)-2-propyn-1-yl]oxy]-3-methoxyphenyl]ethyl]-3-methyl-2-[(methylsulfonyl)amino]-butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(b41) "Tetracycline antibiotic fungicides" (FRAC code 41) inhibit growth of fungi by affecting protein synthesis. Examples include oxytetracycline.

(b42) "Thiocarbamate fungicides" (FRAC code 42) include methasulfocarb.

(b43) "Benzamide fungicides" (FRAC code 43) inhibit growth of fungi by delocalization of spectrin-like proteins. Examples include pyridinylmethyl benzamide fungicides such as fluopicolide (now FRAC code 7, pyridinylethyl benzamides).

(b44) "Microbial fungicides" (FRAC code 44) disrupt fungal pathogen cell membranes. Microbial fungicides include *Bacillus* species such as *Bacillus amyloliquefaciens* strains QST 713, FZB24, MB1600, D747 and the fungicidal lipopeptides which they produce.

(b45) "$Q_xI$ fungicides" (FRAC code 45) inhibit Complex III mitochondrial respiration in fungi by affecting ubiquinone reductase at an unknown ($Q_x$) site of the cytochrome bc1 complex. Inhibiting mitochondrial respiration prevents normal fungal growth and development. $Q_xI$ fungicides include triazolopyrimidylamines such as ametoctradin (5-ethyl-6-octyl[1,2,4]triazolo[1,5-a]pyrimidin-7-amine).

(b46) "Plant extract fungicides" are proposed to act by cell membrane disruption. Plant extract fungicides include terpene hydrocarbons and terpene alcohols such as the extract from *Melaleuca alternifolia* (tea tree).

(b47) "Host plant defense induction fungicides" (FRAC code P) induce host plant defense mechanisms. Host plant defense induction fungicides include benzothiadiazoles, benzisothiazole and thiadiazole-carboxamide fungicides. The benzothiadiazoles include acibenzolar-S-methyl. The benzisothiazoles include probenazole. The thiadiazole-carboxamides include tiadinil and isotianil.

(b48) "Multi-site contact fungicides" inhibit fungal growth through multiple sites of action and have contact/preventive activity. This class of fungicides includes: (b48.1) "copper fungicides" (FRAC code M1)", (b48.2) "sulfur fungicides" (FRAC code M2), (b48.3) "dithiocarbamate fungicides" (FRAC code M3), (b48.4) "phthalimide fungicides" (FRAC code M4), (b48.5) "chloronitrile fungicides" (FRAC code M5), (b48.6) "sulfamide fungicides" (FRAC code M6), (b48.7) multi-site contact "guanidine fungicides" (FRAC code M7), (b48.8) "triazine fungicides" (FRAC code M8), (b48.9) "quinone fungicides" (FRAC code M9), (b48.10) "quinoxaline fungicides" (FRAC code M10) and (b48.11) "maleimide fungicides" (FRAC code M11). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. Multi-site contact "guanidine fungicides" include, guazatine, iminoctadine albesilate and iminoctadine triacetate. "Triazine fungicides" include anilazine. "Quinone fungicides" include dithianon. "Quinoxaline fungicides" include quinomethionate (also known as chinomethionate). "Maleimide fungicides" include fluoroimide.

(b49) "Fungicides other than fungicides of classes (b1) through (b48)" include certain fungicides whose mode of action may be unknown. These include: (b49.1), "phenyl-acetamide fungicides" (FRAC code U6), (b49.2) "aryl-phenyl-ketone fungicides" (FRAC code U8), (b49.3) "guanidine fungicides" (FRAC code U12), (b49.4) "thiazolidine fungicides" (FRAC code U13), (b49.5) "pyrimidinone-hydrazone fungicides" (FRAC code U14) and (b49.6) compounds that bind to oxysterol-binding protein as described in PCT Patent Publication WO 2013/009971. The phenyl-acetamides include cyflufenamid and N-[[(cyclopropyl-methoxy)amino][6-(difluoromethoxy)-2,3-difluorophenyl]-methylene]-benzeneacetamide. The aryl-phenyl ketones include benzophenones such as metrafenone, and benzo-ylpyridines such as pyriofenone (5-chloro-2-methoxy-4-methyl-3-pyridinyl)(2,3,4-trimethoxy-6-methylphenyl)methanone). The quanidines include dodine. The thiazolidines include flutianil ((2Z)-2-[[2-fluoro-5-(trifluoromethyl)phenyl]thio]-2-[3-(2-methoxyphenyl)-2-thiazolidinylidene]acetonitrile). The pyrimidinonehydrazones include ferimzone. The (b49.6) class includes oxathiapiprolin (1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone) and its R-enantiomer which is 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]-ethanone (Registry Number 1003319-79-6). The (b49) class also includes bethoxazin, flometoquin (2-ethyl-3,7-dimethyl-6-[4-(trifluoromethoxy)phenoxy]-4-quinolinyl methyl carbonate), fluoroimide, neoasozin (ferric methanearsonate), picarbutrazox (1,1-dimethylethyl N-[6-[[[[((Z)1-methyl-1H-tetrazol-5-yl)phenylmethylene]amino]oxy]methyl]-2-pyridinyl] carbamate), pyrrolnitrin, quinomethionate, tebufloquin (6-(1,1-dimethylethyl)-8-fluoro-2,3-dimethyl-4-quinolinyl acetate), tolnifanide (N-(4-chloro-2-nitrophenyl)-N-ethyl-4-methylbenzenesulfonamide), 2-butoxy-6-iodo-3-propyl-4H-1-benzopyran-4-one, 3-butyn-1-yl N-[6-[[[[(1-methyl-1H-tetrazol-5-yl)phenylmethylene]amino]oxy]methyl]-2-pyridinyl]-carbamate, (N-(4-chloro-2-nitrophenyl)-N-ethyl-4-methylbenzenesulfonamide), N'-[4-[4-chloro-3-(trifluoromethyl)phenoxy]-2,5-dimethylphenyl]-N-ethyl-N-methylmethanimidamide, N-[[(cyclopropylmethoxy)amino][6-(difluoromethoxy)-2,3-difluorophenyl]-methylene] benzeneacetamide, 2,6-dimethyl-1H,5H-[1,4]dithiino[2,3-c:5,6-c']dipyrrole-1,3,5,7(2H,6H)-tetrone, 5-fluoro-2-[(4-methylphenyl)methoxy]-4-pyrimidinamine, 5-fluoro-2-[(4-fluorophenyl)methoxy]-4-pyrimidinamine and 4-fluorophenyl N-[1-[[[1-(4-cyano-phenyl)ethyl]sulfonyl]methyl]propyl]carbamate, pentyl N-[6-[[[[(1-methyl-1H-tetrazol-5-yl)phenylmethylene]amino]oxy]methyl]-2-pyridinyl]carbamate, pentyl N-[4-[[[[(1-methyl-1H-tetrazol-5-yl)phenylmethylene]amino]oxy]methyl]-2-thiazolyl] carbamate and pentyl N-[6-[[[[(Z)-(1-methyl-1H-tetrazol-5-yl)phenylmethylene]amino]oxy]methyl]-2-pyridinyl]-carbamate. The (b46) class further includes mitosis- and cell division-inhibiting fungicides besides those of the particular classes described above (e.g., (b1), (b10) and (b22)).

Additional "Fungicides other than fungicides of classes (1) through (46)" whose mode of action may be unknown, or may not yet be classified include a fungicidal compound selected from components (b49.7) through (b49.12), as shown below.

Component (b49.7) relates to a compound of Formula b49.7

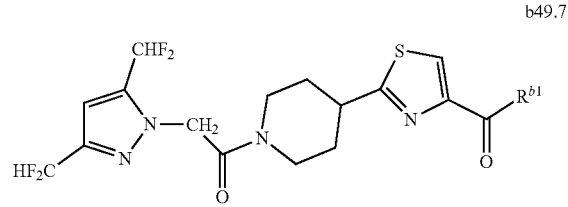

wherein R$^{b1}$ is

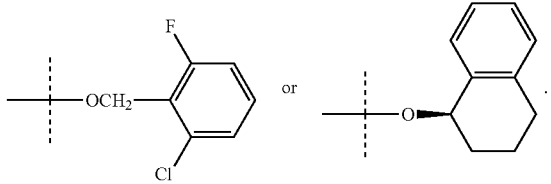

Examples of a compound of Formula b49.7 include (b49.7a) (2-chloro-6-fluorophenyl)-methyl 2-[1-[2-[3,5-bis(difluoromethyl)-1H-pyrazol-1-yl]acetyl]-4-piperidinyl]-4-thiazolecarboxylate (Registry Number 1299409-40-7) and (b49.7b) (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate (Registry Number 1299409-42-9). Methods for preparing compounds of Formula b46.2 are described in PCT Patent Publications WO 2009/132785 and WO 2011/051243.

Component (b49.8) relates to a compound of Formula b49.8

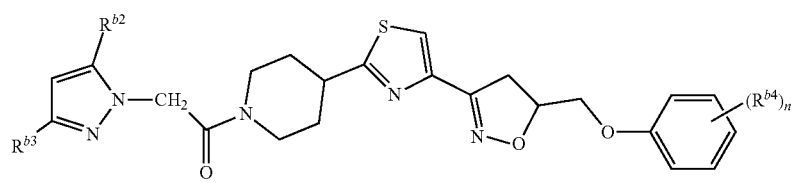

b49.8 wherein $R^{b2}$ is $CH_3$, $CF_3$ or $CHF_2$; $R^{b3}$ is $CH_3$, $CF_3$ or $CHF_2$; $R^{b4}$ is halogen or cyano; and n is 0, 1, 2 or 3. Examples of a compound of Formula b49.8 include (b49.8a) 1-[4-[4-[5-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone. Methods for preparing compounds of Formula b49.8 are described in PCT Patent Application PCT/US11/64324.

Component (b4799) relates to a compound of Formula b49.9

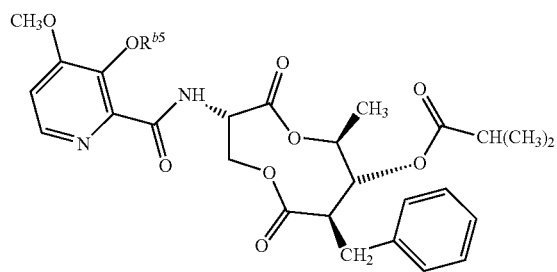

b49.9 wherein $R^{b5}$ is —$CH_2OC(O)CH(CH_3)_2$, —$C(O)CH_3$, —$CH_2OC(O)CH_3$,

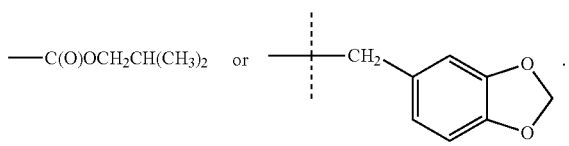

Examples of a compound of Formula b49.9 include (b49.9a) [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate (Registry Number 517875-34-2), (b49.9b) (3S,6S,7R,8R)-3-[[[3-(acetyloxy)-4-methoxy-2-pyridinyl]-carbonyl]amino]-6-methyl-4,9-dioxo-8-(phenylmethyl)-1,5-dioxonan-7-yl 2-methylpropanoate (Registry Number 234112-93-7), (b49.9c) (3S,6S,7R,8R)-3[[[3[(acetyloxy)-methoxy]-4-methoxy-2-pyridinyl]carbonyl]amino]-6-methyl-4,9-dioxo-8-(phenylmethyl)-1,5-dioxonan-7-yl 2-methylpropanoate (Registry Number 517875-31-9), (b49.9d) (3S,6S,7R,8R)-3-[[[4-methoxy-3-[[(2-methyl-propoxy)carbonyl]oxy]-2-pyridinyl]carbonyl]-amino]6-methyl-4,9-dioxo-8-(phenylmethyl)-1,5-dioxonan-7-yl 2-methylpropanoate (Registry Number 328256-72-0), and (b49.9e) N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenyl-methyl)L-arabinonoyl]-L-serine, (1→4')-lactone (Registry Number 1285706-70-8). Methods for preparing compounds of Formula b49.9 are described in PCT Patent Publications WO 99/40081, WO 2001/014339, WO 2003/035617 and WO 2011044213.

Component (b49.10) relates to a compound of Formula b49.10

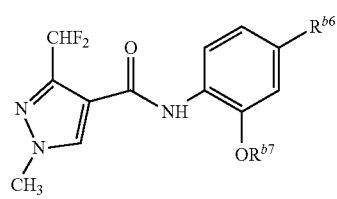

b49.10 wherein $R^{b6}$ is H or F, and $R^{b7}$ is —$CF_2CHFCF_3$ or —$CF_2CF_2H$. Examples of a compound of Formula b49.10 are (b49.10a) 3-(difluoromethyl)-N-[4-fluoro-2-(1,1,2,3,3,3-hexafluoro-propoxy)phenyl]-1-methyl-1H-pyrazole-4-carboxamide (Registry Number 1172611-40-3) and (b49.10b) 3-(difluoromethyl)-1-methyl-N-[2-(1,1,2,2-tetrafluoroethoxy)phenyl]-1H-pyrazole 4-carboxamide (Registry Number 923953-98-4). Compounds of Formula 49.10 can be prepared by methods described in PCT Patent Publication WO 2007/017450.

Component b49.11 relates a compound of Formula b49.11

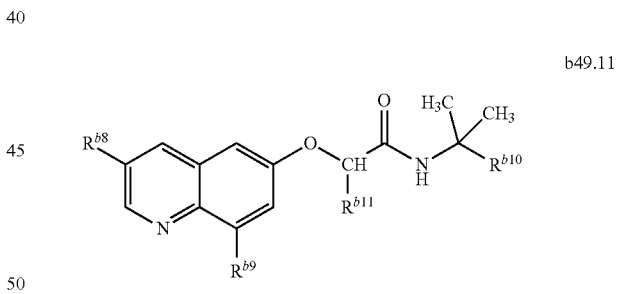

b49.11 wherein
$R^{b8}$ is halogen, $C_1$-$C_4$ alkoxy or $C_2$-$C_4$ alkynyl;
$R^{b9}$ is H, halogen or $C_1$-$C_4$ alkyl;
$R^{b10}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{b11}$ is methyl or —$Y^{b13}$—$R^{b12}$;
$R^{b12}$ is $C_1$-$C_2$ alkyl; and
$Y^{b13}$ is $CH_2$, O or S.
Examples of compounds of Formula b49.11 include (b49.11a) 2-[(3-bromo-6-quinolinyl)-oxy]-N-(1,1-dimethyl-2-butyn-1-yl)-2-(methylthio)acetamide, (b49.11b) 2[(3-ethynyl-6-quinolinyl)oxy]-N-[1-(hydroxymethyl)-1-methyl-2-propyn-1-yl]-2-(methylthio)acetamide, (b49.11c) N-(1,1-dimethyl-2-butyn-1-yl)-2-[(3-ethynyl-6-quinolinyl)

oxy]-2-(methylthio)-acetamide, (b49.11 d) 2-[(3-bromo-8-methyl-6-quinolinyl)oxy]-N-(1,1-dimethyl-2-propyn-1-yl)-2-(methylthio)acetamide and (b49.11e) 2-[(3-bromo-6-quinolinyl)oxy]-N-(1,1-di-methylethyl)butanamide.

Compounds of Formula b49.11, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098.

Component 49.12 relates to N'-[4-[[3-[(4-chlorophenyl)methyl]-1,2,4-thiadiazol-5-yl]oxy]-2,5-dimethylphenyl]-N-ethyl-N-methylmethanimidamide, which is believed to inhibit C24-methyl transferase involved in the biosynthesis of sterols.

Therefore of note is a mixture (i.e. composition) comprising a compound of Formula 1 and at least one fungicidal compound selected from the group consisting of the afore-described classes (1) through (49). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (49). Also of particular note is a composition comprising said mixture (in fungicidally effective amount) and further comprising at least one additional surfactant selected from the group consisting of surfactants, solid diluents and liquid diluents.

Examples of component (b) fungicides include acibenzolar-S-methyl, aldimorph, ametoctradin, amisulbrom, anilazine, azaconazole, azoxystrobin, benalaxyl (including benalaxyl-M), benodanil, benomyl, benthiavalicarb (including benthiavalicarb-isopropyl), benzovindiflupyr, bethoxazin, binapacryl, biphenyl, bitertanol, bixafen, blasticidin-S, boscalid, bromuconazole, bupirimate, buthiobate, captafol, captan, carbendazim, carboxin, carpropamid, chloroneb, chlorothalonil, chlozolinate, clotrimazole, copper hydroxide, copper oxychloride, copper sulfate, coumoxystrobin, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole (including diniconazole-M), dinocap, dithianon, dithiolanes, dodemorph, dodine, econazole, edifenphos, enoxastrobin (also known as enestroburin), epoxiconazole, etaconazole, ethaboxam, ethirimol, etridiazole, famoxadone, fenamidone, fenarimol, fenaminstrobin, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, flometoquin, fluazinam, fludioxonil, flufenoxystrobin, fluindapyr, flumorph, fluopicolide, fluopyram, flouroimide, fluoxastrobin, fluquinconazole, flusilazole, flusulfamide, flutianil, flutolanil, flutriafol, fluxapyroxad, folpet, fthalide, fuberidazole, furalaxyl, furametpyr, guazatine, hexaconazole, hymexazole, imazalil, imibenconazole, iminoctadine albesilate, iminoctadine triacetate, iodocarb, ipconazole, iprobenfos, iprodione, iprovalicarb, isoconazole, isofetamid, isoprothiolane, isopyrazam, isotianil, kasugamycin, kresoxim-methyl, mancozeb, mandepropamid, mandestrobin, maneb, mepanipyrim, mepronil, meptyldinocap, metalaxyl (including metalaxyl-M/mefenoxam), metconazole, methasulfocarb, metiram, metominostrobin, metrafenone, miconazole, myclobutanil, naftifine, neo-asozin, nuarimol, octhilinone, ofurace, orysastrobin, oxadixyl, oxathiapiprolin, oxolinic acid, oxpoconazole, oxycarboxin, oxytetracycline, pefurazoate, penconazole, pencycuron, penflufen, penthiopyrad, phosphorous acid (including salts thereof, e.g., fosetyl-aluminum), picarbutrazox, picoxystrobin, piperalin, polyoxin, probenazole, prochloraz, procymidone, propamacarb, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyrisoxazole, pyroquilon, pyrrolnitrin, quinconazole, quinomethionate, quinoxyfen, quintozene, sedaxane, silthiofam, simeconazole, spiroxamine, streptomycin, sulfur, tebuconazole, tebufloquin, teclofthalam, tecnazene, terbinafine, tetraconazole, thiabendazole, thifluzamide, thiophanate, thiophanate-methyl, thiram, tiadinil, tolclofos-methyl, tolnifanide, tolprocarb, tolyfluanid, triadimefon, triadimenol, triarimol, triticonazole, triazoxide, tribasic copper sulfate, tricyclazole, triclopyricarb, tridemorph, trifloxystrobin, triflumizole, triforine, trimorphamide, uniconazole, uniconazole-P, validamycin, valifenalate (also known as valiphenal), vinclozolin, zineb, ziram, zoxamide, (3S,6S,7R,8R)-3-[[[3-[(acetyloxy)methoxy]-4-methoxy-2-pyridinyl]carbonyl]amino]-6-methyl-4,9-dioxo-8-(phenylmethyl)-1,5-dioxonan-7-yl 2-methylpropanoate, (3S,6S,7R,8R)-3-[[[3-(acetyloxy)-4-methoxy-2-pyridinyl]carbonyl]amino]-6-methyl-4,9-dioxo-8-(phenylmethyl)-1,5-dioxonan-7-yl 2-methylpropanoate, N-[[3-(1,3-benzodioxol-5-ylmethoxy)-4-methoxy-2-pyridinyl]carbonyl]-O-[2,5-dideoxy-3-O-(2-methyl-1-oxopropyl)-2-(phenylmethyl)-L-arabinonoyl]-L-serine, (1→4')-lactone, N-[2-(1S,2R)-[1,1'-bicyclopropyl]-2-ylphenyl]-3-(difluoromethyl)-1-methyl-1H-pyrazole-4-carboxamide, 2-[(3-bromo-6-quinolinyl)oxy]-N-(1,1-dimethyl-2-butyn-1-yl)-2-(methylthio)acetamide, 2-[(3-bromo-6-quinolinyl)oxy]-N-(1,1-dimethylethyl)butanamide, 2-[(3-bromo-8-methyl-6-quinolinyl)oxy]-N-(1,1-dimethyl-2-propyn-1-yl)-2-(methylthio)acetamide, 2-butoxy-6-iodo-3-propyl-4H-1-benzopyran-4-one, 3-butyn-1-yl N-[6-[[[[(1-methyl-1H-tetrazol-5-yl)phenylmethylene]amino]oxy]methyl]-2-pyridinyl]carbamate, α-(1-chlorocyclopropyl)-α-[2-(2,2-dichlorocyclopropyl)ethyl]-1H-1,2,4-triazole-1-ethanol, 2-[2-(1-chlorocyclopropyl)-4-(2,2-dichlorocyclopropyl)-2-hydroxybutyl]-1,2-dihydro-3H-1,2,4-triazole-3-thione, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chloro-phenyl)-2-(2,4-difluorophenyl)-2-oxiranyl]methyl]-1,2-dihydro-3H-1,2,4-triazole-3-thione, rel-1-[[(2R,3S)-3-(2-chlorophenyl)-2-(2,4-difluorophenyl)-2-oxiranyl]methyl]-5-(2-propen-1-ylthio)-1H-1,2,4-triazole, 3-[5-(4-chlorophenyl)-2,3-dimethyl-3-isoxazolidinyl]pyridine, (2-chloro-6-fluorophenyl)methyl 2-[1-[2-[3,5-bis(difluoromethyl)-1H-pyrazol-1-yl]acetyl]-4-piperidinyl]-4-thiazolecarboxylate, N'-[4-[[3-[(4-chlorophenyl)methyl]-1,2,4-thiadiazol-5-yl]oxy]-2,5-dimethylphenyl]-N-ethyl-N-methyl-methanimidamide, N-[2-[4-[[3-(4-chloro-phenyl)-2-propyn-1-yl]oxy]-3-methoxyphenyl]ethyl]-3-methyl-2-[(methylsulfonyl)amino]-butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, N'-[4-[4-chloro-3-(trifluoromethyl)phenoxy]-2,5-dimethylphenyl]-N-ethyl-N-methylmethanimidamide, N-cyclopropyl-3-(difluoromethyl)-5-fluoro-1-methyl-N-[[2-(1-methylethyl)phenyl]methyl]-1H-pyrazole-4-carboxamide, N-[[(cyclopropylmethoxy)amino][6-(difluoromethoxy)-2,3-difluorophenyl]methylene]-benzeneacetamide, N-[2-(2,4- dichlorophenyl)-2-methoxy-1-methylethyl]-3-(difluoromethyl)-1-methyl-1H-pyrazole-4-carboxamide, N-(3',4'-difluoro[1,1'-biphenyl]-2-yl)-3-(trifluoromethyl)-2-pyrazinecarboxamide, 3-(difluoromethyl)-N-(2,3-dihydro-1,1,3-trimethyl-1H-inden-4-yl)-1-methyl-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, 5,8-difluoro-N-[2-[3-methoxy-4-[[4-(trifluoromethyl)-2-pyridinyl]oxy]phenyl]ethyl]-4-quinazolinamine, 3-(difluoromethyl)-1-methyl-N-[2-(1,1,2,2-tetrafluoroethoxy)phenyl]-1H-pyrazole-4-carboxamide, 1-[4-[4-[5R-[(2,6-difluorophenoxy)methyl]-4,5-dihydro-3-isoxazolyl]-2-thiazolyl]-1-piperdinyl]-2-[5-methyl-3-(trifluoromethyl)-1H-pyrazol-1-yl]ethanone, N-(1,1-dimethyl-2-butyn-1-yl)-2-[(3-ethynyl-6-quinolinyl)oxy]-2-(methylthio)-acetamide, 2,6-dimethyl-1H,5H-[1,4]dithiino[2,3-c:5,6-c']dipyrrole-1,3,5,7(2H,6H)-tetrone, 2-[(3-ethynyl-6-quinolinyl)oxy]-N-[1-(hydroxymethyl)-1-methyl-2-propyn-1-yl]-2-(methyl-thio)acetamide, 4-fluorophenyl N-[1-[[[1-(4-cyanophenyl)ethyl]sulfonyl]methyl]-propyl]carbamate, 5-fluoro-2-[(4-fluorophenyl)methoxy]-4-pyrimidinamine, 5-fluoro-2-[(4-methylphenyl)methoxy]-4-pyrimidinamine, (3S,6S,7R,8R)-3-[[[4-methoxy-3-[[(2-methyl-propoxy)carbonyl]oxy]-2-pyridinyl]carbonyl]amino]-6-methyl-4,9-dioxo-8-(phenylmethyl)-1,5-dioxonan-7-yl-2-methylpropanoate, α-(methoxyimino)-N-methyl-2-[[[1-[3-(trifluoro-methyl)phenyl]ethoxy]imino]methyl]benzeneacetamide, [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl 2-methylpropanoate, pentyl N-[6-[[[[(1-methyl-1H-tetrazol-5-yl)phenylmethylene]amino]oxy]methyl]-2-pyridinyl]carbamate, pentyl N-[4-[[[[(1-methyl-1H-tetrazol-5-yl)phenylmethylene]amino]oxy]methyl]-2-thiazolyl]carbamate, and pentyl N-[6-[[[[(Z)-(1-methyl-1H-tetrazol-5-yl)phenylmethylene]amino]oxy]methyl]-2-pyridinyl]carbamate and (1R)-1,2,3,4-tetrahydro-1-naphthalenyl 2-[1-[2-[3,5-bis(difluoromethyl)-1H-pyrazol-1-yl]acetyl]-4-piperidinyl]-4-thiazolecarboxylate. Therefore of note is a fungicidal composition comprising as component (a) a compound of Formula 1 (or an N-oxide or salt thereof) and as component (b) at least one fungicide selected from the preceding list.

Of particular note are combinations of compounds of Formula 1 (or an N-oxide or salt thereof) (i.e. Component (a) in compositions) with azoxystrobin, benzovindiflupyr, bixafen, captan, carpropamid, chlorothalonil, copper hydroxide, copper oxychloride, copper sulfate, cymoxanil, cyproconazole, cyprodinil, diethofencarb, difenoconazole, dimethomorph, epoxiconazole, ethaboxam, fenarimol, fenhexamid, fluazinam, fludioxonil, fluindapyr, fluopyram, flusilazole, flutianil, flutriafol, fluxapyroxad, folpet, iprodione, isofetamid, isopyrazam, kresoxim-methyl, mancozeb, mandestrobin, meptyldinocap, metalaxyl (including metalaxyl-M/mefenoxam), metconazole, metrafenone, myclobutanil, oxathiapiprolin, penflufen, penthiopyrad, phosphorous acid (including salts thereof, e.g., fosetyl-aluminum), picoxystrobin, propiconazole, proquinazid, prothioconazole, pyraclostrobin, pyrimethanil, sedaxane spiroxamine, sulfur, tebuconazole, thiophanate-methyl, trifloxystrobin, zoxamide, α-(1-chlorocyclopropyl)-α-[2-(2,2-dichlorocyclopropyl)ethyl]-1H-1,2,4-triazole-1-ethanol, 2-[2-(1chlorocyclopropyl)-4-(2,2-dichlorocyclopropyl)-2-hydroxybutyl]-1,2-dihydro-3H-1,2,4-triazole-3-thione, N-[2-(2,4-dichlorophenyl)-2-methoxy-1-methylethyl]-3-(difluoromethyl)-1-methyl-1H-pyrazole-4-carboxamide, 3-(difluoromethyl)-N-(2,3-dihydro-1,1,3-trimethyl-1H-inden-4-yl)-1-methyl-1H-pyrazole-4-carboxamide, 1-[4-[4-[5R-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 1,1-di-methylethyl N-[6-[[[[(1-methyl-1H-tetrazol-5-yl)phenylmethylene]amino]oxy]methyl]-2-pyridinyl]carbamate, 2,6-dimethyl-1H,5H-[1,4]dithiino[2,3-c:5,6-c']dipyrrole-1,3,5,7(2H,6H)-tetrone, 5-fluoro-2-[(4-fluorophenyl)methoxy]-4-pyrimidinamine, 5-fluoro-2-[(4-methylphenyl)methoxy]-4-pyrimidinamine, (αS)-[3-(4-chloro-2-fluorophenyl)-5-(2,4-difluorophenyl)-4-isoxazolyl]-3-pyridinemethanol, rel-1-[[(2R,3S)-3-(2-chlorophenyl)-2-(2,4-difluorophenyl)-2-oxiranyl]methyl]-1H-1,2,4-triazole, rel-2-[[(2R,3S)-3-(2-chloro-phenyl)-2-(2,4-difluorophenyl)-2-oxiranyl]methyl]-1,2-dihydro-3H-1,2,4-triazole-3-thione, and rel-1-[[[(2R,3S)-3-(2-chlorophenyl)-2-(2,4-difluorophenyl)-2-oxiranyl]methyl]-5-(2-propen-1-ylthio)-1H-1,2,4-triazole (i.e. as Component (b) in compositions).

Examples of other biologically active compounds or agents with which compounds of this invention can be formulated are: invertebrate pest control compounds or agents such as abamectin, acephate, acetamiprid, acrinathrin, afidopyropen ([(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H, 11H-naphtho[2,1-b]pyrano[3,4-e]pyran-4-yl]methyl cyclopropanecarboxy-late), amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyclaniliprole (3-bromo-N-[2-bromo-4-chloro-6-[[(1-cyclopropyl-ethyl)amino]carbonyl]phenyl]-1-(3-chloro-2-pyridinyl)-1H-pyrazole-5-carboxamide), cycloxaprid ((5S,8R)-1-[(6-chloro-3-pyridinyl)methyl]-2,3,5,6,7,8-hexahydro-9-nitro-5,8-epoxy-1H-imidazo[1,2-a]azepine), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, flufenoxystrobin (methyl (αE)-2-[[2-chloro-4-(trifluoromethyl)phenoxy]methyl]-α-(methoxymethylene)benzeneacetate), flufensulfone (5-chloro-2-[(3,4,4-trifluoro-3-buten-1-yl)sulfonyl]thiazole), flupiprole (1-[2,6-dichloro-4-(trifluoromethyl)phenyl]-5-[(2-methyl-2-propen-1-yl)amino]-4-[(trifluoro-methyl)sulfinyl]-1H-pyrazole-3-carbonitrile), flupyradifurone (4-[[(6-chloro-3-pyridinyl)-methyl](2,2-difluoroethyl)amino]-2(5H)-furanone), tau-fluvalinate, flufenerim (UR-50701), flufenoxuron, fonophos, halofenozide, heptafluthrin ([2,3,5,6-tetrafluoro-4-(methoxymethyl)phenyl]methyl 2,2-dimethyl-3-[(1Z)-3,3,3-trifluoro-1-propen-1-yl]cyclo-propanecarboxylate), hexaflumuron, hydramethylnon, imidacloprid, indoxacarb, isofenphos, lufenuron, malathion, meperfluthrin ([2,3,5,6-tetrafluoro-4-(methoxymethyl)phenyl]methyl (1R,3S)-3-(2,2-dichloroethenyl)-2,2-dimethylcyclopropanecarboxylate), metaflumizone, metaldehyde, methamidophos, methidathion, methomyl, methoprene, methoxychlor, methoxyfenozide, metofluthrin, milbemycin oxime, momfluorothrin ([2,3,5,6-tetrafluoro-4-(methoxymethyl)phenyl]methyl-3-(2-cyano-1-propen-1-yl)-2,2-dimethylcyclopropanecarboxylate), monocrotophos, nicotine, nitenpyram, nithiazine, novaluron, noviflumuron (XDE-007), oxamyl, pyflubumide (1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide), parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriminostrobin (methyl (αE)-2-[[[2-[(2,4-dichlorophenyl)amino]-6-(trifluoromethyl)-4-pyrimidinyl]oxy] methyl]-α-(methoxy-methylene)benzeneacetate), pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Also in certain instances, combinations of a compound of the invention with other biologically active compounds or agents can result in a less-than-additive (i.e. safening) effect on organisms beneficial to the agronomic environment. For example, a compound of the invention may safen a herbicide on crop plants or protect a beneficial insect species (e.g., insect predators, pollinators such as bees) from an insecticide.

Fungicides of note for formulation with compounds of Formula 1 to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, flufenoxystrobin, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Invertebrate pest control compounds or agents with which compounds of Formula 1 can be formulated to provide mixtures useful in seed treatment include but are not limited to abamectin, acetamiprid, acrinathrin, afidopyropen, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyclaniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, fluensulfone, flufenoxuron, flufiprole, flupyradifurone, fluvalinate, formetanate, fosthiazate, heptafluthrin, hexaflumuron, hydramethylnon, imidacloprid, indoxacarb, lufenuron, meperfluthrin, metaflumizone, methiocarb, methomyl, methoprene, methoxyfenozide, momfluorothrin, nitenpyram, nithiazine, novaluron, oxamyl, pyflubumide, pymetrozine, pyrethrin, pyridaben, pyriminostrobin, pyridalyl, pyriproxyfen, ryanodine, spinetoram, spinosad, spirodiclofen, spiromesifen, spirotetramat, sulfoxaflor, tebufenozide, tetramethrin, tetramethylfluthrin, thiacloprid, thiamethoxam, thiodicarb, thiosultap-sodium, tralomethrin, triazamate, triflumuron, *Bacillus thuringiensis* delta-endotoxins, strains of *Bacillus thuringiensis* and strains of Nucleo polyhydrosis viruses.

Compositions comprising compounds of Formula 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtilis* and *Pasteuria penetrans*. A suitable *Bacillus firmus* strain is strain CNCM I-1582 (GB-126) which is commercially available as BioNem™. A suitable *Bacillus cereus* strain is strain NCMM I-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum.*

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradyrhizobium japonicum*. These inocculants can optionally include one or more lipo-chitooligosaccharides (LCOs), which are nodulation (Nod) factors produced by rhizobia bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The following TESTS demonstrate the control efficacy of compounds of this invention on specific pathogens. The pathogen control protection afforded by the compounds is not limited, however, to these species. See Index Tables A through T below for compound descriptions. The following abbreviations are used in the Index Tables: Me means methyl, CN means cyano, $NO_2$ means nitro, Et means ethyl, n-Pr means n-propyl, i-Pr means isopropyl, c-Pr means cyclopropyl, i-Bu means iso-butyl, t-Bu means tert-butyl, Ph means phenyl, MeO means methoxy, EtO means ethoxy and Ac means acetyl. The abbreviation "Cmpd. No." stands for "Compound Number", and the abbreviation "Ex." stands for "Example" and is followed by a number indicating in which example the compound is prepared. $^{19}F$ NMR spectra are reported in ppm relative to trichlorofluoromethane in $CDCl_3$ solution unless indicated otherwise. The numerical value reported in the column "MS" is the molecular weight of the highest isotopic abundance positively charged parent ion (M+1) formed by addition of $H^+$ (molecular weight of 1) to the molecule having the highest isotopic abundance, or the highest isotopic abundance negatively charged ion (M-1) formed by loss of $H^+$ (molecular weight of 1). The presence of molecular ions containing one or more higher atomic weight isotopes of lower abundance (e.g., $^{37}Cl$, $^{81}Br$) is not reported. The reported MS peaks were observed by mass spectrometry using electrospray ionization (ESI) or atmospheric pressure chemical ionization (APCI).

INDEX TABLE A

| Cmpd. No. | $(R^2)_x$ | L | $^{19}F$ NMR | MS |
|---|---|---|---|---|
| 1 | 3-(EtOC(=O)), 4-Br, 5-Me | $CH_2$ | −65.40 | |
| 2 (Ex. 12) | 4-(EtOC(=O)) | CH(Me) | −65.44 | |
| 6 | 3-N≡C | $CH_2$ | −65.39 | |
| 7 | 5-N≡C | $CH_2$ | −65.39 | |
| 17 | 4-(CH(=O)) | $CH_2$ | −65.34 | |
| 18 | 4-(MeOC(=O)NHN=CH) | $CH_2$ | −65.34 | |
| 19 | 4-($Me_2$NN=CH) | $CH_2$ | −65.35 | |
| 20 | 4-(OH—N=CH) | $CH_2$ | −65.34, −66.15 | |
| 21 | 4-(MeOC(=O)) | $CH_2$ | −65.41 | |
| 25 | 4-(MeOH=CH) | $CH_2$ | −65.34 | |
| 26 | 4-(OHC(=O)$CH_2$ON=CH) | $CH_2$ | −65.34 | |
| 55 | 4-(OHC(=O)) | $CH_2$ | −65.39 | |
| 56 | 4-(HC≡C$CH_2$OC(=O)) | $CH_2$ | −65.39 | |
| 57 | 4-(N≡C$CH_2$OC(=O)) | $CH_2$ | −65.38 | |
| 58 | 4-(i-PrOC(=O)) | $CH_2$ | −65.39 | |
| 59 | 4-(MeO$CH_2$$CH_2$OC(=O)) | $CH_2$ | −65.39 | |
| 60 | 4-(n-PrOC(=O)) | $CH_2$ | −65.39 | |
| 61 | 4-(MeNHC(=O)) | $CH_2$ | −64.74$^a$ | |
| 62 | 4-($Me_2$NC(=O)) | $CH_2$ | −65.41 | |
| 63 | 4-(i-PrNHC(=O)) | $CH_2$ | −64.74$^a$ | |
| 64 | 4-($CH_2$=CH$CH_2$NHC(=O)) | $CH_2$ | −64.74$^a$ | |
| 65 | 4-(N≡C$CH_2$NHC(=O)) | $CH_2$ | −64.74$^a$ | |
| 66 | 3-Me, 4-(EtOC(=O)), 5-Me | $CH_2$ | −65.35 | |
| 67 | 4-(EtNHC(=O)) | $CH_2$ | −64.73$^a$ | |
| 68 | 4-(n-PrNHC(=O)) | $CH_2$ | −64.74$^a$ | |
| 69 | 4-(c-PrNHC(=O)) | $CH_2$ | −64.75$^a$ | |
| 78 | 4-(t-BuNHC(=O) | $CH_2$ | −65.38 | |
| 79 | 3-(EtOC(=O)), 5-Et | $CH_2$ | −65.42 | |
| 80 | 3-(EtOC(=O)), 5-i-Pr | $CH_2$ | −65.39 | |
| 81 | 3-Et, 5-(EtOC(=O)) | $CH_2$ | −65.43 | |
| 82 | 3-i-Pr, 5-(EtOC(=O)) | $CH_2$ | −65.41 | |
| 83 (Ex. 10) | 4-(EtOC(=O)) | $CH_2$ | −65.38 | |
| 85 | 3-Ph | $CH_2$ | −65.35 | |
| 95 (Ex. 2) | 4-N≡C | $CH_2$ | −65.33 | |
| 97 | 3-Br | $CH_2$ | | 375 (M + 1) |

INDEX TABLE A-continued

| Cmpd. No. | (R²)ₓ | L | ¹⁹F NMR | MS |
|---|---|---|---|---|
| 98 | 3-t-Bu | CH₂ | | 351 (M + 1) |
| 109 | 3-Me, 5-(EtOC(=O)) | CH₂ | −65.47 | |
| 110 | 3-(EtOC(=O)), 5-Me | CH₂ | −65.53 | |
| 111 | 3-CF₃, 4-(EtOC(=O)) | CH₂ | −65.38 | |
| 114 | 3-(EtOC(=O)) | CH₂ | | 367 (M + 1) |
| 122 | 3-(4-Cl—Ph | CH₂ | | 405 (M + 1) |
| 127 | 3-Me, 5-CF₃ | CH₂ | −65.42 | |
| 132 | 3-CF₃, 5-Me | CH₂ | −65.43 | |
| 140 | 3,5-di-(OHC(=O)) | CH₂ | | 381 (M + 1) |
| 142 | 3-(2-Cl—Ph) | CH₂ | | 405 (M + 1) |
| 144 | 3,5-di-CF₃ | CH₂ | | 431 (M + 1) |
| 145 | 3,5-di-Me | CH₂ | | 323 (M + 1) |
| 146 | 3-(2-Cl—Ph), 4-Br | CH₂ | | 485 (M + 1) |
| 153 | 3-CF₃ | CH₂ | −65.35, −61.93 | |
| 154 | 3,5-di-(EtOC(=O)) | CH₂ | −65.42 | |
| 162 | — | CH₂ | −65.36 | |
| 163 | 4-Br | CH₂ | −65.34 | |
| 166 | 4-(CH₂=CHCH₂OC(=O)) | CH₂ | −65.39 | |
| 167 | 4-(CH₂=CBrCH₂OC(=O)) | CH₂ | −65.39 | |
| 168 | 4-(CH₂=CHCF₂OC(=O)) | CH₂ | −65.39, −83.18 | |
| 169 | 4-(Me₂C=CHCH₂OC(=O)) | CH₂ | −65.39 | |
| 170 | 4-(CH₂=C(Me)CH₂OC(=O)) | CH₂ | −65.39 | |
| 171 | 4-(i-BuOC(=O)) | CH₂ | −65.39 | |
| 172 | 4-(MeOC(=O))-cyclopropyl-NHC(=O)) | CH₂ | −65.39 | |
| 173 | 4-(N≡C-cyclopropyl-NHC(=O)) | CH₂ | −65.39 | |
| 174 | 3,4,5-tri-(EtOC(=O)) | CH₂ | −65.48 | |
| 179 | 3-(OHC(=O)), 5-Me | CH₂ | −65.40 | |
| 180 | 3-(CF₃C(=O)OC(=O)), 5-Me | CH₂ | −65.40, −72.88 | |
| 181 | 3-(N≡CCH₂NHC(=O)), 5-Me | CH₂ | −65.39 | |
| 182 | 3-(Me₂NC(=O)), 5-Me | CH₂ | −65.40 | |
| 183 | 3-(MeOCH₂CH₂NHC(=O)), 5-Me | CH₂ | −65.40 | |
| 184 | 3-(N≡CCH₂OC(=O)), 5-Me | CH₂ | −65.40 | |
| 185 | 3-(N≡CCH₂OC(=O)), 5-Me | CH₂ | −65.40 | |
| 186 | 3-(CH₂=CHCH₂OC(=O)), 5-Me | CH₂ | −65.41 | |
| 187 | 3-(EtOC(=O)), 5-t-Bu | CH₂ | −65.44 | |
| 212 | 4-(CF₃CH₂NHC(=O)) | CH₂O | | 436 (M + 1) |
| 213 | 4-(MeOCH₂CH₂NHC(=O)) | CH₂O | | 412 (M + 1) |
| 214 | 4-(N≡CCH₂NHC(=O)) | CH₂O | | 393 (M + 1) |
| 215 | 4-(1H-pyrazol-1-yl-CH₂CH₂NHC(=O)) | CH₂O | | 448 (M + 1) |
| 216 | 4-(c-PrCH₂OC(=O)) | CH₂O | | 409 (M + 1) |
| 217 | 4-(n-PrOC(=O)) | CH₂O | | 397 (M + 1) |
| 218 | 4-[(tetrahydro-2H-pyran-2-yl)ON=C(Me)CH₂OC(=O)] | CH₂ | | 492 (M − 1) |
| 219 | 4-(n-BuON=C(Me)CH₂OC(=O)) | CH₂ | | 466 (M + 1) |
| 220 | 4-(t-BuON=C(Me)CH₂OC(=O)) | CH₂ | | 466 (M + 1) |
| 221 | 4-(EtON=C(Me)CH₂OC(=O)) | CH₂ | | 438 (M + 1) |
| 222 | 4-(i-PrON=C(Me)CH₂OC(=O)) | CH₂ | | 452 (M + 1) |
| 223 | 4-(HO—N=C(Me)CH₂OC(=O)) | CH₂ | | 410 (M + 1) |
| 241 | 4-(EtOC(=O)) | CH₂SCH₂ | | 411 (M − 1) |
| 242 | 4-(EtOC(=O)) | CH₂S(O)CH₂ | | 429 (M + 1) |
| 243 | 4-(EtOC(=O)) | CH₂S(O)₂CH₂ | | 445 (M + 1) |
| 244 | 4-(PhC(=O)CH₂OC(=O)) | CH₂ | | 457 (M + 1) |
| 245 | 4-(MeON=C(Ph)CH₂OC(=O)) | CH₂ | | 486 (M + 1) |
| 268 | 4-(2-EtO—Ph—OCH₂CH₂OC(=O)) | CH₂ | −65.30 | |
| 269 | 4-(Me-oxetanyl-CH₂OC(=O)) | CH₂ | −65.30 | |

INDEX TABLE A-continued

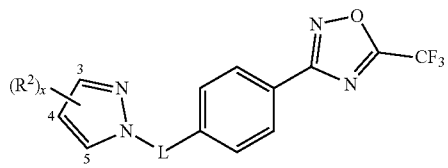

| Cmpd. No. | $(R^2)_x$ | L | $^{19}F$ NMR | MS |
|---|---|---|---|---|
| 270 | 4-(i-PrONHC(=O)) | $CH_2$ | $-64.70^a$ | |
| 272 | 4-(MeONHC(=O)) | $CH_2$ | $-64.50^a$ | |
| 273 | 4-(t-BuONHC(=O)) | $CH_2$ | | 408 (M + 1) |
| 274 | 4-(N≡CCH$_2$CH$_2$CH$_2$OC(=O)) | $CH_2$ | $-65.30$ | |
| 275 | 4-(MeOC(=O)CH=CHCH$_2$OC(=O)) | $CH_2$ | $-65.30$ | |
| 276 | 4-(EtOC(=O)) | $CH_2$ | $-65.33$ | |
| 299 | 4-(Ph—C≡CCH$_2$OC(=O)) | $CH_2$ | $-65.30$ | |
| 300 | 4-(N≡CCH(Me)OC(=O)) | $CH_2$ | | 392 (M + 1) |
| 301 | 4-(4-CN—Ph—CH$_2$OC(=O)) | $CH_2$ | $-65.30$ | |
| 308 | 4-(EtOC(=O)) | $CH_2CH_2O$ | | 395 (M − 1) |
| 339 | 4-(EtC≡CCH$_2$OC(=O)) | $CH_2$ | $-65.30$ | |
| 340 | 4-((1-Me-2-pyrrolidinyl)CH$_2$OC(=O)) | $CH_2$ | $-65.30$ | |
| 348 | 4-(Me)$_3$SiC≡CCH$_2$OC(=O)) | $CH_2$ | | 449 (M + 1) |
| 349 | 4-(MeC(=O)CH$_2$OC(=O)) | $CH_2$ | | 395 (M + 1) |
| 350 | 4-(MeON=C(Me)CH$_2$OC(=O)) | $CH_2$ | | 424 (M + 1) |
| 359 | 4-N≡C | $CH_2CH_2CH_2$ | | 348 (M + 1) |
| 360 | 3-Ph | $CH_2CH_2CH_2$ | | 399 (M + 1) |
| 361 | 3-(4-Cl—Ph) | $CH_2CH_2CH_2$ | | 433 (M + 1) |
| 362 | 4-(EtOC(=O)) | $CH_2OCH_2$ | | 397 (M + 1) |
| 363 | 4-(HOC(=O)) | $CH_2CH_2CH_2$ | | 367 (M + 1) |
| 364 | 4-(CH$_2$=C(Me)CH$_2$OC(=O)) | $CH_2CH_2CH_2$ | | 422 (M + 1) |
| 365 | 4-(n-PrOC(=O)) | $CH_2CH_2CH_2$ | | 409 (M + 1) |
| 373 | 4-(CH$_2$=CHCH$_2$OC(=O)) | $CH_2CH_2CH_2$ | | 407 (M + 1) |
| 374 | 4-(CH≡CCH$_2$OC(=O)) | $CH_2CH_2CH_2$ | | 405 (M + 1) |
| 376 | 4-(EtOC(=O)) | $CH_2O$ | | 383 (M + 1) |
| 378 | 4-(EtOC(=O)CH$_2$NHC(=O)) | $CH_2$ | $-65.30$ | |
| 379 | 4-(N≡CCH$_2$N(Me)C(=O)) | $CH_2$ | | 391 (M + 1) |
| 380 | 4-(EtONHC(=O)) | $CH_2$ | $-64.70^a$ | |
| 381 | 4-NH$_2$ | $CH_2$ | | 310 (M + 1) |
| 382 | 4-NO$_2$ | $CH_2$ | $-65.40$ | |
| 383 | 4-I | $CH_2$ | $-65.40$ | |
| 384 | 4-(EtO—N=CH) | $CH_2$ | $-65.35$ | |
| 385 | 4-(n-PrO—N=CH) | $CH_2$ | $-65.33$ | |
| 386 | 4-(CH$_2$=CHCH$_2$O—N=CH) | $CH_2$ | $-65.35$ | |
| 387 | 4-(CH≡CCH$_2$O—N=CH) | $CH_2$ | $-65.34$ | |
| 388 | 4-(i-PrO—N=CH) | $CH_2$ | $-65.36$ | |
| 389 | 4-(CH$_3$C(=O)NHN=CH) | $CH_2$ | $-65.35$ | |
| 390 | MeS(=O)$_2$CH$_2$CH$_2$OC(=O)) | $CH_2$ | $-65.30$ | |
| 391 | 4-((EtO)$_2$CHCH$_2$C(=O)) | $CH_2$ | $-65.30$ | |
| 392 | 4-(F$_2$CHCH$_2$O(=O)) | $CH_2$ | | 403 (M + 1) |
| 406 | 4-(Me)$_2$NC(=O) | $CH_2CH_2CH_2$ | $-65.37$ | 394 (M + 1) |
| 410 | 4-(n-BuOC(=O)) | $CH_2$ | $-65.30$ | |
| 411 | 4-(c-PrCH$_2$OC(=O)) | $CH_2$ | $-65.30$ | |
| 412 | 4-(PhCH$_2$OC(=O)) | $CH_2$ | $-65.30$ | |
| 415 | 4-(MeNHC(=O)) | $CH_2CH_2CH_2$ | $-65.37$ | |
| 427 | 4-(MeOC(=O)) | $CH_2CH_2CH_2$ | | 381 (M + 1) |
| 428 | 4-(EtOC(=O)) | $CH_2CH_2CH_2$ | | 395 (M + 1) |
| 434 | 4-(MeSCH$_2$C(=O)CH$_2$OC(=O)) | $CH_2$ | | 441 (M + H) |
| 435 | 4-CN | $CH_2CH_2CH_2$ | $-65.35$ | |
| 436 | 4-(MeOC(=O)) | $CH_2CH_2CH_2$ | $-65.36$ | |
| 437 | 4-(EtOC(=O)) | $CH_2CH_2CH_2$ | $-65.38$ | |
| 441 | 4-(MeC(=O)NH | $CH_2$ | $-65.40$ | |
| 442 | 4-(MeS(=O)$_2$NH | $CH_2$ | $-65.40$ | |
| 443 | 4-(EtOC(=O)NH | $CH_2$ | $-65.40$ | |
| 447 | 4-(CH$_3$(CH$_2$)$_4$OC(=O)) | $CH_2$ | $-65.30$ | |
| 448 | 4-(ClCH$_2$CH$_2$CH$_2$O(=O)) | $CH_2$ | $-65.30$ | |
| 449 | 4-(CF$_3$CH$_2$NHC(=O)) | $CH_2$ | | 420 (M + 1) |
| 474 | 4-(MeO(CH$_2$)$_3$OC(=O)) | $CH_2$ | $-65.30$ | |
| 475 | 4-((4-morpholinyl)CH$_2$CH$_2$OC(=O)) | $CH_2$ | $-65.30$ | |
| 476 | 4-(EtOC(=O)CH$_2$OC(=O)) | $CH_2$ | $-65.30$ | |
| 477 | 4-(ClCH$_2$CH$_2$OC(=O)) | $CH_2$ | $-65.30$ | |
| 478 | 4-(BrCH$_2$CH$_2$OC(=O)) | $CH_2$ | $-85.30$ | |
| 479 | 4-((2-pyridinyl)(CH$_2$OC(=O)) | $CH_2$ | $-65.30$ | |
| 480 | 4-((Me)$_2$CHCH$_2$CH$_2$OC(=O)) | $CH_2$ | $-65.30$ | |
| 481 | 4-(sec-BuOC(=O)) | $CH_2$ | $-65.40$ | |
| 482 | 4-(CH$_2$=C(Cl)CH$_2$OC(=O)) | $CH_2$ | $-65.30$ | |
| 483 | 4-((3-pyridinyl)CH$_2$NHC(=O)) | $CH_2$ | $-65.30$ | |
| 484 | 4-(PhCH$_2$NH(=O)) | $CH_2$ | $-65.30$ | |

INDEX TABLE A-continued

| Cmpd. No. | (R²)ₓ | L | ¹⁹F NMR | MS |
|---|---|---|---|---|
| 485 | 4-(PhNH(=O)) | CH₂ | −65.30 | |
| 486 | 4-(CH₂=C(CN)CH₂OC(=O)) | CH₂ | | 404 (M + 1) |
| 494 | 4-(MeON=C(CH₂Cl)CH₂OC(=O)) | CH₂ | | 458 (M + 1) |
| 495 | 4-(ClCH₂C(=O)CH₂OC(=O)) | CH₂ | | 429 (M + 1) |
| 496 | 4-[(2,2-dimethyl-1,3-dioxolan-4-yl)CH₂OC(=O)] | CH₂ | | 453 (M + 1) |
| 503 | 3-(F₂S) | CH₂ | −65.31, +72.69(d), +84.24(quint) | |
| 504 | 5-(F₅S) | CH₂ | −65.33, +63.66(d), +80.27(quint) | |

A dash "—" in the (R²)ₓ column means that no R² substituent is present and the remaining carbon valences are occupied by the hydrogen atoms. In the L column, the atom to the right is connect to the phenyl ring and the atom to the left is connected to the pyrazolyl ring.

ᵃ ¹⁹F NMR in DMSO-d₆ solution.

INDEX TABLE B

| Cmpd. No. | (R²)ₓ | L | ¹⁹F NMR | MS |
|---|---|---|---|---|
| 30 | 3-Br, 5-NO₂ | CH₂ | −65.40 | |
| 32 | 5-Br, 6-Me | CH₂ | −65.42 | |
| 34 | 3-Me, 4-Br | CH₂ | −65.41 | |
| 39 | 4-I, 6-Cl | CH₂ | −65.41 | |
| 41 | 6-(MeOC(=O)) | CH₂ | −65.42 | |
| 43 | 3-(MeON(Me)C(=O)) | CH₂ | −65.41 | |
| 44 | 3-(N=CCH₂NHC(=O)) | CH₂ | −65.40 | |
| 45 | 3-(MeNHC(=O)) | CH₂ | −65.41 | |
| 46 | 3-(MeOCH₂CH₂NHC(=O)) | CH₂ | −65.41 | |
| 47 | 7-(MeOC(=O)) | CH₂ | −65.45 | |
| 48 | 5-(MeOC(=O)) | CH₂ | | 403 (M + 1) |
| 49 (Ex. 4) | 4-(MeOC(=O)) | CH₂ | −65.42 | |
| 51 | 3-Me, 5-Br | CH₂ | −65.41 | |
| 53 | 4-Cl, 6-Br | CH₂ | −65.40 | |
| 94 | 5-NO₂ | CH₂ | −65.39 | |
| 99 | 3-Me | CH₂ | −65.43 | |
| 100 | 4-Me | CH₂ | −65.42 | |
| 101 | 7-Me | CH₂ | −65.43 | |
| 104 | 3-N=C | CH₂ | −65.40 | |
| 105 | 4-N=C | CH₂ | −65.41 | |
| 106 | 5-N=C | CH₂ | −65.41 | |
| 112 | 3-Br | CH₂ | −65.41 | |
| 115 | 5-NH₂ | CH₂ | | 360 (M + 1) |
| 116 | 3-Cl | CH₂ | −65.41 | |
| 117 | 3-(EtOC(=O)) | CH₂ | −65.42 | |
| 119 | 5-Cl | CH₂ | −65.42 | |
| 120 | 3-CN, 6-MeO | CH₂ | −65.40 | |
| 125 | 4-F | CH₂ | −65.42 | |
| 126 | 5-MeO | CH₂ | −65.42 | |
| 128 | 5-Br | CH₂ | −65.41 | |
| 134 | 3-(MeOC(=O)) | CH₂ | −65.41 | |
| 143 | — | CH₂ | | 345 (M + 1) |

INDEX TABLE B-continued

| Cmpd. No. | (R²)ₓ | L | ¹⁹F NMR | MS |
|---|---|---|---|---|
| 148 | 3-(Me₂NC(=O)) | CH₂ | −65.41 | |
| 341 | 4-(MeOC(=O)) | CH₂ | −65.40 | |

A dash "—" in the (R²)ₓ column means that no R² substituent is present and the remaining carbon valences are occupied by the hydrogen atoms.

INDEX TABLE C

| Cmpd. No. | (R²)ₓ | L | ¹⁹F NMR |
|---|---|---|---|
| 33 | 5-Br, 6-Me | CH₂ | −65.39 |
| 35 | 5-(MeOC(=O)) | CH₂ | −65.39 |
| 36 (Ex. 4) | 4-(MeOC(=O)) | CH₂ | −65.39 |
| 37 | 3-Me, 4-Br | CH₂ | −65.39 |
| 38 | 4-I, 6-Cl | CH₂ | −65.38 |
| 42 | 6-(MeOC(=O)) | CH₂ | −65.39 |
| 50 | 7-(MeOC(=O)) | CH₂ | −65.42 |
| 52 | 3-Me, 5-Br | CH₂ | −65.40 |
| 54 | 4-Cl, 6-Br | CH₂ | −65.38 |
| 102 | 4-Me | CH₂ | −65.39 |
| 103 | 7-Me | CH₂ | −65.40 |
| 107 | 4-N=C | CH₂ | −65.39 |
| 108 | 5-N=C | CH₂ | −65.38 |
| 113 | 3-Br | CH₂ | −65.40 |

INDEX TABLE C-continued

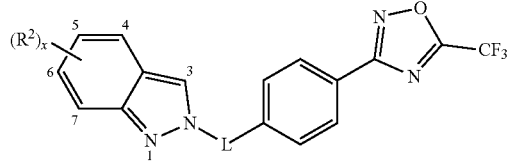

| Cmpd. No. | $(R^2)_x$ | L | $^{19}F$ NMR |
|---|---|---|---|
| 121 | 3-N≡C, 6-MeO | $CH_2$ | −65.39 |
| 123 | 3-(EtOC(=O)) | $CH_2$ | −65.44 |
| 130 | 4-F | $CH_2$ | −65.39 |
| 131 | 5-MeO | $CH_2$ | −65.39 |
| 133 | 5-Br | $CH_2$ | −65.39 |
| 141 | 3-(MeOC(=O)) | $CH_2$ | −65.41 |

INDEX TABLE D

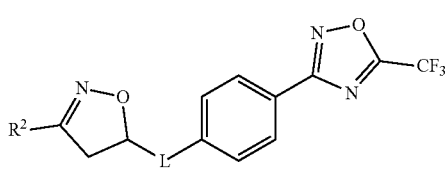

| Cmpd. No. | $R^2$ | L | $^{19}F$ NMR |
|---|---|---|---|
| 12 (Ex. 13) | $Me_2NC(=O)$ | $CH_2$ | −65.36 |
| 29 | EtOC(=O) | $CH_2$ | −65.36 |
| 164 | $NH_2C(=O)$ | $CH_2$ | −65.37 |
| 165 | MeNHC(=O) | $CH_2$ | −65.36 |
| 175 | EtNHC(=O) | $CH_2$ | −65.36 |
| 176 | CH≡CCH$_2$NHC(=O) | $CH_2$ | −65.34 |
| 177 | 1-azetidinyl-C(=O) | $CH_2$ | −65.36 |

INDEX TABLE E

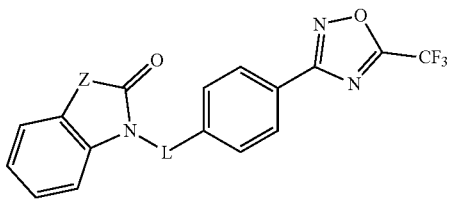

| Cmpd. No. | Z | L | $^{19}F$ NMR | MS |
|---|---|---|---|---|
| 87 | C=O | $CH_2$ | −65.38 | |
| 118 | O | $CH_2$ | −65.41 | |
| 156 | S | $CH_2$ | | 378 (M + 1) |
| 159 (Ex. 7) | N—Me | $CH_2$ | | 375 (M + 1) |
| 161 | $CF_2$ | $CH_2$ | −65.41 | |

INDEX TABLE F

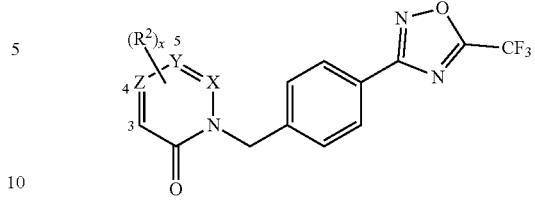

| Cmpd. No. | X | Y | Z | $(R^2)_x$ | $^{19}F$ NMR | MS |
|---|---|---|---|---|---|---|
| 3 | N | CH | C | 4-Cl | | 357 (M + 1) |
| 4 (Ex. 3) | N | C | CH | 5-Cl | | 357 (M + 1) |
| 5 | N | C | C | 4,5-di-Cl | | 391 (M + 1) |
| 27 | N | C | C | 4-MeO, 5-Cl | | 387 (M + 1) |
| 28 | N | CH | C | 4-MeO | | 353 (M + 1) |
| 417 | CH | CH | CH | 3-CN | −65.30 | |
| 418 | CH | N | CH | 3-(EtOC(=O)) | −65.30 | |
| 419 | CH | C | N | 5-(EtOC(=O)) | −65.30 | |
| 420 | CH | C | CH | 5-(MeOC(=O)) | −65.30 | |
| 421 | CH | CH | C | 4-MeO | −65.30 | |
| 422 | CH | CH | CH | 3-(MeOC(=O)) | −65.30 | |
| 423 | CH | CH | N | 3-(MeOC(=O)) | | 381 (M + 1) |

INDEX TABLE G

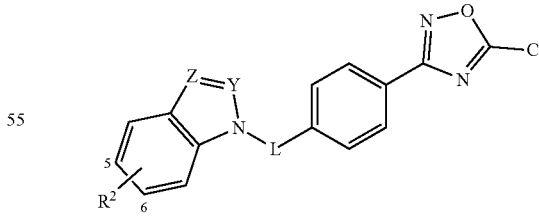

| Cmpd. No. | Z | L | $^{19}F$ NMR |
|---|---|---|---|
| 8 | (N≡C)CH | $CH_2$ | −65.44 |
| 14 | O | CH(C≡N) | −65.32 |
| 96 | O | $CH_2$ | −65.36 |
| 150 | C=O | $CH_2$ | −65.36 |

INDEX TABLE H

| Cmpd. No. | Z | Y | $R^2$ | L | $^{19}F$ NMR | MS |
|---|---|---|---|---|---|---|
| 22 | N | N | 5-(MeOC(=O)) | $CH_2$ | | 404 (M + 1) |
| 88 | CH | CH | 6-CN | $CH_2$ | −65.38 | |
| 91 | N | CH | — | $CH_2$ | −65.38 | |
| 92 | N | N | — | $CH_2$ | −65.39 | |

A dash "—" in the $R^2$ column means that no $R^2$ substituent is present and the remaining carbon valences are occupied by hydrogen atoms.

INDEX TABLE I

| Cmpd. No. | Z | Y | L | $^{19}$F NMR |
|---|---|---|---|---|
| 11 | C(=O) | S(=O)$_2$ | CH$_2$ | −65.41 |
| 90 (Ex. 9) | C(=O) | C(=O) | CH$_2$ | −65.39 |
| 155 | S | C(=O) | CH$_2$ | −65.40 |
| 160 | CH$_2$ | CH$_2$ | CH$_2$ | −65.41 |

INDEX TABLE J

| Cmpd. No. | R$^2$ | L | Z | R$^5$ | $^{19}$F NMR | MS | m.p. (° C.) |
|---|---|---|---|---|---|---|---|
| 70 | 4-(EtOC(=O)) | CH$_2$ | S | H | −65.39 | | |
| 71 (Ex. 11) | 4-Br | CH$_2$ | S | H | −65.41 | | |
| 72 | 3-Br | CH$_2$ | S | H | −65.39 | | |
| 73 | 3-(EtOC(=O)), 5-Me | CH$_2$ | S | H | −65.44 | | |
| 76 | 3-CN, 4-Br | CH$_2$ | S | H | −65.36 | | |
| 77 | 4-Br, 5-CN | CH$_2$ | S | H | −65.38 | | |
| 188 | 4-(MeOC(=O)) | CH$_2$ | S | H | −65.40 | | |
| 189 | 4-CN | CH$_2$ | S | H | −65.41 | | |
| 190 | 4-(CH=CCH$_2$OC(=O)) | CH$_2$ | S | H | −65.39 | | |
| 192 | 4-(EtOC(=O)) | CH(Me) | S | H | −65.47 | | |
| 197 | 4-CH(=O) | CH$_2$ | S | H | −65.38 | | |
| 198 | 4-(n-PrOC(=O)) | CH$_2$ | S | H | −65.39 | | |
| 199 | 4-(CH$_2$=CHCH$_2$OC(=O)) | CH$_2$ | S | H | −65.44 | | |
| 200 | 4-(i-PrOC(=O)) | CH$_2$ | S | H | −65.39 | | |
| 209 | 4-(HOC(=O)) | CH$_2$ | S | MeO | | | 141-152.3 |
| 210 | 4-(EtOC(=O)) | CH$_2$ | O | H | | | 65-80.9 |
| 211 | 4-(n-PrOC(=O)) | CH$_2$ | O | H | | | 53.5-64.1 |
| 246 | 4-(EtOC(=O)) | CH(Me) | S | H | | 387 (M + 1) | |
| 247 | 4-(EtOC(=O)) | CH(Me) | S | H | | 387 (M + 1) | |
| 248 | 4-(n-PrOC(=O)) | CH(Me) | S | H | | 401 (M + 1) | |
| 249 | 4-(n-PrOC(=O)) | CH(Me) | S | H | | 401 (M+) | |
| 491 | 4-(CH=CCH$_2$NHC(=O)) | CH$_2$ | S | H | | 371 (M + 1) | |
| 493 | 4-(n-PrOC(=O)) | CH(Me) | S | H | | | |
| 336 | 4-(EtOC(=O)) | CH$_2$ | S | MeO | | | 126.2-128.3 |
| 439 | 4-(n-PrOC(=O)) | CH$_2$ | S | MeO | | 417 (M + H) | |
| 440 | 4-(CH$_2$=CHCH$_2$OC(=O)) | CH$_2$ | S | MeO | | 415 (M + H) | |

INDEX TABLE K

| Cmpd. No. | R$^1$ | L | $^{19}$F NMR | m.p. (° C.) |
|---|---|---|---|---|
| 191 | c-Pr | NHCH$_2$ | −65.46 | |
| 194 | 5-cyano-1-methyl-1H-indazol-3-yl | CH$_2$ | −65.41 | |

INDEX TABLE K-continued

[Structure: thienyl ring with R¹-L substituent at 5-position and 1,2,4-oxadiazole-CF₃ at 2-position]

| Cmpd. No. | R¹ | L | $^{19}$F NMR | m.p. (° C.) |
|---|---|---|---|---|
| 195 | 5-MeO-1-methyl-1H-indazol-yl | CH₂ | −65.41 | |
| 196 | 1H-indol-1-yl | CH₂ | −65.46 | |
| 201 | ethyl 2-methylthiazole-4-carboxylate-yl | CH₂ | | 80-84 |
| 202 | N-(cyclopropylmethyl)-2-methylthiazole-4-carboxamide-yl | CH₂ | | 415 (M + 1) |
| 323 | tetrahydro-1,1-dioxido-2H-1,2-thiazin-2-yl | CH₂ | | 368 (M + 1) |
| 324 | 1,1-dioxido-2-isothiazolidinyl | CH₂ | | 376 (M + 23) |
| 325 | 3-oxo-4-morpholinyl | CH₂ | | 334 (M + 1) |
| 375 | 2-Me-5-F—Ph | OCH₂ | −65.46 | |
| 438 | 2-Me—Ph | OCH₂ | −66.04 | |

In the L column, the atom to the right is connect to the thienyl ring and the atom to left is connected to R¹.

INDEX TABLE L

[Structure: R²-substituted isoxazoline-thienyl-oxadiazole-CF₃]

| Cmpd. No. | R¹ | L | MS | m.p. (° C.) |
|---|---|---|---|---|
| 366 | EtOC(=O) | CH₂ | | 88.7-93.2 |
| 367 | HOC(=O) | CH₂ | | 111.5-125.6 |
| 368 | MeNHC(=O) | CH₂ | | 95.3-120.3 |
| 369 | EtNHC(=O) | CH₂ | | 145-147 |
| 429 | CH≡CCH₂NHC(=O) | CH₂ | | 113.5-119 |
| 430 | (Et)₂NC(=O) | CH₂ | 403 (M + 1) | |
| 460 | (Me)₂NC(=O) | CH₂ | 375 (M + 1) | |
| 461 | MeOCH₂CH₂NHC(=O) | CH₂ | | 55.2-78.1 |

INDEX TABLE M

[Structure: R¹-L-pyrazol-1-yl with 1,2,4-oxadiazole-CF₃ at 4-position]

| Cmpd. No. | R¹ | L | $^{19}$F NMR |
|---|---|---|---|
| 305 | 4-(EtOC(=O))-1H-pyrazol-1-yl | CH₂ | −65.39 |
| 306 | Me₂N-C(=O)-5-methyl-4,5-dihydroisoxazol-3-yl | CH₂ | −65.38 |
| 307 | 4-(EtOC(=O))-1H-pyrazol-1-yl | CH₂CH₂ | −65.44 |
| 310 | 4-(MeOC(=O))—Ph | CH₂CH₂ | −65.43 |
| 311 | 4-(MeOC(=O))—Ph | CH₂ | −65.43 |
| 326 | 3-(5-trifluoromethyl-1,2,4-oxadiazol-3-yl)-1H-pyrazol-1-yl | CH₂CH₂CH₂ | −65.43 |

INDEX TABLE N

[Structure: R² on thiazole/oxazole ring (Z), connected via L to phenyl bearing 3-(5-CF₃-1,2,4-oxadiazol-3-yl)]

| Cmpd No. | R² | Z | L | m.p. (° C.) | MS |
|---|---|---|---|---|---|
| 203 | (N≡C)₂CHNHC(=O) | O | CH₂ | | 403 (M + 1) |
| 204 | ClCH₂CH₂NHC(=O) | O | CH₂ | | 401 (M + 1) |
| 205 | 3,3-difluoro-1-piperidinyl-C(=O) | O | CH₂ | | 444 (M + 1) |
| 206 | (Me)₃SiCH₂CH₂NHC(=O) | O | CH₂ | | 439 (M + 1) |
| 207 | 3,3-difluoro-1-pyrrolidinyl-C(=O) | S | CH₂ | | 445 (M + 1) |
| 208 | Cl₂C=CHCH₂NHC(=O) | S | CH₂ | | 463 (M + 1) |
| 225 | F₂CHCH₂NHC(=O) | O | CH₂ | | 403 (M + 1) |
| 226 | 2,2-difluorocyclopropyl-CH₂NHC(=O) | O | CH₂ | | 429 (M + 1) |
| 227 | 1-pyrrolidinyl-C(=O) | O | CH₂ | | 393 (M + 1) |
| 228 | 4,4-difluoro-1-piperidinyl-C(=O) | O | CH₂ | | 443 (M + 1) |
| 229 | N≡CCH₂CH₂NHC(=O) | O | CH₂ | | 392 (M + 1) |
| 230 | N≡CC(Me)₂NHC(=O) | O | CH₂ | | 406 (M + 1) |
| 231 | N≡C-C(cyclopropyl)-NHC(=O) | O | CH₂ | | 404 (M + 1) |
| 252 | EtOC(=O) | O | CH₂ | | 368 (M + 1) |
| 253 | HOC(=O) | O | CH₂ | | 340 (M + 1) |
| 254 | NH₂C(=O) | O | CH₂ | | 339 (M + 1) |
| 256 | N≡C | O | CH₂ | | 319 (M + 1) |
| 257 | MeOCH₂CH₂NHC(=O) | O | CH₂ | | 397 (M + 1) |
| 258 | N≡CCH₂NHC(=O) | O | CH₂ | | 378 (M + 1) |
| 259 | i-PrNHC(=O)) | O | CH₂ | | 381 (M + 1) |
| 260 | c-PrNHC(=O) | O | CH₂ | | 379 (M + 1) |
| 261 | 1-azetidinyl-C(=O) | O | CH₂ | | 379 (M + 1) |
| 262 | Et₂NC(=O) | O | CH₂ | | 395 (M + 1) |
| 263 | 4-morpholinyl-C(=O) | O | CH₂ | | 409 (M + 1) |
| 264 | 1H-pyrazol-1-yl-CH₂CH₂NHC(=O) | O | CH₂ | 125-126 | 433 (M + 1) |
| 265 | 1-methyl-1H-pyrazol-3-yl-CH₂NHC(=O) | O | CH₂ | | 433 (M + 1) |
| 277 | 2-thiazolyl-CH₂NHC(=O) | O | CH₂ | | 436 (M + 1) |
| 278 | (MeO)₂CHCH₂NHC(=O) | O | CH₂ | | 427 (M + 1) |
| 279 | (MeOCH₂)₂CHNHC(=O) | O | CH₂ | | 441 (M + 1) |
| 280 | EtNHC(=O) | O | CH₂ | | 367 (M + 1) |
| 315 | (Me)₂NC(=O) | O | CH₂ | | 367 (M + 1) |
| 316 | F₃CCH₂NHC(=O) | O | CH₂ | | 421 (M + 1) |
| 327 | c-PrCH₂NHC(=O) | O | CH₂ | | 393 (M + 1) |
| 328 | CF₃CF₂CH₂NHC(=O) | O | CH₂ | | 471 (M + 1) |
| 329 | 3-thietanyl-NHC(=O) | O | CH₂ | | 411 (M + 1) |
| 330 | CF₃CH₂CH₂NHC(=O) | O | CH₂ | 104-105 | 435 (M + 1) |
| 331 | CF₃C(Me)₂NHC(=O) | O | CH₂ | | 449 (M + 1) |
| 332 | tetrahydro-2-oxo-3-furanyl-NHC(=O)) | O | CH₂ | | 423 (M + 1) |
| 334 | CH₂=CHCH₂OC(=O) | O | CH₂ | | 380 (M + 1) |
| 335 | i-BuOC(=O) | O | CH₂ | | 396 (M + 1) |
| 342 | c-PrNHC(=O) | S | CH₂ | 112-116 | |
| 343 | H₂NC(=O) | S | CH₂ | 195-199 | |
| 344 | EtOC(=O) | S | CH₂ | 109-113 | |
| 345 | HOC(=O) | S | CH₂ | 200-204 | |
| 370 | N≡C | S | CH₂ | 97-101 | |
| 393 | N≡CCH₂NHC(=O) | S | CH₂ | 143-147 | |
| 394 | MeOCH₂NHC(=O) | S | CH₂ | 83-87 | |
| 395 | 4,4-difluorocyclohexyl-NHC(=O) | O | CH₂ | | 457 (M + 1) |
| 396 | H-pyrazol-1-yl-CH₂CH₂NHC(=O) | S | CH₂ | | 449 (M + 1) |
| 397 | CF₃CH₂CH₂NHC(=O) | S | CH₂ | | 451 (M + 1) |
| 398 | CF₃(CH₂)₃NHC(=O) | O | CH₂ | | 449 (M + 1) |
| 399 | Cl₂C=CHCH₂NHC(=O) | O | CH₂ | | 447 (M + 1) |
| 400 | FCH₂CH₂NHC(=O) | O | CH₂ | | 385 (M + 1) |
| 401 | CF₃OCH₂CH₂NHC(=O) | O | CH₂ | | 451 (M + 1) |
| 402 | 3,3-di-F-pyrolidin-1-yl-C(=O) | O | CH₂ | | 429 (M + 1) |
| 403 (Ex. 18) | MeOC(=O) | O | CH₂O | | 370 (M + 1) |
| 404 | EtOC(=O) | S | CH₂O | | 400 (M + 1) |
| 463 | CF₃CH₂NHC(=O) | S | CH₂ | | 437 (M + 1) |
| 464 | MeOCH₂NHC(=O) | O | CH₂O | | 413 (M + 1) |
| 465 | CF₃CH₂NHC(=O) | O | CH₂O | | 437 (M + 1) |
| 466 | 1H-pyrazol-1-yl-CH₂CH₂NHC(=O) | O | CH₂O | | 449 (M + 1) |
| 467 | CF₃CH₂CH₂NHC(=O) | O | CH₂O | | 451 (M + 1) |
| 468 | N≡CCH₂NHC(=O) | O | CH₂O | | 394 (M + 1) |
| 469 | MeOCH₂CH₂NHC(=O) | S | CH₂O | | 429 (M + 1) |

INDEX TABLE N-continued

| Cmpd No. | R² | Z | L | m.p. (° C.) | MS |
|---|---|---|---|---|---|
| 470 | CF₃CH₂NHC(=O) | S | CH₂O | | 453 (M + 1) |
| 471 | 1H-pyrazol-1-yl-CH₂CH₂NHC(=O) | S | CH₂O | | 465 (M + 1) |
| 472 | CF₃CH₂CH₂NHC(=O) | S | CH₂O | | 467 (M + 1) |
| 473 | N≡CCH₂NHC(=O) | S | CH₂O | | 410 (M + 1) |
| 487 | 4-morpholinyl-C(=O) | S | CH₂ | 86-90 | |
| 488 | EtNHC(=O) | S | CH₂ | 71-75 | |
| 489 | (MeOCH₂)₂CHNHC(=O) | S | CH₂ | | 457 (M + 1) |
| 490 | MeOC(=O) | O | CH₂ | | 354 (M + 1) |

In the L column, the atom to the right is connect to the phenyl ring and the atom to left is connected to the R¹ ring.

INDEX TABLE O

| Cmpd No. | R² | L | ¹⁹F NMR | MS |
|---|---|---|---|---|
| 13 (Ex. 14) | — | NHCH(C≡N) | -65.31 | |
| 15 | — | N(Ac)CH(C≡N) | -65.34 | |
| 281 | 4-(CF₃CH₂NHC(=O)) | CH₂ | | 430 (M + 1) |
| 282 | 4-(MeOCH₂CH₂NHC(=O)) | CH₂ | | 406 (M + 1) |
| 283 | 4-(N≡CCH₂NHC(=O)) | CH₂ | | 387 (M + 1) |
| 284 | 3-(MeOCH₂CH₂NHC(=O)) | CH₂ | | 406 (M + 1) |
| 285 | 3-(N≡CCH₂NHC(=O)) | CH₂ | | 387 (M + 1) |
| 309 | 4-MeO | CH(OH) | -65.37 | |
| 354 | 4-(MeOC(=O)) | CH₂O | -65.41 | |
| 451 | — | CH₂ | -65.37 | |
| 453 | 4-(EtOC(=O)) | CH₂ | | 376 (M - 1) |
| 454 | 3-(EtOC(=O)) | CH₂ | | 376 (M - 1) |
| 497 | 2-Me | CH(OH) | | 333 (M - 1) |
| 498 | 3-F | CH(OH) | | 337 (M - 1) |
| 499 | 3-Cl | CH(OH) | | 353 (M - 1) |
| 500 | 4-F | CH(OH) | | 337 (M - 1) |
| 501 | 4-Me | CH(OH) | | 333 (M - 1) |

A dash "—" in the (R²)ₓ column means that no R² substituent is present and the remaining carbon valences are occupied by hydrogen atoms.
In the L column, the atom to the right is connect to the J phenyl ring and the atom to left is connected to the R¹ phenyl ring bearing (R²)ₓ.

INDEX TABLE P

| Cmpd No. | Z | R² | L | MS |
|---|---|---|---|---|
| 286 | S | CF₃CH₂NHC(=O) | CH₂ | 436 (M + 1) |
| 287 | S | MeOCH₂CH₂NHC(=O) | CH₂ | 412 (M + 1) |
| 288 | S | N≡CCH₂NHC(=O) | CH₂ | 393 (M + 1) |
| 289 | S | 1H-pyrazol-1-yl-CH₂CH₂NHC(=O) | CH₂ | 448 (M + 1) |

INDEX TABLE P-continued

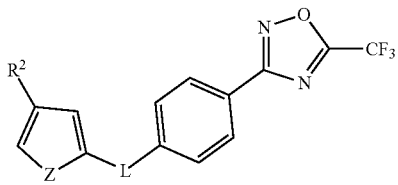

| Cmpd No. | Z | R² | L | MS |
|---|---|---|---|---|
| 290 | S | c-PrCH₂NHC(=O) | CH₂ | 408 (M + 1) |
| 292 | O | MeOCH₂CH₂NHC(=O) | CH₂ | 396 (M + 1) |
| 293 | O | 1H-pyrazol-1-yl-CH₂CH₂NHC(=O)) | CH₂ | 432 (M + 1) |
| 294 | O | N≡CCH₂NHC(=O) | CH₂ | 377 (M + 1) |
| 291 | O | CF₃CH₂NHC(=O) | CH₂ | 420 (M − 1) |
| 455 | S | MeOC(=O) | CH₂ | 368 (M − 1) |
| 456 | O | MeOC(=O) | CH₂ | 352 (M − 1) |

INDEX TABLE Q

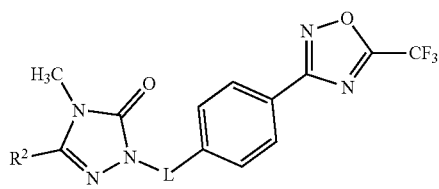

| Cmpd No. | R² | L | ¹⁹F NMR | MS |
|---|---|---|---|---|
| 235 | Et | CH₂ | −65.36 | 354 (M + 1) |
| 236 | c-Pr | CH₂ | −65.36 | 366 (M + 1) |
| 237 | i-Pr | CH₂ | −65.36 | 368 (M + 1) |
| 238 | n-Pr | CH₂ | −65.36 | 368 (M + 1) |
| 239 | CF₃ | CH₂CH₂ | −65.37, −66.17 | 408 (M + 1) |
| 240 | CF₃ | CH₂CH₂CH₂ | −65.37, −66.17 | 422 (M + 1) |
| 267 | CF₃ | CH₂ | −65.37, −66.17 | 394 (M + 1) |

INDEX TABLE R

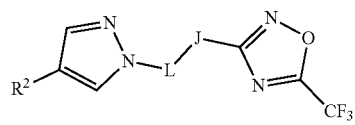

| Cmpd No. | R² | L | J | ¹⁹F NMR | MS | m.p. (° C.) |
|---|---|---|---|---|---|---|
| 193 | EtOC(=O) | CH₂ | thiophene | −65.38 | | |
| 234 | EtOC(=O) | CH₂ | N-methyl pyridinone | −65.19 | | |
| 250 | n-PrOC(=O) | CH₂ | thiophene | −65.41 | | |
| 251 | i-PrOC(=O) | CH₂ | thiophene | −65.41 | | |
| 271 | EtOC(=O) | CH₂ | thiophene | | 371 (M + 1) | |
| 304 | EtOC(=O) | CH₂ | fluorodimethylphenyl | | 385 (M + 1) | |
| 346 | EtOC(=O) | CH₂ | dimethyl pyridazinone | | 385 (M + 1) | |

INDEX TABLE R-continued

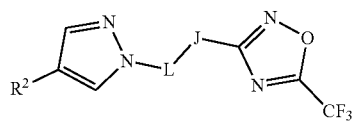

| Cmpd No. | R² | L | J | ¹⁹F NMR | MS | m.p. (° C.) |
|---|---|---|---|---|---|---|
| 347 | EtOC(=O) | CH₂CH₂ | (1-methyl-6-oxo-pyridazin-3-yl) | | 399 (M + 1) | |
| 358 | EtOC(=O) | CH₂CH₂CH₂ | (1-methyl-6-oxo-pyridazin-3-yl) | | 413 (M + 1) | |
| 377 | HOC(=O) | CH₂ | (2,4-disubstituted thiophene) | −65.38 | | |
| 416 | n-PrOC(=O) | CH₂ | (2,6-naphthalenediyl) | | | 100.7-130 |
| 424 | EtOC(=O) | CH₂ | (2,5-pyridinediyl) | −65.30 | | |
| 457 | EtOC(=O) | CH₂ | (2,6-naphthalenediyl) | | 417 (M + 1) | |
| 458 | EtOC(=O) | CH₂ | (1-methyl-piperidin-4-yl) | | 374 (M + 1) | |
| 459 | EtOC(=O) | CH₂CH₂ | (1-methyl-piperidin-4-yl) | | 388 (M + 1) | |

In the J column the bond to the left is connected to L and the bond to the right is connected to the oxadiazolyl ring.

INDEX TABLE S

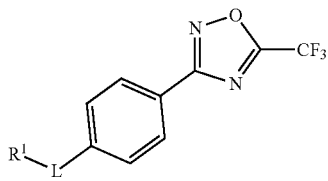

| Cmpd No. | R¹ | L | ¹⁹F NMR | MS |
|---|---|---|---|---|
| 9 | 3-cyano-1H-1,2,4-triazol-1-yl | CH₂ | −65.38 | |
| 10 | 3-cyano-4H-1,2,4-triazol-4-yl | CH₂ | −65.39 | |
| 16 | 4-(MeOC(=O))-1H-1,2,3-triazol-1-yl | CH₂ | −65.35 | |

INDEX TABLE S-continued
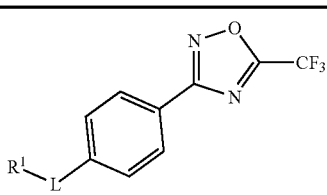
| Cmpd No. | R¹ | L | ¹⁹F NMR | MS |
|---|---|---|---|---|
| 23 | 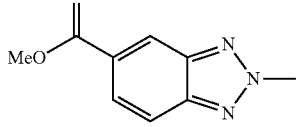 | CH$_2$ | | 404 (M + 1) |
| 24 (Ex. 8) | 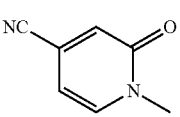 | CH$_2$ | −65.39 | |
| 31 | 4-Me-5-MeS-2H-1,2,3-triazol-2-yl | CH$_2$ | −65.40 | |
| 40 | 4-MeS-5-Me-1H-1,2,3-triazol-1-yl | CH$_2$ | −65.39 | |
| 74 (Ex. 15) | 4-(MeOC(=O))-4,5-dihydro-2-oxazolyl | CH$_2$ | −65.33 | 356 (M + 1) |
| 75 (Ex. 17) | 4-(NH$_2$C(=O))-4,5-dihydro-2-oxazolyl | CH$_2$ | −65.32 | 341 (M + 1) |
| 84 | 5-Br-4-(EtOC(=O))-2H-1,2,3-triazol-2-yl | CH$_2$ | −70.14 | |
| 86 | 1H-pyrrolo[2,3-b]pyridin-1-yl | CH$_2$ | −65.40 | |
| 89 | 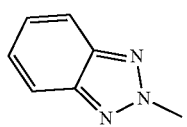 | CH$_2$ | −65.35 | |
| 93 | 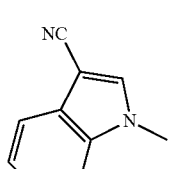 | CH$_2$ | −65.38 | |
| 124 | 3-(EtOC(=O))-1-pyrrolidinyl | CH$_2$ | −65.46 | |
| 129 | 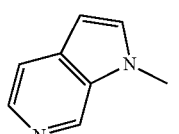 | CH$_2$ | −65.39 | |
| 135 | 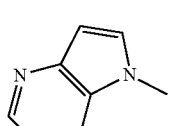 | CH$_2$ | −65.40 | |
| 136 (Ex. 5) | 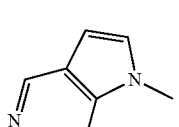 | CH$_2$ | −65.40 | |
| 137 |  | CH$_2$ | −65.40 | |
| 138 | 3-(MeOC(=O))-4H-1,2,4-triazol-4-yl | CH$_2$ | −65.41 | |

INDEX TABLE S-continued
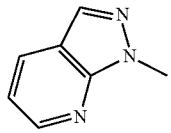
| Cmpd No. | R¹ | L | ¹⁹F NMR | MS |
|---|---|---|---|---|
| 139 | 3-(MeOC(=O))-1H-1,2,4-triazol-1-yl | CH₂ | −65.41 | |
| 147 (Ex. 1) | 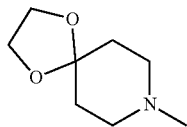 | CH₂ | −65.43 | |
| 149 | 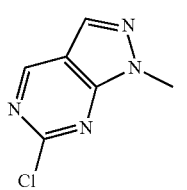 | CH₂ | −65.38 | |
| 151 | 3-cyano-1-pyrrolidinyl | CH₂ | −65.41 | 323 (M + 1) |
| 152 | 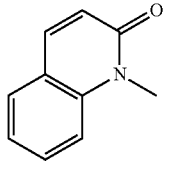 | CH₂ | −65.37 | 381 (M + 1) |
| 157 | 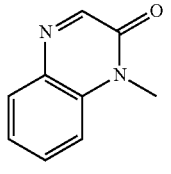 | CH₂ | −65.42 | |
| 158 (Ex. 6) | 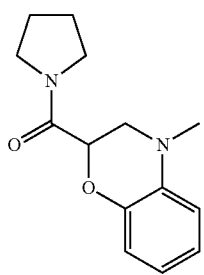 | CH₂ | −65.40 | |
| 178 (Ex. 16) | 4-(Me₂NC(=O))-4,5-dihydro-2-oxazolyl | CH₂ | −65.36 | 370 (M + 1) |
| 255 | 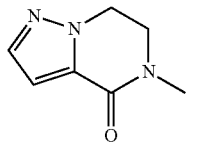 | CH₂ | | 473 (M + 1) |
| 297 |  | CH₂ | | 364 (M + 1) |
| 298 | 2-Me-4-thiazolyl | CH₂O | | 342 (M + 1) |

INDEX TABLE S-continued

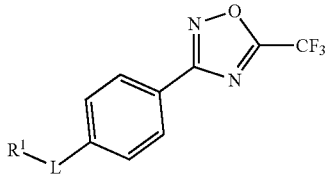

| Cmpd No. | R¹ | L | ¹⁹F NMR | MS |
|---|---|---|---|---|
| 303 | 4-(EtOC(=O))-1H-1,2,3-triazol-1-yl | CH₂ | −65.30 | |
| 312 | 3-(MeOC(=O))-5-isoxazolyl | CH₂O | | 369 (M − 1) |
| 313 | 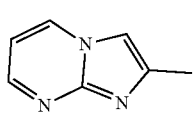 | CH₂O | | 361 (M + 1) |
| 314 | 3-(Me₂NC(=O))-5-isoxazolyl | CH₂O | | 383 (M + 1) |
| 317 | 5-(MeOC(=O))-2-thienyl | CH₂O | | 383 (M − 1) |
| 318 | 3-isoxazolyl | CH₂O | | 312 (M + 1) |
| 319 | 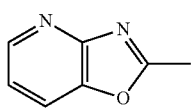 | CH₂O | | 362 (M + 1) |
| 320 | 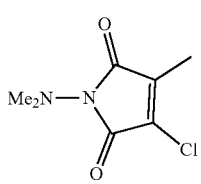 | CH₂O | | 363 (M + 1) |
| 321 | tetrahydro-1,1-dioxido-2H-1,2-thiazin-2-yl | CH₂ | | 362 (M + 1) |
| 322 | 1,1-dioxido-2-isothiazolidinyl | CH₂ | | 370 (M + 23) |
| 337 | 1H-1,2,4-triazol-1-yl | CH₂O | | 312 (M + 1) |
| 338 | 3,5-dimethyl-4-isoxazolyl | CH₂O | | 340 (M + 1) |
| 351 | 3,4-dihydro-2(1H)-isoquinolinyl | CH₂ | −65.40 | |
| 352 | 5-(EtNHC(=O))-2-thienyl | CH₂O | | 398 (M + 1) |
| 353 | 3-pyridinyl | CH₂O | | 322 (M + 1) |
| 355 | 2-benzoxazolyl | CH₂O | | 362 (M + 1) |
| 356 | 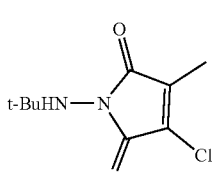 | O | −65.32 | |
| 357 | 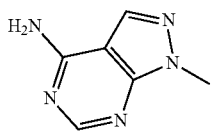 | O | −65.35 | |
| 371 | 2-oxo-1-pyrrolidinyl | CH₂ | | 312 (M + 1) |
| 372 | 3-oxo-4-morpholinyl | CH₂ | | 327 (M + 1) |
| 407 | 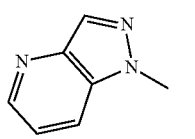 | CH₂ | −65.30 | |
| 408 |  | CH₂ | −65.40 | |

INDEX TABLE S-continued

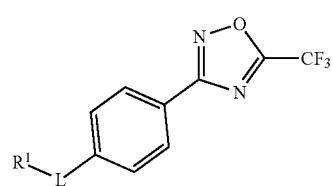

| Cmpd No. | R¹ | L | ¹⁹F NMR | MS |
|---|---|---|---|---|
| 409 | (4-azaindazole, N-methyl) | $CH_2$ | | 346 (M + 1) |
| 414 | 5-bromo-pyrazolo[3,4-b]pyridine, 2-methyl | $CH_2$ | −65.30 | |
| 413 | 5-bromo-pyrazolo[3,4-b]pyridine, 1-methyl | $CH_2$ | −65.30 | |
| 431 | 3-methyl-3-(ethoxycarbonyl)-2-oxopyrrolidine | $CH_2$ | | 384 (M + 1) |
| 432 | 3-methyl-3-(ethoxycarbonyl)-2-oxopiperidine | $CH_2$ | | 398 (M + 1) |
| 433 | 6-chloro-pyrazolo[3,4-d]pyrimidine, 2-methyl | $CH_2$ | −65.30 | |
| 444 | 4-iodo-pyrazolo[3,4-b]pyridine, 1-methyl | $CH_2$ | −65.40 | |
| 445 | 4-iodo-pyrazolo[3,4-b]pyridine, 2-methyl | $CH_2$ | | 472 (M + 1) |

INDEX TABLE S-continued

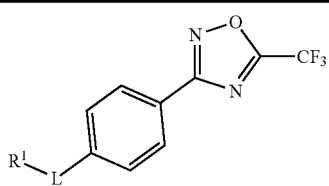

| Cmpd No. | R¹ | L | ¹⁹F NMR | MS |
|---|---|---|---|---|
| 446 | 3-amino-1-methyl-1H-pyrazolo[3,4-b]pyridin-5-yl | CH₂ | −65.40 | |
| 450 | 5-(CF₃C(=O))-2-furanyl | CH₂ | −65.35, −73.25 | |
| 452 | methyl 2-methyl-5-thiazolecarboxylate-4-yl | O | | 372 (M + 1) |
| 462 | 7-methyl-6-oxo-5,6,7,8-tetrahydroimidazo[1,5-a]pyrimidin-yl | CH₂ | | 364 (M + 1) |
| 492 | 2,7-dimethyl-6-oxo-5,6,7,8-tetrahydroimidazo[1,5-a]pyrimidin-yl | CH₂ | | 379 (M + 1) |

INDEX TABLE T

| Cmpd No. | Structure | ¹⁹F NMR | AP+ (M + 1) |
|---|---|---|---|
| 224 | Me₂N-C(=O)-isoxazoline-CH₂CH₂-O-phenyl-oxadiazole-CF₃ | −65.37 | 399 (M + 1) |
| 232 | 2-fluorobenzyl-pyridinone-oxadiazole-CF₃ | −65.23 | |
| 233 | 3-methoxybenzyl-pyridinone-oxadiazole-CF₃ | −65.24 | |

INDEX TABLE T-continued

| Cmpd No. | Structure | $^{19}$F NMR | AP+ (M + 1) |
|---|---|---|---|
| 426 | Me₂N-isoxazoline-CH₂-N(piperidine)-1,2,4-oxadiazole-CF₃ | −65.43 | 376 (M + 1) |
| 502 | Me₂N-isoxazoline-CH₂-O-phenyl-1,2,4-oxadiazole-CF₃ | −65.34 | |

Biological Examples of the Invention

General protocol for preparing test suspensions for Tests A-C: the test compounds were first dissolved in acetone in an amount equal to 3% of the final volume and then suspended at the desired concentration (in ppm) in acetone and purified water (50/50 mix by volume) containing 250 ppm of the surfactant PEG400 (polyhydric alcohol esters). The resulting test suspensions were then used in Tests A-C.

Test A

The test suspension was sprayed to the point of run-off on soybean seedlings. The following day the seedlings were inoculated with a spore suspension of *Phakopsora pachyrhizi* (the causal agent of Asian soybean rust) and incubated in a saturated atmosphere at 22° C. for 24 h and then moved to a growth chamber at 22° C. for 8 days, after which time visual disease ratings were made.

Test B

The test suspension was sprayed to the point of run-off on wheat seedlings. The following day the seedlings were inoculated with a spore suspension of *Zymoseptoria tritici* (the causal agent of wheat leaf blotch) and incubated in a saturated atmosphere at 24° C. for 48 h, and then moved to a growth chamber at 20° C. for 17 days, after which time visual disease ratings were made.

Test C

The test suspension was sprayed to the point of run-off on wheat seedlings. The following day the seedlings were inoculated with a spore suspension of *Puccinia recondita* f. sp. *tritici*; (the causal agent of wheat leaf rust) and incubated in a saturated atmosphere at 20° C. for 24 h, and then moved to a growth chamber at 20° C. for 6 days, after which time visual disease ratings were made.

Test D

The test suspension was sprayed to the point of run-off on wheat seedlings. The following day the seedlings were inoculated with a spore suspension of *Erysiphe graminis* f. sp. *tritici*, (the causal agent of wheat powdery mildew) and incubated in a saturated atmosphere at 20° C. for 8 days, after which time visual disease ratings were made. Of the compounds tested the following provided very good to excellent disease control (80% or greater): 85, 192, 263, 282, 337, 353, 455, 454, 490 and 497.

Results for Tests A-C are given in Table A. In the Table, a rating of 100 indicates 100% disease control and a rating of 0 indicates no disease control (relative to the controls). A dash (-) indicates the compound was not tested. The test suspensions were sprayed at the concentration listed in the column "Rate in ppm", unless otherwise indicated. An asterisk "*" next to the rating indicates a 250 ppm test suspension was used, a double asterisk "" next to the rating indicates a 100 ppm test suspension was used, and a triple asterisk "*" next to the rating indicates a 50 ppm test suspension was used.

TABLE A

| Cmpd No. | Rate in ppm | Test A | Test B | Test C |
|---|---|---|---|---|
| 1 | 10 | 100 | — | 68 |
| 2 | 10 | 100 | 98** | 99 |
| 3 | 50 | 100 | — | 100 |
| 4 | 50 | 100 | — | 100 |
| 5 | 50 | 100 | — | 94 |
| 6 | 250 | 100 | 0 | 100 |
| 7 | 250 | 100 | 0 | 100 |
| 8 | 270 | 100 | 18 | 100 |
| 9 | 260 | 100 | 100 | 100 |
| 10 | 270 | 100 | 5 | 100 |
| 11 | 10 | 100 | — | 74 |
| 12 | 255 | 100 | 98 | 100 |
| 13 | 250 | 100 | 85 | 100 |
| 14 | 250 | 100 | 86 | 100 |
| 15 | 250 | 100 | 0 | 96 |
| 16 | 260 | 100 | 93 | 100 |
| 17 | 250 | 100 | 98 | 100 |
| 18 | 250 | 100 | 93 | 100 |
| 19 | 250 | 100 | 100 | 100 |
| 20 | 250 | 100 | 99 | 100 |
| 21 | 10 | 100 | 97** | 100 |
| 22 | 10 | 100 | — | 96 |
| 23 | 10 | 100 | — | 100 |
| 24 | 10 | 100 | — | 95 |
| 25 | 250 | 100 | 86* | 100 |
| 26 | 250 | 100 | 46* | 100 |
| 27 | 50 | 100 | — | 100 |
| 28 | 50 | 100 | — | 100 |
| 29 | 10 | 73 | 94* | 19 |
| 30 | 10 | 25 | — | 0 |
| 31 | 10 | 100 | — | 100 |
| 32 | 10 | 96 | — | 68 |
| 33 | 10 | 100 | — | 68 |
| 34 | 10 | 71 | — | 55 |
| 35 | 10 | 100 | — | 98 |

TABLE A-continued

| Cmpd No. | Rate in ppm | Test A | Test B | Test C |
|---|---|---|---|---|
| 36 | 10 | 100 | — | 100 |
| 37 | 10 | 99 | — | 86 |
| 38 | 10 | 78 | — | 68 |
| 39 | 10 | 44 | — | 28 |
| 40 | 10 | 100 | — | 92 |
| 41 | 10 | 100 | — | 98 |
| 42 | 10 | 100 | — | 92 |
| 43 | 10 | 100 | — | 96 |
| 44 | 10 | 100 | — | 95 |
| 45 | 10 | 100 | — | 99 |
| 46 | 10 | 100 | — | 100 |
| 47 | 10 | 100 | — | 74 |
| 48 | 10 | 100 | — | 89 |
| 49 | 10 | 100 | — | 100 |
| 50 | 10 | 13 | — | 28 |
| 51 | 10 | 99 | — | 68 |
| 52 | 10 | 99 | — | 80 |
| 53 | 10 | 0 | — | 9 |
| 54 | 10 | 99 | — | 68 |
| 55 | 10 | 100 | — | 99 |
| 56 | 10 | 100 | 68** | 100 |
| 57 | 10 | 100 | 99** | 100 |
| 58 | 10 | 100 | 83** | 100 |
| 59 | 10 | 100 | 58** | 100 |
| 60 | 10 | 100 | 75** | 100 |
| 61 | 10 | 100 | — | 100 |
| 62 | 10 | 100 | — | 100 |
| 63 | 10 | 100 | — | 100 |
| 64 | 10 | 100 | — | 100 |
| 65 | 10 | 100 | — | 100 |
| 66 | 255 | 100 | — | 100 |
| 67 | 10 | 100 | — | 99 |
| 68 | 10 | 100 | — | 100 |
| 69 | 10 | 100 | — | 100 |
| 70 | 255 | 100 | 96 | 100 |
| 71 | 250 | 100 | 36 | 100 |
| 72 | 50 | 99 | — | 100 |
| 73 | 10 | 100 | — | 86 |
| 74 | 10 | 99 | — | 51 |
| 75 | 10 | 100 | — | 68 |
| 76 | 270 | 100 | 41 | 99 |
| 77 | 50 | 100 | — | 100 |
| 78 | 10 | 100 | — | 100 |
| 79 | 10 | 100 | — | 68 |
| 80 | 10 | 100 | — | 68 |
| 81 | 10 | 100 | — | 0 |
| 82 | 10 | 0 | — | 0 |
| 83 | 250 | 100 | 79 | 100 |
| 84 | 250 | 100 | 66 | 100 |
| 85 | 250 | 100*** | 9 | 100 |
| 86 | 250 | 100 | 89 | 100 |
| 87 | 250 | 100 | 82 | 100 |
| 88 | 250 | 100 | 93 | 100 |
| 89 | 250 | 100 | 83 | 100 |
| 90 | 250 | 100 | 33 | 99 |
| 91 | 250 | 100 | 96 | 100 |
| 92 | 250 | 0 | 96 | 100 |
| 93 | 250 | 100 | 39 | 99 |
| 94 | 250 | 100 | 35 | 78 |
| 95 | 250 | 100 | 87 | 100 |
| 96 | 250 | 100 | 0 | 99 |
| 97 | 50 | 99 | — | 100 |
| 98 | 50 | 99 | — | 68 |
| 99 | 10 | 100 | — | 68 |
| 100 | 10 | 100 | — | 86 |
| 101 | 50 | 100 | — | 100 |
| 102 | 10 | 100 | — | 99 |
| 103 | 10 | 100 | — | 97 |
| 104 | 10 | 100 | — | 68 |
| 105 | 50 | 100 | — | 100 |
| 106 | 50 | 100 | — | 100 |
| 107 | 10 | 100 | — | 90 |
| 108 | 50 | 100 | — | 100 |
| 109 | 50 | 100 | — | 77 |
| 110 | 10 | 100 | — | 91 |
| 111 | 255 | 100 | 0 | 86 |
| 112 | 10 | 92 | — | 0 |
| 113 | 10 | 99 | — | 0 |
| 114 | 250 | 100 | 0 | 100 |
| 115 | 10 | 98 | — | 95 |
| 116 | 265 | 100 | 25 | 99 |
| 117 | 255 | 88 | 0 | 41 |
| 118 | 250 | 100 | 0 | 98 |
| 119 | 265 | 100 | 54 | 100 |
| 120 | 260 | 99 | 0 | 68 |
| 121 | 10 | 87 | — | 0 |
| 122 | 250 | 100 | 0 | 68 |
| 123 | 255 | 100 | 21 | 99 |
| 124 | 260 | 100 | 50 | 100 |
| 125 | 260 | 100 | 55 | 100 |
| 126 | 260 | 100 | — | 100 |
| 127 | 10 | 0 | — | 0 |
| 128 | 255 | 100 | 19 | 100 |
| 129 | 260 | 100 | 0 | 89 |
| 130 | 260 | 100 | 89 | 100 |
| 131 | 10 | 100 | — | 99 |
| 132 | 270 | 100 | 0 | 95 |
| 133 | 255 | 100 | 59 | 100 |
| 134 | 255 | 100 | 0 | 80 |
| 135 | 10 | 96 | — | 0 |
| 136 | 10 | 100 | — | 68 |
| 137 | 10 | 100 | — | 41 |
| 138 | 260 | 100 | 96 | 100 |
| 139 | 255 | 100 | 62 | 100 |
| 140 | 10 | 0 | — | 0 |
| 141 | 10 | 100 | — | 88 |
| 142 | 250 | 100 | 57 | 100 |
| 143 | 250 | 100 | 71 | 100 |
| 144 | 250 | 36 | 0 | 0 |
| 145 | 250 | 100 | 0 | 100 |
| 146 | 250 | 100 | 0 | 0 |
| 147 | 10 | 100 | — | 100 |
| 148 | 10 | 100 | — | 96 |
| 149 | 260 | 100 | 72 | 100 |
| 150 | 255 | 100 | 19 | 100 |
| 151 | 50 | 100 | — | 98 |
| 152 | 10 | 100 | — | 100 |
| 153 | 250 | 100 | 0 | 89 |
| 154 | 50 | 100 | — | 100 |
| 155 | 10 | 60 | — | 0 |
| 156 | 255 | 100 | 86 | 100 |
| 157 | 10 | 100 | — | 100 |
| 158 | 270 | 100 | 90 | 100 |
| 159 | 260 | 100 | 87 | 100 |
| 160 | 10 | 99 | — | 98 |
| 161 | 265 | 100 | 33 | 99 |
| 162 | 250 | 100 | 0 | 100 |
| 163 | 250 | 100 | 0 | 100 |
| 164 | 250 | 100 | 88 | 100 |
| 165 | 260 | 100 | 95 | 100 |
| 166 | 10 | 100 | 90** | 100 |
| 167 | 10 | 100 | — | 100 |
| 168 | 10 | 100 | — | 100 |
| 169 | 10 | 100 | — | 99 |
| 170 | 10 | 100 | 97** | 100 |
| 171 | 10 | 100 | 37** | 100 |
| 172 | 10 | 100 | — | 99 |
| 173 | 10 | 100 | — | 96 |
| 174 | 10 | 85 | — | 91 |
| 175 | 255 | 100 | 95 | 100 |
| 176 | 250 | 100 | 92 | 100 |
| 177 | 250 | 100 | 97 | 100 |
| 178 | 10 | 96 | — | 68 |
| 179 | 10 | 98 | — | 9 |
| 180 | 10 | 97 | — | 0 |
| 181 | 10 | 100 | — | 100 |
| 182 | 10 | 100 | — | 100 |
| 183 | 10 | 100 | — | 100 |
| 184 | 10 | 100 | — | 55 |
| 185 | 10 | 100 | — | 98 |
| 186 | 10 | 100 | — | 74 |
| 187 | 10 | 0 | — | 0 |
| 188 | 10 | 100 | — | 100 |
| 189 | 50 | 100 | — | 100 |
| 190 | 10 | 100 | — | 100 |
| 191 | 50 | 100 | 96* | 100 |

TABLE A-continued

| Cmpd No. | Rate in ppm | Test A | Test B | Test C |
|---|---|---|---|---|
| 192 | 10 | 100 | 99* | 100 |
| 193 | 50 | 100 | 28* | 100 |
| 194 | 10 | 100 | — | 100 |
| 195 | 10 | 100 | — | 98 |
| 196 | 10 | 100 | — | 93 |
| 197 | 10 | 99 | — | 98 |
| 198 | 10 | 100 | 94** | 99 |
| 199 | 10 | 100 | — | 100 |
| 200 | 10 | 100 | — | 100 |
| 201 | — | — | — | — |
| 202 | — | — | — | — |
| 203 | 10 | 100 | — | 86 |
| 204 | 10 | 100 | — | 100 |
| 205 | 10 | 100 | — | 89 |
| 206 | 10 | 98 | — | 68 |
| 207 | 10 | 100 | — | 86 |
| 208 | 10 | 100 | — | 86 |
| 209 | — | — | — | — |
| 210 | 50 | 100 | 63* | 99 |
| 211 | 50 | 100 | 70* | 100 |
| 212 | 10 | 100 | 79* | 100 |
| 213 | 10 | 100 | 82* | 74 |
| 214 | 10 | 100 | 73* | 74 |
| 215 | 10 | 99 | 90* | 74 |
| 216 | 10 | 100 | 9* | 74 |
| 217 | — | — | 35* | — |
| 218 | — | — | — | — |
| 219 | — | — | — | — |
| 220 | — | — | — | — |
| 221 | 10 | 100 | — | 95 |
| 222 | 10 | 100 | — | 97 |
| 223 | — | — | — | — |
| 224 | 50 | 100 | 81* | 89 |
| 225 | 10 | 100 | 99* | 100 |
| 226 | 10 | 100 | 94* | 100 |
| 227 | 10 | 100 | 99* | 97 |
| 228 | 10 | 100 | 99* | 79 |
| 229 | 10 | 100 | 94* | 100 |
| 230 | 10 | 100 | 99* | 99 |
| 231 | 10 | 100 | 95* | 97 |
| 232 | 250 | 100 | 68 | 100 |
| 233 | 50 | 97 | 90* | 100 |
| 234 | 10 | 100 | 87* | 88 |
| 235 | 250 | 100 | 87 | 100 |
| 236 | 250 | 100 | 83 | 100 |
| 237 | 250 | 100 | 94 | 100 |
| 238 | 250 | 100 | 87 | 100 |
| 239 | 250 | 100 | 0 | 100 |
| 240 | 250 | 100 | 4 | 100 |
| 241 | 10 | 100 | — | 100 |
| 242 | 10 | 100 | — | 99 |
| 243 | 10 | 98 | — | 85 |
| 244 | — | — | — | — |
| 245 | — | — | — | — |
| 246 | — | — | — | — |
| 247 | — | — | — | — |
| 248 | — | — | — | — |
| 249 | — | — | — | — |
| 250 | 10 | 100 | — | 74 |
| 251 | 10 | 100 | — | 74 |
| 252 | 10 | 100 | 92* | 84 |
| 253 | 10 | 98 | 46* | 74 |
| 254 | 10 | 100 | 70* | 100 |
| 255 | — | — | — | — |
| 256 | 10 | 100 | 98* | 99 |
| 257 | 10 | 100 | 99* | 100 |
| 258 | 10 | 100 | 99* | 99 |
| 259 | 10 | 100 | 99* | 99 |
| 260 | 10 | 100 | 47* | 100 |
| 261 | 10 | 100 | 88* | 99 |
| 262 | 10 | 100 | 96* | 98 |
| 263 | 10 | 100 | 95* | 94 |
| 264 | 10 | 100 | 99* | 99 |
| 265 | 10 | 100 | 93* | 100 |
| 267 | 50 | 99 | — | 74 |
| 268 | 10 | 100 | — | 86 |
| 269 | 10 | 100 | — | 100 |
| 270 | 10 | 100 | — | 100 |
| 271 | 10 | 99 | — | 68 |
| 272 | 10 | 100 | — | 100 |
| 273 | 10 | 100 | — | 100 |
| 274 | 10 | 100 | — | 100 |
| 275 | 10 | 100 | — | 100 |
| 276 | 50 | 100 | 35* | 80 |
| 277 | 10 | 100 | 99* | 100 |
| 278 | 10 | 100 | 98* | 100 |
| 279 | 10 | 100 | 94* | 100 |
| 280 | 10 | 100 | 99* | 99 |
| 281 | 10 | 100 | 34* | 95 |
| 282 | 10 | 100 | 94* | 97 |
| 283 | 10 | 100 | 0* | 98 |
| 284 | 10 | 100 | 91* | 100 |
| 285 | 10 | 100 | 94* | 97 |
| 286 | 10 | 100 | 3* | 100 |
| 287 | 10 | 100 | 98* | 100 |
| 288 | 10 | 100 | 91* | 100 |
| 289 | 10 | 100 | 80* | 100 |
| 290 | 10 | 100 | 53* | 100 |
| 291 | 10 | 100 | 13* | 97 |
| 292 | 10 | 100 | 96* | 85 |
| 293 | 10 | 100 | 91* | 79 |
| 294 | 10 | 100 | 50* | 79 |
| 297 | 10 | 100 | — | 93 |
| 298 | 10 | 50 | 73* | 0 |
| 299 | 10 | 100 | — | 86 |
| 300 | 10 | 94 | — | 9 |
| 301 | 10 | 100 | — | 100 |
| 303 | 10 | 100 | — | 100 |
| 304 | 10 | 100 | — | 100 |
| 305 | 50 | 44 | 0* | 0 |
| 306 | 50 | 0 | 10* | 0 |
| 307 | 50 | 0 | 0* | 0 |
| 308 | 10 | 0 | — | 0 |
| 309 | 50 | 100 | — | 68 |
| 310 | 50 | 0 | 0* | 0 |
| 311 | 50 | 0 | 0* | 0 |
| 312 | 10 | 0 | 0* | 0 |
| 313 | 10 | 77 | 14* | 0 |
| 314 | 10 | 99 | 86* | 0 |
| 315 | 10 | 100 | 97* | 99 |
| 316 | 10 | 100 | 5* | 100 |
| 317 | 10 | 0 | 54* | 0 |
| 318 | 10 | 0 | 11* | 0 |
| 319 | 10 | 97 | 33* | 0 |
| 320 | 10 | 97 | 33* | 0 |
| 321 | 250 | 100 | 99* | 100 |
| 322 | 250 | 100 | 95* | 100 |
| 323 | 250 | 100 | 92* | 100 |
| 324 | 250 | 100 | 80* | 100 |
| 325 | 250 | 100 | 36* | 100 |
| 326 | 250 | 84 | 1* | 67 |
| 327 | 10 | 100 | 94* | 100 |
| 328 | 10 | 100 | 0* | 100 |
| 329 | 10 | 100 | 98* | 98 |
| 330 | 10 | 100 | 96* | 100 |
| 331 | 10 | 99 | 97* | 94 |
| 332 | 10 | 100 | 99* | 99 |
| 334 | 10 | 99 | 92* | 86 |
| 335 | 10 | 100 | 73* | 94 |
| 336 | 10 | 0 | — | 0 |
| 337 | 10 | 99 | 78* | 82 |
| 338 | 10 | 99 | 10* | 0 |
| 339 | 10 | 100 | — | 98 |
| 340 | 10 | 100 | — | 94 |
| 341 | 10 | 100 | — | 100 |
| 342 | 10 | 100 | 99* | 100 |
| 343 | 10 | 100 | 97* | 100 |
| 344 | 10 | 100 | 96* | 93 |
| 345 | 10 | 96 | 50* | 68 |
| 346 | 10 | 0 | 0* | 0 |
| 347 | 10 | 0 | 0* | 0 |
| 348 | 10 | 100 | — | 96 |
| 349 | 10 | 100 | — | 100 |
| 350 | 10 | 100 | — | 99 |
| 351 | 10 | 92 | — | 67 |
| 352 | 10 | 87 | 0* | 68 |

TABLE A-continued

| Cmpd No. | Rate in ppm | Test A | Test B | Test C |
|---|---|---|---|---|
| 353 | 10 | 0 | 73* | 0 |
| 354 | 10 | 0 | 20* | 0 |
| 355 | 10 | 0 | 4* | 0 |
| 356 | 250 | 99 | 96* | 94 |
| 357 | 250 | 98 | 99* | 91 |
| 358 | 10 | 0 | 0* | 0 |
| 359 | 10 | 100 | 99* | 95 |
| 360 | 10 | — | — | 68 |
| 361 | 10 | — | — | 0 |
| 362 | 50 | 100 | — | 100 |
| 363 | 50 | 100 | — | 100 |
| 364 | 50 | 100 | — | 100 |
| 365 | 50 | 100 | 80* | 99 |
| 366 | 50 | 100 | — | 100 |
| 367 | 50 | 96 | — | 67 |
| 368 | 50 | 100 | — | 100 |
| 369 | 50 | 100 | — | 100 |
| 370 | 250 | 100 | 98* | 100 |
| 371 | 250 | 100 | 95* | 100 |
| 372 | 250 | 100 | 99* | 100 |
| 373 | 250 | 100 | 99* | 100 |
| 374 | 10 | 100 | — | 96 |
| 375 | 10 | 100 | — | 98 |
| 376 | 10 | 100 | 49* | 68 |
| 377 | 10 | — | — | — |
| 378 | 10 | 100 | — | 98 |
| 379 | 10 | 100 | — | 97 |
| 380 | 10 | 100 | — | 100 |
| 381 | 10 | 0 | — | 0 |
| 382 | 10 | 100 | — | 96 |
| 383 | 10 | 71 | — | 68 |
| 384 | 10 | 100 | — | 100 |
| 385 | 10 | 100 | — | 100 |
| 386 | 10 | 100 | — | 100 |
| 387 | 10 | 100 | — | 99 |
| 388 | 10 | 100 | — | 100 |
| 389 | 10 | 100 | — | 100 |
| 390 | 10 | 100 | — | 100 |
| 391 | 10 | 100 | — | 100 |
| 392 | 10 | 100 | — | 100 |
| 393 | 10 | 100 | 94* | 100 |
| 394 | 10 | 100 | 99* | 100 |
| 395 | 10 | 95 | 0* | 97 |
| 396 | 10 | 100 | 28* | 100 |
| 397 | 10 | 100 | 82* | 98 |
| 398 | 10 | 100 | 80* | 97 |
| 399 | 10 | 100 | 10* | 99 |
| 400 | 10 | 100 | 99* | 100 |
| 401 | 10 | 100 | 77* | 99 |
| 402 | 10 | 100 | 96* | 90 |
| 403 | 10 | 60 | 47* | 0 |
| 404 | 10 | 0 | 0* | 68 |
| 406 | 10 | 100 | — | 93 |
| 407 | 10 | 100 | — | 100 |
| 408 | 10 | 100 | — | 100 |
| 409 | 10 | 100 | — | 100 |
| 410 | 10 | 100 | — | 100 |
| 411 | 10 | 100 | — | 100 |
| 412 | 10 | 100 | — | 100 |
| 413 | 10 | 100 | — | 68 |
| 414 | 10 | 100 | — | 100 |
| 415 | 10 | 100 | — | 96 |
| 416 | 50 | 77 | — | 0 |
| 417 | 10 | 100 | — | 100 |
| 418 | 10 | 100 | — | 99 |
| 419 | 10 | 96 | — | 99 |
| 420 | 10 | 100 | — | 100 |
| 421 | 10 | 100 | — | 100 |
| 422 | 10 | 90 | — | 93 |
| 423 | 10 | 86 | — | 80 |
| 424 | 10 | 100 | — | 96 |
| 426 | 250 | 0 | 9* | 0 |
| 427 | 50 | 100 | — | 67 |
| 428 | 50 | 100 | — | 100 |
| 429 | 50 | 100 | — | 100 |
| 430 | 50 | 100 | — | 100 |
| 431 | 50 | 99 | — | 98 |
| 432 | 50 | 100 | — | 92 |
| 433 | 10 | 100 | — | 99 |
| 434 | 10 | 100 | — | 98 |
| 435 | 10 | 100 | — | 74 |
| 436 | 10 | 100 | — | 74 |
| 437 | 10 | 100 | — | 86 |
| 438 | 10 | — | — | — |
| 439 | 10 | 0 | — | 0 |
| 440 | 10 | 0 | — | 0 |
| 441 | 10 | 87 | — | 9 |
| 442 | 10 | 44 | — | 0 |
| 443 | 10 | 100 | — | 74 |
| 444 | 10 | 96 | — | 86 |
| 445 | 10 | 100 | — | 99 |
| 446 | 10 | 99 | — | 86 |
| 447 | 10 | 100 | — | 100 |
| 448 | 10 | 100 | — | 100 |
| 449 | 10 | 100 | — | 100 |
| 450 | 10 | 94 | 41* | 0 |
| 451 | 10 | 99 | 8* | 0 |
| 452 | 10 | 81 | 59* | 0 |
| 453 | 10 | 92 | 50* | 0 |
| 454 | 10 | 100 | 47* | 0 |
| 455 | 10 | 100 | 66* | 0 |
| 456 | 10 | 100 | 65* | 68 |
| 457 | 50 | 77 | — | 0 |
| 458 | 50 | 0 | 0* | 0 |
| 459 | 50 | 0 | 0* | 0 |
| 460 | 50 | 100 | — | 99 |
| 461 | 50 | 100 | — | 100 |
| 462 | 10 | 100 | — | 89 |
| 463 | 10 | 100 | 65* | 100 |
| 464 | 10 | 79 | 94* | 23 |
| 465 | 10 | 100 | 0* | 80 |
| 466 | 10 | 100 | 3* | 55 |
| 467 | 10 | 97 | 6* | 68 |
| 468 | 10 | 84 | 22* | 0 |
| 469 | 10 | 96 | 65* | 86 |
| 470 | 10 | 100 | 0* | 94 |
| 471 | 10 | 77 | 15* | 80 |
| 472 | 10 | 77 | 22* | 0 |
| 473 | 10 | 94 | 28* | 89 |
| 474 | 10 | 100 | — | 100 |
| 475 | 10 | 100 | — | 91 |
| 476 | 10 | 100 | — | 86 |
| 477 | 10 | 100 | — | 100 |
| 478 | 50 | 81 | — | 19 |
| 479 | 10 | 100 | — | 100 |
| 480 | 10 | 100 | — | 98 |
| 481 | 10 | 100 | — | 100 |
| 482 | 10 | 100 | — | 100 |
| 483 | 10 | 100 | — | 54 |
| 484 | 10 | 100 | — | 100 |
| 485 | 10 | 100 | — | 99 |
| 486 | 10 | 100 | — | 89 |
| 487 | 10 | 100 | 98** | 100 |
| 488 | 10 | 100 | 99* | 100 |
| 489 | 10 | 100 | 92* | 99 |
| 490 | 10 | 100 | 94* | 74 |
| 491 | | — | — | — |
| 492 | 10 | 100 | — | 85 |
| 493 | 10 | 100 | — | 100 |
| 494 | 10 | 100 | 47* | 0 |
| 495 | 10 | 100 | 43* | 0 |
| 496 | 10 | 100 | 48* | 0 |
| 497 | 10 | 100 | 5* | 0 |
| 498 | 10 | 100 | 43* | 0 |
| 499 | 250 | 100 | 48* | 100 |
| 500 | 250 | 100 | 5* | 100 |
| 501 | 10 | 100 | — | 0 |
| 502 | 250 | 100 | 62 | 100 |
| 503 | | — | — | — |
| 504 | | — | — | — |

What is claimed is:

1. A compound selected from Formula 1, tautomers, N-oxides, and salts thereof,

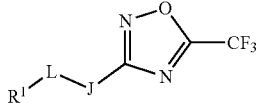

1 wherein
$R^1$ is

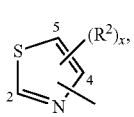

U-1

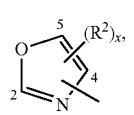

U-2

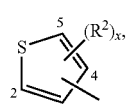

U-4

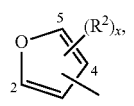

U-5

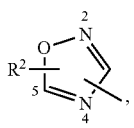

U-8

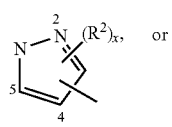

U-12    or

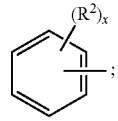

U-69 wherein the floating bond on $R^1$ is connected to L in Formula 1 through any available carbon or nitrogen atom of the depicted ring;

x is 0, 1 or 2;

L is $(CR^{4a}R^{4b})_n$, $OCH_2$, $CH_2O$, $OCH_2CH_2$, $CH_2CH_2O$ or $CH_2OCH_2$; wherein the atom to the left is connected to $R^1$, and the atom to the right is connected to J;

J is

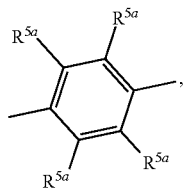

J-63 wherein the bond projecting to the left is bonded to L, and the bond projecting to the right is bonded to the oxadiazole ring in Formula 1;

each $R^{5a}$ is independently H or $R^5$; provided that at most only two $R^{5a}$ substituents are other than H;

each $R^2$ is independently halogen, cyano, —CH(=O), —C(=O)OH, —C(=O)NR$^{3a}$R$^{3b}$, —C(R$^6$)=NR$^7$ or —U—V-Q; or $C_1$-$C_6$ alkyl, $C_2$-$C_6$ alkenyl, $C_2$-$C_6$ alkynyl, $C_3$-$C_7$ cycloalkyl, $C_1$-$C_6$ alkoxy, $C_2$-$C_6$ alkenyloxy, $C_2$-$C_6$ alkynyloxy, $C_3$-$C_7$ cycloalkoxy, $C_1$-$C_6$ alkylthio, $C_2$-$C_6$ alkoxycarbonyl, $C_3$-$C_6$ alkenyloxycarbonyl, $C_3$-$C_6$ alkynyloxycarbonyl, $C_4$-$C_7$ cycloalkoxycarbonyl, $C_2$-$C_6$ alkylcarbonyloxy or $C_2$-$C_6$ alkylcarbonylamino, each optionally substituted with up to 2 substituents independently selected from $R^{10}$;

each $R^{3a}$ is independently H, cyano, hydroxy, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl;

each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ halocycloalkyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from cyano, $C_2$-$C_4$ alkylcarbonyl, $C_2$-$C_4$ alkoxycarbonyl and $C_3$-$C_{15}$ trialkylsilyl;

each $R^{4a}$ and $R^{4b}$ is independently H, halogen, methyl or methoxy;

each $R^5$ is methoxy;

each $R^6$ is independently H or methyl;

each $R^7$ is independently $C_1$-$C_4$ alkoxy, $C_2$-$C_4$ alkenyloxy or $C_2$-$C_4$ alkynyloxy, each optionally substituted with up to 1 substituent selected from cyano, hydroxy and —C(=O)OH;

each $R^{10}$ is independently halogen, cyano, $C_1$-$C_4$ alkyl, $C_1$-$C_4$ haloalkyl, $C_1$-$C_4$ alkoxy, $C_1$-$C_4$ haloalkoxy, $C_2$-$C_4$ alkoxyalkoxy, $C_1$-$C_4$ alkylsulfonyl, $C_1$-$C_4$ haloalkylsulfonyl, $C_2$-$C_4$ alkylcarbonyl, $C_2$-$C_4$ haloalkylcarbonyl, $C_2$-$C_5$ alkoxycarbonyl or —C(R$^{13}$)=NOR$^{14}$;

each U is independently a direct bond, C(=O)O or C(=O)NR$^{17}$, wherein the atom to the left is connected to $R^1$, and the atom to the right is connected to V;

each V is independently a direct bond, $C_1$-$C_3$ alkylene, $C_2$-$C_4$ alkenylene or $C_3$-$C_4$ alkynylene;

each Q is independently phenyl, each optionally substituted with up to 2 substituents independently selected from $R^{12}$; or pyridinyl, pyrazolyl, imidazolyl, triazolyl, thiazolyl, oxazolyl, isoxazolyl, thienyl, isoxazolinyl, piperidinyl, morpholinyl or piperazinyl, each ring optionally substituted with up to 2 substituents independently selected from $R^{12}$;

each $R^{12}$ is independently halogen, cyano, $C_1$-$C_2$ alkyl, $C_1$-$C_2$ haloalkyl or $C_1$-$C_2$ alkoxy;

each $R^{13}$ is independently H, halogen, methyl or methoxy;

each $R^{14}$ is independently H, $C_1$-$C_2$ alkyl, $C_1$-$C_2$ haloalkyl, $C_2$-$C_4$ alkenyl, $C_2$-$C_4$ alkylcarbonyl or $C_2$-$C_4$ alkoxycarbonyl;

each $R^{17}$ is independently H, cyano, methyl or halomethyl;

n is 1, 2, or 3;

provided that:
(a) when $R^1$ is 1H-pyrazol-1-yl substituted with 1-2 substituents selected from $CH_3$ and J is unsubstituted phenyl, then L is other than $CH_2CH_2$, $CH_2CHF$ or $CH(CH_3)$;
(b) the compound of Formula 1 is not

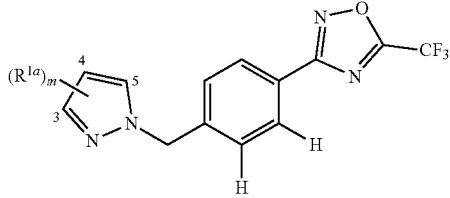

wherein:
each $R^{1a}$ may be the same or different;
m is 0; or
m is 1; $R^{1a}$ is at the 3-position and is Cl or —CH(=O); or
m is 1; $R^{1a}$ is at the 4-position and is halogen, cyano, —CH(=O), OHC(=O), $C_2$-$C_5$ alkoxycarbonyl, $NH_2C(=O)$, $CH_3NHC(=O)$, $CH_3CH_2NHC(=O)$, cyclopropyl-$CH_2NHC(=O)$, $(CH_3)_2NC(=O)$, $(CH_3CH_2)_2NC(=O)$, $CH_3ONHC(=O)$, $CH_3OCH_2CH_2NHC(=O)$, $C\equiv CCH_2NHC(=O)$, $CH_3ON(CH_3)C(=O)$, $CH_3ON=CH$ $CH_3CH_2ON=CH$, $CH_3CH_2CH_2ON=CH$, $(CH_3)_2CHON=CH$ or $C\equiv CCH_2ON=CH$; or
m is 2; $R^{1a}$ is at the 3- and 4-positions and is cyano, $CF_2H$, $CH_3OCH_2$, $C_2$-$C_3$ alkoxycarbonyl, cyclopropyl, phenyl or 4-chlorophenyl; or
m is 2; $R^{1a}$ is at the 3- and 5-positions and is cyano, $CH_3$, —CH(=O), $CF_2H$, cyclopropyl, $C_2$-$C_3$ alkoxycarbonyl, 4-fluorophenyl, 2,4-difluorophenyl, 2,5-difluorophenyl or 4-methoxyphenyl; or
m is 2; $R^{1a}$ is at the 4- and 5-positions and is $CF_2H$, cyclopropyl, $CH_3OCH_2$ or $C_2$-$C_3$ alkoxycarbonyl;
(c) the compound of Formula 1 is not
ethyl 1-[1-[4-[5-(trifluoromethyl)-1,2,4-oxadiazol-3-yl]phenyl]ethyl]-1H-pyrazole-4-carboxylate;
ethyl 1-[2-[4-[5-(trifluoromethyl)-1,2,4-oxadiazol-3-yl]phenyl]ethyl]-1H-pyrazole-4-carboxylate;
ethyl 1-[2-fluoro-2-[4-[5-(trifluoromethyl)-1,2,4-oxadiazol-3-yl]phenyl]ethyl]-1H-pyrazole-4-carboxylate;
3-[4-[[(1-methyl-1H-pyrazol-3-yl)oxy]methyl]phenyl]-5-(trifluoromethyl)-1,2,4-oxadiazole;
3-[4-[[(5-methyl-1H-pyrazol-3-yl)oxy]methyl]phenyl]-5-(trifluoromethyl)-1,2,4-oxadiazole;
3-[4-[(2-fluorophenoxy)methyl]phenyl]-5-(trifluoromethyl)-1,2,4-oxadiazole;
3-[4-[(2,6-difluorophenoxy)methyl]phenyl]-5-(trifluoromethyl)-1,2,4-oxadiazole;
3-[4-(phenoxymethyl)phenyl]-5-(trifluoromethyl)-1,2,4-oxadiazole;
3-[4-[(4-fluorophenoxy)methyl]phenyl]-5-(trifluoromethyl)-1,2,4-oxadiazole;
3-[4-[(3,5-diethyl-1H-pyrazol-1-yl)methyl]phenyl]-5-(trifluoromethyl)-1,2,4-oxadiazole; and
3-[2-methoxy-4-(phenoxymethyl)phenyl]-5-(trifluoromethyl)-1,2,4-oxadiazole.

2. A compound of claim 1 wherein:
$R^1$ is U-1, U-2 or U-12;
L is $(CR^{4a}R^{4b})_n$;
J is J 63;
each $R^2$ is independently —C(=O)$NR^{3a}R^{3b}$, —C($R^6$)=$NR^7$ or —U—V—Q; or $C_2$-$C_6$ alkoxycarbonyl, $C_3$-$C_6$ alkenyloxycarbonyl or $C_3$-$C_6$ alkynyloxycarbonyl, each optionally substituted with up to 1 substituent selected from $R^{10}$;
each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl;
each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from $C_2$-$C_4$ alkylcarbonyl and $C_2$-$C_4$ alkoxycarbonyl;
each $R^{4a}$ and $R^{4b}$ is independently H or methyl;
each $R^6$ is independently H;
each $R^7$ is independently $C_1$-$C_4$ alkoxy, $C_2$-$C_4$ alkenyloxy or $C_2$-$C_4$ alkynyloxy;
each $R^{10}$ is independently halogen, $C_1$-$C_4$ alkyl, $C_1$-$C_4$ haloalkyl, $C_1$-$C_4$ alkoxy, $C_1$-$C_4$ haloalkoxy, $C_2$-$C_4$ alkylcarbonyl, $C_2$-$C_4$ haloalkylcarbonyl, $C_2$-$C_5$ alkoxycarbonyl or —C($R^{13}$)=$NOR^{14}$;
each V is independently a direct bond, $C_1$-$C_3$ alkylene or $C_2$-$C_4$ alkenylene;
each Q is independently phenyl, each optionally substituted with up to 2 substituents independently selected from $R^{12}$; or pyridinyl, pyrazolyl, imidazolyl, triazolyl, thiazolyl or oxazolyl, each ring optionally substituted with up to 2 substituents independently selected from $R^{12}$;
each $R^{12}$ is independently halogen, methyl or methoxy; and
each $R^{14}$ is independently H, methyl, halomethyl, $C_2$-$C_4$ alkylcarbonyl or $C_2$-$C_4$ alkoxycarbonyl.

3. A compound of claim 2 wherein:
$R^1$ is U-2 or U-12;
$R^{5a}$ is H;
each $R^2$ is independently —C(=O)$NR^{3a}R^{3b}$; or $C_2$-$C_6$ alkoxycarbonyl, optionally substituted with up to 1 substituent selected from $R^{10}$;
each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_2$-$C_4$ alkoxyalkyl or $C_3$-$C_5$ alkoxycarbonylalkyl;
each $R^{3b}$ is independently H, $C_1$-$C_6$ alkyl, $C_1$-$C_6$ haloalkyl, $C_2$-$C_6$ alkenyl or $C_2$-$C_6$ haloalkenyl, each optionally substituted with up to 1 substituent selected from $C_2$-$C_4$ alkylcarbonyl and $C_2$-$C_4$ alkoxycarbonyl; and
each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl or $C_2$-$C_5$ alkoxycarbonyl.

4. A compound of claim 3 wherein:
$R^1$ is U-2 connected at its 2-position to L; or
$R^1$ is U-12 connected at its 1-position to L;
each $R^2$ is independently —C(=O)$NR^{3a}R^{3b}$ or $C_2$-$C_6$ alkoxycarbonyl; and
n is 1.

5. A compound of claim 1 wherein:
$R^1$ is U-1, U-2, U-4, U-5 or U-12;
L is $CH_2$, $CH_2CH_2$, $OCH_2$ or $CH_2O$;
each $R^{5a}$ is H;
each $R^2$ is independently —C(=O)$NR^{3a}R^{3b}$, —C($R^6$)=$NR^7$ or —U—V-Q; or $C_2$-$C_6$ alkoxycarbonyl, $C_3$-$C_6$ alkenyloxycarbonyl or $C_3$-$C_6$ alkynyloxycarbonyl, each optionally substituted with up to 1 substituent selected from $R^{10}$;
each U is a direct bond;
each V is independently a direct bond, $C_1$-$C_3$ alkylene or $C_2$-$C_4$ alkenylene;
each Q is independently phenyl, each optionally substituted with up to 2 substituents independently selected from $R^{12}$; or pyridinyl, pyrazolyl, imidazolyl, triazolyl, thiazolyl or oxazolyl, each ring optionally substituted with up to 2 substituents independently selected from $R^{12}$.

6. A compound of claim 5 wherein:
$R^1$ is U-2 or U-12;
x is 1 or 2;
L is $CH_2$ or $CH_2O$;
each $R^2$ is independently —C(=O)$NR^{3a}R^{3b}$; or $C_2$-$C_6$ alkoxycarbonyl, optionally substituted with up to 1 substituent selected from $R^{10}$;
each $R^{3a}$ is independently H, $C_1$-$C_4$ alkyl, $C_1$-$C_4$ haloalkyl, $C_2$-$C_4$ alkenyl, $C_2$-$C_4$ alkynyl, $C_1$-$C_4$ alkoxy, $C_2$-$C_4$ alkoxyalkyl, $C_2$-$C_4$ alkylcarbonyl, $C_2$-$C_4$ haloalkylcarbonyl or $C_3$-$C_5$ alkoxycarbonylalkyl;
each $R^{3b}$ is independently H, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_4$-$C_{10}$ cycloalkylalkyl, $C_4$-$C_{10}$ halocycloalkylalkyl, $C_2$-$C_6$ alkoxyalkyl or $C_2$-$C_6$ haloalkoxyalkyl, each optionally substituted with up to 1 substituent selected from $C_2$-$C_4$ alkylcarbonyl and $C_2$-$C_4$ alkoxycarbonyl; and
each $R^{10}$ is independently halogen, $C_1$-$C_4$ alkyl, $C_1$-$C_4$ alkoxy, $C_2$-$C_4$ alkylcarbonyl, $C_2$-$C_4$ haloalkylcarbonyl or $C_2$-$C_5$ alkoxycarbonyl.

7. A compound of claim 6 wherein:
$R^1$ is U-2 connected at its 2-position to L; or
$R^1$ is U-12 connected at its 1-position to L; and
x is 1.

8. A compound of claim 1 that is:

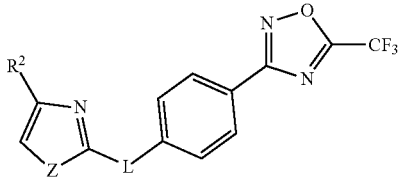

wherein:
$R^2$ is ClCH$_2$CH$_2$NHC(=O); Z is O and L is CH$_2$; or
$R^2$ is F$_2$CHCH$_2$NHC(=O); Z is O and L is CH$_2$; or
$R^2$ is N≡CCH$_2$CH$_2$NHC(=O); Z is O and L is CH$_2$; or
$R^2$ is MeOCH$_2$CH$_2$NHC(=O); Z is O and L is CH$_2$; or
$R^2$ is 1H-pyrazol-1-yl-CH$_2$CH$_2$NHC(=O); Z is O and L is CH$_2$; or
$R^2$ is CF$_3$CH$_2$CH$_2$NHC(=O); Z is O and L is CH$_2$; or
$R^2$ is MeOCH$_2$CH$_2$NHC(=O); Z is S and L is CH$_2$; or
$R^2$ is FCH$_2$CH$_2$NHC(=O); Z is O and L is CH$_2$; or
$R^2$ is CF$_3$OCH$_2$CH$_2$NHC(=O); Z is O and L is CH$_2$; or
$R^2$ is CF$_3$CH$_2$NHC(=O); Z is S and L is CH$_2$; or
$R^2$ is CF$_3$CH$_2$NHC(=O); Z is O and L is CH$_2$.

9. A compound of claim 1 that is:

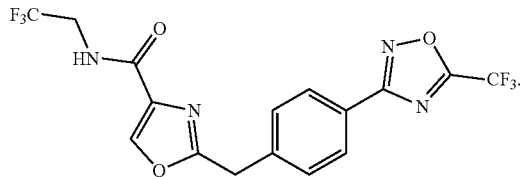 [SMILES: O=C(NCC(F)(F)F)c1coc(Cc2ccc(-c3noc(C(F)(F)F)n3)cc2)n1]

10. A compound of claim 1 that is:

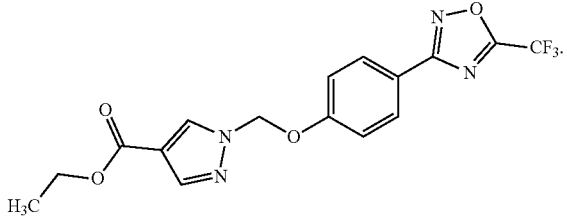 [SMILES: CCOC(=O)c1cnn(COc2ccc(-c3noc(C(F)(F)F)n3)cc2)c1]

11. A fungicidal composition comprising (a) a compound of claim 1; and (b) at least one fungicide.

12. A fungicidal composition comprising (a) a compound of claim 1; and (b) at least one additional component selected from the group consisting of surfactants, solid diluents and liquid diluents.

13. A method for controlling plant diseases caused by fungal plant pathogens comprising applying to the plant or portion thereof, or to the plant seed, a fungicidally effective amount of a compound of claim 1.

14. A method for controlling plant diseases caused by Basidiomycetes fungal plant pathogens comprising applying to the plant or portion thereof, or to the plant seed, a fungicidally effective amount of a compound of claim 1.

* * * * *